United States Patent
Brentjens et al.

(10) Patent No.: US 10,918,665 B2
(45) Date of Patent: *Feb. 16, 2021

(54) CHIMERIC ANTIGEN RECEPTORS TARGETING B-CELL MATURATION ANTIGEN AND USES THEREOF

(71) Applicants: MEMORIAL SLOAN KETTERING CANCER CENTER, New York, NY (US); EUREKA THERAPEUTICS, INC., Emeryville, CA (US)

(72) Inventors: Renier J. Brentjens, New York, NY (US); Eric L. Smith, New York, NY (US); Cheng Liu, Emeryville, CA (US)

(73) Assignees: MEMORIAL SLOAN KETTERING CANCER CENTER, New York, NY (US); EUREKA THERAPEUTICS, INC., Emeryville, CA (US)

( * ) Notice: Subject to any disclaimer, the term of this patent is extended or adjusted under 35 U.S.C. 154(b) by 356 days.

This patent is subject to a terminal disclaimer.

(21) Appl. No.: 15/613,638

(22) Filed: Jun. 5, 2017

(65) Prior Publication Data

US 2018/0360880 A1   Dec. 20, 2018

Related U.S. Application Data

(63) Continuation of application No. PCT/US2015/064112, filed on Dec. 4, 2015.

(60) Provisional application No. 62/088,309, filed on Dec. 5, 2014.

(51) Int. Cl.
| | |
|---|---|
| *A61K 35/17* | (2015.01) |
| *C07K 16/28* | (2006.01) |
| *C07K 14/725* | (2006.01) |
| *C07K 14/705* | (2006.01) |
| *A61P 35/00* | (2006.01) |

(52) U.S. Cl.
CPC .............. *A61K 35/17* (2013.01); *A61P 35/00* (2018.01); *C07K 14/7051* (2013.01); *C07K 14/70521* (2013.01); *C07K 16/2878* (2013.01); *C07K 2317/34* (2013.01); *C07K 2317/622* (2013.01); *C07K 2317/73* (2013.01); *C07K 2317/92* (2013.01); *C07K 2319/02* (2013.01); *C07K 2319/03* (2013.01); *C07K 2319/33* (2013.01); *C12N 2740/10043* (2013.01); *C12N 2840/203* (2013.01)

(58) Field of Classification Search
None
See application file for complete search history.

(56) References Cited

U.S. PATENT DOCUMENTS

| | | | |
|---|---|---|---|
| 4,956,778 A | 9/1990 | Naito | |
| 5,091,513 A | 2/1992 | Huston et al. | |
| 5,132,405 A | 7/1992 | Huston et al. | |
| 7,083,785 B2 | 8/2006 | Browning et al. | |
| 7,605,236 B2 | 10/2009 | Ruben et al. | |
| 8,399,645 B2 | 3/2013 | Campana et al. | |
| 8,497,118 B2 | 7/2013 | Jensen | |
| 8,802,374 B2 | 8/2014 | Jensen | |
| 9,034,324 B2 | 5/2015 | Kalled et al. | |
| 2005/0196754 A1 | 9/2005 | Drmanac et al. | |
| 2009/0169562 A1 | 7/2009 | Throsby et al. | |
| 2011/0117093 A1 | 5/2011 | Ruben et al. | |
| 2012/0082661 A1 | 4/2012 | Kalled et al. | |
| 2013/0336964 A1 | 12/2013 | Rovati et al. | |
| 2014/0161828 A1 | 6/2014 | Armitage et al. | |
| 2014/0193433 A1 | 7/2014 | Borges et al. | |
| 2014/0243504 A1 | 8/2014 | Davis et al. | |
| 2015/0051266 A1 | 2/2015 | Kochenderfer | |
| 2016/0046724 A1 | 2/2016 | Brogdon et al. | |
| 2018/0118842 A1 | 5/2018 | Brentjens et al. | |
| 2018/0360880 A1 | 12/2018 | Brentjens et al. | |
| 2019/0161553 A1 | 5/2019 | Sather et al. | |

FOREIGN PATENT DOCUMENTS

| | | |
|---|---|---|
| JP | 2011-178691 A | 9/2011 |
| WO | WO 2008/116149 A2 | 9/2008 |
| WO | WO 2010/054007 A1 | 5/2010 |
| WO | WO 2010/104949 A2 | 9/2010 |
| WO | WO 2011/085103 A2 | 7/2011 |
| WO | WO 2012/066058 A1 | 5/2012 |
| WO | WO 2012/079000 A1 | 6/2012 |
| WO | WO 2012/143498 A1 | 10/2012 |
| WO | WO 2013/072406 A1 | 5/2013 |
| WO | WO 2013/072415 A1 | 5/2013 |
| WO | WO 2013/154760 A1 | 10/2013 |
| WO | WO 2014/087010 A1 | 6/2014 |
| WO | WO 2014/089335 A2 | 6/2014 |

(Continued)

OTHER PUBLICATIONS

Clinical Trial Identifier NCT02546167, "CART-BCMA Cells for Multiple Myeloma," Retrieved on https://clinicaltrials.gov/ct2/show/NCT02546167. Retrieved on Oct. 22, 2018.
Dimopoulos et al. "Current treatment landscape for relapsed and/or refractory multiple myeloma," Nat Rev Clin Oncol (2015) 12:42-54.
Nasonov et al., "Belimumab: advancement in treatment of Systemic Lupus Erythematosus (SLE)," Federal State Budgetary Institution 'Scientific Research Institute for Rheumatology', RAMS, Moscow, 54(5):13-19 (2012) [with full English translation].
U.S. Appl. No. 15/613,986 (US 2018/0118842), filed Jun. 5, 2017 (May 3, 2018).
U.S. Appl. No. 15/613,986, Nov. 2, 2018 Notice of Allowance.
U.S. Appl. No. 15/613,986, Aug. 3, 2018 Response to Non-Final Office Action.

(Continued)

*Primary Examiner* — Nelson B Moseley, II
(74) *Attorney, Agent, or Firm* — Baker Botts L.L.P.

(57) ABSTRACT

The presently disclosed subject matter provides for methods and compositions for treating multiple myeloma. It relates to chimeric antigen receptors (CARs) that specifically target B cell maturation antigen (BMCA), and immunoresponsive cells comprising such CARs. The presently disclosed BMCA-specific CARs have enhanced immune-activating properties, including anti-tumor activity.

57 Claims, 29 Drawing Sheets

Specification includes a Sequence Listing.

(56) References Cited

FOREIGN PATENT DOCUMENTS

| WO | WO 2014/134165 A1 | 9/2014 |
|---|---|---|
| WO | WO 2014/191128 A1 | 12/2014 |
| WO | WO 2015/142675 A2 | 9/2015 |
| WO | WO 2015/158671 A1 | 10/2015 |
| WO | WO 2016/014565 A2 | 1/2016 |
| WO | WO 2016/014789 A2 | 1/2016 |
| WO | WO 2016/090320 A1 | 6/2016 |
| WO | WO 2016/090327 A2 | 6/2016 |
| WO | WO 2016/094304 A2 | 6/2016 |

OTHER PUBLICATIONS

U.S. Appl. No. 15/613,986, May 3, 2018 Non-Final Office Action.
Bataille et al., "The phenotype of normal, reactive and malignant plasma cells. Identification of 'many and multiple myelomas' and of new targets for myeloma therapy," Haematologica 91:1234-1240 (2006).
Bertilaccio et al., "Low-Dose Lenalidomide Improves CAR-Based Immunotherapy in CLL by Reverting T-Cell Defects In Vivo," Blood 122:4171 (2013).
Boyd et al., "The Clinical Impact and Molecular Biology of del(17p) in Multiple Myeloma Treated with Conventional or Thalidomide-Based Therapy," Genes, Chromosomes & Cancer 50:765-774 (2011).
Brentjens et al., "CD19-Targeted T Cells Rapidly Induce Molecular Remissions in Adults with Chemotherapy-Refractory Acute Lymphoblastic Leukemia," Science Translational Medicine 5:177ra38 (2013).
Brentjens et al., "Eradication of systemic B-cell tumors by genetically targeted human T lymphocytes co-stimulated by CD80 and interleukin-15," Nature Medicine 9(3):279-286 (2003).
Brentjens et al., "Genetically Targeted T cells Eradicate Systemic Acute Lymphoblastic Leukemia Xenografts," Clin Cancer Res. 13(18):5426-5435 (2007).
Brentjens et al., "Safety and persistence of adoptively transferred autologous CD19-targeted T cells in patients with relapsed or chemotherapy refractory B-cell leukemias," Blood 118(18):4817-4828 (2011).
Brown et al., "Tolerance to single, but not multiple, amino acid replacements in antibody V-H CDR2: A means of minimizing B cell wastage from somatic hypermutation?", The Journal of Immunology, The American Association of Immunologists, 156(9):3285-3291 (1996).
Carpenter et al., "B-cell Maturation Antigen is a Promising Target for Adoptive T-cell Therapy of Multiple Myeloma," Clin Cancer Res. 19(8):2048-2060 (2013).
Davila et al., "Efficacy and Toxicity Management of 19-28z CAR T Cell Therapy in B Cell Acute Lymphoblastic Leukemia," Science Translational Medicine 6:224ra25 (2014).
Dudley et al., "Adoptive Cell Therapy for Patients With Metastatic Melanoma: Evaluation of Intensive Myeloablative Chemoradiation Preparative Regimens," J Clin Oncol. 26(32):5233-5239 (2008).
Frigyesi et al., "Robust isolation of malignant plasma cells in multiple myeloma," Blood 123(9):1336-1340 (2014).
Gade et al., "Targeted Elimination of Prostate Cancer by Genetically Directed Human T Lymphocytes," Cancer Res. 65:9080-9088 (2005).
Gahrton et al., "Allogeneic Bone Marrow Transplantation in Multiple Myeloma," The N. Engl. J. Med 325(18):1267-1273 (1991).
Gong et al., "Cancer Patient T Cells Genetically Targeted to Prostate-Specific Membrane Antigen Specifically Lyse Prostate Cancer Cells and Release Cytokines in Response to Prostate-Specific Membrane Antigen," Neoplasia 1(2):123-127 (1999).
Hollyman et al., "Manufacturing Validation of Biologically Functional T Cells Targeted to CD19 Antigen for Autologous Adoptive Cell Therapy," J. Immunother 32(2):169-180 (2009).
Hunder et al., "Treatment of Metastatic Melanoma with Autologous CD4+ T Cells against NY-ESO-1," N. Engl. J. Med 358(25):2698-2703 (2008).

International Search Report dated Mar. 3, 2016 in International Application No. PCT/US15/64112.
Kershaw et al., "Gene-Engineered T Cells as a Superior Adjuvant Therapy for Metastatic Cancer," J Immunol 173:2143-2150 (2004).
Krause et al., "Antigen-dependent CD28 Signaling Selectively Enhances Survival and Proliferation in Genetically Modified Activated Human Primary T Lymphocytes," J. Exp. Med. 188(4):619-626 (1998).
Lyddane et al., "Cutting Edge: CD28 Controls Dominant Regulatory T Cell Activity during Active Immunization," J. Immunol. 176:3306-3310 (2006).
Maher et al., "Human T-lymphocyte cytotoxicity and proliferation directed by a single chimeric TCRζ/CD28 receptor," Nat. Biotechnol. 20:70-75 (2002).
Maus et al., "T Cells Expressing Chimeric Antigen Receptors Can Cause Anaphylaxis in Humans," Cancer Immunol Res 1(1):26-31 (2013).
Morgan et al., "Case Report of a Serious Adverse Event Following the Administration of T Cells Transduced With a Chimeric Antigen Receptor Recognizing *ERBB2*," Molecular Therapy 18(4):843-851 (2010).
Pegram et al., "Tumor-targeted T cells modified to secrete IL-12 eradicate systemic tumors without need for prior conditioning," Blood 119(18):4133-4141 (2012).
Riviere et al., "Novel Strategies for Cancer Therapy: The Potential of Genetically Modified T Lymphocytes," Curr Hematol Rep 3:290-297 (2004).
Rosenberg et al., "Adoptive cell transfer: a clinical path to effective cancer immunotherapy," Nature Reviews Cancer 8:299-308 (2008).
Sadelain et al., "The basic principles of chimeric antigen receptor (CAR) design," Cancer Discovery 3(4):388-398 (2013).
Sadelain et al., "The promise and potential pitfalls of chimeric antigen receptors," Curr Opin Immunol 21:215-223 (2009).
Shaughnessy et al., "A validated gene expression model of high-risk multiple myeloma is defined by deregulated expression of genes mapping to chromosome 1," Blood 109:2276-2284 (2007).
Siegel et al., "Cancer Statistics, 2013," CA Cancer J Clin. 63:11-30 (2013).
Stephan et al., "T cell-encoded CD80 and 4-1BBL induce auto- and transcostimulation, resulting in potent tumor rejection," Nat. Med 13(12):1440-1449 (2007).
Supplemental Partial European Search Report dated May 4, 2018 in Application No. EP 15864826.
Tai et al., "Novel afucosylated anti-B cell maturation antigen-monomethyl auristatin F antibody-drug conjugate (GSK2857916) induces potent and selective anti-multiple myeloma activity," Blood (Feb. 25, 2014) (38 pages).
U.S. Appl. No. 16/178,571 (Copy not submitted herewith pursuant to the waiver of 37 C.F. R. § 1.98(a)(2)(iii) issued by the Office of Sep. 21, 2004)., filed May 30, 2019, Juno Therapeutics, Inc.
Ali et al., "T cells expressing an anti-B-cell maturation antigen chimeric antigen receptor cause remissions of multiple myeloma," Blood 128(13):1688-1700 (2016).
Kuester et al., "Pharmacokinetics of Monoclonal Antibodies," in Pharmacokinetics and Pharmacodynamics of Biotech Drugs, ed. Bernd Meibohm, Wiley-VCH, chapter 3, pp. 45-91 (2006).
Lefranc et al., "IMGT unique numbering for immunoglobulin and T cell receptor variable domains and Ig superfamily V-like domains," Dev Comp Immunol 27(1):55-77 (2003).
Ryan et al., "Antibody targeting of B-cell maturation antigen on malignant plasma cells," Molecular cancer therapeutics 6(11):3009-3018 (2007).
Tai et al., "Antibody-Based Therapies in Multiple Myeloma," Bone Marrow Research Article ID: 924058 (2011).
Tai et al., "Targeting B-cell maturation antigen in multiple myeloma," Immunotherapy 7(11):1187-1199 (2015).
Extended European Search Report dated Jul. 24, 2018 in Application No. EP 15864826.
Garfall et al., "Immunotherapy with Chimeric Antigen Receptors for Multiple Myeloma," Discov Med., 17(91):37-46 (2014).
Gershoni et al., "Epitope mapping: the first step in developing epitope-based vaccines," BioDrugs, 21(3):145-156 (2007).

(56) References Cited

OTHER PUBLICATIONS

Maus et al., "Zoom Zoom: Racing CARs for Multiple Myeloma," Clin Cancer Res., 19(8):1917-1919 (2013).
Coico (Koyko) et al., "Immunology," translation from English, edited by N.B. Serebryanaya, Mosow, "Akademiya," 2008, p. 37 (in Russian).
Parkman R., "Clonal Analysis of Murine Graft-vs-Host Disease. I. Phenotypic and Functional Analysis of T Lymphocyte Clones," J. Immunol. (1986) 136(10):3543-3548.
Yeger, L., "Clinical Immunology and Allergology," (1990) 2nd ed., translation from German, Mosow, Meditsina in 3 volumes, vol. 1, pp. 219-222 (in Russian).
Kochenderfer et. al., "Adoptive transfer of syngeneic T cells transduced with a chimeric antigen receptor that recognizes murine CD19 can eradicate lymphoma and normal B cells," Blood, 116(19):3875-3886 (2010).
Ozhegov, S.I. The Thesaurus of the Russian Language: 80,000 words and idioms / S.I. Ozhegov and N.Yu Shvedova; Russian Academy of Sciences, Institute of the Russian Language named after V.V. Vinogradov.—4th Edition, updated—Moscow: [A Temp}, 2006. 1:375 (with full English translation).
U.S. Appl. No. 15/613,986, filed Nov. 2, 2018 Notice of Allowance.
U.S. Appl. No. 15/613,986, filed Aug. 3, 2018 Response to Non-Final Office Action.
U.S. Appl. No. 15/613,986, filed May 3, 2018 Non-Final Office Action.
Allen, "Ligand-Targeted Therapeutics in Anticancer Therapy," Nat. Rev. Cancer 2:750-763 (2002).
Altschul et al., "Basic Local Alignment Search Tool," J. Mol. Biol. 215(3):403-410 (1990).
Altschul et al., "Gapped BLAST and PSI-BLAST: a new generation of protein database search programs," Nucleic Acids Res. 25(17):3389-3402 (1997).
Amon et al., "Monoclonal Antibodies for Immunotargeting of Drugs in Cancer Therapy," in Monoclonal Antibodies and Cancer Therapy, Reisfeld et al. (eds.), pp. 243-256 (Alan R. Liss, Inc. 1985).
Azinovic et al., "Survival benefit associated with human anti-mouse antibody (HAMA) in patients with B-cell malignancies," Cancer Immunol Immunother 55:1451-1458 (2006).
Bird et al., "Single-Chain Antigen-Binding Proteins," Science 242(4877):423-426 (1988).
Brennan et al., "Preparation of Bispecific Antibodies by Chemical Recombination of Monoclonal Immunoglobulin G$_{1}$ Fragments," Science 229(4708):81-83 (1985).
Brocks et al., "A TNF receptor antagonistic scFv, which is not secreted in mammalian cells, is expressed as a soluble mono- and bivalent scFv derivative in insect cells," Immunotechnology 3:173-184 (1997).
Caron et al., "Engineered Humanized Dimeric Forms of IgG are More Effective Antibodies," J Exp. Med 176:1191-1195 (1992).
Casset et al., "A peptide mimetic of an anti-CD4 monoclonal antibody by rational design," Biochemical and Biophysical Research Communications 307:198-205 (2003).
Chen et al., "Selection and Analysis of an Optimized Anti-VEGF Antibody: Crystal Structure of an Affinity-matured Fab in Complex with Antigen," J. Mol. Biol. 293:865-881 (1999).
Creative Biomart, Anti-Human TNFRSF17 scFv Stable Cell Line-CHO. (Aug. 30, 2013) [according to the properties of the posted document] (Retrieved from the Internet Mar. 23, 2016: <http://www.creativebiomart.net/pdf/CSC-P0544,TNFRSF17.pdf>); p. 1.
Cuesta et al., "Multivalent antibodies: when design surpasses evolution," Trends in Biotechnology 28:355-362 (2010).
De Pascalis et al., "Grafting of "Abbreviated" Complementarity-Determining Regions Containing Specificity-Determining Residues Essential for Ligand Contact to Engineer a Less Immunogenic Humanized Monoclonal Antibody," The Journal of Immunology 169:3076-3084 (2002).
Extended European Search Report dated Jul. 17, 2018 in Application No. 15864646.3.
Fife et al., "Inhibition of T cell activation and autoimmune diabetes using a B cell surface-linked CTLA-4 agonist," J Clin Invst 116(8):2252-2261 (2006).
Flatman et al., "Process analytics for purification of monoclonal antibodies," J Chromatogr. B 848:79-87 (2007).
Giomarelli et al., "Inhibition of thrombin-induced platelet aggregation using human single-chain Fv antibodies specific for TREM-like transcript- I," Thromb Haemost 97:955-963 (2007).
Glennie et al., "Preparation and performance of bispecific F(ab' gamma)2 antibody containing thioether-linked Fab' gamma fragments," J. Immunol. 139:2367-2375 (1987).
Harris et al., "Crystallographic Structure of an Intact IgG1 Monoclonal Antibody," Journal of Molecular Biology 275:861-872 (1998).
Hellstrom et al., "Antibodies for Drug Delivery," in Controlled Drug Delivery (2nd Ed.), Robinson et al. (eds.), pp. 623-653 (Marcel Dekker, Inc. 1987).
Ho et al., "Inhibition of Cocaine Binding to the Human Dopamine Transporter by a Single Chain Anti-Idiotypic Antibody: Its Cloning, Expression and Functional Properties," BioChim Biophys Acta 1638(3):257-266 (2003).
Huston et al., "Protein engineering of antibody binding sites: Recovery of specific activity in an anti-digoxin single-chain Fv analogue produced in *Escherichia coli*," PNAS USA 85:5879-5883 (1988).
International Search Report dated May 31, 2016 in International Application No. PCT/US15/64119.
Kabat et al., Sequences of Proteins of Immunological Interest, 4th Edition, U.S. Department of Health and Human Services, National Institutes of Health (1987).
Kabat et al., Sequences of Proteins of Immunological Interest, vol. 1, Fifth Edition, U.S. Department of Health and Human Services, NIH Publication No. 91-3242 (1991).
Karpovsky et al., "Production of Target-Specific Effector Cells Using Hetero-Cross-Linked Aggregates Containing Anti-Target Cell and Anti-Fcγ Receptor Antibodies," J. Exp. Med. 160:1686-1701 (1984).
Klechevsky et al., "Antitumor activity of immunotoxins with T-cell receptor-like specificity against human melanoma xenografts," Cancer Res 68(15):6360-6367 (2008).
Kuester et al., "Pharmacokinetics of Monoclonal Antibodies," in Pharmacokinetics and Pharmacodynamics of Biotech Drugs, ed. Bernd Meibohm, Wiley-VHC, chapter 3, p. 45-91 (2006).
Lamminmaki et al., "Crystal Structure of a Recombinant Anti-estradiol Fab Fragment in Complex with 17/3-Estradiol," J. Biol. Chem. 276(39):36687-36694 (2001).
Ledbetter et al., "Agonistic Activity of a CD40-Specific Single-Chain Fv Constructed from the Variable Regions of mAb G28-5," Crit Rev Immunol. 17:427-435 (1997).
Liu et al., "Heteroantibody duplexes target cells for lysis by cytotoxic T lymphocytes," PNAS USA 82:8648-8652 (1985).
MacCallum et al., "Antibody-antigen Interactions: Contact Analysis and Binding Site Topography," J. Mol. Biol. 262:732-745 (1996).
McCafferty et al., "Phage antibodies: filamentous phage displaying antibody variable domains," Nature 348:552-554 (1990).
McKay Brown et al., "Tolerance to single, but not multiple, amino acid replacements in antibody V-H CDR2: A means of minimizing B cell wastage from somatic hypermutation?" The Journal of Immunology, The American Association of Immunologists, 156(9):3285-3291 (1996).
Meyers et al., "Optimal alignments in linear space," Cabios 4(1):11-17 (1988).
Moosmayer et al., "A single-chain TNF receptor antagonist is an effective inhibitor of TNF mediated cytotoxicity," Ther Immunol. 2:31-40 (1995).
Needleman et al., "A General Method Applicable to the Search for Similarities in the Amino Acid Sequence of Two Proteins," J. Mol. Biol. 48:443-453 (1970).
Order, S. "Analysis, Results, and Future Prospective of the Therapeutic Use of Radiolabeled Antibody in Cancer Therapy," in Monoclonal Antibodies for Cancer Detection and Therapy, Baldwin et al. (eds.), pp. 303-316 (Academic Press 1985).

(56) References Cited

OTHER PUBLICATIONS

Padlan et al., "Structure of an antibody-antigen complex: Crystal structure of the HyHEL-10 Fab-lysozyme complex," PNAS USA 86:5938-5942 (1989).
Partial Supplementary European Search Report dated May 2, 2018 in Application No. 15864646.3.
Pastan et al., "Immunotoxins in Cancer Therapy," Curr. Opin. Investig. Drugs 3(7):1089-1091 (2002).
Paulus, "Preparation and Biomedical Applications of Bispecific Antibodies," Behring Ins. Mitt. 78:118-132 (1985).
Payne, "Progress in immunoconjugate cancer therapeutics," Cancer Cell 3:207-212 (2003).
Persic et al., "An integrated vector system for the eukaryotic expression of antibodies or their fragments after selection from phage display libraries," Gene 187:9-18 (1997).
Peter et al., "Protective effects of an anti-melanocortin-4 receptor scFv derivative in lipopolysaccharide-induced cachexia in rats," J Cachexia Sarcopenia Muscle 4:79-88 (2013).
Peter et al., "scFv Single Chain Antibody Variable Fragment as Inverse Agonist of the β2-Adrenergic Receptor," J Biol. Chem. 278(38):36740-36747 (2003).
Queen et al., "A humanized antibody that binds to the interleukin 2 receptor," PNAS USA 86:10029-10033 (1989).
Ramadoss et al., "An Anti-B Cell Maturation Antigen Bispecific Antibody for Multiple Myeloma," J. Am. Chem. Soc., 137:5288-5291 (2015).
Riechmann et al., "Reshaping human antibodies for therapy," Nature 332:323-327 (1988).
Ritter et al., "Serological Analysis of Human Anti-Human Antibody Responses in Colon Cancer Patients Treated with Repeated Doses of Humanized Monoclonal Antibody A33," Cancer Res 61:6851-6859 (2001).
Roberts et al., "Vaccination with CD20 peptides induces a biologically active, specific immune response in mice," Blood 99:3748-3755 (2002).
Rudikoff et al., "Single amino acid substitution altering antigen-binding specificity," PNAS USA 79:1979-1983 (1982).
Saito et al., "Drug delivery strategy utilizing conjugation via reversible disulfide linkages: role and site of cellular reducing activities," Adv. Drug Delivery Rev. 55:199-215 (2003).
Senter et al., "Selective activation of anticancer prodrugs by monoclonal antibody—enzyme conjugates," Adv. Drug Deliv. Rev. 53:247-264 (2001).
Shen et al., "Engineering Peptide Linkers for scFv Immunosensors," Anal. Chem. 80(6):1910-1917 (2008).
Shieh et al., "Transgenic Expression of Single-Chain Anti-CTLA-4 Fv on 13 Cells Protects Nonobese Diabetic Mice from Autoimmune Diabetes," J Immunol 183:2277-2285 (2009).
Thorpe et al., "The Preparation and Cytotoxic Properties of Antibody-Toxin Conjugates," Immunol. Rev., 62:119-158 (1982).
Thorpe, "Antibody Carriers of Cytotoxic Agents in Cancer Therapy: A Review," Monoclonal Antibodies '84: Biological and Clinical Applications, pp. 475-506 (1985).
Tjandra et al., "Development of human anti-murine antibody (HAMA) response in patients," Immunol Cell Biol. 68:367-376 (1990).
Tomimatsu et al., "Production of Human Monoclonal Antibodies against FcεRIα by a Method Combining in-vitro Immunization with Phage Display," Biosci. Biotechnol. Biochem 73(7):1465-1469 (2009).
Trail et al., "Monoclonal antibody drug immunoconjugates for targeted treatment of cancer," Cancer Immunol. Immunother. 52:328-337 (2003).
Vajdos et al., "Comprehensive Functional Maps of the Antigen-binding Site of an Anti-ErbB2 Antibody Obtained with Shotgun Scanning Mutagenesis," J. Mol. Biol. 320:415-428 (2002).
Ward et al., "Binding activities of a repertoire of single immunoglobulin variable domains secreted from *Escherichia coli*," Nature 341:544-546 (1989).
White et al., "Antibody-Targeted Immunotherapy for Treatment of Malignancy," Annu. Rev. Med., 52:125-145 (2001).
Wu et al., "Humanization of a Murine Monoclonal Antibody by Simultaneous Optimization of Framework and CDR Residues," J. Mol. Biol. 294:151-162 (1999).
Xie et al., "Direct demonstration of MuSK involvement in acetylcholine receptor clustering through identification of agonist ScFv," Nat Biotech 15:768-771 (1997).
Yasmina et al., "Probing the binding mechanism and affinity of tanezumab, a recombinant humanized anti-NGF monoclonal antibody, using a repertoire of biosensors," Protein Science 17:1326-1335 (2008).
Zhao et al., "Characteristics of an scFv Antibody Fragment That Binds to Immunoglobulin G of Graves' Disease Patients and Inhibits Autoantibody-Mediated Thyroid-Stimulating Activity," Hyrbidoma 27(6):445-451 (2008).
Dondelinger et al., "Understanding the Significance and Implications of Antibody Numbering and Antigen-Binding Surface/Residue Definition," Frontiers in Immunnology, vol. 9, pp. 1-15, (2018).
U.S. Appl. No. 15/613,986 (U.S. Pat. No. 10,562,972), filed Jun. 5, 2017 (Feb. 18, 2020).
U.S. Appl. No. 16/732,089 (US 2020/0123266), filed Dec. 31, 2019 (Apr. 23, 2020).
U.S. Appl. No. 16/844,610 (US 2020/0276239), filed Apr. 9, 2020 (Sep. 3, 2020).
U.S. Appl. No. 16/844,759 (US 2020/0276240), filed Apr. 9, 2020 (Sep. 3, 2020).
U.S. Appl. No. 15/613,986, filed Jan. 31, 2019 Amendment and Request for Continued Examination (RCE).
U.S. Appl. No. 15/613,986, filed Feb. 21, 2019 Non-Final Office Action.
U.S. Appl. No. 15/613,986, filed May 21, 2019 Response to Non-Final Office Action.
U.S. Appl. No. 15/613,986, filed Jul. 11, 2019 Notice of Allowance.
U.S. Appl. No. 15/613,986, filed Sep. 19, 2019 Request for Continued Examination (RCE).
U.S. Appl. No. 15/613,986, filed Oct. 2, 2019 Notice of Allowance.
U.S. Appl. No. 15/613,986, filed Dec. 31, 2019 Issue Fee Payment.
U.S. Appl. No. 16/732,089, filed Mar. 9, 2020 Non-Final Office Action.
U.S. Appl. No. 16/732,089, filed Jun. 4, 2020 Response to Non-Final Office Action.
U.S. Appl. No. 16/732,089, filed Jun. 26, 2020 Notice of Allowance.
U.S. Appl. No. 16/732,089, filed Sep. 3, 2020 Request for Continued Examination (RCE).
U.S. Appl. No. 16/844,610, filed Jun. 22, 2020 Non-Final Office Action.
U.S. Appl. No. 16/844,759, filed Jun. 24, 2020 Notice of Allowance.
Clinical Trial Identifier NCT02215967, "Study of T Cells Targeting B-Cell Maturation Antigen for Previously Treated Multiple Myeloma," first posted Aug. 13, 2014, accessible at https://clinicaltrials.gov/ct2/show/NCT02215967.
Examination Report (Communication pursuant to Article 94(3) EPC) dated Apr. 2, 2020 for European Patent Application No. 15864826.1.

Epitope: amino acid #7-27

```
1           11          21          31          41          51
LQMAGQCSQN  EYFDSLLHAC  IPCQLRCSSN  TPPLTCQRYC  NASVTNSVKG  TNA
```

|              | 1     | 2     | 3     | 4     | 5     | 6     | 7     | 8     | 9     | 10    | 11    | 12    |
|--------------|-------|-------|-------|-------|-------|-------|-------|-------|-------|-------|-------|-------|
| ET140-3 mIgG | 0.084 | 0.076 | 0.086 | 0.094 | 0.08  | 0.127 | 0.381 | 0.178 | 2.249 | 0.758 | 1.067 | 2.08  |
| ET140-24 mIgG| 0.084 | 0.079 | 0.08  | 0.081 | 0.073 | 0.105 | 0.087 | 0.083 | 0.104 | 0.115 | 0.094 | 0.137 |
| ET140-54 mIgG| 0.069 | 0.076 | 0.083 | 0.073 | 0.069 | 0.095 | 0.075 | 0.073 | 0.087 | 0.087 | 0.085 | 0.139 |
| 901 mIgG     | 0.084 | 0.075 | 0.089 | 0.088 | 0.073 | 0.118 | 0.087 | 0.078 | 0.116 | 0.094 | 0.108 | 0.186 |
|              | 13    | 14    | 15    | 16    | 17    | 18    | 19    | 20    | 21    | 22    | 23    | 24    |
| ET140-3 mIgG | 1.027 | 0.124 | 0.328 | 0.266 | 0.155 | 0.097 | 0.098 | 0.087 | 0.089 | 0.131 | 0.113 | 0.382 |
| ET140-24 mIgG| 0.143 | 0.105 | 0.268 | 0.231 | 0.15  | 0.099 | 0.104 | 0.083 | 0.086 | 0.098 | 0.109 | 0.357 |
| ET140-54 mIgG| 0.138 | 0.104 | 0.276 | 0.263 | 0.146 | 0.105 | 0.099 | 0.081 | 0.077 | 0.111 | 0.101 | 0.325 |
| 901 mIgG     | 0.252 | 0.126 | 0.305 | 0.282 | 0.162 | 0.112 | 0.126 | 0.094 | 0.089 | 0.12  | 0.114 | 0.354 |
|              | 25    | 26    | 27    | 28    | 29    | 30    | 31    | 32    | 33    | 34    | 35    | 36    |
| ET140-3 mIgG | 0.583 | 0.225 | 0.12  | 0.109 | 0.109 | 0.111 | 0.107 | 0.099 | 0.116 | 0.099 | 0.072 | 0.089 |
| ET140-24 mIgG| 0.537 | 0.212 | 0.1   | 0.101 | 0.09  | 0.083 | 0.085 | 0.092 | 0.083 | 0.069 | 0.076 | 0.084 |
| ET140-54 mIgG| 0.494 | 0.2   | 0.103 | 0.093 | 0.083 | 0.08  | 0.08  | 0.092 | 0.084 | 0.07  | 0.071 | 0.085 |
| 901 mIgG     | 0.492 | 0.162 | 0.098 | 0.096 | 0.09  | 0.086 | 0.087 | 0.094 | 0.086 | 0.079 | 0.072 | 0.088 |
|              | 37    | 38    | 39    |       |       |       |       |       |       |       |       |       |
| ET140-3 mIgG | 0.085 | 0.08  | 0.072 | 0.074 | 0.07  | 0.066 | 0.068 | 0.072 | 0.074 | 0.065 | 0.07  | 0.069 |
| ET140-24 mIgG| 0.086 | 0.071 | 0.071 | 0.079 | 0.092 | 0.084 | 0.077 | 0.077 | 0.078 | 0.068 | 0.064 | 0.069 |
| ET140-54 mIgG| 0.083 | 0.069 | 0.074 | 0.078 | 0.065 | 0.065 | 0.07  | 0.069 | 0.066 | 0.067 | 0.069 | 0.061 |
| 901 mIgG     | 0.09  | 0.075 | 0.085 | 0.083 | 0.084 | 0.078 | 0.071 | 0.075 | 0.068 | 0.066 | 0.064 | 0.066 |

FIG. 20

SEQUENCE LISTING

```
<160> NUMBER OF SEQ ID NOS: 280

<210> SEQ ID NO 1
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
```

35                  40                  45
Trp Leu Gly Arg Thr Tyr Tyr Arg Ser Lys Tyr Asn Asp Tyr Ala
    50                  55                  60
Val Ser Val Lys Ser Arg Ile Thr Ile Asn Pro Asp Thr Ser Lys Asn
65                  70                  75                  80
Gln Phe Ser Leu Gln Leu Asn Ser Val Thr Pro Glu Asp Thr Ala Val
                85                  90                  95
Tyr Tyr Cys Ala Arg Gln Gly Tyr Ser Tyr Gly Tyr Ser Asp Val
            100                 105                 110
Trp Gly Gln Gly Thr Leu Val Thr Val Ser Ser
        115                 120

<210> SEQ ID NO 2
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Ser Val Leu Thr Gln Pro Pro Ser Val Ser Val Ala Pro Arg Gln
1               5                   10                  15
Arg Val Thr Ile Ser Cys Ser Gly Ser Ser Ser Asn Ile Gly His Asn
            20                  25                  30
Asp Val Ser Trp Tyr Gln His Leu Pro Gly Lys Ala Pro Arg Leu Leu
        35                  40                  45
Ile Tyr Phe Asp Asp Leu Leu Pro Ser Gly Val Ser Asp Arg Phe Ser
    50                  55                  60
Ala Ser Lys Ser Gly Thr Ser Ala Ser Leu Ala Ile Ser Gly Leu Gln
65                  70                  75                  80
Ser Glu Asp Glu Ala Asp Tyr Tyr Cys Ala Ala Trp Asp Gly Ser Leu
                85                  90                  95
Asn Ala Phe Val Phe Gly Thr Gly Thr Lys Val Thr Val Leu Gly
            100                 105                 110

<210> SEQ ID NO 3
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
caggtacagc tgcagcagtc aggtccagga ctggtgaagc cctcgcagac cctctcactc      60
acctgtgcca tctccgggga cagtgtctct agcaacagtg ctgcttggaa ctggatcagg     120
cagtccccat cgagaggcct tgagtggctg gaaggacat actacaggtc caagtggtat      180
aatgattatg cagtatctgt gaaaagtcga ataaccatca cccagacac atccaagaac      240 cagttctccc tgcagctgaa ctctgtgact cccgaggaca cggctgtgta ttactgtgcg     300
cgccagggtt actcttacta cggttactct gatgtttggg gtcaaggtac tctggtgacc     360
gtctcctca                                                             369

<210> SEQ ID NO 4
<211> LENGTH: 333
<212> TYPE: DNA
<213> ORGANISM: Artificial Sequence

```
<220> FEATURE:
<223> OTHER INFORMATION: Description of Artificial Sequence: Synthetic
      polynucleotide

<400> SEQUENCE: 4
cagtctgtgc tgactcagcc accctcggtg tctgtagccc ccaggcagag ggtcaccatc    60
tcgtgttctg gaagcagctc caacatcgga cataatgatg taagctggta ccagcatctc   120
ccagggaagg ctcccagact cctcatctat tttgatgacc tgctgccgtc agggtctct    180 gaccgattct ctgcctccaa gtctggcacc tcagcctccc tggccatcag tgggctccag   240
tctgaggatg aggctgatta ttactgtgca gcatgggatg gcagcctgaa tgcctttgtc   300
ttcggaactg ggaccaaggt caccgtccta ggt                                333

<210> SEQ ID NO 5
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Tyr Gly Phe Ser Gly Ser Arg Phe Tyr Asp Thr
            100                 105                 110

Trp Gly Gln Gly Thr Leu Val Thr Val Ser Ser
        115                 120

<210> SEQ ID NO 6
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gln Pro Val Leu Thr Gln Pro Pro Ser Val Ser Glu Ala Pro Arg Gln
1               5                   10                  15

Arg Val Thr Ile Ser Cys Ser Gly Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Phe Asp Asp Leu Leu Ser Ser Gly Val Ser Asp Arg Phe Ser
    50                  55                  60

Gly Ser Lys Ser Gly Thr Ser Ala Ser Leu Ala Ile Ser Gly Leu Gln
65                  70                  75                  80
```

Ser Glu Asp Glu Ala Asp Tyr Tyr Cys Ala Ala Trp Asp Asp Ser Leu
            85                  90                  95

Asn Gly Tyr Val Phe Gly Thr Gly Thr Lys Val Thr Val Leu Gly
            100                 105                 110

<210> SEQ ID NO 7
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
caggtacagc tgcagcagtc aggtccagga ctggtgaagc cctcgcagac cctctcactc      60
acctgtgcca tctccgggga cagtgtctct agcaacagtg ctgcttggaa ctggatcagg     120
cagtccccat cgagaggcct tgagtggctg ggaaggacat actacaggtc aagtggtat     180 aatgattatg cagtatctgt gaaaagtcga ataaccatca cccagacac atccaagaac     240 cagttctccc tgcagctgaa ctctgtgact cccgaggaca cggctgtgta ttactgtgcg     300
cgctacggtt tctctggttc tcgtttctac gatacttggg gtcaaggtac tctggtgacc     360
gtctcctca                                                            369

<210> SEQ ID NO 8
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
cagcctgtgc tgactcagcc accctcggtg tctgaagccc ccaggcagag ggtcaccatc      60
tcctgttctg gaagcagctc caacatcgga aataatgctg taaactggta ccagcagctc     120
ccaggaaagg ctcccaaact cctcatctat tttgatgatc tgctgtcctc aggggtctct     180
gaccgattct ctggctccaa gtctggcacc tcagcctccc tggccatcag tgggctccag     240
tctgaagatg aggctgatta ttactgtgca gcatgggatg acagcctgaa tggttatgtc     300
ttcggaactg ggaccaaggt caccgtccta ggt                                 333

<210> SEQ ID NO 9
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Tyr Ser Lys Ser Ile Val Ser Tyr Met Asp Tyr Trp
            100                 105                 110

Gly Gln Gly Thr Leu Val Thr Val Ser Ser
        115                 120

<210> SEQ ID NO 10
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Leu Pro Val Leu Thr Gln Pro Pro Ser Thr Ser Gly Thr Pro Gly Gln
1               5                   10                  15

Arg Val Thr Val Ser Cys Ser Gly Ser Ser Ser Asn Ile Gly Ser Asn
            20                  25                  30

Val Val Phe Trp Tyr Gln Gln Leu Pro Gly Thr Ala Pro Lys Leu Val
        35                  40                  45

Ile Tyr Arg Asn Asn Gln Arg Pro Ser Gly Val Pro Asp Arg Phe Ser
    50                  55                  60

Val Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Tyr Val Phe Gly Thr Gly Thr Lys Val Thr Val Leu Gly
            100                 105                 110

<210> SEQ ID NO 11
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
gaggtccagc tggtgcagtc tggagctgag gtgaagaagc ctgggtcctc ggtgaaggtc      60
tcctgcaagg cttctggagg caccttcagc agctatgcta tcagctgggt gcgacaggcc    120
cctggacaag ggcttgagtg gatgggaagg atcatcccta tccttggtat agcaaactac    180
gcacagaagt tccagggcag agtcaccatg accgaggaca tcctacagac acagcctac    240 atggagctga gcagcctgag atctgaggac acggccgtgt attactgtgc gcgctctggt    300
tactctaaat ctatcgtttc ttacatggat tactggggtc aaggtactct ggtgaccgtc    360
tcctca                                                               366

<210> SEQ ID NO 12
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
ctgcctgtgc tgactcagcc cccctccacg tctgggaccc ccgggcagag ggtcaccgtc      60

```
tcttgttctg gaagcagctc caacatcgga agtaatgttg tattctggta ccagcagctc    120
ccaggcacgg ccccaaaact tgtcatctat aggaataatc aacggccctc aggggtccct    180
gaccgattct ctgtctccaa gtctggcacc tcagcctccc tggccatcag tgggctccgg    240
tccgaggacg aggctgatta ttattgtgca gcttgggatg acagcctgag tggttatgtc    300
ttcggaactg ggaccaaggt caccgtccta ggt                                 333
```

<210> SEQ ID NO 13
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Gln Trp Gly Gly Val Leu Asp Tyr Trp Gly Gln Gly Thr
            100                 105                 110

Leu Val Thr Val Ser Ser
        115
```

<210> SEQ ID NO 14
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

```
Gln Ser Val Val Thr Gln Pro Pro Ser Val Ser Gly Ala Pro Gly Gln
1               5                   10                  15

Arg Val Thr Ile Ser Cys Ser Gly Ser Ser Ser Asn Ile Gly Ala Arg
            20                  25                  30

Tyr Asp Val Gln Trp Tyr Gln Gln Leu Pro Gly Thr Ala Pro Lys Leu
        35                  40                  45

Leu Ile Phe Gly Asn Asn Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Ala Ser Val Phe Gly Gly Gly Thr Lys Leu Thr Val Leu Gly
            100                 105                 110
```

```
<210> SEQ ID NO 15
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
gaggtccagc tggtacagtc tggggctgag gtgaagaagc ctggggcctc agtgaaggtt     60
tcctgcaagg catctggata caccttcacc agctactata tgcactgggt gcgacaggcc    120
cctggacaag gcttgagtg gatgggaata atcaaccca gtggtggtag cacaagctac     180
gcacagaagt tccagggcag agtcaccatg accagggaca cgtccacgag cacagtctac    240
atggagctga gcagcctgag atctgaggac acggccgtgt attactgtgc gcgctctcag    300
tggggtggtg ttctggatta ctgggtcaa ggtactctgg tgaccgtctc ctca           354

<210> SEQ ID NO 16
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
cagtctgtcg tgacgcagcc gccctcagtg tctggggccc cagggcagag ggtcaccatc     60
tcctgcagtg ggagcagctc caacatcggg gcacgttatg atgttcagtg gtaccagcag    120
cttccaggaa cagcccccaa actcctcatc tttggtaaca acaatcggcc ctcagggtc     180 cctgaccgat tctctggctc caagtctggc acgtcagcct ccctggccat cactgggctc    240
caggctgagg atgaggctga ttattactgc cagtcctatg acagcagcct gagtgcttcg    300
gtgttcggcg agggaccaa gctgaccgtc ctaggt                               336

<210> SEQ ID NO 17
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Val Glu Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Gly Tyr Glu Ser Trp Gly Ser Tyr Glu Val Ile Asp Arg
            100                 105                 110

Trp Gly Gln Gly Thr Leu Val Thr Val Ser Ser
        115                 120
```

<210> SEQ ID NO 18
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Ala Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Arg Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Val Val Phe Gly Gly Gly Thr Lys Leu Thr Val Leu Gly
            100                 105                 110

<210> SEQ ID NO 19
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
caggtgcagc tggtggagtc tggggctgag gtgaagaagc ctgggtcctc ggtgaaggtc      60
tcctgcaagg cttctggagg caccttcagc agctatgcta tcagctgggt gcgacaggcc    120
cctggacaag gcttgagtg gatgggaagg atcatcccta tccttggtat agcaaactac     180
gcacagaagt tccagggcag agtcacgatt accgcggacg aatccacgag cacagcctac    240
atggagctga gcagcctgag atctgaggac acggccgtat attactgtgc gcgcactggt    300
tacgaatctt ggggttctta cgaagttatc gatcgttggg gtcaaggtac tctggtgacc    360
gtctcctca                                                             369

<210> SEQ ID NO 20
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
caggctgtgc tgactcagcc accctcagcg tctgggaccc ccgggcagag ggtcaccatc      60
tcttgttctg gaagcagctc caacatcgga agtaatactg taaactggta ccggcagctc    120
ccaggaacgg cccccaaact cctcatctat agtaataatc agcggccctc agggtccct     180 gaccgattct ctggctccaa gtctggcacc tcagcctccc tggccatcag tgggctccag    240
tctgaggatg aggctgatta ttactgtgca gcatgggatg acagcctgaa tggtgtggta    300
ttcggcggag ggaccaagct gaccgtccta ggt                                        333

<210> SEQ ID NO 21
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Val Gln Leu Val Gln Ser Gly Ala Glu Val Lys Pro Gly Ser
1               5                   10                  15

Ser Val Lys Val Ser Cys Lys Ala Ser Gly Thr Phe Ser Ser Tyr
                20                  25                  30

Ala Ile Ser Trp Val Arg Gln Ala Pro Gly Gln Gly Leu Glu Trp Met
            35                  40                  45

Gly Arg Ile Ile Pro Ile Leu Gly Ile Ala Asn Tyr Ala Gln Lys Phe
50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Tyr Ser His Asp Met Trp Ser Glu Asp Trp Gly
            100                 105                 110

Gln Gly Thr Leu Val Thr Val Ser Ser
        115                 120

<210> SEQ ID NO 22
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Leu Pro Val Leu Thr Gln Pro Pro Ser Ala Ser Gly Thr Pro Gly Gln
1               5                   10                  15

Arg Val Thr Ile Ser Cys Ser Gly Arg Ser Ser Asn Ile Gly Ser Asn
                20                  25                  30

Ser Val Asn Trp Tyr Arg Gln Leu Pro Gly Ala Ala Pro Lys Leu Leu
            35                  40                  45

Ile Tyr Ser Asn Asn Gln Arg Pro Pro Gly Val Pro Val Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Thr Tyr Tyr Cys Ala Thr Trp Asp Asp Asn Leu
                85                  90                  95

Asn Val His Tyr Val Phe Gly Thr Gly Thr Lys Val Thr Val Leu Gly
            100                 105                 110

<210> SEQ ID NO 23
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

```
caggtgcagc tggtgcagtc tggggctgag gtgaagaagc ctgggtcctc ggtgaaggtc    60
tcctgcaagg cttctggagg caccttcagc agctatgcta tcagctgggt gcgacaggcc   120
cctggacaag gcttgagtg gatgggaagg atcatcccta tccttggtat agcaaactac   180
gcacagaagt tccagggcag agtcacgatt accgcggaca atccacgag cacagcctac   240 atggagctga gcagcctgag atctgaggac acggccgtgt attactgtgc gcgcggtggt   300
tactactctc atgacatgtg gtctgaagat tggggtcaag gtactctggt gaccgtctcc   360
tca                                                                 363
```

<210> SEQ ID NO 24
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24

```
ctgcctgtgc tgactcagcc accctcagcg tctgggaccc ccgggcagag ggtcaccatc    60
tcttgttctg gacgcagttc caacatcggg agtaattctg ttaactggta tcgacaactc   120
ccaggagcgg cccccaaact cctcatctat agtaataatc agcggccccc aggggtccct   180
gtgcgattct ctggctccaa gtctggcacc tcagcctccc tggccatcag tgggctccag   240
tctgaagatg aggccactta ttactgtgca acatgggatg acaatctgaa tgttcactat   300
gtcttcggaa ctgggaccaa ggtcaccgtc ctaggt                             336
```

<210> SEQ ID NO 25
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

```
Gln Val Gln Leu Gln Glu Ser Gly Pro Gly Leu Val Lys Pro Ser Gly
1               5                   10                  15

Thr Leu Ser Leu Thr Cys Gly Val Ser Gly Gly Ser Ile Ser Asn Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Lys Tyr Asn Pro Ser Leu
    50                  55                  60

Arg Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Arg Asp Asn Trp Lys Thr Pro Thr Thr Lys Ile Asp Gly Phe
            100                 105                 110

Asp Ile Trp Gly Gln Gly Thr Met Val Thr Val Ser Ser
        115                 120                 125
```

<210> SEQ ID NO 26
<211> LENGTH: 117
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 26

Gln Pro Val Leu Thr Gln Pro Pro Ser Ala Ser Ala Ser Leu Gly Ala
1               5                   10                  15

Ser Val Thr Leu Thr Cys Thr Leu Ser Ser Gly Tyr Ser Asn Tyr Lys
            20                  25                  30

Val Asp Trp Tyr Gln Gln Arg Pro Gly Lys Gly Pro Arg Phe Val Met
        35                  40                  45

Arg Val Gly Thr Gly Gly Ile Val Gly Ser Lys Gly Asp Gly Ile Pro
    50                  55                  60

Asp Arg Phe Ser Val Leu Gly Ser Gly Leu Asn Arg Tyr Leu Thr Ile
65                  70                  75                  80

Lys Asn Ile Gln Glu Glu Asp Glu Gly Asp Tyr His Cys Gly Ala Asp
                85                  90                  95

His Gly Ser Gly Ser Asn Phe Val Tyr Val Phe Gly Thr Gly Thr Lys
            100                 105                 110

Val Thr Val Leu Gly
        115

<210> SEQ ID NO 27
<211> LENGTH: 375
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 27
caggtgcagc tgcaggagtc gggcccagga ctggtgaagc cttcggggac cctgtccctc         60
acctgcggtg tctctggtgg ctccatcagc aatagtaact ggtggagttg ggtccgccag        120
ccccccggga aggggctgga gtggattggg gaaatctatc atagtgggag caccaagtac        180
aacccgtccc tcaggagtcg agtcaccata tcagtagaca agtccaagaa ccagttctcc        240
ctaaaattga gctctgtgac cgccgcggac acggccgtat attactgtgc gagacgagat        300
aactggaaga ccccccactac caaaattgat ggttttgata tctggggcca agggacaatg        360
gtcaccgtct cttca                                                         375

<210> SEQ ID NO 28
<211> LENGTH: 351
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 28
cagcctgtgc tgactcagcc accttctgca tcagcctccc tgggagcctc ggtcacactc         60
acctgcaccc tgagcagcgg ctacagtaat tataaagtgg actggtacca gcagagacca        120
gggaagggcc cccggtttgt gatgcgagtg ggcactggtg ggattgtggg atccaagggg        180
gatggcatcc ctgatcgctt ctcagtcttg ggctcaggcc tgaatcggta cctgaccatc        240
aagaacatcc aggaagaaga tgagggtgac tatcactgtg gggcagacca tggcagtggg        300
agcaacttcg tgtatgtctt cggaactggg accaaggtca ccgtcctagg t                351

<210> SEQ ID NO 29

<210> SEQ ID NO 29
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gln Trp Gly Ser Ser Trp Asp Tyr Trp Gly Gln Gly Thr
            100                 105                 110

Leu Val Thr Val Ser Ser
        115
```

<210> SEQ ID NO 30
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys Arg
            100                 105
```

<210> SEQ ID NO 31
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31

```
caggtccagc tggtacagtc tggggctgag gtgaagaagc ctggggcctc agtgaaggtc    60
tcctgcaagg cttctggata caccttcacc ggctactata tgcactgggt gcgacaggcc    120
```

```
cctggacaag ggcttgagtg gatgggatgg atcaaccct a acagtggtgg cacaaactat      180
gcacagaagt tcagggcag ggtcaccatg accaggaca cgtccatcag cacagcctac         240
atggagctga gcaggctgag atctgacgac acggccgtgt attactgtgc gcgctctcag       300
tggggttctt cttgggatta ctggggtcaa ggtactctgg tgaccgtctc ctca             354
```

<210> SEQ ID NO 32
<211> LENGTH: 324
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 32

```
gacatccagt tgacccagtc tccatcctcc ctgtctgcat ctgtaggaga cagagtcacc       60
atcacttgcc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct    240
gaagattttg caacttacta ctgtcaacag agttacagta ccccctccgac gttcggccaa    300 gggaccaagg tggagatcaa acgt                                             324
```

<210> SEQ ID NO 33
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 33

```
Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Ser Tyr His Leu Tyr Gly Tyr Asp Ser Trp Gly Gln Gly
            100                 105                 110

Thr Leu Val Thr Val Ser Ser
        115
```

<210> SEQ ID NO 34
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 34

Gln Pro Val Leu Thr Gln Pro Pro Ser Ala Ser Ala Ser Leu Gly Ala

```
                1               5                   10                  15
Ser Val Thr Leu Thr Cys Thr Leu Ser Asn Asp Tyr Thr Asn Tyr Lys
                20                  25                  30

Val Asp Trp Tyr Gln Gln Arg Pro Gly Lys Gly Pro Arg Phe Val Met
                35                  40                  45

Arg Val Gly Pro Gly Gly Ile Val Gly Ser Lys Gly Asp Gly Ile Pro
                50                  55                  60

Asp Arg Phe Ser Val Leu Gly Ser Gly Leu Asn Arg Tyr Leu Thr Ile
65                  70                  75                  80

Lys Asn Ile Gln Glu Glu Asp Glu Ser Asp Tyr His Cys Gly Ala Asp
                85                  90                  95

His Gly Thr Gly Ser Asn Phe Val Tyr Val Phe Gly Gly Gly Thr Lys
                100                 105                 110

Leu Thr Val Leu Gly
                115
```

<210> SEQ ID NO 35
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35

```
gaggtgcagc tggtggagtc cggggctgag gtgaagaagc ctggggcctc agtgaaggtc      60
tcctgcaagg cttctggata caccttcacc ggctactata tgcactgggt gcgacaggcc     120
cctggacaag gcttgagtg gatgggatgg atcaaccctaa cagtggtgg cacaaactat      180 gcacagaagt tcagggcag ggtcaccatg accagggaca cgtccatcag cacagcctac      240
atggagctga gcaggctgag atctgacgac acggccgtat attactgtgc gcgctcttct      300
taccatctgt acggttacga ttcttggggt caaggtactc tggtgaccgt ctcctca        357
```

<210> SEQ ID NO 36
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36

```
cagcctgtgc tgactcagcc accttctgca tcagcctccc tgggagcctc ggtcactctc      60
acctgcaccc tgagcaacga ctacactaat tataaagtgg actggtacca gcagagacca     120
gggaagggcc cccggtttgt gatgcgagtg ggccctggtg ggattgtggg atccaagggg     180
gatggcatcc ctgatcgctt ctcagtcttg ggctcaggcc tgaatcgata cctgaccatc     240
aagaacatcc aggaggagga tgagagtgac taccactgtg gggcggacca tggcaccggg     300
agcaacttcg tgtacgtgtt cggcggaggg accaagctga ccgtcctagg t              351
```

<210> SEQ ID NO 37
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Ser Thr Ala Asn Tyr Ala Gln Lys Phe
50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gln Pro Trp Thr Trp Tyr Ser Pro Tyr Asp Gln Trp Gly Gln
            100                 105                 110

Gly Thr Leu Val Thr Val Ser Ser
        115                 120

<210> SEQ ID NO 38
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gln Pro Val Leu Thr Gln Pro Pro Ser Ala Ser Ala Ser Leu Gly Ala
1               5                   10                  15

Ser Val Thr Leu Thr Cys Thr Leu Ser Ser Gly Tyr Ser Asn Tyr Lys
            20                  25                  30

Val Asp Trp Tyr Gln Gln Arg Pro Gly Lys Gly Pro Arg Phe Leu Met
        35                  40                  45

Arg Val Asp Thr Gly Gly Ile Val Gly Ser Lys Gly Asp Gly Ile Pro
50                  55                  60

Asp Arg Phe Ser Val Ser Gly Ser Gly Leu Asn Arg Tyr Leu Thr Ile
65                  70                  75                  80

Lys Asn Ile Gln Glu Glu Asp Glu Ser Asp Tyr His Cys Gly Ala Asp
                85                  90                  95

His Gly Ser Gly Ser Asn Phe Val Trp Val Phe Gly Gly Gly Thr Lys
            100                 105                 110

Leu Thr Val Leu Gly
        115

<210> SEQ ID NO 39
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
caggtgcagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag ggcttgagtg gatgggaggg atcatcccta tctttagtac agcaaactac     180
gcacagaagt tccagggcag agtcaccatg accacagaca catccacgag cacagcctac     240
```

```
atggagctga ggagcctgag atctgacgac acggccgtgt attactgtgc gcgccagccg    300
tggacttggt actctccgta cgatcagtgg ggtcaaggta ctctggtgac cgtctcctca    360
```

<210> SEQ ID NO 40
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40

```
cagcctgtgc tgactcagcc accttctgca tcagcctccc tgggagcctc ggtcacactc     60
acctgcaccc tgagcagcgg ctacagtaat tataaagtgg actggtatca acagagacca    120
gggaagggcc cccggtttct gatgcgagta gacaccggtg ggattgtggg atccaagggg    180
gatggcatcc ctgatcgctt ctcagtctcg ggctcaggtc tgaatcggta cctgaccatc    240
aagaacattc aggaagagga tgagagtgac taccactgtg gggcagacca tggcagtggg    300
agcaacttcg tgtgggtgtt cggcggaggg accaagctga ccgtcctagg t             351
```

<210> SEQ ID NO 41
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Glu Val Gln Leu Val Glu Thr Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Thr Trp Val Arg Gln Ala Pro Gly Lys Gly Leu Glu Trp Val
        35                  40                  45

Ser Ala Ile Thr Pro Gly Gly Asp Arg Thr Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Gly Tyr Met Ile Asp Met Trp Gly Gln Gly Thr Leu
            100                 105                 110

Val Thr Val Ser Ser
        115

<210> SEQ ID NO 42
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

```
Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Leu Thr Phe Gly Gly Gly Thr Lys Val Glu Ile Lys
            100                 105                 110

Arg

<210> SEQ ID NO 43
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
gaggtgcagc tggtggagac tgggggaggc ctggtacagc ctggggggtc cctgagactc      60
tcctgtgctg cctctggatt cacctttagc acctatgcca tgacctgggt ccgccaggct     120
ccagggaagg gctggagtg gtctcagct attactcctg gtggtgatcg cacatactac       180
gcagactccg tgaagggccg tttcactatc tccagagaca attccaggaa cacgctgtat     240
ctgcaaatga acagcctgag agccgaggac acggccgtat attactgtgc gcgctactac     300
ggttacatga tcgatatgtg gggtcaaggt actctggtga ccgtctcctc a              351

<210> SEQ ID NO 44
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
gatgttgtga tgactcagtc tccactctcc ctgcccgtca cccctggaga gccggcctcc      60
atctcctgca ggtctagtca gagcctcctg catagtaatg gatacaacta tttggattgg     120
tacctgcaga agccagggca gtctccacag ctcctgatct atttgggttc taatcgggcc     180
tccggggtcc ctgacaggtt cagtggcagt ggatcaggca cagattttac actgaaaatc     240
agcagagtgg aggctgagga tgttggggtt tattactgca tgcaagctct acaaactcct     300
ctcactttcg gcggagggac caaggtggaa atcaaacgt                            339

<210> SEQ ID NO 45
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Gln Met Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Gly Tyr
             20                  25                  30
```

Tyr Val His Trp Leu Arg Gln Ala Pro Gly Gln Gly Leu Glu Trp Met
            35                  40                  45

Gly Trp Ile Asn Pro Asn Ser Gly Gly Thr Asn Asn Ala Gln Glu Phe
 50                  55                  60

Gln Gly Arg Ile Thr Met Thr Arg Asp Thr Ser Ile Asn Thr Ala Tyr
 65                  70                  75                  80

Met Glu Leu Ser Arg Leu Arg Ser Asp Thr Ala Val Tyr Tyr Cys
                 85                  90                  95

Ala Arg Ser Gln Trp Gly Gly Thr Tyr Asp Tyr Trp Gly Gln Gly Thr
                100                 105                 110

Leu Val Thr Val Ser Ser
            115

<210> SEQ ID NO 46
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Ser Tyr Val Leu Thr Gln Pro Pro Ser Ala Ser Gly Thr Pro Gly Gln
 1               5                  10                  15

Arg Val Thr Ile Ser Cys Ser Gly Ser Ser Ser Asn Ile Gly Ser Asn
             20                  25                  30

Thr Val Asn Trp Tyr Gln Gln Val Pro Gly Thr Ala Pro Lys Leu Leu
            35                  40                  45

Ile Tyr Ser Asn Asn Gln Arg Pro Ser Gly Val Pro Asp Arg Phe Ser
 50                  55                  60

Gly Ser Lys Ser Gly Ala Ser Ala Ser Leu Ala Ile Ser Trp Leu Gln
 65                  70                  75                  80

Ser Glu Asp Glu Ala Asp Tyr Tyr Cys Ala Ala Trp Asp Asp Ser Leu
                 85                  90                  95

Asn Gly Trp Val Phe Gly Gly Gly Thr Lys Leu Thr Val Leu Gly
                100                 105                 110

<210> SEQ ID NO 47
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
cagatgcagc tggtgcagtc tggggctgag gtgaagaagc ctggggcctc agtgaaggtc      60
tcctgcaagg cttctggata caccttcacc ggctattatg tacactggtt gcgacaggcc     120
cctggacaag ggcttgagtg gatgggttgg atcaacccta acagtggcgg cacaaacaat     180
gcacaggagt tccaaggcag gatcaccatg accagggaca cgtccatcaa cacagcctac     240
atggagctga gcaggctgag atctgacgac acggccgtgt attactgtgc gcgctctcag     300
tggggtggta cttacgatta ctggggtcaa ggtactctgg tgaccgtctc ctca           354

<210> SEQ ID NO 48
<211> LENGTH: 333
<212> TYPE: DNA
<213> ORGANISM: Artificial Sequence

```
<220> FEATURE:
<223> OTHER INFORMATION: Description of Artificial Sequence: Synthetic
      polynucleotide

<400> SEQUENCE: 48
tcctatgtgc tgactcagcc accctcagcg tctgggaccc ccgggcagag ggtcaccatc      60
tcttgttctg gaagcagctc caacatcgga agtaatactg taaactggta ccagcaggtc     120
ccaggaacgg ccccccaaact cctcatctat agtaataatc agcggccctc aggggtccct    180
gaccgattct ctggctccaa gtctggcgcc tcagcctccc tggccatcag ttggctccag     240
tctgaggatg aggctgatta ttactgtgca gcatgggatg acagcctgaa tggttgggtg     300
ttcggcggag ggaccaagct gaccgtccta ggt                                  333

<210> SEQ ID NO 49
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Asp Phe Thr Thr Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Val
        50                  55                  60

Arg Gly Arg Val Thr Ile Ser Ala Asp Lys Ser Ile Asn Thr Ala Tyr
65                  70                  75                  80

Leu Gln Trp Ser Ser Leu Glu Ala Ser Asp Thr Ala Met Tyr Tyr Cys
                85                  90                  95

Ala Arg Met Trp Thr Phe Ser Gln Asp Gly Trp Gly Gln Gly Thr Leu
            100                 105                 110

Val Thr Val Ser Ser
        115

<210> SEQ ID NO 50
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Gln Ala Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Tyr
                20                  25                  30

Thr Val Ser Trp Tyr Gln Gln Leu Pro Gly Thr Ala Pro Lys Phe Leu
            35                  40                  45

Ile Tyr Ser Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Gln
65                  70                  75                  80
```

```
Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Val Thr Val Leu Gly
            100                 105                 110

<210> SEQ ID NO 51
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
gaggtgcagc tggtgcagtc tggagcagag gtgaaaaagc cgggggagtc tctgaagatc      60
tcctgtaagg gttctggata tgactttacc acctactgga tcgggtgggt cgcgccagatg    120 cccgggaagg gcctggagtg gatggggatc atctatcctg gtgactctga taccagatac    180
agcccgtccg tccgaggccg ggtcaccatc tcagccgaca gtccatcaa caccgcctat     240 ttgcagtgga gtagcctgga ggcctccgac accgccatgt attactgtgc gcgcatgtgg    300
actttctctc aggatggttg gggtcaaggt actctggtga ccgtctcctc a             351

<210> SEQ ID NO 52
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
caggctgtgc tgactcagcc accctcagcg tctgggaccc ccgggcagag ggtcaccatc      60
tcttgttctg gaagcagctc caacatcgga agttatactg taagctggta ccagcaactc    120
ccaggaacgg cccccaaatt cctcatctat tctaataatc agcggccctc agggggtccct  180 gaccgattct ctggctccaa gtctggcacc tcagcctccc tggccatcag tgggctccag    240
tctgaggatg aggctgatta ttactgtgct gcatgggatg acagcctgaa tggttatgtc    300
ttcggaactg ggaccaaggt caccgtccta ggt                                  333

<210> SEQ ID NO 53
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Glu Val Gln Leu Val Gln Ser Gly Ala Glu Met Lys Lys Pro Gly Ala
1               5                   10                  15

Ser Leu Lys Leu Ser Cys Lys Ala Ser Gly Tyr Thr Phe Ile Asp Tyr
            20                  25                  30

Tyr Val Tyr Trp Met Arg Gln Ala Pro Gly Gln Gly Leu Glu Ser Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Met Tyr Tyr Cys
```

```
                    85                  90                  95
Ala Arg Ser Gln Arg Asp Gly Tyr Met Asp Tyr Trp Gly Gln Gly Thr
            100                 105                 110

Leu Val Thr Val Ser Ser
        115
```

<210> SEQ ID NO 54
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

```
Gln Ser Ala Leu Thr Gln Pro Ala Ser Val Ser Ala Ser Pro Gly Gln
1               5                   10                  15

Ser Ile Ala Ile Ser Cys Thr Gly Thr Ser Ser Asp Val Gly Trp Tyr
            20                  25                  30

Gln Gln His Pro Gly Lys Ala Pro Lys Leu Met Ile Tyr Glu Asp Ser
        35                  40                  45

Lys Arg Pro Ser Gly Val Ser Asn Arg Phe Ser Gly Ser Lys Ser Gly
    50                  55                  60

Asn Thr Ala Ser Leu Thr Ile Ser Gly Leu Gln Ala Glu Asp Glu Ala
65                  70                  75                  80

Asp Tyr Tyr Cys Ser Ser Asn Thr Arg Ser Ser Thr Leu Val Phe Gly
                85                  90                  95

Gly Gly Thr Lys Leu Thr Val Leu Gly
            100                 105
```

<210> SEQ ID NO 55
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55

```
gaagtgcagc tggtgcagtc tggggctgag atgaagaagc ctggggcctc actgaagctc    60
tcctgcaagg cttctggata caccttcatc gactactatg tatactggat gcgacaggcc   120
cctggacaag gcttgagtc catgggatgg atcaaccta acagtggtgg cacaaactat     180
gcacagaagt tcagggcag gtcaccatg accaggaca cgtccatcag cacagcctac      240
atggagctga gcaggctgag atctgacgac accgccatgt attactgtgc gcgctcccag   300
cgtgacggtt acatggatta ctggggtcaa ggtactctgg tgaccgtctc ctca          354
```

<210> SEQ ID NO 56
<211> LENGTH: 315
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56

```
caatctgccc tgactcagcc tgcctccgtg tctgcgtctc ctggacagtc gatcgccatc    60
tcctgcactg gaaccagcag tgacgttggt tggtatcaac agcacccagg caaagccccc   120
aaactcatga tttatgagga cagtaagcgg ccctcagggg tttctaatcg cttctctggc   180
```

-continued

```
tccaagtctg gcaacacggc ctccctgacc atctctgggc tccaggctga ggacgaggct    240
gattattact gcagctcaaa tacaagaagc agcactttgg tgttcggcgg agggaccaag    300
ctgaccgtcc taggt                                                     315
```

<210> SEQ ID NO 57
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 57

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Arg Leu Glu Trp Met
        35                  40                  45

Gly Trp Ile Asn Pro Asn Ser Gly Gly Thr Asn Tyr Ala Gln Lys Phe
    50                  55                  60

Gln Asp Arg Ile Thr Val Thr Arg Asp Thr Ser Ser Asn Thr Gly Tyr
65                  70                  75                  80

Met Glu Leu Thr Arg Leu Arg Ser Asp Asp Thr Ala Val Tyr Tyr Cys
                85                  90                  95

Ala Arg Ser Pro Tyr Ser Gly Val Leu Asp Lys Trp Gly Gln Gly Thr
            100                 105                 110

Leu Val Thr Val Ser Ser
        115
```

<210> SEQ ID NO 58
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 58

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Phe Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Val Thr Val Leu Gly
            100                 105                 110
```

<210> SEQ ID NO 59
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59
caggtccagc tggtacagtc tggggctgag gtgaagaagc ctggggcctc agtgaaggtc     60
tcctgcaagg cttctggata caccttcacc gactactata tgcactgggt gcgacaggcc    120
cctggacaac ggcttgagtg gatgggatgg atcaaccctc acagtggtgg cacaaactat    180
gcacagaagt ttcaggacag gatcaccgtg accagggaca cctccagcaa cacaggctac    240
atggagctga ccaggctgag atctgacgac acggccgtgt attactgtgc gcgctctccg    300
tactctggtg tttctggataa atgggggtcaa ggtactctgg tgaccgtctc ctca        354

<210> SEQ ID NO 60
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60
cagtctgtgc tgacgcagcc gccctcagtg tctggggccc cagggcagag ggtcaccatc     60
tcctgcactg ggagcagctc caacatcggg gcaggttttg atgtacactg gtaccagcag    120
cttccaggaa cagccccaa actcctcatc tatggtaaca gcaatcggcc ctcagggtc      180
cctgaccgat tctctggctc caagtctggc acctcagcct ccctggccat cactgggctc    240
caggctgagg atgaggctga ttattactgc cagtcctatg acagcagcct gagtggttat    300
gtcttcggaa ctgggaccaa ggtcaccgtc ctaggt                              336

<210> SEQ ID NO 61
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Tyr Gly Ser Tyr Arg Trp Glu Asp Ser Trp Gly Gln
            100                 105                 110

Gly Thr Leu Val Thr Val Ser Ser
        115                 120

<210> SEQ ID NO 62
<211> LENGTH: 112

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Gln Ala Val Leu Thr Gln Pro Pro Ser Ala Ser Gly Thr Pro Gly Gln
1               5                   10                  15
Arg Val Thr Ile Ser Cys Ser Gly Ser Ser Ser Asn Ile Gly Ser Asn
            20                  25                  30
Tyr Val Phe Trp Tyr Gln Gln Leu Pro Gly Thr Ala Pro Lys Leu Leu
        35                  40                  45
Ile Tyr Ser Asn Asn Gln Arg Pro Ser Gly Val Pro Asp Arg Phe Ser
    50                  55                  60
Gly Ser Lys Ser Gly Thr Ser Ala Ser Leu Ala Ile Ser Gly Leu Arg
65                  70                  75                  80
Ser Glu Asp Glu Ala Asp Tyr Tyr Cys Ala Ala Trp Asp Asp Ser Leu
                85                  90                  95
Ser Ala Ser Tyr Val Phe Gly Thr Gly Thr Lys Val Thr Val Leu Gly
            100                 105                 110

<210> SEQ ID NO 63
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63
caggtgcagc tggtgcagtc tggggctgag gtgaagaagc ctgggtcctc ggtgaaggtc    60
tcctgcaagg cttctggagg caccttcagc agctatgcta tcagctgggt gcgacaggcc   120
cctggacaag gcttgagtg gatgggaagg atcatccta tccttggtac agcaaactac    180
gcacagaagt tccagggcag agtcacgatt accgcggacg aatccacgag cacagcctac   240
atggagctga gcagcctgag atctgaggac acggccgtgt attactgtgc gcgctctggt   300
tacggttctt accgttggga agattcttgg ggtcaaggta ctctggtgac cgtctcctca   360

<210> SEQ ID NO 64
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64
caggctgtgc tgactcagcc accctcagcg tctgggaccc ccgggcagag ggtcaccatc    60
tcttgttctg gaagcagctc caacatcgga agtaattacg tattctggta ccagcagctc   120
ccaggaacgg cccccaaact cctcatctat agtaataatc agcggccctc agggtccct    180
gaccgattct ctggctccaa gtctggcacc tcagcctccc tggccatcag tgggctccgg   240
tccgaggatg aggctgatta ttactgtgca gcatgggatg acagcctgag tgcctcttat   300
gttttcggaa ctgggaccaa ggtcaccgtc ctaggt                              336

<210> SEQ ID NO 65
<211> LENGTH: 116
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 65

```
Glu Val Gln Leu Val Gln Ser Gly Ala Glu Val Lys Lys Pro Gly Glu
1               5                   10                  15
Ser Leu Lys Ile Ser Cys Lys Gly Ser Gly Tyr Ser Phe Thr Ser Tyr
            20                  25                  30
Trp Ile Gly Trp Val Arg Gln Met Pro Gly Lys Gly Leu Glu Trp Met
        35                  40                  45
Gly Ile Ile Tyr Pro Gly Asp Ser Asp Thr Arg Tyr Ser Pro Ser Phe
    50                  55                  60
Gln Gly His Val Thr Ile Ser Ala Asp Lys Ser Ile Ser Thr Ala Tyr
65                  70                  75                  80
Leu Gln Trp Ser Ser Leu Lys Ala Ser Asp Thr Ala Met Tyr Tyr Cys
                85                  90                  95
Ala Arg Tyr Ser Gly Ser Phe Asp Asn Trp Gly Gln Gly Thr Leu Val
            100                 105                 110
Thr Val Ser Ser
            115
```

<210> SEQ ID NO 66
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 66

```
Ser Tyr Glu Leu Thr Gln Pro Pro Ser Ala Ser Gly Thr Pro Gly Gln
1               5                   10                  15
Arg Val Thr Met Ser Cys Ser Gly Thr Ser Ser Asn Ile Gly Ser His
            20                  25                  30
Ser Val Asn Trp Tyr Gln Gln Leu Pro Gly Thr Ala Pro Lys Leu Leu
        35                  40                  45
Ile Tyr Thr Asn Asn Gln Arg Pro Ser Gly Val Pro Asp Arg Phe Ser
    50                  55                  60
Gly Ser Lys Ser Gly Thr Ser Ala Ser Leu Ala Ile Ser Gly Leu Gln
65                  70                  75                  80
Ser Glu Asp Glu Ala Asp Tyr Tyr Cys Ala Ala Trp Asp Gly Ser Leu
                85                  90                  95
Asn Gly Leu Val Phe Gly Gly Gly Thr Lys Leu Thr Val Leu Gly
            100                 105                 110
```

<210> SEQ ID NO 67
<211> LENGTH: 348
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 67

```
gaggtgcagc tggtgcagtc tggagcagag gtgaaaaagc ccggggagtc tctgaagatc      60
tcctgtaagg gttctggata cagctttacc agctactgga tcggctgggt gcgccagatg     120
cccgggaaag gcctggagtg gatggggatc atctatcctg gtgactctga taccagatac     180
```

```
agcccgtcct tccaaggcca cgtcaccatc tcagctgaca agtccatcag cactgcctac    240
ctgcagtgga gcagcctgaa ggcctcggac accgccatgt attactgtgc gcgctactct    300
ggttctttcg ataactgggg tcaaggtact ctggtgaccg tctcctca                 348

<210> SEQ ID NO 68
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68
tcctatgagc tgactcagcc accctcagcg tctgggaccc ccgggcagag ggtcaccatg    60
tcttgttctg gaaccagctc caacatcgga agtcactctg taaactggta ccagcagctc   120
ccaggaacgg cccccaaact cctcatctat actaataatc agcggccctc agggggtccct   180 gaccgattct ctggctccaa gtctggcacc tcagcctccc tggccatcag tggcctccag   240
tctgaggatg aggctgatta ttactgtgca gcatgggatg gcagcctgaa tggtctggta   300
ttcggcggag ggaccaagct gaccgtccta ggt                                333

<210> SEQ ID NO 69
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ser Arg Gly Gly Gly Gly Ser Gly Gly Gly Ser Gly Gly Gly Gly
1               5                   10                  15

Ser Leu Glu Met Ala
            20

<210> SEQ ID NO 70
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
tctagaggtg gtggtggtag cggcggcggc ggctctggtg gtggtggatc cctcgagatg    60
gcc                                                                 63

<210> SEQ ID NO 71
<211> LENGTH: 184
<212> TYPE: PRT
<213> ORGANISM: Homo sapiens

<400> SEQUENCE: 71

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45
```

```
Val Lys Gly Thr Asn Ala Ile Leu Trp Thr Cys Leu Gly Leu Ser Leu
 50                  55                  60

Ile Ile Ser Leu Ala Val Phe Val Leu Met Phe Leu Leu Arg Lys Ile
 65                  70                  75                  80

Asn Ser Glu Pro Leu Lys Asp Glu Phe Lys Asn Thr Gly Ser Gly Leu
                 85                  90                  95

Leu Gly Met Ala Asn Ile Asp Leu Glu Lys Ser Arg Thr Gly Asp Glu
                100                 105                 110

Ile Ile Leu Pro Arg Gly Leu Glu Tyr Thr Val Glu Glu Cys Thr Cys
            115                 120                 125

Glu Asp Cys Ile Lys Ser Lys Pro Lys Val Asp Ser Asp His Cys Phe
130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
            180

<210> SEQ ID NO 72
<211> LENGTH: 255
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Gln Ser Val Leu Thr Gln Pro Pro Ser Val Ser Val Ala Pro Arg Gln
 1                   5                  10                  15

Arg Val Thr Ile Ser Cys Ser Gly Ser Ser Ser Asn Ile Gly His Asn
                 20                  25                  30

Asp Val Ser Trp Tyr Gln His Leu Pro Gly Lys Ala Pro Arg Leu Leu
             35                  40                  45

Ile Tyr Phe Asp Asp Leu Leu Pro Ser Gly Val Ser Asp Arg Phe Ser
 50                  55                  60

Ala Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Gly Ser Leu
                 85                  90                  95

Asn Ala Phe Val Phe Gly Thr Gly Thr Lys Val Thr Val Leu Gly Ser
                100                 105                 110

Arg Gly Gly Gly Gly Ser Gly Gly Gly Ser Gly Gly Gly Gly Ser
            115                 120                 125

Leu Glu Met Ala Gln Val Gln Leu Gln Gln Ser Gly Pro Gly Leu Val
            130                 135                 140

Lys Pro Ser Gln Thr Leu Ser Leu Thr Cys Ala Ile Ser Gly Asp Ser
145                 150                 155                 160

Val Ser Ser Asn Ser Ala Ala Trp Asn Trp Ile Arg Gln Ser Pro Ser
                165                 170                 175

Arg Gly Leu Glu Trp Leu Gly Arg Thr Tyr Tyr Arg Ser Lys Trp Tyr
            180                 185                 190

Asn Asp Tyr Ala Val Ser Val Lys Ser Arg Ile Thr Ile Asn Pro Asp
                195                 200                 205

Thr Ser Lys Asn Gln Phe Ser Leu Gln Leu Asn Ser Val Thr Pro Glu
            210                 215                 220
```

```
Asp Thr Ala Val Tyr Tyr Cys Ala Arg Gln Gly Tyr Tyr Gly
225                 230                 235                 240

Tyr Ser Asp Val Trp Gly Gln Gly Thr Leu Val Thr Val Ser Ser
            245                 250                 255

<210> SEQ ID NO 73
<211> LENGTH: 255
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Gln Pro Val Leu Thr Gln Pro Pro Ser Val Ser Glu Ala Pro Arg Gln
1               5                   10                  15

Arg Val Thr Ile Ser Cys Ser Gly Ser Ser Asn Ile Gly Asn Asn
            20                  25                  30

Ala Val Asn Trp Tyr Gln Gln Leu Pro Gly Lys Ala Pro Lys Leu Leu
            35                  40                  45

Ile Tyr Phe Asp Asp Leu Leu Ser Ser Gly Val Ser Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Val Thr Val Leu Gly Ser
            100                 105                 110

Arg Gly Gly Gly Gly Ser Gly Gly Gly Gly Ser Gly Gly Gly Gly Ser
        115                 120                 125

Leu Glu Met Ala Gln Val Gln Leu Gln Gln Ser Gly Pro Gly Leu Val
    130                 135                 140

Lys Pro Ser Gln Thr Leu Ser Leu Thr Cys Ala Ile Ser Gly Asp Ser
145                 150                 155                 160

Val Ser Ser Asn Ser Ala Ala Trp Asn Trp Ile Arg Gln Ser Pro Ser
                165                 170                 175

Arg Gly Leu Glu Trp Leu Gly Arg Thr Tyr Tyr Arg Ser Lys Trp Tyr
            180                 185                 190

Asn Asp Tyr Ala Val Ser Val Lys Ser Arg Ile Thr Ile Asn Pro Asp
        195                 200                 205

Thr Ser Lys Asn Gln Phe Ser Leu Gln Leu Asn Ser Val Thr Pro Glu
    210                 215                 220

Asp Thr Ala Val Tyr Tyr Cys Ala Arg Tyr Gly Phe Ser Gly Ser Arg
225                 230                 235                 240

Phe Tyr Asp Thr Trp Gly Gln Gly Thr Leu Val Thr Val Ser Ser
            245                 250                 255

<210> SEQ ID NO 74
<211> LENGTH: 254
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Leu Pro Val Leu Thr Gln Pro Pro Ser Thr Ser Gly Thr Pro Gly Gln
1               5                   10                  15
```

```
Arg Val Thr Val Ser Cys Ser Gly Ser Ser Asn Ile Gly Ser Asn
            20                  25                  30

Val Val Phe Trp Tyr Gln Gln Leu Pro Gly Thr Ala Pro Lys Leu Val
        35                  40                  45

Ile Tyr Arg Asn Asn Gln Arg Pro Ser Gly Val Pro Asp Arg Phe Ser
50                  55                  60

Val Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Tyr Val Phe Gly Thr Gly Thr Lys Val Thr Val Leu Gly Ser
            100                 105                 110

Arg Gly Gly Gly Gly Ser Gly Gly Gly Ser Gly Gly Gly Gly Ser
            115                 120                 125

Leu Glu Met Ala Glu Val Gln Leu Val Gln Ser Gly Ala Glu Val Lys
130                 135                 140

Lys Pro Gly Ser Ser Val Lys Val Ser Cys Lys Ala Ser Gly Gly Thr
145                 150                 155                 160

Phe Ser Ser Tyr Ala Ile Ser Trp Val Arg Gln Ala Pro Gly Gln Gly
            165                 170                 175

Leu Glu Trp Met Gly Arg Ile Ile Pro Ile Leu Gly Ile Ala Asn Tyr
        180                 185                 190

Ala Gln Lys Phe Gln Gly Arg Val Thr Met Thr Glu Asp Thr Ser Thr
            195                 200                 205

Asp Thr Ala Tyr Met Glu Leu Ser Ser Leu Arg Ser Glu Asp Thr Ala
210                 215                 220

Val Tyr Tyr Cys Ala Arg Ser Gly Tyr Ser Lys Ser Ile Val Ser Tyr
225                 230                 235                 240

Met Asp Tyr Trp Gly Gln Gly Thr Leu Val Thr Val Ser Ser
            245                 250

<210> SEQ ID NO 75
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Gln Ser Val Val Thr Gln Pro Pro Ser Val Ser Gly Ala Pro Gly Gln
1               5                   10                  15

Arg Val Thr Ile Ser Cys Ser Gly Ser Ser Asn Ile Gly Ala Arg
            20                  25                  30

Tyr Asp Val Gln Trp Tyr Gln Gln Leu Pro Gly Thr Ala Pro Lys Leu
        35                  40                  45

Leu Ile Phe Gly Asn Asn Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Ala Ser Val Phe Gly Gly Thr Lys Leu Thr Val Leu Gly
            100                 105                 110

Ser Arg Gly Gly Gly Gly Ser Gly Gly Gly Gly Ser Gly Gly Gly Gly
```

```
              115                 120                 125
Ser Leu Glu Met Ala Glu Val Gln Leu Val Gln Ser Gly Ala Glu Val
    130                 135                 140

Lys Lys Pro Gly Ala Ser Val Lys Val Ser Cys Lys Ala Ser Gly Tyr
145                 150                 155                 160

Thr Phe Thr Ser Tyr Tyr Met His Trp Val Arg Gln Ala Pro Gly Gln
                165                 170                 175

Gly Leu Glu Trp Met Gly Ile Ile Asn Pro Ser Gly Gly Ser Thr Ser
            180                 185                 190

Tyr Ala Gln Lys Phe Gln Gly Arg Val Thr Met Thr Arg Asp Thr Ser
        195                 200                 205

Thr Ser Thr Val Tyr Met Glu Leu Ser Ser Leu Arg Ser Glu Asp Thr
    210                 215                 220

Ala Val Tyr Tyr Cys Ala Arg Ser Gln Trp Gly Gly Val Leu Asp Tyr
225                 230                 235                 240

Trp Gly Gln Gly Thr Leu Val Thr Val Ser Ser
                245                 250
```

<210> SEQ ID NO 76
<211> LENGTH: 255
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

```
Gln Ala Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Arg Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Val Val Phe Gly Gly Gly Thr Lys Leu Thr Val Leu Gly Ser
            100                 105                 110

Arg Gly Gly Gly Gly Ser Gly Gly Gly Gly Ser Gly Gly Gly Gly Ser
        115                 120                 125

Leu Glu Met Ala Gln Val Gln Leu Val Glu Ser Gly Ala Glu Val Lys
    130                 135                 140

Lys Pro Gly Ser Ser Val Lys Val Ser Cys Lys Ala Ser Gly Gly Thr
145                 150                 155                 160

Phe Ser Ser Tyr Ala Ile Ser Trp Val Arg Gln Ala Pro Gly Gln Gly
                165                 170                 175

Leu Glu Trp Met Gly Arg Ile Ile Pro Ile Leu Gly Ile Ala Asn Tyr
            180                 185                 190

Ala Gln Lys Phe Gln Gly Arg Val Thr Ile Thr Ala Asp Glu Ser Thr
        195                 200                 205

Ser Thr Ala Tyr Met Glu Leu Ser Ser Leu Arg Ser Glu Asp Thr Ala
    210                 215                 220
```

Val Tyr Tyr Cys Ala Arg Thr Gly Tyr Glu Ser Trp Gly Ser Tyr Glu
225                 230                 235                 240

Val Ile Asp Arg Trp Gly Gln Gly Thr Leu Val Thr Val Ser Ser
            245                 250                 255

<210> SEQ ID NO 77
<211> LENGTH: 254
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Leu Pro Val Leu Thr Gln Pro Pro Ser Ala Ser Gly Thr Pro Gly Gln
1               5                   10                  15

Arg Val Thr Ile Ser Cys Ser Gly Arg Ser Ser Asn Ile Gly Ser Asn
            20                  25                  30

Ser Val Asn Trp Tyr Arg Gln Leu Pro Gly Ala Ala Pro Lys Leu Leu
        35                  40                  45

Ile Tyr Ser Asn Asn Gln Arg Pro Pro Gly Val Pro Val Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Thr Tyr Tyr Cys Ala Thr Trp Asp Asp Asn Leu
                85                  90                  95

Asn Val His Tyr Val Phe Gly Thr Gly Thr Lys Val Thr Val Leu Gly
            100                 105                 110

Ser Arg Gly Gly Gly Gly Ser Gly Gly Gly Ser Gly Gly Gly Gly
        115                 120                 125

Ser Leu Glu Met Ala Gln Val Gln Leu Val Gln Ser Gly Ala Glu Val
130                 135                 140

Lys Lys Pro Gly Ser Ser Val Lys Val Ser Cys Lys Ala Ser Gly Gly
145                 150                 155                 160

Thr Phe Ser Ser Tyr Ala Ile Ser Trp Val Arg Gln Ala Pro Gly Gln
                165                 170                 175

Gly Leu Glu Trp Met Gly Arg Ile Ile Pro Ile Leu Gly Ile Ala Asn
            180                 185                 190

Tyr Ala Gln Lys Phe Gln Gly Arg Val Thr Ile Thr Ala Asp Lys Ser
        195                 200                 205

Thr Ser Thr Ala Tyr Met Glu Leu Ser Ser Leu Arg Ser Glu Asp Thr
210                 215                 220

Ala Val Tyr Tyr Cys Ala Arg Gly Gly Tyr Tyr Ser His Asp Met Trp
225                 230                 235                 240

Ser Glu Asp Trp Gly Gln Gly Thr Leu Val Thr Val Ser Ser
                245                 250

<210> SEQ ID NO 78
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Gln Pro Val Leu Thr Gln Pro Pro Ser Ala Ser Ala Ser Leu Gly Ala
1               5                   10                  15

Ser Val Thr Leu Thr Cys Thr Leu Ser Ser Gly Tyr Ser Asn Tyr Lys
            20                  25                  30

Val Asp Trp Tyr Gln Gln Arg Pro Gly Lys Gly Pro Arg Phe Val Met
        35                  40                  45

Arg Val Gly Thr Gly Gly Ile Val Gly Ser Lys Gly Asp Gly Ile Pro
    50                  55                  60

Asp Arg Phe Ser Val Leu Gly Ser Gly Leu Asn Arg Tyr Leu Thr Ile
65                  70                  75                  80

Lys Asn Ile Gln Glu Glu Asp Glu Gly Asp Tyr His Cys Gly Ala Asp
                85                  90                  95

His Gly Ser Gly Ser Asn Phe Val Tyr Val Phe Gly Thr Gly Thr Lys
            100                 105                 110

Val Thr Val Leu Gly Ser Arg Gly Gly Gly Ser Gly Gly Gly Gly
        115                 120                 125

Ser Gly Gly Gly Gly Ser Leu Glu Met Ala Gln Val Gln Leu Gln Glu
    130                 135                 140

Ser Gly Pro Gly Leu Val Lys Pro Ser Gly Thr Leu Ser Leu Thr Cys
145                 150                 155                 160

Gly Val Ser Gly Gly Ser Ile Ser Asn Ser Asn Trp Trp Ser Trp Val
                165                 170                 175

Arg Gln Pro Pro Gly Lys Gly Leu Glu Trp Ile Gly Glu Ile Tyr His
            180                 185                 190

Ser Gly Ser Thr Lys Tyr Asn Pro Ser Leu Arg Ser Arg Val Thr Ile
        195                 200                 205

Ser Val Asp Lys Ser Lys Asn Gln Phe Ser Leu Lys Leu Ser Ser Val
    210                 215                 220

Thr Ala Ala Asp Thr Ala Val Tyr Tyr Cys Ala Arg Arg Asp Asn Trp
225                 230                 235                 240

Lys Thr Pro Thr Thr Lys Ile Asp Gly Phe Asp Ile Trp Gly Gln Gly
                245                 250                 255

Thr Met Val Thr Val Ser Ser
            260

<210> SEQ ID NO 79
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys Arg Ser Arg Gly Gly
            100                 105                 110

```
Gly Gly Ser Gly Gly Gly Ser Gly Gly Gly Ser Leu Glu Met
        115                 120                 125

Ala Gln Val Gln Leu Val Gln Ser Gly Ala Glu Val Lys Lys Pro Gly
    130                 135                 140

Ala Ser Val Lys Val Ser Cys Lys Ala Ser Gly Tyr Thr Phe Thr Gly
145                 150                 155                 160

Tyr Tyr Met His Trp Val Arg Gln Ala Pro Gly Gln Gly Leu Glu Trp
                165                 170                 175

Met Gly Trp Ile Asn Pro Asn Ser Gly Gly Thr Asn Tyr Ala Gln Lys
            180                 185                 190

Phe Gln Gly Arg Val Thr Met Thr Arg Asp Thr Ser Ile Ser Thr Ala
        195                 200                 205

Tyr Met Glu Leu Ser Arg Leu Arg Ser Asp Asp Thr Ala Val Tyr Tyr
    210                 215                 220

Cys Ala Arg Ser Gln Trp Gly Ser Ser Trp Asp Tyr Trp Gly Gln Gly
225                 230                 235                 240

Thr Leu Val Thr Val Ser Ser
                245

<210> SEQ ID NO 80
<211> LENGTH: 257
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Gln Pro Val Leu Thr Gln Pro Pro Ser Ala Ser Ala Ser Leu Gly Ala
1               5                   10                  15

Ser Val Thr Leu Thr Cys Thr Leu Ser Asn Asp Tyr Thr Asn Tyr Lys
            20                  25                  30

Val Asp Trp Tyr Gln Gln Arg Pro Gly Lys Gly Pro Arg Phe Val Met
        35                  40                  45

Arg Val Gly Pro Gly Gly Ile Val Gly Ser Lys Gly Asp Gly Ile Pro
    50                  55                  60

Asp Arg Phe Ser Val Leu Gly Ser Gly Leu Asn Arg Tyr Leu Thr Ile
65                  70                  75                  80

Lys Asn Ile Gln Glu Glu Asp Glu Ser Asp Tyr His Cys Gly Ala Asp
                85                  90                  95

His Gly Thr Gly Ser Asn Phe Val Tyr Val Phe Gly Gly Thr Lys
            100                 105                 110

Leu Thr Val Leu Gly Ser Arg Gly Gly Gly Ser Gly Gly Gly Gly
        115                 120                 125

Ser Gly Gly Gly Gly Ser Leu Glu Met Ala Glu Val Gln Leu Val Glu
    130                 135                 140

Ser Gly Ala Glu Val Lys Lys Pro Gly Ala Ser Val Lys Val Ser Cys
145                 150                 155                 160

Lys Ala Ser Gly Tyr Thr Phe Thr Gly Tyr Tyr Met His Trp Val Arg
                165                 170                 175

Gln Ala Pro Gly Gln Gly Leu Glu Trp Met Gly Trp Ile Asn Pro Asn
            180                 185                 190

Ser Gly Gly Thr Asn Tyr Ala Gln Lys Phe Gln Gly Arg Val Thr Met
        195                 200                 205

Thr Arg Asp Thr Ser Ile Ser Thr Ala Tyr Met Glu Leu Ser Arg Leu
```

```
            210                 215                 220
Arg Ser Asp Asp Thr Ala Val Tyr Tyr Cys Ala Arg Ser Ser Tyr His
225                 230                 235                 240

Leu Tyr Gly Tyr Asp Ser Trp Gly Gln Gly Thr Leu Val Thr Val Ser
                245                 250                 255

Ser

<210> SEQ ID NO 81
<211> LENGTH: 258
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Gln Pro Val Leu Thr Gln Pro Pro Ser Ala Ser Ala Ser Leu Gly Ala
1               5                   10                  15

Ser Val Thr Leu Thr Cys Thr Leu Ser Ser Gly Tyr Ser Asn Tyr Lys
            20                  25                  30

Val Asp Trp Tyr Gln Gln Arg Pro Gly Lys Gly Pro Arg Phe Leu Met
        35                  40                  45

Arg Val Asp Thr Gly Gly Ile Val Gly Ser Lys Gly Asp Gly Ile Pro
    50                  55                  60

Asp Arg Phe Ser Val Ser Gly Ser Gly Leu Asn Arg Tyr Leu Thr Ile
65                  70                  75                  80

Lys Asn Ile Gln Glu Glu Asp Glu Ser Asp Tyr His Cys Gly Ala Asp
                85                  90                  95

His Gly Ser Gly Ser Asn Phe Val Trp Val Phe Gly Gly Gly Thr Lys
            100                 105                 110

Leu Thr Val Leu Gly Ser Arg Gly Gly Gly Ser Gly Gly Gly Gly
        115                 120                 125

Ser Gly Gly Gly Gly Ser Leu Glu Met Ala Gln Val Gln Leu Val Gln
    130                 135                 140

Ser Gly Ala Glu Val Lys Lys Pro Gly Ser Ser Val Lys Val Ser Cys
145                 150                 155                 160

Lys Ala Ser Gly Gly Thr Phe Ser Ser Tyr Ala Ile Ser Trp Val Arg
                165                 170                 175

Gln Ala Pro Gly Gln Gly Leu Glu Trp Met Gly Gly Ile Ile Pro Ile
            180                 185                 190

Phe Ser Thr Ala Asn Tyr Ala Gln Lys Phe Gln Gly Arg Val Thr Met
        195                 200                 205

Thr Thr Asp Thr Ser Thr Ser Thr Ala Tyr Met Glu Leu Arg Ser Leu
    210                 215                 220

Arg Ser Asp Asp Thr Ala Val Tyr Tyr Cys Ala Arg Gln Pro Trp Thr
225                 230                 235                 240

Trp Tyr Ser Pro Tyr Asp Gln Trp Gly Gln Gly Thr Leu Val Thr Val
                245                 250                 255

Ser Ser

<210> SEQ ID NO 82
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 82

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

Arg Ser Arg Gly Gly Gly Gly Ser Gly Gly Gly Gly Ser Gly Gly Gly
        115                 120                 125

Gly Ser Leu Glu Met Ala Glu Val Gln Leu Val Glu Thr Gly Gly Gly
130                 135                 140

Leu Val Gln Pro Gly Gly Ser Leu Arg Leu Ser Cys Ala Ala Ser Gly
145                 150                 155                 160

Phe Thr Phe Ser Thr Tyr Ala Met Thr Trp Val Arg Gln Ala Pro Gly
                165                 170                 175

Lys Gly Leu Glu Trp Val Ser Ala Ile Thr Pro Gly Gly Asp Arg Thr
            180                 185                 190

Tyr Tyr Ala Asp Ser Val Lys Gly Arg Phe Thr Ile Ser Arg Asp Asn
        195                 200                 205

Ser Arg Asn Thr Leu Tyr Leu Gln Met Asn Ser Leu Arg Ala Glu Asp
    210                 215                 220

Thr Ala Val Tyr Tyr Cys Ala Arg Tyr Tyr Gly Tyr Met Ile Asp Met
225                 230                 235                 240

Trp Gly Gln Gly Thr Leu Val Thr Val Ser Ser
                245                 250

<210> SEQ ID NO 83
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Ser Tyr Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Val Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Ala Ser Ala Ser Leu Ala Ile Ser Trp Leu Gln
65                  70                  75                  80

Ser Glu Asp Glu Ala Asp Tyr Tyr Cys Ala Ala Trp Asp Asp Ser Leu
                85                  90                  95

```
Asn Gly Trp Val Phe Gly Gly Thr Lys Leu Thr Val Leu Gly Ser
                100                 105                 110

Arg Gly Gly Gly Ser Gly Gly Gly Ser Gly Gly Gly Ser
            115                 120                 125

Leu Glu Met Ala Gln Met Gln Leu Val Gln Ser Gly Ala Glu Val Lys
130                 135                 140

Lys Pro Gly Ala Ser Val Lys Val Ser Cys Lys Ala Ser Gly Tyr Thr
145                 150                 155                 160

Phe Thr Gly Tyr Tyr Val His Trp Leu Arg Gln Ala Pro Gly Gln Gly
                165                 170                 175

Leu Glu Trp Met Gly Trp Ile Asn Pro Asn Ser Gly Thr Asn Asn
            180                 185                 190

Ala Gln Glu Phe Gln Gly Arg Ile Thr Met Thr Arg Asp Thr Ser Ile
        195                 200                 205

Asn Thr Ala Tyr Met Glu Leu Ser Arg Leu Arg Ser Asp Asp Thr Ala
210                 215                 220

Val Tyr Tyr Cys Ala Arg Ser Gln Trp Gly Gly Tyr Asp Tyr Trp
225                 230                 235                 240

Gly Gln Gly Thr Leu Val Thr Val Ser Ser
            245                 250

<210> SEQ ID NO 84
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Gln Ala Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Tyr
            20                  25                  30

Thr Val Ser Trp Tyr Gln Gln Leu Pro Gly Thr Ala Pro Lys Phe Leu
        35                  40                  45

Ile Tyr Ser Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Val Thr Val Leu Gly Ser
                100                 105                 110

Arg Gly Gly Gly Ser Gly Gly Gly Gly Ser Gly Gly Gly Gly Ser
            115                 120                 125

Leu Glu Met Ala Glu Val Gln Leu Val Gln Ser Gly Ala Glu Val Lys
130                 135                 140

Lys Pro Gly Glu Ser Leu Lys Ile Ser Cys Lys Gly Ser Gly Tyr Asp
145                 150                 155                 160

Phe Thr Thr Tyr Trp Ile Gly Trp Val Arg Gln Met Pro Gly Lys Gly
                165                 170                 175

Leu Glu Trp Met Gly Ile Ile Tyr Pro Gly Asp Ser Asp Thr Arg Tyr
            180                 185                 190

Ser Pro Ser Val Arg Gly Arg Val Thr Ile Ser Ala Asp Lys Ser Ile
```

```
              195                 200                 205
Asn Thr Ala Tyr Leu Gln Trp Ser Ser Leu Glu Ala Ser Asp Thr Ala
    210                 215                 220

Met Tyr Tyr Cys Ala Arg Met Trp Thr Phe Ser Gln Asp Gly Trp Gly
225                 230                 235                 240

Gln Gly Thr Leu Val Thr Val Ser Ser
                245

<210> SEQ ID NO 85
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Gln Ser Ala Leu Thr Gln Pro Ala Ser Val Ser Ala Ser Pro Gly Gln
1               5                   10                  15

Ser Ile Ala Ile Ser Cys Thr Gly Thr Ser Ser Asp Val Gly Trp Tyr
            20                  25                  30

Gln Gln His Pro Gly Lys Ala Pro Lys Leu Met Ile Tyr Glu Asp Ser
        35                  40                  45

Lys Arg Pro Ser Gly Val Ser Asn Arg Phe Ser Gly Ser Lys Ser Gly
50                  55                  60

Asn Thr Ala Ser Leu Thr Ile Ser Gly Leu Gln Ala Glu Asp Glu Ala
65                  70                  75                  80

Asp Tyr Tyr Cys Ser Ser Asn Thr Arg Ser Ser Thr Leu Val Phe Gly
                85                  90                  95

Gly Gly Thr Lys Leu Thr Val Leu Gly Ser Arg Gly Gly Gly Gly Ser
            100                 105                 110

Gly Gly Gly Gly Ser Gly Gly Gly Ser Leu Glu Met Ala Glu Val
        115                 120                 125

Gln Leu Val Gln Ser Gly Ala Glu Met Lys Lys Pro Gly Ala Ser Leu
    130                 135                 140

Lys Leu Ser Cys Lys Ala Ser Gly Tyr Thr Phe Ile Asp Tyr Tyr Val
145                 150                 155                 160

Tyr Trp Met Arg Gln Ala Pro Gly Gln Gly Leu Glu Ser Met Gly Trp
                165                 170                 175

Ile Asn Pro Asn Ser Gly Gly Thr Asn Tyr Ala Gln Lys Phe Gln Gly
            180                 185                 190

Arg Val Thr Met Thr Arg Asp Thr Ser Ile Ser Thr Ala Tyr Met Glu
        195                 200                 205

Leu Ser Arg Leu Arg Ser Asp Asp Thr Ala Met Tyr Tyr Cys Ala Arg
    210                 215                 220

Ser Gln Arg Asp Gly Tyr Met Asp Tyr Trp Gly Gln Gly Thr Leu Val
225                 230                 235                 240

Thr Val Ser Ser

<210> SEQ ID NO 86
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86
```

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
                20                  25                  30

Phe Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
        50                  55                  60

Ser Gly Ser Lys Ser Gly Thr Ser Ala Ser Leu Ala Ile Thr Gly Leu
65              70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Val Thr Val Leu Gly
            100                 105                 110

Ser Arg Gly Gly Gly Gly Ser Gly Gly Gly Ser Gly Gly Gly Gly
            115                 120                 125

Ser Leu Glu Met Ala Gln Val Gln Leu Val Gln Ser Gly Ala Glu Val
            130                 135                 140

Lys Lys Pro Gly Ala Ser Val Lys Val Ser Cys Lys Ala Ser Gly Tyr
145             150                 155                 160

Thr Phe Thr Asp Tyr Tyr Met His Trp Val Arg Gln Ala Pro Gly Gln
            165                 170                 175

Arg Leu Glu Trp Met Gly Trp Ile Asn Pro Asn Ser Gly Gly Thr Asn
            180                 185                 190

Tyr Ala Gln Lys Phe Gln Asp Arg Ile Thr Val Thr Arg Asp Thr Ser
            195                 200                 205

Ser Asn Thr Gly Tyr Met Glu Leu Thr Arg Leu Arg Ser Asp Asp Thr
            210                 215                 220

Ala Val Tyr Tyr Cys Ala Arg Ser Pro Tyr Ser Gly Val Leu Asp Lys
225             230                 235                 240

Trp Gly Gln Gly Thr Leu Val Thr Val Ser Ser
            245                 250

<210> SEQ ID NO 87
<211> LENGTH: 253
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Gln Ala Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Tyr Val Phe Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Arg
65              70                  75                  80

Ser Glu Asp Glu Ala Asp Tyr Tyr Cys Ala Ala Trp Asp Asp Ser Leu
                85                  90                  95

Ser Ala Ser Tyr Val Phe Gly Thr Gly Thr Lys Val Thr Val Leu Gly

```
                    100                 105                 110
Ser Arg Gly Gly Gly Ser Gly Gly Gly Ser Gly Gly Gly
            115                 120                 125

Ser Leu Glu Met Ala Gln Val Gln Leu Val Gln Ser Gly Ala Glu Val
            130                 135                 140

Lys Lys Pro Gly Ser Ser Val Lys Val Ser Cys Lys Ala Ser Gly Gly
145                 150                 155                 160

Thr Phe Ser Ser Tyr Ala Ile Ser Trp Val Arg Gln Ala Pro Gly Gln
                165                 170                 175

Gly Leu Glu Trp Met Gly Arg Ile Ile Pro Ile Leu Gly Thr Ala Asn
            180                 185                 190

Tyr Ala Gln Lys Phe Gln Gly Arg Val Thr Ile Thr Ala Asp Glu Ser
            195                 200                 205

Thr Ser Thr Ala Tyr Met Glu Leu Ser Ser Leu Arg Ser Glu Asp Thr
        210                 215                 220

Ala Val Tyr Tyr Cys Ala Arg Ser Gly Tyr Gly Ser Tyr Arg Trp Glu
225                 230                 235                 240

Asp Ser Trp Gly Gln Gly Thr Leu Val Thr Val Ser Ser
                245                 250

<210> SEQ ID NO 88
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Ser Tyr Glu Leu Thr Gln Pro Pro Ser Ala Ser Gly Thr Pro Gly Gln
1               5                   10                  15

Arg Val Thr Met Ser Cys Ser Gly Thr Ser Ser Asn Ile Gly Ser His
            20                  25                  30

Ser Val Asn Trp Tyr Gln Gln Leu Pro Gly Thr Ala Pro Lys Leu Leu
        35                  40                  45

Ile Tyr Thr Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Gly Ser Leu
                85                  90                  95

Asn Gly Leu Val Phe Gly Gly Gly Thr Lys Leu Thr Val Leu Gly Ser
            100                 105                 110

Arg Gly Gly Gly Gly Ser Gly Gly Gly Ser Gly Gly Gly Gly Ser
            115                 120                 125

Leu Glu Met Ala Glu Val Gln Leu Val Gln Ser Gly Ala Glu Val Lys
            130                 135                 140

Lys Pro Gly Glu Ser Leu Lys Ile Ser Cys Lys Gly Ser Gly Tyr Ser
145                 150                 155                 160

Phe Thr Ser Tyr Trp Ile Gly Trp Val Arg Gln Met Pro Gly Lys Gly
                165                 170                 175

Leu Glu Trp Met Gly Ile Ile Tyr Pro Gly Asp Ser Asp Thr Arg Tyr
            180                 185                 190

Ser Pro Ser Phe Gln Gly His Val Thr Ile Ser Ala Asp Lys Ser Ile
        195                 200                 205
```

```
Ser Thr Ala Tyr Leu Gln Trp Ser Ser Leu Lys Ala Ser Asp Thr Ala
    210                 215                 220

Met Tyr Tyr Cys Ala Arg Tyr Ser Gly Ser Phe Asp Asn Trp Gly Gln
225                 230                 235                 240

Gly Thr Leu Val Thr Val Ser Ser
                245
```

<210> SEQ ID NO 89
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

```
Val Ser Ser Asn Ser Ala Ala Trp Asn
1               5
```

<210> SEQ ID NO 90
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

```
Tyr Arg Ser Lys Trp Tyr Asn
1               5
```

<210> SEQ ID NO 91
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

```
Ala Arg Gln Gly Tyr Ser Tyr Tyr Gly Tyr Ser Asp Val
1               5                   10
```

<210> SEQ ID NO 92
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

```
Ser Ser Asn Ile Gly His Asn Asp
1               5
```

<210> SEQ ID NO 93
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

```
Phe Asp Asp
1
```

<210> SEQ ID NO 94
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Ala Ala Trp Asp Gly Ser Leu Asn Ala Phe Val
1               5                   10

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Val Ser Ser Asn Ser Ala Ala Trp Asn
1               5

<210> SEQ ID NO 96
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Tyr Arg Ser Lys Trp Tyr Asn
1               5

<210> SEQ ID NO 97
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Ala Arg Tyr Gly Phe Ser Gly Ser Arg Phe Tyr Asp Thr
1               5                   10

<210> SEQ ID NO 98
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Ser Ser Asn Ile Gly Asn Asn Ala
1               5

<210> SEQ ID NO 99
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 99

Phe Asp Asp
1

<210> SEQ ID NO 100
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ala Ala Trp Asp Asp Ser Leu Asn Gly Tyr Val
1               5                   10

<210> SEQ ID NO 101
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gly Gly Thr Phe Ser Ser Tyr Ala
1               5

<210> SEQ ID NO 102
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Ile Ile Pro Ile Leu Gly Ile Ala
1               5

<210> SEQ ID NO 103
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Ala Arg Ser Gly Tyr Ser Lys Ser Ile Val Ser Tyr Met Asp Tyr
1               5                   10                  15

<210> SEQ ID NO 104
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Ser Ser Asn Ile Gly Ser Asn Val
1               5

<210> SEQ ID NO 105
<211> LENGTH: 3
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 105

Arg Asn Asn
1

<210> SEQ ID NO 106
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Ala Ala Trp Asp Asp Ser Leu Ser Gly Tyr Val
1               5                   10

<210> SEQ ID NO 107
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Gly Tyr Thr Phe Thr Ser Tyr Tyr
1               5

<210> SEQ ID NO 108
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Ile Asn Pro Ser Gly Gly Ser Thr
1               5

<210> SEQ ID NO 109
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Ala Arg Ser Gln Trp Gly Gly Val Leu Asp Tyr
1               5                   10

<210> SEQ ID NO 110
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Ser Ser Asn Ile Gly Ala Arg Tyr Asp
1               5
```

<210> SEQ ID NO 111
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gly Asn Asn
1

<210> SEQ ID NO 112
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Gln Ser Tyr Asp Ser Ser Leu Ser Ala Ser Val
1               5                   10

<210> SEQ ID NO 113
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Gly Gly Thr Phe Ser Ser Tyr Ala
1               5

<210> SEQ ID NO 114
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Ile Ile Pro Ile Leu Gly Ile Ala
1               5

<210> SEQ ID NO 115
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Ala Arg Thr Gly Tyr Glu Ser Trp Gly Ser Tyr Glu Val Ile Asp Arg
1               5                   10                  15

<210> SEQ ID NO 116
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 116

Ser Ser Asn Ile Gly Ser Asn Thr
1               5

<210> SEQ ID NO 117
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Ser Asn Asn
1

<210> SEQ ID NO 118
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Ala Ala Trp Asp Asp Ser Leu Asn Gly Val Val
1               5                   10

<210> SEQ ID NO 119
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Gly Gly Thr Phe Ser Ser Tyr Ala
1               5

<210> SEQ ID NO 120
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Ile Ile Pro Ile Leu Gly Ile Ala
1               5

<210> SEQ ID NO 121
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Ala Arg Gly Gly Tyr Tyr Ser His Asp Met Trp Ser Glu Asp
1               5                   10

<210> SEQ ID NO 122
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Ser Ser Asn Ile Gly Ser Asn Ser
1               5

<210> SEQ ID NO 123
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Ser Asn Asn
1

<210> SEQ ID NO 124
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Ala Thr Trp Asp Asp Asn Leu Asn Val His Tyr Val
1               5                   10

<210> SEQ ID NO 125
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Gly Gly Ser Ile Ser Asn Ser Asn Trp
1               5

<210> SEQ ID NO 126
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Ile Tyr His Ser Gly Ser Thr
1               5

<210> SEQ ID NO 127
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Ala Arg Arg Asp Asn Trp Lys Thr Pro Thr Thr Lys Ile Asp Gly Phe
```

Asp Ile

<210> SEQ ID NO 128
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Ser Gly Tyr Ser Asn Tyr Lys
1               5

<210> SEQ ID NO 129
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Val Gly Thr Gly Gly Ile Val Gly
1               5

<210> SEQ ID NO 130
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Gly Ala Asp His Gly Ser Gly Ser Asn Phe Val Tyr Val
1               5                   10

<210> SEQ ID NO 131
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Gly Tyr Thr Phe Thr Gly Tyr Tyr
1               5

<210> SEQ ID NO 132
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Ile Asn Pro Asn Ser Gly Gly Thr
1               5

<210> SEQ ID NO 133
<211> LENGTH: 11
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 133

Ala Arg Ser Gln Trp Gly Ser Ser Trp Asp Tyr
1               5                   10

<210> SEQ ID NO 134
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Gln Ser Ile Ser Ser Tyr
1               5

<210> SEQ ID NO 135
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Ala Ala Ser
1

<210> SEQ ID NO 136
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Gln Gln Ser Tyr Ser Thr Pro Pro Thr
1               5

<210> SEQ ID NO 137
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Gly Tyr Thr Phe Thr Gly Tyr Tyr
1               5

<210> SEQ ID NO 138
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Ile Asn Pro Asn Ser Gly Gly Thr
1               5
```

<210> SEQ ID NO 139
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Ala Arg Ser Ser Tyr His Leu Tyr Gly Tyr Asp Ser
1               5                   10

<210> SEQ ID NO 140
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Asn Asp Tyr Thr Asn Tyr Lys
1               5

<210> SEQ ID NO 141
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Val Gly Pro Gly Gly Ile Val Gly
1               5

<210> SEQ ID NO 142
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Gly Ala Asp His Gly Thr Gly Ser Asn Phe Val Tyr Val
1               5                   10

<210> SEQ ID NO 143
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Gly Gly Thr Phe Ser Ser Tyr Ala
1               5

<210> SEQ ID NO 144
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Ile Ile Pro Ile Phe Ser Thr Ala
1               5

<210> SEQ ID NO 145
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Ala Arg Gln Pro Trp Thr Trp Tyr Ser Pro Tyr Asp Gln
1               5                   10

<210> SEQ ID NO 146
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Ser Gly Tyr Ser Asn Tyr Lys
1               5

<210> SEQ ID NO 147
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Val Asp Thr Gly Gly Ile Val Gly
1               5

<210> SEQ ID NO 148
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Gly Ala Asp His Gly Ser Gly Ser Asn Phe Val Trp Val
1               5                   10

<210> SEQ ID NO 149
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Gly Phe Thr Phe Ser Thr Tyr Ala
1               5

<210> SEQ ID NO 150
<211> LENGTH: 8
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 150

Ile Thr Pro Gly Gly Asp Arg Thr
1               5

<210> SEQ ID NO 151
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Ala Arg Tyr Tyr Gly Tyr Met Ile Asp Met
1               5                   10

<210> SEQ ID NO 152
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Gln Ser Leu Leu His Ser Asn Gly Tyr Asn Tyr
1               5                   10

<210> SEQ ID NO 153
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Leu Gly Ser
1

<210> SEQ ID NO 154
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Met Gln Ala Leu Gln Thr Pro Leu Thr
1               5

<210> SEQ ID NO 155
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Gly Tyr Thr Phe Thr Gly Tyr Tyr
1               5
```

<210> SEQ ID NO 156
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Ile Asn Pro Asn Ser Gly Gly Thr
1               5

<210> SEQ ID NO 157
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Ala Arg Ser Gln Trp Gly Gly Thr Tyr Asp Tyr
1               5                   10

<210> SEQ ID NO 158
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Ser Ser Asn Ile Gly Ser Asn Thr
1               5

<210> SEQ ID NO 159
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Ser Asn Asn
1

<210> SEQ ID NO 160
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Ala Ala Trp Asp Asp Ser Leu Asn Gly Trp Val
1               5                   10

<210> SEQ ID NO 161
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Gly Tyr Asp Phe Thr Thr Tyr Trp
1               5

<210> SEQ ID NO 162
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Ile Tyr Pro Gly Asp Ser Asp Thr
1               5

<210> SEQ ID NO 163
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Ala Arg Met Trp Thr Phe Ser Gln Asp Gly
1               5                   10

<210> SEQ ID NO 164
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Ser Ser Asn Ile Gly Ser Tyr Thr
1               5

<210> SEQ ID NO 165
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Ser Asn Asn
1

<210> SEQ ID NO 166
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Ala Ala Trp Asp Asp Ser Leu Asn Gly Tyr Val
1               5                   10

<210> SEQ ID NO 167
<211> LENGTH: 8

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Gly Tyr Thr Phe Ile Asp Tyr Tyr
1               5

<210> SEQ ID NO 168
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Ile Asn Pro Asn Ser Gly Gly Thr
1               5

<210> SEQ ID NO 169
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Ala Arg Ser Gln Arg Asp Gly Tyr Met Asp Tyr
1               5                   10

<210> SEQ ID NO 170
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Ile Ser Cys Thr Gly Thr Ser Ser Asp
1               5

<210> SEQ ID NO 171
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Glu Asp Ser
1

<210> SEQ ID NO 172
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Ser Ser Asn Thr Arg Ser Ser Thr Leu Val
```

```
<210> SEQ ID NO 173
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Gly Tyr Thr Phe Thr Asp Tyr Tyr
1               5

<210> SEQ ID NO 174
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Ile Asn Pro Asn Ser Gly Gly Thr
1               5

<210> SEQ ID NO 175
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Ala Arg Ser Pro Tyr Ser Gly Val Leu Asp Lys
1               5                   10

<210> SEQ ID NO 176
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Ser Ser Asn Ile Gly Ala Gly Phe Asp
1               5

<210> SEQ ID NO 177
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Gly Asn Ser
1

<210> SEQ ID NO 178
<211> LENGTH: 11
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 178

Gln Ser Tyr Asp Ser Ser Leu Ser Gly Tyr Val
1               5                   10

<210> SEQ ID NO 179
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Gly Gly Thr Phe Ser Ser Tyr Ala
1               5

<210> SEQ ID NO 180
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Ile Ile Pro Ile Leu Gly Thr Ala
1               5

<210> SEQ ID NO 181
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Ala Arg Ser Gly Tyr Gly Ser Tyr Arg Trp Glu Asp Ser
1               5                   10

<210> SEQ ID NO 182
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Ser Ser Asn Ile Gly Ser Asn Tyr
1               5

<210> SEQ ID NO 183
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Ser Asn Asn
1

<210> SEQ ID NO 184

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Ala Ala Trp Asp Asp Ser Leu Ser Ala Ser Tyr Val
1               5                   10

<210> SEQ ID NO 185
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Gly Tyr Ser Phe Thr Ser Tyr Trp
1               5

<210> SEQ ID NO 186
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Ile Tyr Pro Gly Asp Ser Asp Thr
1               5

<210> SEQ ID NO 187
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Ala Arg Tyr Ser Gly Ser Phe Asp Asn
1               5

<210> SEQ ID NO 188
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Ser Ser Asn Ile Gly Ser His Ser
1               5

<210> SEQ ID NO 189
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189
```

Thr Asn Asn
1

<210> SEQ ID NO 190
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Ala Ala Trp Asp Gly Ser Leu Asn Gly Leu Val
1               5                   10

<210> SEQ ID NO 191
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Met Ala Leu Pro Val Thr Ala Leu Leu Leu Pro Leu Ala Leu Leu Leu
1               5                   10                  15

His Ala Ala Arg
            20

<210> SEQ ID NO 192
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
atggctctcc cagtgactgc cctactgctt cccctagcgc ttctcctgca tgcagctcgt        60

<210> SEQ ID NO 193
<211> LENGTH: 220
<212> TYPE: PRT
<213> ORGANISM: Homo sapiens

<400> SEQUENCE: 193

Met Leu Arg Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
                20                  25                  30

Asp Asn Ala Val Asn Leu Ser Cys Lys Tyr Ser Tyr Asn Leu Phe Ser
            35                  40                  45

Arg Glu Phe Arg Ala Ser Leu His Lys Gly Leu Asp Ser Ala Val Glu
        50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

```
Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
                180                 185                 190

Asn Met Thr Pro Arg Arg Pro Gly Pro Thr Arg Lys His Tyr Gln Pro
                195                 200                 205

Tyr Ala Pro Pro Arg Asp Phe Ala Ala Tyr Arg Ser
    210                 215                 220

<210> SEQ ID NO 194
<211> LENGTH: 321
<212> TYPE: DNA
<213> ORGANISM: Homo sapiens

<400> SEQUENCE: 194
attgaagtta tgtatcctcc tccttaccta gacaatgaga agagcaatgg aaccattatc      60
catgtgaaag ggaaacacct tgtccaagt cccctatttc ccggaccttc taagcccttt     120
tgggtgctgg tggtggttgg tggagtcctg gcttgctata gcttgctagt aacagtggcc    180
tttattattt tctgggtgag gagtaagagg agcaggctcc tgcacagtga ctacatgaac    240
atgactcccc gccgccccgg gcccacccgc aagcattacc agccctatgc cccaccacgc    300
gacttcgcag cctatcgctc c                                              321

<210> SEQ ID NO 195
<211> LENGTH: 163
<212> TYPE: PRT
<213> ORGANISM: Homo sapiens

<400> SEQUENCE: 195

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
                20                  25                  30

Tyr Leu Leu Asp Gly Ile Leu Phe Ile Tyr Gly Val Ile Leu Thr Ala
            35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Arg Arg Lys Asn Pro Gln Glu Gly Leu Tyr Asn Glu
                100                 105                 110

Leu Gln Lys Asp Lys Met Ala Glu Ala Tyr Ser Glu Ile Gly Met Lys
            115                 120                 125

Gly Glu Arg Arg Arg Gly Lys Gly His Asp Gly Leu Tyr Gln Gly Leu
    130                 135                 140

Ser Thr Ala Thr Lys Asp Thr Tyr Asp Ala Leu His Met Gln Ala Leu
145                 150                 155                 160

Pro Pro Arg
```

<210> SEQ ID NO 196
<211> LENGTH: 339
<212> TYPE: DNA
<213> ORGANISM: Homo sapiens

<400> SEQUENCE: 196

```
agagtgaagt tcagcaggag cgcagacgcc cccgcgtacc agcagggcca gaaccagctc      60
tataacgagc tcaatctagg acgaagagag gagtacgatg ttttggacaa gagacgtggc     120
cgggaccctg adatgggggg aaagccgaga aggaagaacc ctcaggaagg cctgtacaat     180
gaactgcaga agataagat ggcggaggcc tacagtgaga ttgggatgaa aggcgagcgc      240 cggagggca aggggcacga tggcctttac cagggtctca gtacagccac caaggacacc     300
tacgacgccc ttcacatgca ggccctgccc cctcgctaa                            339
```

<210> SEQ ID NO 197
<211> LENGTH: 255
<212> TYPE: PRT
<213> ORGANISM: Homo sapiens

<400> SEQUENCE: 197

```
Met Gly Asn Ser Cys Tyr Asn Ile Val Ala Thr Leu Leu Val Leu
1               5                   10                  15

Asn Phe Glu Arg Thr Arg Ser Leu Gln Asp Pro Cys Ser Asn Cys
            20                  25                  30

Pro Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
50                  55                  60

Cys Arg Gln Cys Lys Gly Val Phe Arg Thr Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255
```

<210> SEQ ID NO 198
<211> LENGTH: 277
<212> TYPE: PRT

<213> ORGANISM: Homo sapiens

<400> SEQUENCE: 198

```
Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
        35                  40                  45

Gly Asn Gly Met Val Ser Arg Cys Ser Arg Ser Gln Asn Thr Val Cys
    50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
    130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205

Val Pro Gly Gly Arg Ala Val Ala Ala Ile Leu Gly Leu Gly Leu Val
    210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
            275
```

<210> SEQ ID NO 199
<211> LENGTH: 199
<212> TYPE: PRT
<213> ORGANISM: Homo sapiens

<400> SEQUENCE: 199

```
Met Lys Ser Gly Leu Trp Tyr Phe Phe Leu Phe Cys Leu Arg Ile Lys
1               5                   10                  15

Val Leu Thr Gly Glu Ile Asn Gly Ser Ala Asn Tyr Glu Met Phe Ile
            20                  25                  30

Phe His Asn Gly Gly Val Gln Ile Leu Cys Lys Tyr Pro Asp Ile Val
        35                  40                  45

Gln Gln Phe Lys Met Gln Leu Leu Lys Gly Gly Gln Ile Leu Cys Asp
    50                  55                  60

Leu Thr Lys Thr Lys Gly Ser Gly Asn Thr Val Ser Ile Lys Ser Leu
```

```
                65                  70                  75                  80
Lys Phe Cys His Ser Gln Leu Ser Asn Asn Ser Val Ser Phe Phe Leu
                85                  90                  95

Tyr Asn Leu Asp His Ser His Ala Asn Tyr Tyr Phe Cys Asn Leu Ser
                100                 105                 110

Ile Phe Asp Pro Pro Phe Lys Val Thr Leu Thr Gly Gly Tyr Leu
                115                 120                 125

His Ile Tyr Glu Ser Gln Leu Cys Cys Gln Leu Lys Phe Trp Leu Pro
        130                 135                 140

Ile Gly Cys Ala Ala Phe Val Val Cys Ile Leu Gly Cys Ile Leu
145                 150                 155                 160

Ile Cys Trp Leu Thr Lys Lys Lys Tyr Ser Ser Val His Asp Pro
                165                 170                 175

Asn Gly Glu Tyr Met Phe Met Arg Ala Val Asn Thr Ala Lys Lys Ser
                180                 185                 190

Arg Leu Thr Asp Val Thr Leu
        195
```

<210> SEQ ID NO 200
<211> LENGTH: 223
<212> TYPE: PRT
<213> ORGANISM: Homo sapiens

<400> SEQUENCE: 200

```
Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
                20                  25                  30

Val Phe Cys Lys Ala Met His Val Ala Gln Pro Ala Val Val Leu Ala
                35                  40                  45

Ser Ser Arg Gly Ile Ala Ser Phe Val Cys Glu Tyr Ala Ser Pro Gly
            50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
                100                 105                 110

Asn Leu Thr Ile Gln Gly Leu Arg Ala Met Asp Thr Gly Leu Tyr Ile
                115                 120                 125

Cys Lys Val Glu Leu Met Tyr Pro Pro Pro Tyr Tyr Leu Gly Ile Gly
        130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
                180                 185                 190

Arg Ser Pro Leu Thr Thr Gly Val Tyr Val Lys Met Pro Pro Thr Glu
                195                 200                 205

Pro Glu Cys Glu Lys Gln Phe Gln Pro Tyr Phe Ile Pro Ile Asn
        210                 215                 220
```

<210> SEQ ID NO 201
<211> LENGTH: 288

```
<212> TYPE: PRT
<213> ORGANISM: Homo sapiens

<400> SEQUENCE: 201

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 202
<211> LENGTH: 525
<212> TYPE: PRT
<213> ORGANISM: Homo sapiens

<400> SEQUENCE: 202

Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
            20                  25                  30

Trp Ala Gln Glu Gly Ala Pro Ala Gln Leu Pro Cys Ser Pro Thr Ile
        35                  40                  45

Pro Leu Gln Asp Leu Ser Leu Leu Arg Arg Ala Gly Val Thr Trp Gln
    50                  55                  60
```

His Gln Pro Asp Ser Gly Pro Pro Ala Ala Ala Pro Gly His Pro Leu
 65                  70                  75                  80

Ala Pro Gly Pro His Pro Ala Ala Pro Ser Ser Trp Gly Pro Arg Pro
                 85                  90                  95

Arg Arg Tyr Thr Val Leu Ser Val Gly Pro Gly Leu Arg Ser Gly
            100                 105                 110

Arg Leu Pro Leu Gln Pro Arg Val Gln Leu Asp Glu Arg Gly Arg Gln
            115                 120                 125

Arg Gly Asp Phe Ser Leu Trp Leu Arg Pro Ala Arg Ala Asp Ala
            130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
            195                 200                 205

Gly Arg Val Pro Val Arg Glu Ser Pro His His Leu Ala Glu Ser
210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
            260                 265                 270

Gly Ala Gly Ser Arg Val Gly Leu Pro Cys Arg Leu Pro Ala Gly Val
            275                 280                 285

Gly Thr Arg Ser Phe Leu Thr Ala Lys Trp Thr Pro Pro Gly Gly Gly
            290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
            355                 360                 365

Cys Glu Val Thr Pro Val Ser Gly Gln Glu Arg Phe Val Trp Ser Ser
            370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
            420                 425                 430

Pro Gly Ala Gln Arg Ser Gly Arg Ala Pro Gly Ala Leu Pro Ala Gly
            435                 440                 445

His Leu Leu Leu Phe Leu Ile Leu Gly Val Leu Ser Leu Leu Leu Leu
            450                 455                 460

Val Thr Gly Ala Phe Gly Phe His Leu Trp Arg Arg Gln Trp Arg Pro
465                 470                 475                 480

Arg Arg Phe Ser Ala Leu Glu Gln Gly Ile His Pro Pro Gln Ala Gln

```
                    485                 490                 495
Ser Lys Ile Glu Glu Leu Glu Gln Glu Pro Glu Pro Glu Pro
                500                 505                 510

Glu Pro Glu Pro Glu Pro Glu Pro Glu Gln Leu
            515                 520                 525

<210> SEQ ID NO 203
<211> LENGTH: 370
<212> TYPE: PRT
<213> ORGANISM: Homo sapiens

<400> SEQUENCE: 203

Met Leu Gly Gln Val Val Thr Leu Ile Leu Leu Leu Leu Lys Val
1               5                   10                  15

Tyr Gln Gly Lys Gly Cys Gln Gly Ser Ala Asp His Val Val Ser Ile
                20                  25                  30

Ser Gly Val Pro Leu Gln Leu Gln Pro Asn Ser Ile Gln Thr Lys Val
                35                  40                  45

Asp Ser Ile Ala Trp Lys Lys Leu Leu Pro Ser Gln Asn Gly Phe His
        50                  55                  60

His Ile Leu Lys Trp Glu Asn Gly Ser Leu Pro Ser Asn Thr Ser Asn
65                  70                  75                  80

Asp Arg Phe Ser Phe Ile Val Lys Asn Leu Ser Leu Leu Ile Lys Ala
                85                  90                  95

Ala Gln Gln Gln Asp Ser Gly Leu Tyr Cys Leu Glu Val Thr Ser Ile
                100                 105                 110

Ser Gly Lys Val Gln Thr Ala Thr Phe Gln Val Phe Val Phe Glu Ser
                115                 120                 125

Leu Leu Pro Asp Lys Val Glu Lys Pro Arg Leu Gln Gly Gln Gly Lys
            130                 135                 140

Ile Leu Asp Arg Gly Arg Cys Gln Val Ala Leu Ser Cys Leu Val Ser
145                 150                 155                 160

Arg Asp Gly Asn Val Ser Tyr Ala Trp Tyr Arg Gly Ser Lys Leu Ile
                165                 170                 175

Gln Thr Ala Gly Asn Leu Thr Tyr Leu Asp Glu Glu Val Asp Ile Asn
                180                 185                 190

Gly Thr His Thr Tyr Thr Cys Asn Val Ser Asn Pro Val Ser Trp Glu
                195                 200                 205

Ser His Thr Leu Asn Leu Thr Gln Asp Cys Gln Asn Ala His Gln Glu
            210                 215                 220

Phe Arg Phe Trp Pro Phe Leu Val Ile Ile Val Ile Leu Ser Ala Leu
225                 230                 235                 240

Phe Leu Gly Thr Leu Ala Cys Phe Cys Val Trp Arg Arg Lys Arg Lys
                245                 250                 255

Glu Lys Gln Ser Glu Thr Ser Pro Lys Glu Phe Leu Thr Ile Tyr Glu
                260                 265                 270

Asp Val Lys Asp Leu Lys Thr Arg Arg Asn His Glu Gln Glu Gln Thr
            275                 280                 285

Phe Pro Gly Gly Gly Ser Thr Ile Tyr Ser Met Ile Gln Ser Gln Ser
                290                 295                 300

Ser Ala Pro Thr Ser Gln Glu Pro Ala Tyr Thr Leu Tyr Ser Leu Ile
305                 310                 315                 320

Gln Pro Ser Arg Lys Ser Gly Ser Arg Lys Arg Asn His Ser Pro Ser
                325                 330                 335
```

```
Phe Asn Ser Thr Ile Tyr Glu Val Ile Gly Lys Ser Gln Pro Lys Ala
                340                 345                 350

Gln Asn Pro Ala Arg Leu Ser Arg Lys Glu Leu Glu Asn Phe Asp Val
            355                 360                 365

Tyr Ser
    370

<210> SEQ ID NO 204
<211> LENGTH: 289
<212> TYPE: PRT
<213> ORGANISM: Homo sapiens

<400> SEQUENCE: 204

Met Lys Thr Leu Pro Ala Met Leu Gly Thr Gly Lys Leu Phe Trp Val
1               5                   10                  15

Phe Phe Leu Ile Pro Tyr Leu Asp Ile Trp Asn Ile His Gly Lys Glu
                20                  25                  30

Ser Cys Asp Val Gln Leu Tyr Ile Lys Arg Gln Ser Glu His Ser Ile
            35                  40                  45

Leu Ala Gly Asp Pro Phe Glu Leu Glu Cys Pro Val Lys Tyr Cys Ala
        50                  55                  60

Asn Arg Pro His Val Thr Trp Cys Lys Leu Asn Gly Thr Thr Cys Val
65                  70                  75                  80

Lys Leu Glu Asp Arg Gln Thr Ser Trp Lys Glu Glu Lys Asn Ile Ser
                85                  90                  95

Phe Phe Ile Leu His Phe Glu Pro Val Leu Pro Asn Asp Asn Gly Ser
                100                 105                 110

Tyr Arg Cys Ser Ala Asn Phe Gln Ser Asn Leu Ile Glu Ser His Ser
            115                 120                 125

Thr Thr Leu Tyr Val Thr Asp Val Lys Ser Ala Ser Glu Arg Pro Ser
        130                 135                 140

Lys Asp Glu Met Ala Ser Arg Pro Trp Leu Leu Tyr Arg Leu Leu Pro
145                 150                 155                 160

Leu Gly Gly Leu Pro Leu Leu Ile Thr Thr Cys Phe Cys Leu Phe Cys
                165                 170                 175

Cys Leu Arg Arg His Gln Gly Lys Gln Asn Glu Leu Ser Asp Thr Ala
            180                 185                 190

Gly Arg Glu Ile Asn Leu Val Asp Ala His Leu Lys Ser Glu Gln Thr
        195                 200                 205

Glu Ala Ser Thr Arg Gln Asn Ser Gln Val Leu Leu Ser Glu Thr Gly
    210                 215                 220

Ile Tyr Asp Asn Asp Pro Asp Leu Cys Phe Arg Met Gln Glu Gly Ser
225                 230                 235                 240

Glu Val Tyr Ser Asn Pro Cys Leu Glu Glu Asn Lys Pro Gly Ile Val
                245                 250                 255

Tyr Ala Ser Leu Asn His Ser Val Ile Gly Pro Asn Ser Arg Leu Ala
            260                 265                 270

Arg Asn Val Lys Glu Ala Pro Thr Glu Tyr Ala Ser Ile Cys Val Arg
        275                 280                 285

Ser

<210> SEQ ID NO 205
<211> LENGTH: 20
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 205

Met Glu Thr Asp Thr Leu Leu Leu Trp Val Leu Leu Leu Trp Val Pro
1               5                   10                  15

Gly Ser Thr Gly
            20

<210> SEQ ID NO 206
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
atggaaaccg acaccctgct gctgtgggtg ctgctgctgt gggtgccagg atccacagga    60

<210> SEQ ID NO 207
<211> LENGTH: 1398
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 207
caatctgccc tgactcagcc tgcctccgtg tctgcgtctc ctggacagtc gatcgccatc      60
tcctgcactg gaaccagcag tgacgttggt tggtatcaac agcacccagg caaagccccc    120
aaactcatga tttatgagga cagtaagcgg ccctcagggg tttctaatcg cttctctggc    180
tccaagtctg gcaacacggc ctccctgacc atctctgggc tccaggctga ggacgaggct    240
gattattact gcagctcaaa tacaagaagc agcactttgg tgttcggcgg agggaccaag    300
ctgaccgtcc taggttctag aggtggtggt ggtagcggcg gcggcggctc tggtggtggt    360
ggatccctcg agatggccga agtgcagctg gtgcagtctg gggctgagat gaagaagcct    420
ggggcctcac tgaagctctc ctgcaaggct tctggataca ccttcatcga ctactatgta    480
tactggatgc acaggcccc tggacaaggg cttgagtcca tgggatggat caaccctaac    540
agtggtggca caaactatgc acagaagttt cagggcaggg tcaccatgac cagggacacg    600
tccatcagca cagcctacat ggagctgagc aggctgagat ctgacgacac cgccatgtat    660
tactgtgcgc gctcccagcg tgacggttac atggattact ggggtcaagg tactctggtg    720
accgtctcct cagcggccgc aattgaagtt atgtatcctc ctccttacct agacaatgag    780
aagagcaatg gaaccattat ccatgtgaaa gggaaacacc tttgtccaag tcccctattt    840
cccggacctt ctaagccctt tgggtgctg gtggtggttg gtggagtcct ggcttgctat    900
agcttgctag taacagtggc ctttattatt ttctgggtga ggagtaagag gagcaggctc    960
ctgcacagtg actacatgaa catgactccc cgccgccccg gcccacccg caagcattac   1020 cagccctatg ccccaccacg cgacttcgca gcctatcgct ccagagtgaa gttcagcagg   1080
agcgcagacg ccccgcgta ccagcagggc cagaaccagc tctataacga gctcaatcta   1140
ggacgaagag aggagtacga tgttttggac aagagacgtg gccgggaccc tgagatgggg   1200
ggaaagccga aaggaagaa ccctcaggaa ggcctgtaca atgaactgca gaaagataag   1260
atggcggagg cctacagtga gattggatg aaaggcgagc gccggagggg caaggggcac   1320

```
gatggccttt accagggtct cagtacagcc accaaggaca cctacgacgc ccttcacatg    1380
caggccctgc cccctcgc                                                   1398

<210> SEQ ID NO 208
<211> LENGTH: 1419
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 208
cagtctgtgc tgacgcagcc gccctcagtg tctggggccc cagggcagag ggtcaccatc     60
tcctgcactg ggagcagctc caacatcggg gcaggttttg atgtacactg gtaccagcag    120
cttccaggaa cagcccccaa actcctcatc tatggtaaca gcaatcggcc ctcaggggtc    180
cctgaccgat tctctggctc caagtctggc acctcagcct ccctggccat cactgggctc    240
caggctgagg atgaggctga ttattactgc cagtcctatg acagcagcct gagtggttat    300
gtcttcggaa ctgggaccaa ggtcaccgtc ctaggttcta gaggtggtgg tggtagcggc    360
ggcggcggct ctggtggtgg tggatccctc gagatggccc aggtccagct ggtacagtct    420
ggggctgagg tgaagaagcc tggggcctca gtgaaggtct cctgcaaggc ttctggatac    480
accttcaccg actactatat gcactgggtg cgacaggccc ctggacaacg gcttgagtgg    540
atgggatgga tcaaccctaa cagtggtggc acaaactatg cacagaagtt tcaggacagg    600
gtcaccgtga ccagggacac ctccagcaac acaggctaca tggagctgac caggctgaga    660
tctgacgaca cggccgtgta ttactgtgcg cgctctccgt actctggtgt tctggataaa    720
tggggtcaag gtactctggt gaccgtctcc tcagcggccg caattgaagt tatgtatcct    780
cctccttacc tagacaatga aagagcaatg gaaccatta tccatgtgaa agggaaacac    840 cttttgtccaa gtccctatt tcccggacct tctaagccct tttgggtgct ggtggtggtt    900
ggtggagtcc tggcttgcta tagcttgcta gtaacagtgg cctttattat tttctgggtg    960
aggagtaaga ggagcaggct cctgcacagt gactacatga acatgactcc ccgccgcccc   1020
gggcccaccc gcaagcatta ccagccctat gccccaccac gcgacttcgc agcctatcgc   1080
tccagagtga agttcagcag gagcgcagac gcccccgcgt accagcaggg ccagaaccag   1140
ctctataacg agctcaatct aggacgaaga gaggagtacg atgttttgga caagagacgt   1200
ggccgggacc ctgagatggg gggaaagccg agaaggaaga accctcagga aggcctgtac   1260
aatgaactgc agaaagataa gatggcgag gcctacagtg agattggat gaaaggcgag    1320 cgccggaggg gcaaggggca cgatggcctt taccagggtc tcagtacagc caccaaggac   1380
acctacgacg cccttcacat gcaggccctg cccctcgc                          1419

<210> SEQ ID NO 209
<211> LENGTH: 1410
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 209
tcctatgagc tgactcagcc accctcagcg tctgggaccc ccgggcagag ggtcaccatg     60
tcttgttctg gaaccagctc caacatcgga agtcactcta taaactggta ccagcagctc    120
ccaggaacgg cccccaaact cctcatctat actaataatc agcggccctc agggtccct    180
```

```
gaccgattct ctggctccaa gtctggcacc tcagcctccc tggccatcag tggcctccag    240
tctgaggatg aggctgatta ttactgtgca gcatgggatg gcagcctgaa tggtctggta    300
ttcggcggag ggaccaagct gaccgtccta ggttctagag gtggtggtgg tagcggcggc    360
ggcggctctg gtggtggtgg atccctcgag atggccgagg tgcagctggt gcagtctgga    420
gcagaggtga aaaagcccgg ggagtctctg aagatctcct gtaagggttc tggatacagc    480
tttaccagct actggatcgg ctgggtgcgc cagatgcccg ggaaaggcct ggagtggatg    540
gggatcatct atcctggtga ctctgatacc agatacagcc cgtccttcca aggccacgtc    600
accatctcag ctgacaagtc catcagcact gcctacctgc agtggagcag cctgaaggcc    660
tcggacaccg ccatgtatta ctgtgcgcgc tactctggtt ctttcgataa ctggggtcaa    720
ggtactctgg tgaccgtctc ctcagcggcc gcaattgaag ttatgtatcc tcctccttac    780
ctagacaatg agaagagcaa tggaaccatt atccatgtga agggaaaaca cctttgtcca    840
agtcccctat ttcccggacc ttctaagccc ttttgggtgc tggtggtggt tgtggagtc    900 ctggcttgct atagcttgct agtaacagtg gcctttatta ttttctgggt gaggagtaag    960
aggagcaggc tcctgcacag tgactacatg aacatgactc cccgccgccc cgggcccacc    1020
cgcaagcatt accagcccta tgccccacca cgcgacttcg cagcctatcg ctccagagtg    1080
aagttcagca ggagcgcaga cgcccccgcg taccagcagg gccagaacca gctctataac    1140
gagctcaatc taggacgaag agaggagtac gatgttttgg acaagagacg tggccgggac    1200
cctgagatgg ggggaaagcc gagaaggaag aaccctcagg aaggcctgta caatgaactg    1260
cagaaagata agatggcgga ggcctacagt gagattggga tgaaaggcga gcgccggagg    1320
ggcaaggggc acgatggcct ttaccagggt ctcagtacag ccaccaagga cacctacgac    1380
gcccttcaca tgcaggccct gccccctcgc                                    1410
```

<210> SEQ ID NO 210
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Gly Gly Gly Gly Ser Gly Gly Gly Gly Ser Gly Gly Gly Gly Ser
1               5                   10                  15

<210> SEQ ID NO 211
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
ggtggaggtg gatcaggtgg aggtggatct ggtggaggtg gatct                    45

<210> SEQ ID NO 212
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 212

Gly Gly Gly Gly Ser
1               5

<210> SEQ ID NO 213
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Ser Gly Gly Ser Gly Gly Ser
1               5

<210> SEQ ID NO 214
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Gly Gly Gly Gly Ser Gly Gly Gly Ser
1               5

<210> SEQ ID NO 215
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Gly Gly Gly Gly Ser Gly Gly Gly Gly Ser
1               5                   10

<210> SEQ ID NO 216
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Gly Gly Gly Gly Ser Gly Gly Gly Gly Ser Gly Gly Gly Gly Gly Gly
1               5                   10                  15

Gly Ser

<210> SEQ ID NO 217
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Gly Gly Gly Gly Ser Gly Gly Gly Gly Ser Gly Gly Gly Gly Ser Gly
1               5                   10                  15

Gly Gly Gly Ser
            20
```

<210> SEQ ID NO 218
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 219
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 219

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 220
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 220

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser
        35

<210> SEQ ID NO 221
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Glu Pro Lys Ser Cys Asp Lys Thr His Thr Cys Pro Pro Cys Pro
1               5                   10                  15

<210> SEQ ID NO 222
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

```
Gly Gly Gly Gly Ser Gly Gly Gly Ser Glu Pro Lys Ser Cys Asp Lys
1               5                   10                  15

Thr His Thr Cys Pro Pro Cys Pro
            20
```

<210> SEQ ID NO 223
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 223

```
Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
                20                  25                  30

Glu Pro Lys Ser Cys Asp Thr Pro Pro Cys Pro Arg Cys Pro Glu
            35                  40                  45

Pro Lys Ser Cys Asp Thr Pro Pro Cys Pro Arg Cys Pro
        50                  55                  60
```

<210> SEQ ID NO 224
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

```
Gly Ser Gly Ser Gly Ser
1               5
```

<210> SEQ ID NO 225
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

```
Ala Ala Ala
1
```

<210> SEQ ID NO 226
<211> LENGTH: 235
<212> TYPE: PRT
<213> ORGANISM: Homo sapiens

<400> SEQUENCE: 226

```
Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
                20                  25                  30

Trp Asn Leu Gly Glu Thr Val Glu Leu Lys Cys Gln Val Leu Leu Ser
            35                  40                  45

Asn Pro Thr Ser Gly Cys Ser Trp Leu Phe Gln Pro Arg Gly Ala Ala
        50                  55                  60

Ala Ser Pro Thr Phe Leu Leu Tyr Leu Ser Gln Asn Lys Pro Lys Ala
```

```
                65                  70                  75                  80
Ala Glu Gly Leu Asp Thr Gln Arg Phe Ser Gly Lys Arg Leu Gly Asp
                    85                  90                  95

Thr Phe Val Leu Thr Leu Ser Asp Phe Arg Arg Glu Asn Glu Gly Cys
                100                 105                 110

Tyr Phe Cys Ser Ala Leu Ser Asn Ser Ile Met Tyr Phe Ser His Phe
                115                 120                 125

Val Pro Val Phe Leu Pro Ala Lys Pro Thr Thr Thr Pro Ala Pro Arg
            130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
                180                 185                 190

Cys Gly Val Leu Leu Leu Ser Leu Val Ile Thr Leu Tyr Cys Asn His
                195                 200                 205

Arg Asn Arg Arg Arg Val Cys Lys Cys Pro Arg Pro Val Val Lys Ser
        210                 215                 220

Gly Asp Lys Pro Ser Leu Ser Ala Arg Tyr Val
225                 230                 235

<210> SEQ ID NO 227
<211> LENGTH: 213
<212> TYPE: DNA
<213> ORGANISM: Homo sapiens

<400> SEQUENCE: 227
cccaccacga cgccagcgcc gcgaccacca accccggcgc ccacgatcgc gtcgcagccc      60
ctgtccctgc gcccagaggc gtgccggcca gcggcggggg cgcagtgca cacgaggggg      120 ctggacttcg cctgtgatat ctacatctgg gcgcccctgg ccgggacttg tggggtcctt     180
ctcctgtcac tggttatcac cctttactgc aac                                  213

<210> SEQ ID NO 228
<211> LENGTH: 126
<212> TYPE: DNA
<213> ORGANISM: Homo sapiens

<400> SEQUENCE: 228
aaacggggca gaaagaagct cctgtatata ttcaaacaac catttatgag accagtacaa      60
actactcaag aggaagatgg ctgtagctgc cgatttccag aagaagaaga aggaggatgt     120
gaactg                                                                126

<210> SEQ ID NO 229
<211> LENGTH: 7671
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 229
ccttctctag gcgccccat atggccatat gagatcttat atggggcacc ccgcccctt       60 gtaaacttcc ctgaccctga catgacaaga gttactaaca gcccctctct ccaagctcac     120
ttacaggctc tctacttagt ccagcacgaa gtctggagac ctctggcggc agcctaccaa     180
```

```
gaacaactgg accgaccggt gccgccacca tggaaaccga caccctgctg ctgtgggtgc      240
tgctgctgtg ggtgccagga tccacaggac tgcctgtgct gactcagcca ccctcagcgt      300
ctgggacccc cgggcagagg gtcaccatct cttgttctgg acgcagttcc aacatcggga      360
gtaattctgt taactggtat cgacaactcc caggagcggc ccccaaactc ctcatctata      420
gtaataatca gcggccccca ggggtccctg tgcgattctc tggctccaag tctggcacct      480
cagcctccct ggccatcagt gggctccagt ctgaagatga ggccacttat tactgtgcaa      540
catgggatga caatctgaat gttcactatg tcttcggaac tgggaccaag gtcaccgtcc      600
taggttctag aggtggtggt ggtagcggcg gcggcggctc tggtggtggt ggatccctcg      660
agatggccca ggtgcagctg gtgcagtctg ggctgaggt gaagaagcct gggtcctcgg      720
tgaaggtctc ctgcaaggct tctggaggca ccttcagcag ctatgctatc agctgggtgc      780
gacaggcccc tggacaaggg cttgagtgga tgggaaggat catccctatc cttggtatag      840
caaactacgc acagaagttc cagggcagag tcacgattac cgcggacaaa tccacgagca      900
cagcctacat ggagctgagc agcctgagat ctgaggcaca ggccgtgtat tactgtgcgc      960
gcggtggtta ctactctcat gacatgtggt ctgaagattg gggtcaaggt actctggtga     1020
ccgtctcctc agcggccgca cccaccacga cgccagcgcc gcgaccacca ccccggcgc      1080 ccacgatcgc gtcgcagccc ctgtccctgc gcccagaggc gtgccggcca gcggcgggg      1140 gcgcagtgca cacgaggggg ctggacttcg cctgtgatat ctacatctgg gcgcccctgg     1200
ccgggacttg tgggtccctt ctcctgtcac tggttatcac cctttactgc aacaaacggg     1260
gcagaaagaa gctcctgtat atattcaaac aaccatttat gagaccagta caaactactc     1320
aagaggaaga tggctgtagc tgccgatttc agaagaagaa agaaggagga tgtgaactga     1380
gagtgaagtt cagcaggagc gcagagcccc ccgcgtacca gcagggccag aaccagctct     1440
ataacgagct caatctagga cgaagagagg agtacgatgt tttggacaag agacgtggcc     1500
gggaccctga gatgggggga aagccgagaa ggaagaaccc tcaggaaggc ctgtacaatg     1560
aactgcagaa agataagatg gcggaggcct acagtgagat tgggatgaaa ggcgagcgcc     1620
ggaggggcaa ggggcacgat ggcctttacc agggtctcag tacagccacc aaggacacct     1680
acgacgccct tcacatgcag gccctgcccc ctcgctaaca gccactcgag gatccggatt     1740
agtccaattt gttaaagaca ggatatcagt ggtccaggct ctagttttga ctcaacaata     1800
tcaccagctg aagcctatag agtacgagcc atagataaaa taaaagattt tatttagtct     1860
ccagaaaaag ggggaatga aagacccccac ctgtaggttt ggcaagctag cttaagtaac     1920 gccatttgc aaggcatgga aaatacata actgagaata gagaagttca gatcaaggtc      1980
aggaacagat ggaacagctg aatatgggcc aaacaggata tctgtggtaa gcagttcctg     2040
ccccggctca gggccaagaa cagatggaac agctgaatat gggccaaaca ggatatctgt     2100
ggtaagcagt tcctgcccg gctcaggggcc aagaacagat ggtccccaga tgcggtccag     2160
ccctcagcag tttctagaga accatcagat gtttccaggg tgcccaagg acctgaaatg      2220 accctgtgcc ttatttgaac taaccaatca gttcgcttct cgcttctgtt cgcgcgcttc     2280
tgctccccga gctcaataaa agagcccaca acccctcact cggggcgcca gtcctccgat     2340
tgactgagtc gcccgggtac ccgtgtatcc aataaaccct cttgcagttg catccgactt     2400
gtggtctcgc tgttccttgg gagggtctcc tctgagtgat tgactacccg tcagcggggg     2460
tctttcacac atgcagcatg tatcaaaatt aatttggttt ttttcttaa gtatttacat     2520 taaatggcca tagtacttaa agttacattg gcttccttga aataaacatg gagtattcag     2580
```

```
aatgtgtcat aaatatttct aattttaaga tagtatctcc attggctttc tactttttct    2640
tttatttttt tttgtcctct gtcttccatt tgttgttgtt gttgtttgtt tgtttgtttg    2700
ttggttggtt ggttaatttt tttttaaaga tcctacacta tagttcaagc tagactatta    2760
gctactctgt aacccagggt gaccttgaag tcatgggtag cctgctgttt tagccttccc    2820
acatctaaga ttacaggtat gagctatcat ttttggtata ttgattgatt gattgattga    2880
tgtgtgtgtg tgtgattgtg tttgtgtgtg tgactgtgaa aatgtgtgta tgggtgtgtg    2940
tgaatgtgtg tatgtatgtg tgtgtgtgag tgtgtgtgtg tgtgtgtgca tgtgtgtgtg    3000
tgtgactgtg tctatgtgta tgactgtgtg tgtgtgtgtg tgtgtgtgtg tgtgtgtgtg    3060
tgtgtgtgtg ttgtgaaaaa atattctatg gtagtgagag ccaacgctcc ggctcaggtg    3120
tcaggttggt ttttgagaca gagtctttca cttagcttgg aattcactgg ccgtcgtttt    3180
acaacgtcgt gactgggaaa accctggcgt tacccaactt aatcgccttg cagcacatcc    3240 cccttttcgcc agctggcgta atagcgaaga ggcccgcacc gatcgccctt cccaacagtt    3300
gcgcagcctg aatggcgaat ggcgcctgat gcggtatttt ctccttacgc atctgtgcgg    3360
tatttcacac cgcatatggt gcactctcag tacaatctgc tctgatgccg catagttaag    3420
ccagccccga cacccgccaa cacccgctga cgcgccctga cgggcttgtc tgctcccggc    3480
atccgcttac agacaagctg tgaccgtctc cgggagctgc atgtgtcaga ggttttcacc    3540
gtcatcaccg aaacgcgcga tgacgaaagg gcctcgtgat acgcctattt ttataggtta    3600
atgtcatgat aataatggtt tcttagacgt caggtggcac ttttcgggga aatgtgcgcg    3660
gaacccctat ttgtttattt ttctaaatac attcaaatat gtatccgctc atgagacaat    3720
aaccctgata aatgcttcaa taatattgaa aaaggaagag tatgagtatt caacatttcc    3780
gtgtcgccct tattcccttt tttgcggcat tttgccttcc tgttttgct  cacccagaaa    3840 cgctggtgaa agtaaaagat gctgaagatc agttgggtgc acgagtgggt tacatcgaac    3900
tggatctcaa cagcggtaag atccttgaga gttttcgccc cgaagaacgt tttccaatga    3960
tgagcacttt taaagttctg ctatgtggcg cggtattatc ccgtattgac gccgggcaag    4020
agcaactcgg tcgccgcata cactattctc agaatgactt ggttgagtac tcaccagtca    4080
cagaaaagca tcttacggat ggcatgacag taagagaatt atgcagtgct gccataacca    4140
tgagtgataa cactgcggcc aacttacttc tgacaacgat cggaggaccg aaggagctaa    4200 ccgcttttt  gcacaacatg ggggatcatg taactcgcct tgatcgttgg gaaccggagc    4260
tgaatgaagc cataccaaac gacgagcgtg acaccacgat gcctgtagca atggcaacaa    4320
cgttgcgcaa actattaact ggcgaactac ttactctagc ttcccggcaa caattaatag    4380
actggatgga ggcggataaa gttgcaggac cacttctgcg ctcggccctt ccggctggct    4440
ggtttattgc tgataaatct ggagccggtg agcgtgggtc tcgcggtatc attgcagcac    4500
tggggccaga tggtaagccc tcccgtatcg tagttatcta cacgacgggg agtcaggcaa    4560
ctatggatga acgaaataga cagatcgctg agataggtgc ctcactgatt aagcattggt    4620
aactgtcaga ccaagtttac tcatatatac tttagattga tttaaaactt cattttaat    4680 ttaaaggat  ctaggtgaag atcctttttg ataatctcat gaccaaaatc ccttaacgtg    4740
agttttcgtt ccactgagcg tcagaccccg tagaaaagat caaggatctc ttgagatc     4800 cttttttct  gcgcgtaatc tgctgcttgc aaacaaaaaa accaccgcta ccagcggtgg    4860
tttgtttgcc ggatcaagag ctaccaactc tttttccgaa ggtaactggc ttcagcagag    4920
```

| | |
|---|---|
| cgcagatacc aaatactgtc cttctagtgt agccgtagtt aggccaccac ttcaagaact | 4980 |
| ctgtagcacc gcctacatac ctcgctctgc taatcctgtt accagtggct gctgccagtg | 5040 |
| gcgataagtc gtgtcttacc gggttggact caagacgata gttaccggat aaggcgcagc | 5100 |
| ggtcgggctg aacgggggt tcgtgcacac agcccagctt ggagcgaacg acctacaccg | 5160 |
| aactgagata cctacagcgt gagcattgag aaagcgccac gcttcccgaa gggagaaagg | 5220 |
| cggacaggta tccggtaagc ggcagggtcg aacaggaga gcgcacgagg gagcttccag | 5280 |
| ggggaaacgc ctggtatctt tatagtcctg tcgggtttcg ccacctctga cttgagcgtc | 5340 |
| gattttgtg atgctcgtca gggggcgga gcctatggaa aaacgccagc aacgcggcct | 5400 |
| ttttacggtt cctggccttt tgctggcctt ttgctcacat gttctttcct gcgttatccc | 5460 |
| ctgattctgt ggataaccgt attaccgcct ttgagtgagc tgataccgct cgccgcagcc | 5520 |
| gaacgaccga gcgcagcgag tcagtgagcg aggaagcgga agagcgccca atacgcaaac | 5580 |
| cgcctctccc cgcgcgttgg ccgattcatt aatgcagctg gcacgacagg tttcccgact | 5640 |
| ggaaagcggg cagtgagcgc aacgcaatta atgtgagtta gctcactcat taggcacccc | 5700 |
| aggctttaca ctttatgctt ccggctcgta tgttgtgtgg aattgtgagc ggataacaat | 5760 |
| ttcacacagg aaacagctat gaccatgatt acgccaagct tgctcttag gagtttccta | 5820 |
| atacatccca aactcaaata tataaagcat ttgacttgtt ctatgcccta ggggcgggg | 5880 |
| ggaagctaag ccagcttttt ttaacattta aaatgttaat tccattttaa atgcacagat | 5940 |
| gtttttattt cataagggtt tcaatgtgca tgaatgctgc aatattcctg ttaccaaagc | 6000 |
| tagtataaat aaaaatagat aaacgtggaa attacttaga gtttctgtca ttaacgtttc | 6060 |
| cttcctcagt tgacaacata aatgcgctgc tgagcaagcc agtttgcatc tgtcaggatc | 6120 |
| aatttcccat tatgccagtc atattaatta ctagtcaatt agttgatttt tattttgac | 6180 |
| atatacatgt gaatgaaaga ccccacctgt aggtttggca agctagctta agtaacgcca | 6240 |
| ttttgcaagg catggaaaaa tacataactg agaatagaaa agttcagatc aaggtcagga | 6300 |
| acagatggaa cagctgaata tgggccaaac aggatatctg tggtaagcag ttcctgcccc | 6360 |
| ggctcagggc caagaacaga tggaacagct gaatatgggc caaacaggat atctgtggta | 6420 |
| agcagttcct gccccggctc agggccaaga acagatggtc cccagatgcg gtccagccct | 6480 |
| cagcagtttc tagagaacca tcagatgttt ccagggtgcc ccaaggacct gaaatgaccc | 6540 |
| tgtgccttat ttgaactaac caatcagttc gcttctcgct tctgttcgcg cgcttatgct | 6600 |
| ccccgagctc aataaaagag cccacaaccc ctcactcggg gcgccagtcc tccgattgac | 6660 |
| tgagtcgccc gggtacccgt gtatccaata aaccctcttg cagttgcatc cgacttgtgg | 6720 |
| tctcgctgtt ccttgggagg gtctcctctg agtgattgac tacccgtcag cggggggtctt | 6780 |
| tcatttgggg gctcgtccgg gatcgggaga ccccctgccca gggaccaccg acccaccacc | 6840 |
| gggaggtaag ctggccagca acttatctgt gtctgtccga ttgtctagtg tctatgactg | 6900 |
| atttatgcg cctgcgtcgg tactagttag ctaactagct ctgtatctgg cggacccgtg | 6960 |
| gtggaactga cgagttcgga acacccggcc gcaaccctgg gagacgtccc agggacttcg | 7020 |
| ggggccgttt tgtggcccg acctgagtcc taaaatcccg atcgtttagg actcttggt | 7080 |
| gcaccccct tagaggaggg atatgtggtt ctggtaggag acgagaacct aaaacagttc | 7140 |
| ccgcctccgt ctgaatttt gctttccggt tgggaccgaa gccgcgccgc gcgtcttgtc | 7200 |
| tgctgcagca tcgttctgtg ttgtctctgt ctgactgtgt ttctgtattt gtctgaaaat | 7260 |
| atgggcccgg gctagactgt taccactccc ttaagtttga ccttaggtca ctggaaagat | 7320 |

```
gtcgagcgga tcgctcacaa ccagtcggta gatgtcaaga agagacgttg ggttaccttc    7380
tgctctgcag aatggccaac ctttaacgtc ggatggccgc gagacggcac ctttaaccga    7440
gacctcatca cccaggttaa gatcaaggtc tttcacctg gcccgcatgg acacccagac    7500
caggtcccct acatcgtgac ctgggaagcc ttggcttttg accccctcc ctgggtcaag    7560 cccttgtac accctaagcc tccgcctcct cttcctccat ccgccccgtc tctcccctt    7620 gaacctcctc gttcgacccc gcctcgatcc tccctttatc cagccctcac t            7671

<210> SEQ ID NO 230
<211> LENGTH: 7653
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 230
ggccctctag gcgcccccat atggccatat gagatcttat atggggcacc cccgccccctt    60 gtaaacttcc ctgaccctga catgacaaga gttactaaca gcccctctct ccaagctcac    120
ttacaggctc tctacttagt ccagcacgaa gtctggagac ctctggcggc agcctaccaa    180
gaacaactgg accgaccggt gccgccacca tggaaaccga caccctgctg ctgtgggtgc    240
tgctgctgtg ggtgccagga tccacaggat cctatgagct gactcagcca ccctcagcgt    300
ctgggacccc cgggcagagg gtcaccatgt cttgttctgg aaccagctcc aacatcggaa    360
gtcactctgt aaactggtac cagcagctcc caggaacggc ccccaaactc ctcatctata    420
ctaataatca gcggccctca ggggtccctg accgattctc tggctccaag tctggcacct    480
cagcctccct ggccatcagt ggcctccagt ctgaggatga ggctgattat tactgtgcag    540
catgggatgg cagcctgaat ggtctggtat cggcggagg gaccaagctg accgtcctag    600
gttctagagg tggtggtggt agcggcggcg cggctctgg tggtggtgga tccctcgaga    660
tggccgaggt gcagctggtg cagtctggag cagaggtgaa aaagcccggg gagtctctga    720 agatcctg taagggttct ggatacagct ttaccagcta ctggatcggc tgggtgcgcc    780
agatgcccgg gaaaggcctg gagtggatgg ggatcatcta tcctggtgac tctgatacca    840
gatacagccc gtccttccaa ggccacgtca ccatctcagc tgacaagtcc atcagcactg    900
cctacctgca gtggagcagc ctgaaggcct cggacaccgc catgtattac tgtgcgcgct    960
actctggttc tttcgataac tggggtcaag gtactctggt gaccgtctcc tcagcggccg    1020
cacccaccac gacgccagcg ccgcgaccac caacccccggc gcccacgatc gcgtcgcagc    1080
ccctgtccct gcgcccagag gcgtgccggc cagcggcggg gggcgcagtg cacacgaggg    1140
ggctggactt cgcctgtgat atctacatct gggcgcccct ggccgggact tgtgggtcc    1200 ttctcctgtc actggttatc ccctttact gcaacaaacg gggcagaaag aagctcctgt    1260
atatattcaa acaaccattt atgagaccag tacaaactac tcaagaggaa gatgctgta    1320 gctgccgatt ccagaagaa gaagaaggag gatgtgaact gagagtgaag ttcagcagga    1380
gcgcagagcc ccccgcgtac cagcagggcc agaaccagct ctataacgag ctcaatctag    1440
gacgaagaga ggagtacgat gttttggaca agagacgtgg ccgggaccct gagatgggggg    1500 gaaagccgag aaggaagaac cctcaggaag gcctgtacaa tgaactgcag aaagataaga    1560
tggcggaggc ctcagtgag attgggatga aggcgagcg ccgaggggc aaggggcacg    1620 atggccttta ccagggtctc agtacagcca ccaaggacac ctacgacgcc ttcacatgc    1680
```

```
aggccctgcc ccctcgctaa cagccactcg aggatccgga ttagtccaat ttgttaaaga    1740
caggatatca gtggtccagg ctctagtttt gactcaacaa tatcaccagc tgaagcctat    1800
agagtacgag ccatagataa aataaaagat tttatttagt ctccagaaaa aggggggaat    1860
gaaagacccc acctgtaggt ttggcaagct agcttaagta acgccatttt gcaaggcatg    1920
gaaaaataca taactgagaa tagagaagtt cagatcaagg tcaggaacag atggaacagc    1980
tgaatatggg ccaaacagga tatctgtggt aagcagttcc tgccccggct cagggccaag    2040
aacagatgga acagctgaat atgggccaaa caggatatct gtggtaagca gttcctgccc    2100
cggctcaggg ccaagaacag atggtcccca gatgcggtcc agccctcagc agtttctaga    2160
gaaccatcag atgtttccag ggtgccccaa ggacctgaaa tgaccctgtg ccttatttga    2220
actaaccaat cagttcgctt ctcgcttctg ttcgcgcgct tctgctcccc gagctcaata    2280
aaagagccca aacccctca ctcggggcgc cagtcctccg attgactgag tcgcccgggt    2340
acccgtgtat ccaataaacc ctcttgcagt tgcatccgac ttgtggtctc gctgttcctt    2400
gggagggtct cctctgagtg attgactacc cgtcagcggg ggtctttcac acatgcagca    2460
tgtatcaaaa ttaatttggt tttttttctt aagtatttac attaaatggc catagtactt    2520
aaagttacat tggcttcctt gaaataaaca tggagtattc agaatgtgtc ataaatattt    2580
ctaattttaa gatagtatct ccattggctt tctacttttt cttttatttt ttttgtcct    2640 ctgtcttcca tttgttgttg ttgttgtttg tttgtttgtt tgttggttgg ttggttaatt    2700 ttttttaaa gatcctacac tatagttcaa gctagactat tagctactct gtaacccagg    2760
gtgaccttga agtcatgggt agcctgctgt tttagccttc ccacatctaa gattacaggt    2820
atgagctatc atttttggta tattgattga ttgattgatt gatgtgtgtg tgtgtgattg    2880
tgtttgtgtg tgtgactgtg aaaatgtgtg tatgggtgtg tgtgaatgtg tgtatgtatg    2940
tgtgtgtgtg agtgtgtgtg tgtgtgtgtg catgtgtgtg tgtgtgactg tgtctatgtg    3000
tatgactgtg tgtgtgtgtg tgtgtgtgtg tgtgtgtgtg tgtgtgtgtg tgttgtgaaa    3060
aaatattcta tggtagtgag agccaacgct ccggctcagg tgtcaggttg gttttttgaga    3120 cagagtcttt cacttagctt ggaattcact ggccgtcgtt ttacaacgtc gtgactggga    3180
aaaccctggc gttacccaac ttaatcgcct tgcagcacat ccccctttcg ccagctggcg    3240
taatagcgaa gaggcccgca ccgatcgccc ttcccaacag ttgcgcagcc tgaatggcga    3300
atggcgcctg atgcggtatt ttctccttac gcatctgtgc ggtatttcac accgcatatg    3360
gtgcactctc agtacaatct gctctgatgc cgcatagtta agccagcccc gacacccgcc    3420
aacacccgct gacgcgccct gacgggcttg tctgctcccg gcatccgctt acagacaagc    3480
tgtgaccgtc tccgggagct gcatgtgtca gaggttttca ccgtcatcac cgaaacgcgc    3540
gatgacgaaa gggcctcgtg atacgcctat ttttataggt taatgtcatg ataataatgg    3600
tttcttagac gtcaggtggc acttttcggg gaaatgtgcg cggaacccct atttgtttat    3660
ttttctaaat acattcaaat atgtatccgc tcatgagaca ataaccctga taaatgcttc    3720
aataatattg aaaaggaag agtatgagta ttcaacattt ccgtgtcgcc cttattccct    3780
tttttgcggc attttgcctt cctgtttttg ctcacccaga aacgctggtg aaagtaaaag    3840
atgctgaaga tcagttgggt gcacgagtgg gttacatcga actggatctc aacagcggta    3900
agatccttga gagttttcgc cccgaagaac gttttccaat gatgagcact tttaaagttc    3960
tgctatgtgg cgcggtatta tcccgtattg acgccgggca agagcaactc ggtcgccgca    4020
```

```
tacactattc tcagaatgac ttggttgagt actcaccagt cacagaaaag catcttacgg    4080
atggcatgac agtaagagaa ttatgcagtg ctgccataac catgagtgat aacactgcgg    4140
ccaacttact tctgacaacg atcggaggac cgaaggagct aaccgctttt ttgcacaaca    4200
tggggatca tgtaactcgc cttgatcgtt gggaaccgga gctgaatgaa gccataccaa    4260
acgacgagcg tgacaccacg atgcctgtag caatggcaac aacgttgcgc aaactattaa    4320
ctggcgaact acttactcta gcttcccggc aacaattaat agactggatg gaggcggata    4380
aagttgcagg accacttctg cgctcggccc ttccggctgg ctggtttatt gctgataaat    4440
ctggagccgg tgagcgtggg tctcgcggta tcattgcagc actggggcca gatggtaagc    4500
cctcccgtat cgtagttatc tacacgacgg ggagtcaggc aactatggat gaacgaaata    4560
gacagatcgc tgagataggt gcctcactga ttaagcattg gtaactgtca gaccaagttt    4620
actcatatat actttagatt gatttaaaac ttcatttta atttaaaagg atctaggtga    4680
agatccttt tgataatctc atgaccaaaa tcccttaacg tgagttttcg ttccactgag    4740
cgtcagaccc cgtagaaaag atcaaaggat cttcttgaga tccttttttt ctgcgcgtaa    4800
tctgctgctt gcaaacaaaa aaccaccgc taccagcggt ggtttgtttg ccggatcaag    4860
agctaccaac tctttttccg aaggtaactg gcttcagcag agcgcagata ccaaatactg    4920
tccttctagt gtagccgtag ttaggccacc acttcaagaa ctctgtagca ccgcctacat    4980
acctcgctct gctaatcctg ttaccagtgg ctgctgccag tggcgataag tcgtgtctta    5040
ccgggttgga ctcaagacga tagttaccgg ataaggcgca gcggtcgggc tgaacggggg    5100
gttcgtgcac acagcccagc ttggagcgaa cgacctacac cgaactgaga tacctacagc    5160
gtgagcattg agaaagcgcc acgcttcccg aagggagaaa ggcggacagg tatccggtaa    5220
gcggcagggt cggaacagga gagcgcacga gggagcttcc agggggaaac gcctggtatc    5280
tttatagtcc tgtcgggttt cgccacctct gacttgagcg tcgatttttg tgatgctcgt    5340
caggggggcg gagcctatgg aaaaacgcca gcaacgcggc cttttacgg ttcctggcct    5400
tttgctggcc ttttgctcac atgttctttc ctgcgttatc ccctgattct gtggataacc    5460
gtattaccgc ctttgagtga gctgataccg ctcgccgcag ccgaacgacc gagcgcagcg    5520
agtcagtgag cgaggaagcg gaagagcgcc caatacgcaa accgcctctc cccgcgcgtt    5580
ggccgattca ttaatgcagc tggcacgaca ggtttcccga ctggaaagcg ggcagtgagc    5640
gcaacgcaat taatgtgagt tagctcactc attaggcacc ccaggcttta cactttatgc    5700
ttccggctcg tatgttgtgt ggaattgtga gcggataaca atttcacaca ggaaacagct    5760
atgaccatga ttacgccaag ctttgctctt aggagtttcc taatacatcc caaactcaaa    5820
tatataaagc atttgacttg ttctatgccc taggggcgg ggggaagcta agccagcttt    5880
ttttaacatt taaaatgtta attccatttt aaatgcacag atgtttttat ttcataaggg    5940
tttcaatgtg catgaatgct gcaatattcc tgttaccaaa gctagtataa ataaaaatag    6000
ataaacgtgg aaattactta gagtttctgt cattaacgtt tccttcctca gttgacaaca    6060
taaatgcgct gctgagcaag ccagtttgca tctgtcagga tcaatttccc attatgccag    6120
tcatattaat tactagtcaa ttagttgatt tttattttg acatatacat gtgaatgaaa    6180
gaccccacct gtaggtttgg caagctagct taagtaacgc cattttgcaa ggcatggaaa    6240
aatacataac tgagaataga aaagttcaga tcaaggtcag gaacagatgg aacagctgaa    6300
tatgggccaa acaggatatc tgtggtaagc agttcctgcc ccggctcagg gccaagaaca    6360
gatggaacag ctgaatatgg gccaaacagg atatctgtgg taagcagttc ctgccccggc    6420
```

```
tcagggccaa gaacagatgg tccccagatg cggtccagcc ctcagcagtt tctagagaac    6480
catcagatgt ttccagggtg ccccaaggac ctgaaatgac cctgtgcctt atttgaacta    6540
accaatcagt tcgcttctcg cttctgttcg cgcgcttatg ctccccgagc tcaataaaag    6600
agcccacaac ccctcactcg gggcgccagt cctccgattg actgagtcgc ccgggtaccc    6660
gtgtatccaa taaaccctct tgcagttgca tccgacttgt ggtctcgctg ttccttggga    6720
gggtctcctc tgagtgattg actacccgtc agcggggtc tttcatttgg gggctcgtcc     6780
gggatcggga gacccctgcc cagggaccac cgacccacca ccgggaggta agctggccag    6840
caacttatct gtgtctgtcc gattgtctag tgtctatgac tgattttatg cgcctgcgtc    6900
ggtactagtt agctaactag ctctgtatct ggcggacccg tggtggaact gacgagttcg    6960
gaacacccgg ccgcaaccct gggagacgtc ccagggactt cgggggccgt ttttgtggcc    7020
cgacctgagt cctaaaatcc cgatcgttta ggactctttg gtgcaccccc cttagaggag    7080
ggatatgtgt ttctggtagg agacgagaac ctaaaacagt tcccgcctcc gtctgaattt    7140
ttgctttcgg tttgggaccg aagccgcgcc gcgcgtcttg tctgctgcag catcgttctg    7200
tgttgtctct gtctgactgt gtttctgtat ttgtctgaaa atatgggccc gggctagact    7260
gttaccactc ccttaagttt gaccttaggt cactggaaag atgtcgagcg atcgctcac    7320 aaccagtcgg tagatgtcaa gaagagacgt tgggttacct tctgctctgc agaatggcca    7380
acctttaacg tcggatggcc gcgagacggc acctttaacc gagacctcat cacccaggtt    7440
aagatcaagg tcttttcacc tggcccgcat ggacacccag accaggtccc ctacatcgtg    7500
acctgggaag ccttggcttt tgacccccct ccctgggtca gcccttgt acaccctaag      7560 cctccgcctc ctcttcctcc atccgccccg tctctccccc ttgaacctcc tcgttcgacc    7620
ccgcctcgat cctcccttta tccagccctc act                                 7653

<210> SEQ ID NO 231
<211> LENGTH: 7668
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 231
ccttctctag gcgccccat atggccatat gagatcttat atggggcacc ccgccccctt       60
gtaaacttcc ctgaccctga catgacaaga gttactaaca gccccctctct ccaagctcac   120 ttacaggctc tctacttagt ccagcacgaa gtctggagac ctctggcggc agcctaccaa    180
gaacaactgg accgaccggt gccgccacca tggaaaccga caccctgctg ctgtgggtgc    240
tgctgctgtg ggtgccagga tccacaggac aggctgtgct gactcagcca ccctcagcgt    300
ctgggacccc cggcagagg gtcaccatct cttgttctgg aagcagctcc aacatcggaa     360
gtaattacgt attctggtac cagcagctcc caggaacggc ccccaaactc ctcatctata    420
gtaataatca gcggccctca ggggtccctg accgattctc tggctccaag tctggcacct    480
cagcctccct ggccatcagt gggctccggt ccgaggatga ggctgattat tactgtgcag    540
catgggatga cagcctgagt gcctcttatg ttttcggaac tgggaccaag gtcaccgtcc    600
taggttctag aggtggtggt ggtagcggcg gcggcggctc tggtggtggt ggatccctcg    660
agatggccca ggtgcagctg gtgcagtctg ggctgaggt gaagaagcct gggtcctcgg     720
tgaaggtctc ctgcaaggct tctggaggca ccttcagcag ctatgctatc agctgggtgc    780
```

```
gacaggcccc tggacaaggg cttgagtgga tgggaaggat catccctatc cttggtacag    840
caaactacgc acagaagttc cagggcagag tcacgattac cgcggacgaa tccacgagca    900
cagcctacat ggagctgagc agcctgagat ctgaggacac ggccgtgtat tactgtgcgc    960
gctctggtta cggttcttac cgttgggaag attcttgggg tcaaggtact ctggtgaccg   1020
tctcctcagc ggccgcaccc accacgacgc cagcgccgcg accaccaacc ccggcgccca   1080
cgatcgcgtc gcagcccctg tccctgcgcc cagaggcgtg ccggcagcg cgggggggcg    1140
cagtgcacac gagggggctg gacttcgcct gtgatatcta catctgggcg ccctggccg    1200
ggacttgtgg ggtccttctc ctgtcactgg ttatcaccct ttactgcaac aaacggggca   1260
gaaagaagct cctgtatata ttcaaacaac catttatgag accagtacaa actactcaag   1320
aggaagatgg ctgtagctgc cgatttccag aagaagaaga aggaggatgt gaactgagag   1380
tgaagttcag caggagcgca gagccccccg cgtaccagca gggccagaac cagctctata   1440
acgagctcaa tctaggacga agagaggagt acgatgtttt ggacaagaga cgtggccggg   1500
accctgagat ggggggaaag ccgagaagga agaaccctca ggaaggcctg tacaatgaac   1560
tgcagaaaga taagatggcg gaggcctaca gtgagattgg gatgaaaggc gagcgccgga   1620
ggggcaaggg gcacgatggc ctttaccagg gtctcagtac agccaccaag gacacctacg   1680
acgcccttca catgcaggcc ctgccccctc gctaacagcc actcgaggat ccggattagt   1740
ccaatttgtt aaagacagga tatcagtggt ccaggctcta gttttgactc aacaatatca   1800
ccagctgaag cctatagagt acgagccata gataaaataa agatttttat ttagtctcca   1860
gaaaaagggg ggaatgaaag accccacctg taggtttggc aagctagctt aagtaacgcc   1920
attttgcaag gcatggaaaa atacataact gagaatagag aagttcagat caaggtcagg   1980
aacagatgga acagctgaat atgggccaaa caggatatct gtggtaagca gttcctgccc   2040
cggctcaggg ccaagaacag atggaacagc tgaatatggg ccaaacagga tatctgtggt   2100
aagcagttcc tgccccggct cagggccaag aacagatggt cccagatgc ggtccagccc    2160
tcagcagttt ctagagaacc atcagatgtt tccagggtgc cccaaggacc tgaaatgacc   2220
ctgtgcctta tttgaactaa ccaatcagtt cgcttctcgc ttctgttcgc gcgcttctgc   2280
tccccgagct caataaaaga gcccacaacc cctcactcgg ggcgccagtc ctccgattga   2340
ctgagtcgcc cgggtacccg tgtatccaat aaaccctctt gcagttgcat ccgacttgtg   2400
gtctcgctgt tccttgggag ggtctcctct gagtgattga ctacccgtca gcggggggtct  2460
ttcacacatg cagcatgtat caaaattaat ttggtttttt tcttaagta tttacattaa    2520
atggccatag tacttaaagt tacattggct tccttgaaat aaacatggag tattcagaat   2580
gtgtcataaa tatttctaat tttaagatag tatctccatt ggctttctac ttttctttt    2640
attttttttt gtcctctgtc ttccattttgt tgttgttgtt gtttgtttgt tgtttgttg   2700
gttggttggt taatttttttt ttaaagatcc tacactatag ttcaagctag actattagct   2760
actctgtaac ccagggtgac cttgaagtca tgggtagcct gctgttttag ccttcccaca   2820
tctaagatta caggtatgag ctatcatttt tggtatattg attgattgat tgattgatgt   2880
gtgtgtgtgt gattgtgttt gtgtgtgtga ctgtgaaaat gtgtgtatgg gtgtgtgtga   2940
atgtgtgtat gtatgtgtgt gtgtgagtgt gtgtgtgtgt gtgtgcatgt gtgtgtgtgt   3000
gactgtgtct atgtgtatga ctgtgtgtgt gtgtgtgtgt gtgtgtgtgt gtgtgtgtgt   3060
gtgtgtgttg tgaaaaaata ttctatggta gtgagagcca acgctccggc tcaggtgtca   3120
```

```
ggttggtttt tgagacagag tctttcactt agcttggaat tcactggccg tcgttttaca    3180
acgtcgtgac tgggaaaacc ctggcgttac ccaacttaat cgccttgcag cacatccccc    3240
tttcgccagc tggcgtaata gcgaagaggc ccgcaccgat cgcccttccc aacagttgcg    3300
cagcctgaat ggcgaatggc gcctgatgcg gtattttctc cttacgcatc tgtgcggtat    3360
ttcacaccgc atatggtgca ctctcagtac aatctgctct gatgccgcat agttaagcca    3420
gccccgacac ccgccaacac ccgctgacgc gccctgacgg gcttgtctgc tcccggcatc    3480
cgcttacaga caagctgtga ccgtctccgg gagctgcatg tgtcagaggt tttcaccgtc    3540
atcaccgaaa cgcgcgatga cgaaagggcc tcgtgatacg cctatttttta taggttaatg    3600
tcatgataat aatggtttct tagacgtcag gtggcacttt tcggggaaat gtgcgcggaa    3660
cccctatttg tttatttttc taaatacatt caaatatgta tccgctcatg agacaataac    3720
cctgataaat gcttcaataa tattgaaaaa ggaagagtat gagtattcaa catttccgtg    3780
tcgcccttat tcccttttttt gcggcatttt gccttcctgt ttttgctcac ccagaaacgc    3840
tggtgaaagt aaaagatgct gaagatcagt tgggtgcacg agtgggttac atcgaactgg    3900
atctcaacag cggtaagatc cttgagagtt ttcgccccga agaacgtttt ccaatgatga    3960
gcacttttaa agttctgcta tgtggcgcgg tattatcccg tattgacgcc gggcaagagc    4020
aactcggtcg ccgcatacac tattctcaga atgacttggt tgagtactca ccagtcacag    4080
aaaagcatct tacggatggc atgacagtaa gagaattatg cagtgctgcc ataaccatga    4140
gtgataacac tgcggccaac ttacttctga caacgatcgg aggaccgaag gagctaaccg    4200
cttttttgca acatggggg gatcatgtaa ctcgccttga tcgttgggaa ccggagctga    4260
atgaagccat accaaacgac gagcgtgaca ccacgatgcc tgtagcaatg gcaacaacgt    4320
tgcgcaaact attaactggc gaactactta ctctagcttc ccggcaacaa ttaatagact    4380
ggatggaggc ggataaagtt gcaggaccac ttctgcgctc ggcccttccg gctggctggt    4440
ttattgctga taaatctgga gccggtgagc gtgggtctcg cggtatcatt gcagcactgg    4500
ggccagatgg taagccctcc cgtatcgtag ttatctacac gacggggagt caggcaacta    4560
tggatgaacg aaatagacag atcgctgaga taggtgcctc actgattaag cattggtaac    4620
tgtcagacca gtttactca tatatacttt agattgattt aaaacttcat ttttaattta    4680
aaaggatcta ggtgaagatc ctttttgata atctcatgac caaaatccct taacgtgagt    4740
tttcgttcca ctgagcgtca gaccccgtag aaaagatcaa aggatcttct tgagatcctt    4800
ttttttctgcg cgtaatctgc tgcttgcaaa caaaaaaacc accgctacca gcggtggttt    4860
gtttgccgga tcaagagcta ccaactcttt ttccgaaggt aactggcttc agcagagcgc    4920
agataccaaa tactgtcctt ctagtgtagc cgtagttagg ccaccacttc aagaactctg    4980
tagcaccgcc tacatacctc gctctgctaa tcctgttacc agtggctgct gccagtggcg    5040
ataagtcgtg tcttaccggg ttggactcaa gacgatagtt accggataag gcgcagcggt    5100
cgggctgaac ggggggttcg tgcacacagc ccagcttgga gcgaacgacc tacaccgaac    5160
tgagatacct acagcgtgag cattgagaaa gcgccacgct tcccgaaggg agaaaggcgg    5220
acaggtatcc ggtaagcggc agggtcggaa caggagagcg cacgagggag cttccagggg    5280
gaaacgcctg gtatctttat agtcctgtcg ggtttcgcca cctctgactt gagcgtcgat    5340
ttttgtgatg ctcgtcaggg gggcggagcc tatggaaaaa cgccagcaac gcggcctttt    5400
tacgttcct ggccttttgc tggccttttg ctcacatgtt ctttcctgcg ttatcccctg    5460
attctgtgga taaccgtatt accgcctttg agtgagctga taccgctcgc cgcagccgaa    5520
```

```
cgaccgagcg cagcgagtca gtgagcgagg aagcggaaga gcgcccaata cgcaaaccgc  5580
ctctccccgc gcgttggccg attcattaat gcagctggca cgacaggttt cccgactgga  5640
aagcgggcag tgagcgcaac gcaattaatg tgagttagct cactcattag gcacccagg   5700
ctttacactt tatgcttccg gctcgtatgt tgtgtggaat tgtgagcgga taacaatttc  5760
acacaggaaa cagctatgac catgattacg ccaagctttg ctcttaggag tttcctaata  5820
catcccaaac tcaaatatat aaagcatttg acttgttcta tgccctaggg ggcgggggga  5880
agctaagcca gcttttttta acatttaaaa tgttaattcc attttaaatg cacagatgtt  5940
tttatttcat aagggtttca atgtgcatga atgctgcaat attcctgtta ccaaagctag  6000
tataaataaa aatagataaa cgtggaaatt acttagagtt tctgtcatta acgtttcctt  6060
cctcagttga caacataaat gcgctgctga gcaagccagt ttgcatctgt caggatcaat  6120
ttcccattat gccagtcata ttaattacta gtcaattagt tgattttttat ttttgacata  6180
tacatgtgaa tgaaagaccc cacctgtagg tttggcaagc tagcttaagt aacgccattt  6240
tgcaaggcat ggaaaaatac ataactgaga atagaaaagt tcagatcaag gtcaggaaca  6300
gatggaacag ctgaatatgg gccaaacagg atatctgtgg taagcagttc ctgccccggc  6360
tcagggccaa gaacagatgg aacagctgaa tatgggccaa acaggatatc tgtggtaagc  6420
agttcctgcc ccggctcagg gccaagaaca gatggtcccc agatgcggtc cagccctcag  6480
cagtttctag agaaccatca gatgtttcca gggtgcccca aggacctgaa atgaccctgt  6540
gccttatttg aactaaccaa tcagttcgct tctcgcttct gttcgcgcgc ttatgctccc  6600
cgagctcaat aaaagagccc acaaccctc actcggggcg ccagtcctcc gattgactga   6660
gtcgcccggg tacccgtgta tccaataaac cctcttgcag ttgcatccga cttgtggtct  6720
cgctgttcct tgggagggtc tcctctgagt gattgactac ccgtcagcgg gggtctttca  6780
tttgggggct cgtccgggat cgggagaccc ctgcccaggg accaccgacc caccaccggg  6840
aggtaagctg gccagcaact tatctgtgtc tgtccgattg tctagtgtct atgactgatt  6900
ttatgcgcct gcgtcggtac tagttagcta actagctctg tatctggcgg acccgtggtg  6960
gaactgacga gttcggaaca cccggccgca acctgggag acgtcccagg gacttcgggg   7020
gccgttttg tggcccgacc tgagtcctaa aatcccgatc gtttaggact ctttggtgca   7080
cccccttag aggagggata tgtggttctg gtaggagacg agaacctaaa acagttcccg   7140
cctccgtctg aattttgct ttcggtttgg gaccgaagcc gcgccgcgcg tcttgtctgc    7200
tgcagcatcg ttctgtgttg tctctgtctg actgtgtttc tgtatttgtc tgaaaatatg   7260
ggcccgggct agactgttac cactcccttta agtttgacct taggtcactg gaaagatgtc  7320
gagcggatcg ctcacaacca gtcggtagat gtcaagaaga gacgttgggt taccttctgc   7380
tctgcagaat ggccaacctt taacgtcgga tggccgcgag acggcacctt taaccgagac   7440
ctcatcaccc aggttaagat caaggtctttt tcacctggcc cgcatggaca cccagaccag   7500
gtcccctaca tcgtgacctg ggaagccttg gcttttgacc ccctccctg ggtcaagccc    7560
tttgtacacc ctaagcctcc gcctcctctt cctccatccg ccccgtctct ccccccttgaa   7620
cctcctcgtt cgacccgcc tcgatcctcc ctttatccag ccctcact                 7668
```

<210> SEQ ID NO 232
<211> LENGTH: 7662
<212> TYPE: DNA
<213> ORGANISM: Artificial Sequence
<220> FEATURE:

<223> OTHER INFORMATION: Description of Artificial Sequence: Synthetic polynucleotide

<400> SEQUENCE: 232

```
ccttctctag gcgcccccat atggccatat gagatcttat atggggcacc cccgcccctt    60
gtaaacttcc ctgaccctga catgacaaga gttactaaca gccctctct ccaagctcac    120
ttacaggctc tctacttagt ccagcacgaa gtctggagac ctctggcggc agcctaccaa   180
gaacaactgg accgaccggt gccgccacca tggaaaccga cacctgctg ctgtgggtgc    240
tgctgctgtg ggtgccagga tccacaggac agtctgtgct gacgcagccg ccctcagtgt   300
ctggggcccc agggcagagg gtcaccatct cctgcactgg gagcagctcc aacatcgggg   360
caggttttga tgtacactgg taccagcagc ttccaggaac agcccccaaa ctcctcatct   420
atggtaacag caatcggccc tcaggggtcc ctgaccgatt ctctggctcc aagtctggca   480
cctcagcctc cctggccatc actgggctcc aggctgagga tgaggctgat tattactgcc   540
agtcctatga cagcagcctg agtggttatg tcttcggaac tgggaccaag gtcaccgtcc   600
taggttctag aggtggtggt ggtagcggcg gcggcggctc tggtggtggt ggatccctcg   660
agatggccca ggtccagctg gtacagtctg ggctgaggt gaagaagcct ggggcctcag   720
tgaaggtctc ctgcaaggct tctggataca ccttcaccga ctactatatg cactgggtgc   780
gacaggcccc tggacaacgg cttgagtgga tgggatggat caaccctaac agtggtggca   840
caaactatgc acagaagttt caggacagga tcaccgtgac cagggacacc tccagcaaca   900
caggctacat ggagctgacc aggctgagat ctgacgacac ggccgtgtat tactgtgcgc   960
gctctccgta ctctggtgtt ctggataaat ggggtcaagg tactctggtg accgtctcct  1020
cagcggccgc acccaccacg acgccagcgc cgcgaccacc aaccccggcg cccacgatcg  1080
cgtcgcagcc cctgtccctg cgcccagagg cgtgccggcc agcggcgggg ggcgcagtgc  1140
acacgagggg gctggacttc gcctgtgata tctacatctg ggcgcccctg gccgggactt  1200
gtgggggtcct tctcctgtca ctggttatca ccctttactg caacaaacgg ggcagaaaga  1260
agctcctgta tatattcaaa caaccattta tgagaccagt acaaactact caagaggaag  1320
atgctgtag ctgccgattt ccagaagaag aagaaggagg atgtgaactg agagtgaagt  1380
tcagcaggag cgcagagccc cccgcgtacc agcagggcca gaaccagctc tataacgagc  1440
tcaatctagg acgaagagag gagtacgatg ttttggacaa gagacgtggc cgggaccctg  1500
agatggggg aaagccgaga aggaagaacc ctcaggaagg cctgtacaat gaactgcaga  1560
aagataagat ggcggaggcc tacagtgaga ttgggatgaa aggcgagcgc cggaggggca  1620
agggcacga tggcctttac cagggtctca gtacagccac caaggacacc tacgacgccc  1680
ttcacatgca ggccctgccc cctcgctaac agccactcga ggatccggat tagtccaatt  1740
tgttaaagac aggatatcag tggtccaggc tctagttttg actcaacaat atcaccagct  1800
gaagcctata gagtacgagc catagataaa ataaaagatt ttatttagtc tccagaaaaa  1860
ggggggaatg aaagacccca cctgtaggtt tggcaagcta gcttaagtaa cgccattttg  1920
caaggcatgg aaaatacat aactgagaat agagaagttc agatcaaggt caggaacaga  1980
tggaacagct gaatatgggc caaacaggat atctgtggta agcagttcct gccccggctc  2040
agggccaaga acagatggaa cagctgaata tgggccaaac aggatatctg tggtaagcag  2100
ttcctgcccc ggctcaggc caagaacaga tggtccccag atgcggtcca gccctcagca  2160
gtttctagag aaccatcaga tgtttccagg gtgccccaag gacctgaaat gaccctgtgc  2220
```

```
cttatttgaa ctaaccaatc agttcgcttc tcgcttctgt tcgcgcgctt ctgctccccg    2280
agctcaataa aagagcccac aacccctcac tcggggcgcc agtcctccga ttgactgagt    2340
cgcccgggta cccgtgtatc caataaaccc tcttgcagtt gcatccgact tgtggtctcg    2400
ctgttccttg ggagggtctc ctctgagtga ttgactaccc gtcagcgggg gtctttcaca    2460
catgcagcat gtatcaaaat taatttggtt ttttttctta agtatttaca ttaaatggcc    2520
atagtactta aagttacatt ggcttccttg aaataaacat ggagtattca gaatgtgtca    2580
taaatatttc taattttaag atagtatctc cattggcttt ctacttttc ttttattttt     2640 ttttgtcctc tgtcttccat tgttgttgt tgttgtttgt ttgtttgttt gttggttggt     2700
tggttaattt ttttttaaag atcctacact atagttcaag ctagactatt agctactctg    2760
taacccaggg tgaccttgaa gtcatgggta gcctgctgtt ttagccttcc cacatctaag    2820
attacaggta tgagctatca tttttggtat attgattgat tgattgattg atgtgtgtgt    2880
gtgtgattgt gtttgtgtgt gtgactgtga aaatgtgtgt atgggtgtgt gtgaatgtgt    2940
gtatgtatgt gtgtgtgtga gtgtgtgtgt gtgtgtgtgc atgtgtgtgt gtgtgactgt    3000
gtctatgtgt atgactgtgt gtgtgtgtgt gtgtgtgtgt gtgtgtgtgt gtgtgtgtgt    3060
gttgtgaaaa atattctat ggtagtgaga gccaacgctc cggctcaggt gtcaggttgg      3120
tttttgagac agagtctttc acttagcttg gaattcactg gccgtcgttt tacaacgtcg    3180
tgactgggaa aaccctggcg ttacccaact taatcgcctt gcagcacatc cccctttcgc    3240
cagctggcgt aatagcgaag aggcccgcac cgatcgccct cccaacagt tgcgcagcct     3300 gaatggcgaa tggcgcctga tgcggtattt tctccttacg catctgtgcg gtatttcaca    3360
ccgcatatgg tgcactctca gtacaatctg ctctgatgcc gcatagttaa gccagccccg    3420
acacccgcca cacccgctg acgcgccctg acgggcttgt ctgctcccgg catccgctta     3480
cagacaagct gtgaccgtct ccgggagctg catgtgtcag aggttttcac cgtcatcacc    3540
gaaacgcgcg atgacgaaag ggcctcgtga tacgcctatt tttataggtt aatgtcatga    3600
taataatggt ttcttagacg tcaggtggca cttttcgggg aaatgtgcgc ggaaccccta    3660
tttgtttatt tttctaaata cattcaaata tgtatccgct catgagacaa taaccctgat    3720
aaatgcttca ataatattga aaaggaaga gtatgagtat tcaacatttc cgtgtcgccc     3780
ttattccctt ttttgcggca ttttgccttc ctgttttgc tcacccagaa acgctggtga     3840
aagtaaaaga tgctgaagat cagttgggtg cacgagtggg ttacatcgaa ctggatctca    3900
acagcggtaa gatccttgag agttttcgcc ccgaagaacg ttttccaatg atgagcactt    3960
ttaaagttct gctatgtggc gcggtattat cccgtattga cgccgggcaa gagcaactcg    4020
gtcgccgcat acactattct cagaatgact tggttgagta ctcaccagtc acagaaaagc    4080
atcttacgga tggcatgaca gtaagagaat tatgcagtgc tgccataacc atgagtgata    4140
acactgcggc caacttactt ctgacaacga tcggaggacc gaaggagcta accgcttttt    4200
tgcacaacat gggggatcat gtaactcgcc ttgatcgttg ggaaccggag ctgaatgaag    4260
ccataccaaa cgacgagcgt gacaccacga tgcctgtagc aatggcaaca acgttgcgca    4320
aactattaac tggcgaacta cttactctag cttcccggca acaattaata gactggatgg    4380
aggcggataa agttgcagga ccacttctgc gctcggccct tccggctggc tggtttattg    4440
ctgataaatc tggagccggt gagcgtgggt ctcgcggtat cattgcagca ctggggccag    4500
atggtaagcc ctcccgtatc gtagttatct acacgacggg gagtcaggca actatggatg    4560
aacgaaatag acagatcgct gagataggtg cctcactgat taagcattgg taactgtcag    4620
```

```
accaagttta ctcatatata ctttagattg atttaaaact tcattttaa tttaaaagga   4680
tctaggtgaa gatccttttt gataatctca tgaccaaaat cccttaacgt gagttttcgt   4740
tccactgagc gtcagacccc gtagaaaaga tcaaaggatc ttcttgagat ccttttttc    4800
tgcgcgtaat ctgctgcttg caaacaaaaa aaccaccgct accagcggtg tttgtttgc    4860
cggatcaaga gctaccaact cttttccga aggtaactgg cttcagcaga gcgcagatac    4920
caaatactgt ccttctagtg tagccgtagt taggccacca cttcaagaac tctgtagcac   4980
cgcctacata cctcgctctg ctaatcctgt taccagtggc tgctgccagt ggcgataagt   5040
cgtgtcttac cgggttggac tcaagacgat agttaccgga taaggcgcag cggtcgggct   5100
gaacggggg ttcgtgcaca cagcccagct tggagcgaac gacctacacc gaactgagat   5160
acctacagcg tgagcattga aaagcgcca cgcttcccga aggagaaag gcggacaggt    5220
atccggtaag cggcagggtc ggaacaggag agcgcacgag ggagcttcca gggggaaacg   5280
cctggtatct ttatagtcct gtcgggtttc gccacctctg acttgagcgt cgattttgt    5340
gatgctcgtc agggggggcgg agcctatgga aaaacgccag caacgcggcc ttttacggt    5400
tcctggcctt ttgctggcct tttgctcaca tgttctttcc tgcgttatcc cctgattctg   5460
tggataaccg tattaccgcc tttgagtgag ctgataccgc tcgccgcagc cgaacgaccg   5520
agcgcagcga gtcagtgagc gaggaagcgg aagagcgccc aatacgcaaa ccgcctctcc   5580
ccgcgcgttg gccgattcat taatgcagct ggcacgacag gtttcccgac tggaaagcgg   5640
gcagtgagcg caacgcaatt aatgtgagtt agctcactca ttaggcaccc caggctttac   5700
actttatgct tccggctcgt atgttgtgtg gaattgtgag cggataacaa tttcacacag   5760
gaaacagcta tgaccatgat tacgccaagc tttgctctta ggagtttcct aatacatccc   5820
aaactcaaat atataaagca tttgacttgt tctatgccct agggggcggg gggaagctaa   5880
gccagctttt tttaacattt aaaatgttaa ttccatttta aatgcacaga tgttttatt    5940
tcataagggt ttcaatgtgc atgaatgctg caatattcct gttaccaaag ctagtataaa   6000
taaaaataga taaacgtgga aattacttag agtttctgtc attaacgttt ccttcctcag   6060
ttgacaacat aaatgcgctg ctgagcaagc cagtttgcat ctgtcaggat caatttccca   6120
ttatgccagt catattaatt actagtcaat tagttgattt ttattttga catatacatg    6180
tgaatgaaag accccacctg taggtttggc aagctagctt aagtaacgcc attttgcaag   6240
gcatggaaaa atacataact gagaatagaa aagttcagat caaggtcagg aacagatgga   6300
acagctgaat atgggccaaa caggatatct gtggtaagca gttcctgccc cggctcaggg   6360
ccaagaacag atggaacagc tgaatatggg ccaaacagga tatctgtggt aagcagttcc   6420
tgccccggct cagggccaag aacagatggt cccagatgc ggtccagccc tcagcagttt    6480
ctagagaacc atcagatgtt tccagggtgc cccaaggacc tgaaatgacc ctgtgcctta   6540
tttgaactaa ccaatcagtt cgcttctcgc ttctgttcgc gcgcttatgc tccccgagct   6600
caataaaaga gcccacaacc cctcactcgg ggcgccagtc ctccgattga ctgagtcgcc   6660
cgggtacccg tgtatccaat aaaccctctt gcagttgcat ccgacttgtg gtctcgctgt   6720
tccttgggag ggtctcctct gagtgattga ctacccgtca gcggggggtct ttcatttggg   6780
ggctcgtccg ggatcgggag acccctgccc agggaccacc gacccaccac cgggaggtaa   6840
gctggccagc aacttatctg tgtctgtccg attgtctagt gtctatgact gattttatgc   6900
gcctgcgtcg gtactagtta gctaactagc tctgtatctg gcggaccgt ggtggaactg    6960
```

| | |
|---|---|
| acgagttcgg aacacccggc cgcaaccctg ggagacgtcc cagggacttc gggggccgtt | 7020 |
| tttgtggccc gacctgagtc ctaaaatccc gatcgtttag gactctttgg tgcacccccc | 7080 |
| ttagaggagg gatatgtggt tctggtagga gacgagaacc taaaacagtt cccgcctccg | 7140 |
| tctgaatttt tgctttcggt ttgggaccga agccgcgccg cgcgtcttgt ctgctgcagc | 7200 |
| atcgttctgt gttgtctctg tctgactgtg tttctgtatt tgtctgaaaa tatgggcccg | 7260 |
| ggctagactt ttaccactcc cttaagtttg accttaggtc actggaaaga tgtcgagcgg | 7320 |
| atcgctcaca accagtcggt agatgtcaag aagagacgtt gggttacctt ctgctctgca | 7380 |
| gaatggccaa cctttaacgt cggatggccg cgagacggca cctttaaccg agacctcatc | 7440 |
| acccaggtta agatcaaggt cttttcacct ggcccgcatg gacacccaga ccaggtcccc | 7500 |
| tacatcgtga cctgggaagc cttggctttt gaccccctc cctgggtcaa gccctttgta | 7560 |
| caccctaagc ctccgcctcc tcttcctcca tccgcccgt ctctcccct tgaacctcct | 7620 |
| cgttcgaccc cgcctcgatc ctccctttat ccagccctca ct | 7662 |

<210> SEQ ID NO 233
<211> LENGTH: 7641
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 233

| | |
|---|---|
| ccttctctag gcgcccccat atggccatat gagatcttat atggggcacc ccgcccctt | 60 |
| gtaaacttcc ctgaccctga catgacaaga gttactaaca gcccctctct ccaagctcac | 120 |
| ttacaggctc tctacttagt ccagcacgaa gtctggagac ctctggcggc agcctaccaa | 180 |
| gaacaactgg accgaccggt gccgccacca tggaaaccga caccctgctg ctgtgggtgc | 240 |
| tgctgctgtg ggtgccagga tccacaggac aatctgccct gactcagcct gcctccgtgt | 300 |
| ctgcgtctcc tggacagtcg atcgccatct cctgcactgg aaccagcagt gacgttggtt | 360 |
| ggtatcaaca gcacccaggc aaagccccca aactcatgat ttatgaggac agtaagcggc | 420 |
| cctcagggt ttctaatcgc ttctctggct ccaagtctgg caacacggcc tccctgacca | 480 |
| tctctgggct ccaggctgag gacgaggctg attattactg cagctcaaat acaagaagca | 540 |
| gcactttggt gttcggcgga gggaccaagc tgaccgtcct aggttctaga ggtggtggtg | 600 |
| gtagcggcgg cggcggctct ggtggtggtg gatccctcga gatggccgaa gtgcagctgg | 660 |
| tgcagtctgg ggctgagatg aagaagcctg ggcctcact gaagctctcc tgcaaggctt | 720 |
| ctggatacac cttcatcgac tactatgtat actggatgcg acaggcccct ggacaagggc | 780 |
| ttgagtccat gggatggatc aaccctaaca gtggtggcac aaactatgca cagaagtttc | 840 |
| agggcagggt caccatgacc agggacacgt ccatcagcac agcctacatg gagctgagca | 900 |
| ggctgagatc tgacgacacc gccatgtatt actgtgcgcg ctcccagcgt gacggttaca | 960 |
| tggattactg gggtcaaggt actctggtga ccgtctcctc agcggccgca cccaccacga | 1020 |
| cgccagcgcc gcgaccacca accccggcgc ccacgatcgc gtcgcagccc ctgtccctgc | 1080 |
| gcccagaggc gtgccggcca gcggcggggg gcgcagtgca cacgagggg ctggacttcg | 1140 |
| cctgtgatat ctacatctgg gcgcccctgg ccgggacttg tggggtcctt ctcctgtcac | 1200 |
| tggttatcac ccttttactgc aacaaacggg gcagaaagaa gctcctgtat atattcaaac | 1260 |
| aaccatttat gagaccagta caaactactc aagaggaaga tggctgtagc tgccgatttc | 1320 |

-continued

| | |
|---|---|
| cagaagaaga agaaggagga tgtgaactga gagtgaagtt cagcaggagc gcagagcccc | 1380 |
| ccgcgtacca gcagggccag aaccagctct ataacgagct caatctagga cgaagagagg | 1440 |
| agtacgatgt tttggacaag agacgtggcc gggaccctga gatgggggga aagccgagaa | 1500 |
| ggaagaaccc tcaggaaggc ctgtacaatg aactgcagaa agataagatg gcggaggcct | 1560 |
| acagtgagat tgggatgaaa ggcgagcgcc ggaggggcaa ggggcacgat ggcctttacc | 1620 |
| agggtctcag tacagccacc aaggacacct acgacgccct tcacatgcag gccctgcccc | 1680 |
| ctcgctaaca gccactcgag gatccggatt agtccaattt gttaaagaca ggatatcagt | 1740 |
| ggtccaggct ctagttttga ctcaacaata tcaccagctg aagcctatag agtacgagcc | 1800 |
| atagataaaa taaaagattt tatttagtct ccagaaaaag gggggaatga agacccccac | 1860 |
| ctgtaggttt ggcaagctag cttaagtaac gccattttgc aaggcatgga aaatacata | 1920 |
| actgagaata gagaagttca gatcaaggtc aggaacagat ggaacagctg aatatgggcc | 1980 |
| aaacaggata tctgtggtaa gcagttcctg ccccggctca gggccaagaa cagatggaac | 2040 |
| agctgaatat gggccaaaca ggatatctgt ggtaagcagt tcctgccccg gctcagggcc | 2100 |
| aagaacagat ggtccccaga tgcggtccag ccctcagcag tttctagaga accatcagat | 2160 |
| gtttccaggg tgccccaagg acctgaaatg accctgtgcc ttatttgaac taaccaatca | 2220 |
| gttcgcttct cgcttctgtt cgcgcgcttc tgctccccga gctcaataaa agagcccaca | 2280 |
| acccctcact cggggcgcca gtcctccgat tgactgagtc gcccgggtac ccgtgtatcc | 2340 |
| aataaaccct cttgcagttg catccgactt gtggtctcgc tgttccttgg gagggtctcc | 2400 |
| tctgagtgat tgactacccg tcagcggggg tctttcacac atgcagcatg tatcaaaatt | 2460 |
| aatttggttt tttttcttaa gtatttacat aaatggcca tagtacttaa agttacattg | 2520 |
| gcttccttga aataaacatg gagtattcag aatgtgtcat aaatatttct aattttaaga | 2580 |
| tagtatctcc attggctttc tactttttct tttattttt tttgtcctct gtcttccatt | 2640 |
| tgttgttgtt gttgtttgtt tgtttgtttg ttggttggtt ggttaatttt tttttaaaga | 2700 |
| tcctacacta tagttcaagc tagactatta gctactctgt aacccagggt gaccttgaag | 2760 |
| tcatgggtag cctgctgttt tagccttccc acatctaaga ttacaggtat gagctatcat | 2820 |
| ttttggtata ttgattgatt gattgattga tgtgtgtgtg tgtgattgtg tttgtgtgtg | 2880 |
| tgactgtgaa aatgtgtgta tgggtgtgtg tgaatgtgtg tatgtatgtg tgtgtgtgag | 2940 |
| tgtgtgtgtg tgtgtgtgca tgtgtgtgtg tgtgactgtg tctatgtgta tgactgtgtg | 3000 |
| tgtgtgtgtg tgtgtgtgtg tgtgtgtgtg tgtgtgtgtg ttgtgaaaaa atattctatg | 3060 |
| gtagtgagag ccaacgctcc ggctcaggtg tcaggttggt ttttgagaca gagtctttca | 3120 |
| cttagcttgg aattcactgg ccgtcgtttt acaacgtcgt gactgggaaa accctggcgt | 3180 |
| tacccaactt aatcgccttg cagcacatcc ccctttcgcc agctggcgta atagcgaaga | 3240 |
| ggcccgcacc gatcgccctt cccaacagtt gcgcagcctg aatggcgaat ggcgcctgat | 3300 |
| gcggtatttt ctccttacgc atctgtgcgg tatttcacac cgcatatggt gcactctcag | 3360 |
| tacaatctgc tctgatgccg catagttaag ccagccccga cacccgccaa cacccgctga | 3420 |
| cgcgccctga cgggcttgtc tgctcccggc atccgcttac agacaagctg tgaccgtctc | 3480 |
| cgggagctgc atgtgtcaga ggttttcacc gtcatcaccg aaacgcgcga tgacgaaagg | 3540 |
| gcctcgtgat acgcctattt ttataggtta atgtcatgat aataatggtt tcttagacgt | 3600 |
| caggtggcac ttttcgggga aatgtgcgcg gaacccctat ttgtttattt ttctaaatac | 3660 |
| attcaaatat gtatccgctc atgagacaat aaccctgata aatgcttcaa taatattgaa | 3720 |

```
aaaggaagag tatgagtatt caacatttcc gtgtcgccct tattccctttt tttgcggcat    3780 tttgccttcc tgttttttgct cacccagaaa cgctggtgaa agtaaaagat gctgaagatc    3840
agttgggtgc acgagtgggt tacatcgaac tggatctcaa cagcggtaag atccttgaga    3900
gttttcgccc cgaagaacgt tttccaatga tgagcacttt taaagttctg ctatgtggcg    3960
cggtattatc ccgtattgac gccgggcaag agcaactcgg tcgccgcata cactattctc    4020
agaatgactt ggttgagtac tcaccagtca cagaaaagca tcttacggat ggcatgacag    4080
taagagaatt atgcagtgct gccataacca tgagtgataa cactgcggcc aacttacttc    4140
tgacaacgat cggaggaccg aaggagctaa ccgcttttttt gcacaacatg ggggatcatg    4200
taactcgcct tgatcgttgg aaccggagc tgaatgaagc cataccaaac gacgagcgtg    4260
acaccacgat gcctgtagca atggcaacaa cgttgcgcaa actattaact ggcgaactac    4320
ttactctagc ttcccggcaa caattaatag actggatgga ggcggataaa gttgcaggac    4380
cacttctgcg ctcggccctt ccggctggct ggtttattgc tgataaatct ggagccggtg    4440
agcgtgggtc tcgcggtatc attgcagcac tggggccaga tggtaagccc tcccgtatcg    4500
tagttatcta cacgacgggg agtcaggcaa ctatggatga acgaaataga cagatcgctg    4560
agataggtgc ctcactgatt aagcattggt aactgtcaga ccaagtttac tcatatatac    4620
tttagattga tttaaaactt cattttttaat ttaaaaggat ctaggtgaag atcctttttg    4680
ataatctcat gaccaaaatc ccttaacgtg agttttcgtt ccactgagcg tcagacccccg    4740 tagaaaagat caaaggatct tcttgagatc cttttttttct gcgcgtaatc tgctgcttgc    4800
aaacaaaaaa accaccgcta ccagcggtgg tttgtttgcc ggatcaagag ctaccaactc    4860
tttttccgaa ggtaactggc ttcagcagag cgcagatacc aaatactgtc cttctagtgt    4920
agccgtagtt aggccaccac ttcaagaact ctgtagcacc gcctacatac ctcgctctgc    4980
taatcctgtt accagtggct gctgccagtg gcgataagtc gtgtcttacc gggttggact    5040
caagacgata gttaccggat aaggcgcagc ggtcgggctg aacggggggt tcgtgcacac    5100
agcccagctt ggagcgaacg acctacaccg aactgagata cctacagcgt gagcattgag    5160
aaagcgccac gcttcccgaa gggagaaagg cggacaggta tccggtaagc ggcagggtcg    5220
gaacaggaga gcgcacgagg gagcttccag ggggaaacgc ctggtatctt tatagtcctg    5280
tcgggtttcg ccacctctga cttgagcgtc gatttttgtg atgctcgtca ggggggcgga    5340
gcctatggaa aaacgccagc aacgcggcct ttttacggtt cctggccttt tgctggcctt    5400
ttgctcacat gttctttcct gcgttatccc ctgattctgt ggataaccgt attaccgcct    5460
ttgagtgagc tgataccgct cgccgcagcc gaacgaccga gcgcagcgag tcagtgagcg    5520
aggaagcgga agagcgccca atacgcaaac cgcctctccc cgcgcgttgg ccgattcatt    5580
aatgcagctg gcacgacagg tttcccgact ggaaagcggg cagtgagcgc aacgcaatta    5640
atgtgagtta gctcactcat taggcacccc aggctttaca ctttatgctt ccggctcgta    5700
tgttgtgtgg aattgtgagc ggataacaat ttcacacagg aaacagctat gaccatgatt    5760
acgccaagct tgctcttag gagtttccta atacatccca aactcaaata tataaagcat    5820
ttgacttgtt ctatgcccta gggggcgggg ggaagctaag ccagcttttt ttaacattta    5880
aaatgttaat tccattttaa atgcacagat gttttttattt cataagggtt tcaatgtgca    5940
tgaatgctgc aatattcctg ttaccaaagc tagtataaat aaaaatagat aaacgtggaa    6000
attacttaga gtttctgtca ttaacgtttc cttcctcagt tgacaacata aatgcgctgc    6060
```

```
tgagcaagcc agtttgcatc tgtcaggatc aatttcccat tatgccagtc atattaatta    6120
ctagtcaatt agttgatttt tattttgac atatacatgt gaatgaaaga ccccacctgt     6180
aggtttggca agctagctta agtaacgcca ttttgcaagg catggaaaaa tacataactg    6240
agaatagaaa agttcagatc aaggtcagga acagatggaa cagctgaata tgggccaaac   6300
aggatatctg tggtaagcag ttcctgcccc ggctcagggc caagaacaga tggaacagct   6360
gaatatgggc caaacaggat atctgtggta agcagttcct gccccggctc agggccaaga   6420
acagatggtc cccagatgcg gtccagccct cagcagtttc tagagaacca tcagatgttt   6480
ccagggtgcc ccaaggacct gaaatgaccc tgtgccttat ttgaactaac caatcagttc   6540
gcttctcgct tctgttcgcg cgcttatgct ccccgagctc aataaaagag cccacaaccc   6600
ctcactcggg gcgccagtcc tccgattgac tgagtcgccc gggtaccgt gtatccaata    6660 aaccctcttg cagttgcatc cgacttgtgg tctcgctgtt ccttgggagg gtctcctctg   6720
agtgattgac tacccgtcag cgggggtctt tcatttgggg gctcgtccgg gatcgggaga   6780
cccctgccca gggaccaccg acccaccacc gggaggtaag ctggccagca acttatctgt   6840
gtctgtccga ttgtctagtg tctatgactg attttatgcg cctgcgtcgg tactagttag   6900
ctaactagct ctgtatctgg cggacccgtg gtggaactga cgagttcgga cacccggcc    6960 gcaaccctgg gagacgtccc agggacttcg ggggccgttt tgtggcccg acctgagtcc    7020 taaaatcccg atcgtttagg actctttggt gcacccccct tagaggaggg atatgtggtt   7080
ctggtaggag acgagaacct aaaacagttc ccgcctccgt ctgaattttt gctttcggtt   7140
tgggaccgaa gccgcgccgc gcgtcttgtc tgctgcagca tcgttctgtg ttgtctctgt   7200
ctgactgtgt ttctgtattt gtctgaaaat atgggcccgg gctagactgt taccactccc    7260
ttaagtttga ccttaggtca ctggaaagat gtcgagcgga tcgctcacaa ccagtcggta   7320
gatgtcaaga agagacgttg ggttaccttc tgctctgcag aatggccaac cttaacgtc    7380 ggatggccgc gagacggcac cttaaccga gacctcatca cccaggttaa gatcaaggtc   7440
ttttcacctg gcccgcatgg acacccagac caggtcccct acatcgtgac ctgggaagcc   7500
ttggcttttg accccctcc ctgggtcaag ccctttgtac accctaagcc tccgcctcct    7560
cttcctccat ccgccccgtc tctccccctt gaacctcctc gttcgacccc gcctcgatcc   7620 tcccttatc cagccctcac t                                              7641
```

<210> SEQ ID NO 234
<211> LENGTH: 1491
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 234

```
atggaaaccg acaccctgct gctgtgggtg ctgctgctgt gggtgccagg atccacagga     60
ctgcctgtgc tgactcagcc accctcagcg tctgggaccc ccgggcagag ggtcaccatc    120
tcttgttctg gacgcagttc caacatcggg agtaattctg ttaactggta tcagcaactc    180
ccaggagcgg cccccaaact cctcatctat agtaataatc agcggccccc agggtccct    240 gtgcgattct ctggctccaa gtctggcacc tcagcctccc tggccatcag tgggctccag   300
tctgaagatg aggccactta ttactgtgca acatgggatg acaatctgaa tgttcactat    360
gtcttcggaa ctgggaccaa ggtcaccgtc ctaggttcta gaggtggtgg tggtagcggc   420
```

| | |
|---|---|
| ggcggcggct ctggtggtgg tggatccctc gagatggccc aggtgcagct ggtgcagtct | 480 |
| ggggctgagg tgaagaagcc tgggtcctcg gtgaaggtct cctgcaaggc ttctggaggc | 540 |
| accttcagca gctatgctat cagctgggtg cgacaggccc ctggacaagg gcttgagtgg | 600 |
| atgggaagga tcatccctat ccttggtata gcaaactacg cacagaagtt ccagggcaga | 660 |
| gtcacgatta ccgcggacaa atccacgagc acagcctaca tggagctgag cagcctgaga | 720 |
| tctgaggaca cggccgtgta ttactgtgcg cgcggtggtt actactctca tgacatgtgg | 780 |
| tctgaagatt ggggtcaagg tactctggtg accgtctcct cagcggccgc aattgaagtt | 840 |
| atgtatcctc ctccttacct agacaatgag aagagcaatg gaaccattat ccatgtgaaa | 900 |
| gggaaacacc tttgtccaag tcccctattt cccggacctt ctaagccctt tgggtgctg | 960 |
| gtggtggttg gtggagtcct ggcttgctat agcttgctag taacagtggc ctttattatt | 1020 |
| ttctgggtga ggagtaagag gagcaggctc ctgcacagtg actacatgaa catgactccc | 1080 |
| cgccgccccg ggcccacccg caagcattac cagccctatg ccccaccacg cgacttcgca | 1140 |
| gcctatcgct ccagagtgaa gttcagcagg agcgcagacg ccccgcgta ccagcagggc | 1200 |
| cagaaccagc tctataacga gctcaatcta ggacgaagag aggagtacga tgttttggac | 1260 |
| aagagacgtg gccgggaccc tgagatgggg ggaaagccga aaggaagaa ccctcaggaa | 1320 |
| ggcctgtaca atgaactgca gaaagataag atggcggagg cctacagtga gattgggatg | 1380 |
| aaaggcgagc gccggagggg caaggggcac gatggccttt accagggtct cagtacagcc | 1440 |
| accaaggaca cctacgacgc ccttcacatg caggccctgc cccctcgcta a | 1491 |

<210> SEQ ID NO 235
<211> LENGTH: 1488
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 235

| | |
|---|---|
| atggaaaccg acaccctgct gctgtgggtg ctgctgctgt gggtgccagg atccacagga | 60 |
| caggctgtgc tgactcagcc accctcagcg tctgggaccc ccgggcagag ggtcaccatc | 120 |
| tcttgttctg gaagcagctc caacatcgga agtaattacg tattctggta ccagcagctc | 180 |
| ccaggaacgg cccccaaact cctcatctat agtaataatc agcggccctc aggggtccct | 240 |
| gaccgattct ctggctccaa gtctggcacc tcagcctccc tggccatcag tgggctccgg | 300 |
| tccgaggatg aggctgatta ttactgtgca gcatgggatg acagcctgag tgcctcttat | 360 |
| gttttcggaa ctgggaccaa ggtcaccgtc ctaggttcta gaggtggtgg tggtagcggc | 420 |
| ggcggcggct ctggtggtgg tggatccctc gagatggccc aggtgcagct ggtgcagtct | 480 |
| ggggctgagg tgaagaagcc tgggtcctcg gtgaaggtct cctgcaaggc ttctggaggc | 540 |
| accttcagca gctatgctat cagctgggtg cgacaggccc ctggacaagg gcttgagtgg | 600 |
| atgggaagga tcatccctat ccttggtaca gcaaactacg cacagaagtt ccagggcaga | 660 |
| gtcacgatta ccgcggacga atccacgagc acagcctaca tggagctgag cagcctgaga | 720 |
| tctgaggaca cggccgtgta ttactgtgcg cgctctggtt acggttctta ccgttgggaa | 780 |
| gattctgggg tcaaggtac tctggtgacc gtctcctcag cggccgcaat tgaagttatg | 840 |
| tatcctcctc cttacctaga caatgagaag agcaatggaa ccattatcca tgtgaaggg | 900 |
| aaacacctttt gtccaagtcc cctatttccc ggaccttcta agccctttgg ggtgctggtg | 960 |

```
gtggttggtg gagtcctggc ttgctatagc ttgctagtaa cagtggcctt tattattttc    1020
tgggtgagga gtaagaggag caggctcctg cacagtgact acatgaacat gactcccgc     1080 cgccccgggc ccacccgcaa gcattaccag ccctatgccc caccacgcga cttcgcagcc    1140
tatcgctcca gagtgaagtt cagcaggagc gcagacgccc ccgcgtacca gcagggccag    1200
aaccagctct ataacgagct caatctagga cgaagagagg agtacgatgt tttggacaag    1260
agacgtggcc gggaccctga gatgggggga aagccgagaa ggaagaaccc tcaggaaggc    1320
ctgtacaatg aactgcagaa agataagatg gcggaggcct acagtgagat tgggatgaaa    1380
ggcgagcgcc ggaggggcaa ggggcacgat ggcctttacc agggtctcag tacagccacc    1440
aaggacacct acgacgccct tcacatgcag gccctgcccc ctcgctaa                 1488
```

<210> SEQ ID NO 236
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Ser Gly Ser Gly Leu Gln Met Ala Gly Gln Cys Ser Gln Asn Glu Tyr
1               5                   10                  15

Phe Asp Ser

<210> SEQ ID NO 237
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Ser Gly Ser Gly Gln Met Ala Gly Gln Cys Ser Gln Asn Glu Tyr Phe
1               5                   10                  15

Asp Ser Leu

<210> SEQ ID NO 238
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Ser Gly Ser Gly Met Ala Gly Gln Cys Ser Gln Asn Glu Tyr Phe Asp
1               5                   10                  15

Ser Leu Leu

<210> SEQ ID NO 239
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Ser Gly Ser Gly Ala Gly Gln Cys Ser Gln Asn Glu Tyr Phe Asp Ser
1               5                   10                  15

```
Leu Leu His

<210> SEQ ID NO 240
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Ser Gly Ser Gly Gly Gln Cys Ser Gln Asn Glu Tyr Phe Asp Ser Leu
1               5                   10                  15

Leu His Ala

<210> SEQ ID NO 241
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Ser Gly Ser Gly Gln Cys Ser Gln Asn Glu Tyr Phe Asp Ser Leu Leu
1               5                   10                  15

His Ala Cys

<210> SEQ ID NO 242
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Ser Gly Ser Gly Cys Ser Gln Asn Glu Tyr Phe Asp Ser Leu Leu His
1               5                   10                  15

Ala Cys Ile

<210> SEQ ID NO 243
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Ser Gly Ser Gly Ser Gln Asn Glu Tyr Phe Asp Ser Leu Leu His Ala
1               5                   10                  15

Cys Ile Pro

<210> SEQ ID NO 244
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Ser Gly Ser Gly Gln Asn Glu Tyr Phe Asp Ser Leu Leu His Ala Cys
```

```
                1               5                  10                  15

Ile Pro Cys

<210> SEQ ID NO 245
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Ser Gly Ser Gly Asn Glu Tyr Phe Asp Ser Leu Leu His Ala Cys Ile
1               5                  10                  15

Pro Cys Gln

<210> SEQ ID NO 246
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Ser Gly Ser Gly Glu Tyr Phe Asp Ser Leu Leu His Ala Cys Ile Pro
1               5                  10                  15

Cys Gln Leu

<210> SEQ ID NO 247
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Ser Gly Ser Gly Tyr Phe Asp Ser Leu Leu His Ala Cys Ile Pro Cys
1               5                  10                  15

Gln Leu Arg

<210> SEQ ID NO 248
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Ser Gly Ser Gly Phe Asp Ser Leu Leu His Ala Cys Ile Pro Cys Gln
1               5                  10                  15

Leu Arg Cys

<210> SEQ ID NO 249
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249
```

Ser Gly Ser Gly Asp Ser Leu Leu His Ala Cys Ile Pro Cys Gln Leu
1               5                   10                  15

Arg Cys Ser

<210> SEQ ID NO 250
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Ser Gly Ser Gly Ser Leu Leu His Ala Cys Ile Pro Cys Gln Leu Arg
1               5                   10                  15

Cys Ser Ser

<210> SEQ ID NO 251
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Ser Gly Ser Gly Leu Leu His Ala Cys Ile Pro Cys Gln Leu Arg Cys
1               5                   10                  15

Ser Ser Asn

<210> SEQ ID NO 252
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Ser Gly Ser Gly Leu His Ala Cys Ile Pro Cys Gln Leu Arg Cys Ser
1               5                   10                  15

Ser Asn Thr

<210> SEQ ID NO 253
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Ser Gly Ser Gly His Ala Cys Ile Pro Cys Gln Leu Arg Cys Ser Ser
1               5                   10                  15

Asn Thr Pro

<210> SEQ ID NO 254
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

```
Ser Gly Ser Gly Ala Cys Ile Pro Cys Gln Leu Arg Cys Ser Ser Asn
1               5                   10                  15

Thr Pro Pro

<210> SEQ ID NO 255
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Ser Gly Ser Gly Cys Ile Pro Cys Gln Leu Arg Cys Ser Ser Asn Thr
1               5                   10                  15

Pro Pro Leu

<210> SEQ ID NO 256
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Ser Gly Ser Gly Ile Pro Cys Gln Leu Arg Cys Ser Ser Asn Thr Pro
1               5                   10                  15

Pro Leu Thr

<210> SEQ ID NO 257
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Ser Gly Ser Gly Pro Cys Gln Leu Arg Cys Ser Ser Asn Thr Pro Pro
1               5                   10                  15

Leu Thr Cys

<210> SEQ ID NO 258
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Ser Gly Ser Gly Cys Gln Leu Arg Cys Ser Ser Asn Thr Pro Pro Leu
1               5                   10                  15

Thr Cys Gln

<210> SEQ ID NO 259
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 259

Ser Gly Ser Gly Gln Leu Arg Cys Ser Ser Asn Thr Pro Pro Leu Thr
1               5                   10                  15

Cys Gln Arg

<210> SEQ ID NO 260
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Ser Gly Ser Gly Leu Arg Cys Ser Ser Asn Thr Pro Pro Leu Thr Cys
1               5                   10                  15

Gln Arg Tyr

<210> SEQ ID NO 261
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Ser Gly Ser Gly Arg Cys Ser Ser Asn Thr Pro Pro Leu Thr Cys Gln
1               5                   10                  15

Arg Tyr Cys

<210> SEQ ID NO 262
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Ser Gly Ser Gly Cys Ser Ser Asn Thr Pro Pro Leu Thr Cys Gln Arg
1               5                   10                  15

Tyr Cys Asn

<210> SEQ ID NO 263
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Ser Gly Ser Gly Ser Ser Asn Thr Pro Pro Leu Thr Cys Gln Arg Tyr
1               5                   10                  15

Cys Asn Ala

<210> SEQ ID NO 264
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 264

Ser Gly Ser Gly Ser Asn Thr Pro Pro Leu Thr Cys Gln Arg Tyr Cys
1               5                   10                  15

Asn Ala Ser

<210> SEQ ID NO 265
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Ser Gly Ser Gly Asn Thr Pro Pro Leu Thr Cys Gln Arg Tyr Cys Asn
1               5                   10                  15

Ala Ser Val

<210> SEQ ID NO 266
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Ser Gly Ser Gly Thr Pro Pro Leu Thr Cys Gln Arg Tyr Cys Asn Ala
1               5                   10                  15

Ser Val Thr

<210> SEQ ID NO 267
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Ser Gly Ser Gly Pro Pro Leu Thr Cys Gln Arg Tyr Cys Asn Ala Ser
1               5                   10                  15

Val Thr Asn

<210> SEQ ID NO 268
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Ser Gly Ser Gly Pro Leu Thr Cys Gln Arg Tyr Cys Asn Ala Ser Val
1               5                   10                  15

Thr Asn Ser

<210> SEQ ID NO 269
<211> LENGTH: 19
<212> TYPE: PRT
<213> ORGANISM: Artificial Sequence
<220> FEATURE:
<223> OTHER INFORMATION: Description of Artificial Sequence: Synthetic

```
                              peptide

<400> SEQUENCE: 269

Ser Gly Ser Gly Leu Thr Cys Gln Arg Tyr Cys Asn Ala Ser Val Thr
1               5                   10                  15

Asn Ser Val

<210> SEQ ID NO 270
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Ser Gly Ser Gly Thr Cys Gln Arg Tyr Cys Asn Ala Ser Val Thr Asn
1               5                   10                  15

Ser Val Lys

<210> SEQ ID NO 271
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Ser Gly Ser Gly Cys Gln Arg Tyr Cys Asn Ala Ser Val Thr Asn Ser
1               5                   10                  15

Val Lys Gly

<210> SEQ ID NO 272
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Ser Gly Ser Gly Gln Arg Tyr Cys Asn Ala Ser Val Thr Asn Ser Val
1               5                   10                  15

Lys Gly Thr

<210> SEQ ID NO 273
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Ser Gly Ser Gly Arg Tyr Cys Asn Ala Ser Val Thr Asn Ser Val Lys
1               5                   10                  15

Gly Thr Asn

<210> SEQ ID NO 274
<211> LENGTH: 19
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 274

Ser Gly Ser Gly Tyr Cys Asn Ala Ser Val Thr Asn Ser Val Lys Gly
1               5                   10                  15

Thr Asn Ala

<210> SEQ ID NO 275
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Thr Ser Gly Gln Ala Gly Gln His His His His His Gly Ala Tyr
1               5                   10                  15

Pro Tyr Asp Val Pro Asp Tyr Ala Ser
            20                  25

<210> SEQ ID NO 276
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276
actagtggcc aggccggcca gcaccatcac catcaccatg gcgcataccc gtacgacgtt      60
ccggactacg cttct                                                      75

<210> SEQ ID NO 277
<211> LENGTH: 4
<212> TYPE: PRT
<213> ORGANISM: Homo sapiens

<400> SEQUENCE: 277

Tyr Val Lys Met
1

<210> SEQ ID NO 278
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Ser Gly Ser Gly
1

<210> SEQ ID NO 279
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Gly Ser Ser Ser Ser
```

```
<210> SEQ ID NO 280
<211> LENGTH: 53
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 280

Leu Gln Met Ala Gly Gln Cys Ser Gln Asn Glu Tyr Phe Asp Ser Leu
1               5                   10                  15

Leu His Ala Cys Ile Pro Cys Gln Leu Arg Cys Ser Ser Asn Thr Pro
            20                  25                  30

Pro Leu Thr Cys Gln Arg Tyr Cys Asn Ala Ser Val Thr Asn Ser Val
        35                  40                  45

Lys Gly Thr Asn Ala
    50
```

CHIMERIC ANTIGEN RECEPTORS TARGETING B-CELL MATURATION ANTIGEN AND USES THEREOF

CROSS-REFERENCE TO RELATED APPLICATIONS

This application is a Continuation of International Application Serial No. PCT/US2015/064112, filed Dec. 4, 2015, which claims priority to U.S. Provisional Patent Application Ser. No. 62/088,309, filed Dec. 5, 2014, the contents of each of which are incorporated by reference in their entirety, and to each of which priority is claimed.

SEQUENCE LISTING

The specification further incorporates by reference the Sequence Listing submitted herewith via EFS on Jun. 5, 2017. Pursuant to 37 C.F.R. § 1.52(e)(5), the Sequence Listing text file, identified as 072734_036000N_SL.txt, is 234,825 bytes and was created on Jun. 5, 2017. The Sequence Listing electronically filed herewith, does not extend beyond the scope of the specification and thus does not contain new matter.

INTRODUCTION

The presently disclosed subject matter provides for methods and compositions for treating cancer. It relates to chimeric antigen receptors (CARs) that specifically target B-cell maturation antigen (BCMA), immunoresponsive cells comprising such CARs, and methods of using such cells for treating cancer (e.g., multiple myeloma).

BACKGROUND OF THE INVENTION

Cell-based immunotherapy is a therapy with curative potential for the treatment of cancer. T cells and other immune cells may be modified to target tumor antigens through the introduction of genetic material coding for artificial or synthetic receptors for antigen, termed Chimeric Antigen Receptors (CARs), specific to selected antigens. Targeted T cell therapy using CARs has shown recent clinical success in treating hematologic malignancies.

Multiple myeloma (MM) is the second most common hematologic malignancy.[8] Approximately 25% of patients have high-risk cytogenetics, which portends a median survival of less then 2 years.[9,10] While recent strides have been made, regardless of cytogenetics, the disease is still considered incurable outside the immuno-therapeutic graft versus myeloma (GvM) effect of an allogeneic transplant. However, allogeneic transplants are limited by ineligibility and high rates of transplant-associated morbidity and mortality.[11] Similar to the GvM effect, a potentially curative T cell effect may be achieved with minimal toxicity through autologous adoptive T cell therapy.

Myeloma may be an ideal disease to test adoptive T cell therapy. First, as indicated above, allogeneic transplants demonstrate that the T cell can be a curative treatment, even with minimal or no concomitant chemotherapy such as after non-myeloablative transplants or post-transplantation donor lymphocyte infusions. Second, conditioning chemotherapy, possibly through the mechanism of depleting regulatory T cells (Tregs), enhances the efficacy of adoptive T cell therapy,[4,12] as such, the immediate post-autologous transplant period could be an optimal time to administer T cells, and myeloma is one of the few diseases where autologous stem cell transplantation is the standard of care. Third, the immunomodulatory drug lenalidomide may improve CAR based therapy, as has been shown in mice,[13] and lenalidomide is commonly used to treat MM. Fourth, adoptive T cell therapy works best in bone marrow predominant disease such as ALL,[6,7] when compared to solid tumors or extra-medullary CLL,[4] and similar to ALL, myeloma is a disease of the bone marrow.

While there are various reasons to expect that adoptive T cell therapy may work well in MM, expanding adoptive T cell therapy to myeloma also poses unique challenges. Unlike other B-cell malignancies, CD19 expression is seen in only 2% of myeloma patients.[14] Furthermore, unlike CD19, the common extracellular immunophenotypic markers in myeloma (CD138, CD38, and CD56) are all co-expressed on other essential cell types, and we predict CARs to any of these targets would lead to unacceptable "off tumor, on target" toxicity[6] which can be fatal even in targets where antibodies are well tolerated, as was the case with a HER2 targeted CAR.[15] Accordingly, there are needs for novel therapeutic strategies to design CARs targeting antigens that are highly expressed in MM cells and limited expression in normal tissues for treating multiple myeloma, which strategies capable of inducing potent tumor eradication with minimal toxicity and immunogenicity.

SUMMARY OF THE INVENTION

The presently disclosed subject matter generally provides chimeric antigen receptors (CARs) that specifically target B-cell maturation antigen (BCMA), immunoresponsive cells comprising such CARs, and uses of these CARs and immunoresponsive cells for treating multiple myeloma.

The presently disclosed subject matter provides CARs. In one non-limiting example, the CAR comprises an extracellular antigen-binding domain, a transmembrane domain and an intracellular domain, where the extracellular antigen-binding domain is a human single-chain variable fragment (scFv) that specifically binds to B cell maturation antigen (BMCA). In certain embodiments, the human scFv specifically binds to BCMA with a binding affinity ($K_D$) of from about $1 \times 10^{-9}$ M to about $3 \times 10^{-6}$ M. In certain embodiments, the human scFv specifically binds to BCMA with a binding affinity ($K_D$) of from about $1 \times 10^{-9}$ M to about $1 \times 10^{-8}$ M.

In certain embodiments, the human scFv comprises a heavy chain variable region comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to an amino acid sequence selected from the group consisting of SEQ ID NOS: 1, 5, 9, 13, 17, 21, 25, 29, 33, 37, 41, 45, 49, 53, 57, 61, and 65.

In certain embodiments, the human scFv comprises a light chain variable region comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to an amino acid sequence selected from the group consisting of SEQ ID NOS: 2, 6, 10, 14, 18, 22, 26, 30, 34, 38, 42, 46, 50, 54, 58, 62, and 66.

In certain embodiments, the human scFv comprises (a) a heavy chain variable region comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to an amino acid sequence selected from the group consisting of SEQ ID NO: 1, 5, 9, 13, 17, 21, 25, 29, 33, 37, 41, 45, 49, 53, 57, 61, and 65; and (b) a light chain variable region comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to an amino acid sequence selected from the group consisting of SEQ ID NOS: 2, 6, 10, 14, 18, 22, 26, 30, 34, 38, 42, 46, 50, 54, 58, 62, and 66.

In certain embodiments, the human scFv comprises a heavy chain variable region comprising an amino acid sequence selected from the group consisting of SEQ ID NOS: 1, 5, 9, 13, 17, 21, 25, 29, 33, 37, 41, 45, 49, 53, 57, 61, and 65, and conservative modifications thereof.

In certain embodiments, the human scFv comprises a light chain variable region comprising an amino acid sequence selected from the group consisting of SEQ ID NOS: 2, 6, 10, 14, 18, 22, 26, 30, 34, 38, 42, 46, 50, 54, 58, 62, and 66, and conservative modifications thereof.

In certain embodiments, the human scFv comprises (a) a heavy chain variable region comprising an amino acid sequence selected from the group consisting of SEQ ID NOS: 1, 5, 9, 13, 17, 21, 25, 29, 33, 37, 41, 45, 49, 53, 57, 61, and 65, and conservative modifications thereof, and (b) a light chain variable region comprising an amino acid sequence selected from the group consisting of SEQ ID NOS: 2, 6, 10, 14, 18, 22, 26, 30, 34, 38, 42, 46, 50, 54, 58, 62, and 66, and conservative modifications thereof.

In certain embodiments, the human scFv comprises a heavy chain variable region comprising amino acids having a sequence selected from the group consisting of: SEQ ID NOS:1, 5, 9, 13, 17, 21, 25, 29, 33, 37, 41, 45, 49, 53, 57, 61, and 65. In certain embodiments, the human scFv comprises a light chain variable region comprising amino acids having a sequence selected from the group consisting of: SEQ ID NOS:2, 6, 10, 14, 18, 22, 26, 30, 34, 38, 42, 46, 50, 54, 58, 62, and 66. In certain embodiments, the human scFv comprises a heavy chain variable region comprising amino acids having the sequence set forth in SEQ ID NO:21. In certain embodiments, the human scFv comprises a heavy chain variable region comprising amino acids having the sequence set forth in SEQ ID NO:53. In certain embodiments, the human scFv comprises a heavy chain variable region comprising amino acids having the sequence set forth in SEQ ID NO:57. In certain embodiments, the human scFv comprises a heavy chain variable region comprising amino acids having the sequence set forth in SEQ ID NO:61. In certain embodiments, the human scFv comprises a heavy chain variable region comprising amino acids having the sequence set forth in SEQ ID NO:65. In certain embodiments, the human scFv comprises a light chain variable region comprising amino acids having the sequence set forth in SEQ ID NO:22. In certain embodiments, the human scFv comprises a light chain variable region comprising amino acids having the sequence set forth in SEQ ID NO:54. In certain embodiments, the human scFv comprises a light chain variable region comprising amino acids having the sequence set forth in SEQ ID NO:58. In certain embodiments, the human scFv comprises a light chain variable region comprising amino acids having the sequence set forth in SEQ ID NO:62. In certain embodiments, the human scFv comprises a light chain variable region comprising amino acids having the sequence set forth in SEQ ID NO:66. In certain embodiments, the extracellular antigen-binding domain comprises (a) a heavy chain variable region comprising amino acids having a sequence set forth in SEQ ID NO:1, and a light chain variable region comprising amino acids having a sequence set forth in SEQ ID NO:2; (b) a heavy chain variable region comprising amino acids having a sequence set forth in SEQ ID NO:5, and a light chain variable region comprising amino acids having a sequence set forth in SEQ ID NO:6; (c) a heavy chain variable region comprising amino acids having a sequence set forth in SEQ ID NO:9, and a light chain variable region comprising amino acids having a sequence set forth in SEQ ID NO:10; (d) a heavy chain variable region comprising amino acids having a sequence set forth in SEQ ID NO:13, and a light chain variable region comprising amino acids having a sequence set forth in SEQ ID NO:14; (e) a heavy chain variable region comprising amino acids having a sequence set forth in SEQ ID NO:17, and a light chain variable region comprising amino acids having a sequence set forth in SEQ ID NO:18; (f) a heavy chain variable region comprising amino acids having a sequence set forth in SEQ ID NO:21, and a light chain variable region comprising amino acids having a sequence set forth in SEQ ID NO:22; (g) a heavy chain variable region comprising amino acids having a sequence set forth in SEQ ID NO:25, and a light chain variable region comprising amino acids having a sequence set forth in SEQ ID NO:26; (h) a heavy chain variable region comprising amino acids having a sequence set forth in SEQ ID NO:29, and a light chain variable region comprising amino acids having a sequence set forth in SEQ ID NO:30; (i) a heavy chain variable region comprising amino acids having a sequence set forth in SEQ ID NO:33, and a light chain variable region comprising amino acids having a sequence set forth in SEQ ID NO:34; (j) a heavy chain variable region comprising amino acids having a sequence set forth in SEQ ID NO:37, and a light chain variable region comprising amino acids having a sequence set forth in SEQ ID NO:38; (k) a heavy chain variable region comprising amino acids having a sequence set forth in SEQ ID NO:41, and a light chain variable region comprising amino acids having a sequence set forth in SEQ ID NO:42; (l) a heavy chain variable region comprising amino acids having a sequence set forth in SEQ ID NO:45, and a light chain variable region comprising amino acids having a sequence set forth in SEQ ID NO:46; (m) a heavy chain variable region comprising amino acids having a sequence set forth in SEQ ID NO:49, and a light chain variable region comprising amino acids having a sequence set forth in SEQ ID NO:50; (n) a heavy chain variable region comprising amino acids having a sequence set forth in SEQ ID NO:53, and a light chain variable region comprising amino acids having a sequence set forth in SEQ ID NO:54; (o) a heavy chain variable region comprising amino acids having a sequence set forth in SEQ ID NO:57, and a light chain variable region comprising amino acids having a sequence set forth in SEQ ID NO:58; (p) a heavy chain variable region comprising amino acids having a sequence set forth in SEQ ID NO:61, and a light chain variable region comprising amino acids having a sequence set forth in SEQ ID NO:62; or (q) a heavy chain variable region comprising amino acids having a sequence set forth in SEQ ID NO:65, and a light chain variable region comprising amino acids having a sequence set forth in SEQ ID NO:66. In certain embodiments, the human scFv comprises a heavy chain variable region comprising amino acids having the sequence set forth in SEQ ID NO:21; and a light chain variable region comprising amino acids having the sequence set forth in SEQ ID NO:22. In certain embodiments, the human scFv comprises a heavy chain variable region comprising amino acids having the sequence set forth in SEQ ID NO:53; and a light chain variable region comprising amino acids having the sequence set forth in SEQ ID NO:54. In certain embodiments, the human scFv comprises a heavy chain variable region comprising amino acids having the sequence set forth in SEQ ID NO:57; and a light chain variable region comprising amino acids having the sequence set forth in SEQ ID NO:58. In certain embodiments, the human scFv comprises a heavy chain variable region comprising amino acids having the sequence set forth in SEQ ID NO:61; and a light chain variable region comprising amino acids having the sequence set forth in SEQ ID NO:62. In certain embodiments, the human scFv comprises a heavy chain variable region comprising amino acids having the sequence set forth in SEQ ID NO:65; and a light chain variable region comprising amino acids having the sequence set forth in SEQ ID NO:66.

In certain non-limiting embodiments, the human scFv comprises both of said heavy and light chains, optionally with a linker sequence, for example a linker peptide, between the heavy chain variable region and the light chain variable region. For example, in certain non-limiting embodiments, the human scFv comprises (i) a heavy chain variable region comprising amino acids having the sequence set forth in SEQ ID NO:53 and (ii) a light chain variable region comprising amino acids having the sequence set forth in SEQ ID NO:54, optionally with (iii) a linker sequence, for example a linker peptide, between the heavy chain variable region and the light chain variable region. In certain embodiments, the human scFv comprises (i) a heavy chain variable region comprising amino acids having the sequence set forth in SEQ ID NO:21 and (ii) a light chain variable region comprising amino acids having the sequence set forth in SEQ ID NO:22, optionally with (iii) a linker sequence, for example a linker peptide, between the heavy chain variable region and the light chain variable region. In certain embodiments, the human scFv comprises (i) a heavy chain variable region comprising amino acids having the sequence set forth in SEQ ID NO:57 and (ii) a light chain variable region comprising amino acids having the sequence set forth in SEQ ID NO:58, optionally with (iii) a linker sequence, for example a linker peptide, between the heavy chain variable region and the light chain variable region. In certain embodiments, the human scFv comprises (i) a heavy chain variable region comprising amino acids having the sequence set forth in SEQ ID NO:61 and (ii) a light chain variable region comprising amino acids having the sequence set forth in SEQ ID NO:62, optionally with (iii) a linker sequence, for example a linker peptide, between the heavy chain variable region and the light chain variable region. In certain embodiments, the human scFv comprises (i) a heavy chain variable region comprising amino acids having the sequence set forth in SEQ ID NO:65 and (ii) a light chain variable region comprising amino acids having the sequence set forth in SEQ ID NO:66, optionally with (iii) a linker sequence, for example a linker peptide, between the heavy chain variable region and the light chain variable region.

In certain embodiments, the human scFv comprises (a) a heavy chain variable region CDR3 comprising an amino acid sequence selected from the group consisting of SEQ ID NOS: 91, 97, 103, 109, 115, 121, 127, 133, 139, 145, 151, 157, 163, 169, 175, 181, and 187; and (b) a light chain variable region CDR3 comprising an amino acid sequence selected from the group consisting of SEQ ID NOS: 94, 100, 106, 112, 118, 124, 130, 136, 142, 148, 154, 160, 166, 172, 178, 184, and 190.

In certain embodiments, the human scFv comprises (a) a heavy chain variable region CDR2 comprising an amino acid sequence selected from the group consisting of SEQ ID NOs: 90, 96, 102, 108, 114, 120, 126, 132, 138, 144, 150, 156, 162, 168, 174, 180, and 186, and conservative modifications thereof and (b) a light chain variable region CDR2 comprising an amino acid sequence selected from the group consisting of SEQ ID NOS: 93, 99, 105, 111, 117, 123, 129, 135, 141, 147, 153, 159, 165, 171, 177, 183, and 189, and conservative modifications thereof.

In certain embodiments, the human scFv comprises (a) a heavy chain variable region CDR1 comprising an amino acid sequence selected from the group consisting of SEQ ID NOs: 89, 95, 101, 107, 113, 119, 125, 131, 137, 143, 149, 155, 161, 167, 173, 179, and 185, and conservative modifications thereof and (b) a light chain variable region CDR1 comprising an amino acid sequence selected from the group consisting of SEQ ID NOS: 92, 98, 104, 110, 116, 122, 128, 134, 140, 146, 152, 158, 164, 170, 176, 182, and 188, and conservative modifications thereof. In certain embodiments, the human scFv comprises: (a) a heavy chain variable region CDR1 comprising an amino acid sequence selected from the group consisting of SEQ ID NOS: 89, 95, 101, 107, 113, 119, 125, 131, 137, 143, 149, 155, 161, 167, 173, 179, and 185; (b) a heavy chain variable region CDR2 comprising an amino acid sequence selected from the group consisting of SEQ ID NOs: 90, 96, 102, 108, 114, 120, 126, 132, 138, 144, 150, 156, 162, 168, 174, 180, and 186; (c) a heavy chain variable region CDR3 comprising an amino acid sequence selected from the group consisting of SEQ ID NOS: 91, 97, 103, 109, 115, 121, 127, 133, 139, 145, 151, 157, 163, 169, 175, 181, and 187; (d) a light chain variable region CDR1 comprising an amino acid sequence selected from the group consisting of SEQ ID NOs: 92, 98, 104, 110, 116, 122, 128, 134, 140, 146, 152, 158, 164, 170, 176, 182, and 188; (e) a light chain variable region CDR2 comprising an amino acid sequence selected from the group consisting of SEQ ID NOs: 93, 99, 105, 111, 117, 123, 129, 135, 141, 147, 153, 159, 165, 171, 177, 183, and 189; and (f) a light chain variable region CDR3 comprising an amino acid sequence selected from the group consisting of SEQ ID NOs: 94, 100, 106, 112, 118, 124, 130, 136, 142, 148, 154, 160, 166, 172, 178, 184, and 190. In certain embodiments, the human scFv comprises (a) a heavy chain variable region CDR1 comprising amino acids having the sequence set forth in SEQ ID NO: 89 or conservative modifications thereof; a heavy chain variable region CDR2 comprising amino acids having the sequence set forth in SEQ ID NO: 90 or conservative modifications thereof; and a heavy chain variable region CDR3 comprising amino acids having the sequence set forth in SEQ ID NO: 91 or conservative modifications thereof; (b) a heavy chain variable region CDR1 comprising amino acids having the sequence set forth in SEQ ID NO: 95 or conservative modifications thereof; a heavy chain variable region CDR2 comprising amino acids having the sequence set forth in SEQ ID NO: 96 or conservative modifications thereof; and a heavy chain variable region CDR3 comprising amino acids having the sequence set forth in SEQ ID NO: 97 or conservative modifications thereof; (c) a heavy chain variable region CDR1 comprising amino acids having the sequence set forth in SEQ ID NO: 101 or conservative modifications thereof; a heavy chain variable region CDR2 comprising amino acids having the sequence set forth in SEQ ID NO: 102 or conservative modifications thereof; and a heavy chain variable region CDR3 comprising amino acids having the sequence set forth in SEQ ID NO: 103 or conservative modifications thereof; (d) a heavy chain variable region CDR1 comprising amino acids having the sequence set forth in SEQ ID NO: 107 or conservative modifications thereof; a heavy chain variable region CDR2 comprising amino acids having the sequence set forth in SEQ ID NO: 108 or conservative modifications thereof; and a heavy chain variable region CDR3 comprising amino acids having the sequence set forth in SEQ ID NO: 109 or conservative modifications thereof; (e) a heavy chain variable region CDR1 comprising amino acids having the sequence set forth in SEQ ID NO: 113 or conservative modifications thereof; a heavy chain variable region CDR2 comprising amino acids having the sequence set forth in SEQ ID NO: 114 or conservative modifications thereof; and a heavy chain variable region CDR3 comprising amino acids having the sequence set forth in SEQ ID NO: 115 or conservative modifications thereof; (f) a heavy chain variable region CDR1 comprising amino acids having the sequence set forth in SEQ ID NO: 119 or conservative modifications thereof; a heavy chain variable region CDR2 comprising amino acids having the sequence set forth in SEQ ID NO: 120 or conservative modifications thereof; and a heavy chain variable region CDR3 comprising amino acids having the sequence set forth in SEQ ID NO: 121 or conservative modifications thereof; (g) a heavy chain variable region CDR1 comprising amino acids having the sequence set forth in SEQ ID NO: 125 or conservative modifications thereof; a heavy chain variable region CDR2 comprising amino acids having the sequence set forth in SEQ ID NO: 126 or conservative modifications thereof; and a heavy chain variable region CDR3 comprising amino acids having the sequence set forth in SEQ ID NO: 127 or conservative modifications thereof; (h) a heavy chain variable region CDR1 comprising amino acids having the sequence set forth in SEQ ID NO: 131 or conservative modifications thereof; a heavy chain variable region CDR2 comprising amino acids having the sequence set forth in SEQ ID NO: 132 or conservative modifications thereof; and a heavy chain variable region CDR3 comprising amino acids having the sequence set forth in SEQ ID NO: 133 or conservative modifications thereof; (i) a heavy chain variable region CDR1 comprising amino acids having the sequence set forth in SEQ ID NO: 137 or conservative modifications thereof; a heavy chain variable region CDR2 comprising amino acids having the sequence set forth in SEQ ID NO: 138 or conservative modifications thereof; and a heavy chain variable region CDR3 comprising amino acids having the sequence set forth in SEQ ID NO: 139 or conservative modifications thereof; (j) a heavy chain variable region CDR1 comprising amino acids having the sequence set forth in SEQ ID NO: 143 or conservative modifications thereof; a heavy chain variable region CDR2 comprising amino acids having the sequence set forth in SEQ ID NO: 144 or conservative modifications thereof; and a heavy chain variable region CDR3 comprising amino acids having the sequence set forth in SEQ ID NO: 145 or conservative modifications thereof; (k) a heavy chain variable region CDR1 comprising amino acids having the sequence set forth in SEQ ID NO: 149 or conservative modifications thereof; a heavy chain variable region CDR2 comprising amino acids having the sequence set forth in SEQ ID NO: 150 or conservative modifications thereof; and a heavy chain variable region CDR3 comprising amino acids having the sequence set forth in SEQ ID NO: 151 or conservative modifications thereof; (l) a heavy chain variable region CDR1 comprising amino acids having the sequence set forth in SEQ ID NO: 155 or conservative modifications thereof; a heavy chain variable region CDR2 comprising amino acids having the sequence set forth in SEQ ID NO: 156 or conservative modifications thereof; and a heavy chain variable region CDR3 comprising amino acids having the sequence set forth in SEQ ID NO: 157 or conservative modifications thereof; (m) a heavy chain variable region CDR1 comprising amino acids having the sequence set forth in SEQ ID NO: 161 or conservative modifications thereof; a heavy chain variable region CDR2 comprising amino acids having the sequence set forth in SEQ ID NO: 162 or conservative modifications thereof; and a heavy chain variable region CDR3 comprising amino acids having the sequence set forth in SEQ ID NO: 163 or conservative modifications thereof; (n) a heavy chain variable region CDR1 comprising amino acids having the sequence set forth in SEQ ID NO: 167 or conservative modifications thereof; a heavy chain variable region CDR2 comprising amino acids having the sequence set forth in SEQ ID NO: 168 or conservative modifications thereof; and a heavy chain variable region CDR3 comprising amino acids having the sequence set forth in SEQ ID NO: 169 or conservative modifications thereof; (o) a heavy chain variable region CDR1 comprising amino acids having the sequence set forth in SEQ ID NO: 173 or conservative modifications thereof; a heavy chain variable region CDR2 comprising amino acids having the sequence set forth in SEQ ID NO: 174 or conservative modifications thereof; and a heavy chain variable region CDR3 comprising amino acids having the sequence set forth in SEQ ID NO: 175 or conservative modifications thereof; (p) a heavy chain variable region CDR1 comprising amino acids having the sequence set forth in SEQ ID NO: 179 or conservative modifications thereof; a heavy chain variable region CDR2 comprising amino acids having the sequence set forth in SEQ ID NO:180 or conservative modifications thereof; and a heavy chain variable region CDR3 comprising amino acids having the sequence set forth in SEQ ID NO: 181 or conservative modifications thereof; or (q) a heavy chain variable region CDR1 comprising amino acids having the sequence set forth in SEQ ID NO: 185 or conservative modifications thereof; a heavy chain variable region CDR2 comprising amino acids having the sequence set forth in SEQ ID NO: 186 or conservative modifications thereof; and a heavy chain variable region CDR3 comprising amino acids having the sequence set forth in SEQ ID NO: 187 or conservative modifications thereof. In certain embodiments, the human scFv comprises: a heavy chain variable region CDR1 comprising amino acids having the sequence set forth in SEQ ID NO: 167; a heavy chain variable region CDR2 comprising amino acids having the sequence set forth in SEQ ID NO: 168; and a heavy chain variable region CDR3 comprising amino acids having the sequence set forth in SEQ ID NO: 169. In certain embodiments, the human scFv comprises: a heavy chain variable region CDR1 comprising amino acids having the sequence set forth in SEQ ID NO: 119; a heavy chain variable region CDR2 comprising amino acids having the sequence set forth in SEQ ID NO: 120; and a heavy chain variable region CDR3 comprising amino acids having the sequence set forth in SEQ ID NO: 121. In certain embodiments, the human scFv comprises: a heavy chain variable region CDR1 comprising amino acids having the sequence set forth in SEQ ID NO: 173; a heavy chain variable region CDR2 comprising amino acids having the sequence set forth in SEQ ID NO: 174; and a heavy chain variable region CDR3 comprising amino acids having the sequence set forth in SEQ ID NO: 175. In certain embodiments, the human scFv comprises: a heavy chain variable region CDR1 comprising amino acids having the sequence set forth in SEQ ID NO: 179; a heavy chain variable region CDR2 comprising amino acids having the sequence set forth in SEQ ID NO: 180; and a heavy chain variable region CDR3 comprising amino acids having the sequence set forth in SEQ ID NO: 181. In certain embodiments, the human scFv comprises: a heavy chain variable region CDR1 comprising amino acids having the sequence set forth in SEQ ID NO: 185; a heavy chain variable region CDR2 comprising amino acids having the sequence set forth in SEQ ID NO: 186; and a heavy chain variable region CDR3 comprising amino acids having the sequence set forth in SEQ ID NO: 187.

In certain embodiments, the human scFv comprises (a) a light chain variable region CDR1 comprising amino acids having the sequence set forth in SEQ ID NO: 92 or conservative modifications thereof; a light chain variable region CDR2 comprising amino acids having the sequence set forth in SEQ ID NO:93 or conservative modifications thereof; and a light chain variable region CDR3 comprising amino acids having the sequence set forth in SEQ ID NO: 94 or conservative modifications thereof; (b) a light chain variable region CDR1 comprising amino acids having the sequence set forth in SEQ ID NO: 98 or conservative modifications thereof; a light chain variable region CDR2 comprising amino acids having the sequence set forth in SEQ ID NO:99 or conservative modifications thereof; and a light chain variable region CDR3 comprising amino acids having the sequence set forth in SEQ ID NO: 100 or conservative modifications thereof; (c) a light chain variable region CDR1 comprising amino acids having the sequence set forth in SEQ ID NO: 104 or conservative modifications thereof; a light chain variable region CDR2 comprising amino acids having the sequence set forth in SEQ ID NO:105 or conservative modifications thereof; and a light chain variable region CDR3 comprising amino acids having the sequence set forth in SEQ ID NO: 106 or conservative modifications thereof; (d) a light chain variable region CDR1 comprising amino acids having the sequence set forth in SEQ ID NO: 110 or conservative modifications thereof; a light chain variable region CDR2 comprising amino acids having the sequence set forth in SEQ ID NO:111 or conservative modifications thereof; and a light chain variable region CDR3 comprising amino acids having the sequence set forth in SEQ ID NO: 112 or conservative modifications thereof; (e) a light chain variable region CDR1 comprising amino acids having the sequence set forth in SEQ ID NO: 116 or conservative modifications thereof; a light chain variable region CDR2 comprising amino acids having the sequence set forth in SEQ ID NO:117 or conservative modifications thereof; and a light chain variable region CDR3 comprising amino acids having the sequence set forth in SEQ ID NO: 118 or conservative modifications thereof; (f) a light chain variable region CDR1 comprising amino acids having the sequence set forth in SEQ ID NO: 122 or conservative modifications thereof; a light chain variable region CDR2 comprising amino acids having the sequence set forth in SEQ ID NO:123 or conservative modifications thereof; and a light chain variable region CDR3 comprising amino acids having the sequence set forth in SEQ ID NO: 124 or conservative modifications thereof; (g) a light chain variable region CDR1 comprising amino acids having the sequence set forth in SEQ ID NO: 128 or conservative modifications thereof; a light chain variable region CDR2 comprising amino acids having the sequence set forth in SEQ ID NO:129 or conservative modifications thereof; and a light chain variable region CDR3 comprising amino acids having the sequence set forth in SEQ ID NO: 130 or conservative modifications thereof; (h) a light chain variable region CDR1 comprising amino acids having the sequence set forth in SEQ ID NO: 134 or conservative modifications thereof; a light chain variable region CDR2 comprising amino acids having the sequence set forth in SEQ ID NO:135 or conservative modifications thereof; and a light chain variable region CDR3 comprising amino acids having the sequence set forth in SEQ ID NO: 136 or conservative modifications thereof; (i) a light chain variable region CDR1 comprising amino acids having the sequence set forth in SEQ ID NO: 140 or conservative modifications thereof; a light chain variable region CDR2 comprising amino acids having the sequence set forth in SEQ ID NO:141 or conservative modifications thereof; and a light chain variable region CDR3 comprising amino acids having the sequence set forth in SEQ ID NO: 142 or conservative modifications thereof; (j) a light chain variable region CDR1 comprising amino acids having the sequence set forth in SEQ ID NO: 146 or conservative modifications thereof; a light chain variable region CDR2 comprising amino acids having the sequence set forth in SEQ ID NO:147 or conservative modifications thereof; and a light chain variable region CDR3 comprising amino acids having the sequence set forth in SEQ ID NO: 148 or conservative modifications thereof; (k) a light chain variable region CDR1 comprising amino acids having the sequence set forth in SEQ ID NO: 152 or conservative modifications thereof; a light chain variable region CDR2 comprising amino acids having the sequence set forth in SEQ ID NO:153 or conservative modifications thereof; and a light chain variable region CDR3 comprising amino acids having the sequence set forth in SEQ ID NO: 154 or conservative modifications thereof; (l) a light chain variable region CDR1 comprising amino acids having the sequence set forth in SEQ ID NO: 158 or conservative modifications thereof; a light chain variable region CDR2 comprising amino acids having the sequence set forth in SEQ ID NO:159 or conservative modifications thereof; and a light chain variable region CDR3 comprising amino acids having the sequence set forth in SEQ ID NO: 160 or conservative modifications thereof; (m) a light chain variable region CDR1 comprising amino acids having the sequence set forth in SEQ ID NO: 164 or conservative modifications thereof; a light chain variable region CDR2 comprising amino acids having the sequence set forth in SEQ ID NO:165 or conservative modifications thereof; and a light chain variable region CDR3 comprising amino acids having the sequence set forth in SEQ ID NO: 166 or conservative modifications thereof; (n) a light chain variable region CDR1 comprising amino acids having the sequence set forth in SEQ ID NO: 170 or conservative modifications thereof; a light chain variable region CDR2 comprising amino acids having the sequence set forth in SEQ ID NO: 171 or conservative modifications thereof; and a light chain variable region CDR3 comprising amino acids having the sequence set forth in SEQ ID NO: 172 or conservative modifications thereof; (o) a light chain variable region CDR1 comprising amino acids having the sequence set forth in SEQ ID NO: 176 or conservative modifications thereof; a light chain variable region CDR2 comprising amino acids having the sequence set forth in SEQ ID NO: 177 or conservative modifications thereof; and a light chain variable region CDR3 comprising amino acids having the sequence set forth in SEQ ID NO: 178 or conservative modifications thereof; (p) a light chain variable region CDR1 comprising amino acids having the sequence set forth in SEQ ID NO: 182 or conservative modifications thereof; a light chain variable region CDR2 comprising amino acids having the sequence set forth in SEQ ID NO: 183 or conservative modifications thereof; and a light chain variable region CDR3 comprising amino acids having the sequence set forth in SEQ ID NO: 184 or conservative modifications thereof; or (q) a light chain variable region CDR1 comprising amino acids having the sequence set forth in SEQ ID NO: 188 or conservative modifications thereof; a light chain variable region CDR2 comprising amino acids having the sequence set forth in SEQ ID NO: 189 or conservative modifications thereof; and a light chain variable region CDR3 comprising amino acids having the sequence set forth in SEQ ID NO: 190 or conservative modifications thereof. In certain embodiments, the human scFv comprises: a light chain variable region CDR1 comprising amino acids having the sequence set forth in SEQ ID NO: 122; a light chain variable region CDR2 comprising amino acids having the sequence set forth in SEQ ID NO: 123; and a light chain variable region CDR3 comprising amino acids having the sequence set forth in SEQ ID NO: 124. In certain embodiments, the human scFv comprises: a light chain variable region CDR1 comprising amino acids having the sequence set forth in SEQ ID NO: 170; a light chain variable region CDR2 comprising amino acids having the sequence set forth in SEQ ID NO: 171; and a light chain variable region CDR3 comprising amino acids having the sequence set forth in SEQ ID NO: 172. In certain embodiments, the human scFv comprises: a light chain variable region CDR1 comprising amino acids having the sequence set forth in SEQ ID NO: 176; a light chain variable region CDR2 comprising amino acids having the sequence set forth in SEQ ID NO: 177; and a light chain variable region CDR3 comprising amino acids having the sequence set forth in SEQ ID NO: 178. In certain embodiments, the human scFv comprises: a light chain variable region CDR1 comprising amino acids having the sequence set forth in SEQ ID NO: 182; a light chain variable region CDR2 comprising amino acids having the sequence set forth in SEQ ID NO: 183; and a light chain variable region CDR3 comprising amino acids having the sequence set forth in SEQ ID NO: 184. In certain embodiments, the human scFv comprises: a light chain variable region CDR1 comprising amino acids having the sequence set forth in SEQ ID NO: 188; a light chain variable region CDR2 comprising amino acids having the sequence set forth in SEQ ID NO: 189; and a light chain variable region CDR3 comprising amino acids having the sequence set forth in SEQ ID NO: 190.

In certain embodiments, the human scFv comprises: (a) a heavy chain variable region CDR1 comprising amino acids having the sequence set forth in SEQ ID NO: 89; a heavy chain variable region CDR2 comprising amino acids having the sequence set forth in SEQ ID NO: 90; a heavy chain variable region CDR3 comprising amino acids having the sequence set forth in SEQ ID NO: 91; a light chain variable region CDR1 comprising amino acids having the sequence set forth in SEQ ID NO: 92; a light chain variable region CDR2 comprising amino acids having the sequence set forth in SEQ ID NO: 93; and a light chain variable region CDR3 comprising amino acids having the sequence set forth in SEQ ID NO: 94; (b) a heavy chain variable region CDR1 comprising amino acids having the sequence set forth in SEQ ID NO: 95; a heavy chain variable region CDR2 comprising amino acids having the sequence set forth in SEQ ID NO: 96; a heavy chain variable region CDR3 comprising amino acids having the sequence set forth in SEQ ID NO: 97; a light chain variable region CDR1 comprising amino acids having the sequence set forth in SEQ ID NO: 98; a light chain variable region CDR2 comprising amino acids having the sequence set forth in SEQ ID NO: 99; and a light chain variable region CDR3 comprising amino acids having the sequence set forth in SEQ ID NO: 100; (c) a heavy chain variable region CDR1 comprising amino acids having the sequence set forth in SEQ ID NO: 101; a heavy chain variable region CDR2 comprising amino acids having the sequence set forth in SEQ ID NO: 102; a heavy chain variable region CDR3 comprising amino acids having the sequence set forth in SEQ ID NO: 103; a light chain variable region CDR1 comprising amino acids having the sequence set forth in SEQ ID NO: 104; a light chain variable region CDR2 comprising amino acids having the sequence set forth in SEQ ID NO: 105; and a light chain variable region CDR3 comprising amino acids having the sequence set forth in SEQ ID NO: 106; (d) a heavy chain variable region CDR1 comprising amino acids having the sequence set forth in SEQ ID NO: 107; a heavy chain variable region CDR2 comprising amino acids having the sequence set forth in SEQ ID NO: 108; a heavy chain variable region CDR3 comprising amino acids having the sequence set forth in SEQ ID NO: 109; a light chain variable region CDR1 comprising amino acids having the sequence set forth in SEQ ID NO: 110; a light chain variable region CDR2 comprising amino acids having the sequence set forth in SEQ ID NO: 111; and a light chain variable region CDR3 comprising amino acids having the sequence set forth in SEQ ID NO: 112; (e) a heavy chain variable region CDR1 comprising amino acids having the sequence set forth in SEQ ID NO: 113; a heavy chain variable region CDR2 comprising amino acids having the sequence set forth in SEQ ID NO: 114; a heavy chain variable region CDR3 comprising amino acids having the sequence set forth in SEQ ID NO: 115; a light chain variable region CDR1 comprising amino acids having the sequence set forth in SEQ ID NO: 116; a light chain variable region CDR2 comprising amino acids having the sequence set forth in SEQ ID NO: 117; and a light chain variable region CDR3 comprising amino acids having the sequence set forth in SEQ ID NO: 118; (f) a heavy chain variable region CDR1 comprising amino acids having the sequence set forth in SEQ ID NO: 119; a heavy chain variable region CDR2 comprising amino acids having the sequence set forth in SEQ ID NO: 120; a heavy chain variable region CDR3 comprising amino acids having the sequence set forth in SEQ ID NO: 121; a light chain variable region CDR1 comprising amino acids having the sequence set forth in SEQ ID NO: 122; a light chain variable region CDR2 comprising amino acids having the sequence set forth in SEQ ID NO: 123; and a light chain variable region CDR3 comprising amino acids having the sequence set forth in SEQ ID NO: 124; (g) a heavy chain variable region CDR1 comprising amino acids having the sequence set forth in SEQ ID NO: 125; a heavy chain variable region CDR2 comprising amino acids having the sequence set forth in SEQ ID NO: 126; a heavy chain variable region CDR3 comprising amino acids having the sequence set forth in SEQ ID NO: 127; a light chain variable region CDR1 comprising amino acids having the sequence set forth in SEQ ID NO: 128; a light chain variable region CDR2 comprising amino acids having the sequence set forth in SEQ ID NO: 129; and a light chain variable region CDR3 comprising amino acids having the sequence set forth in SEQ ID NO: 130; (h) a heavy chain variable region CDR1 comprising amino acids having the sequence set forth in SEQ ID NO: 131; a heavy chain variable region CDR2 comprising amino acids having the sequence set forth in SEQ ID NO: 132; a heavy chain variable region CDR3 comprising amino acids having the sequence set forth in SEQ ID NO: 133; a light chain variable region CDR1 comprising amino acids having the sequence set forth in SEQ ID NO: 134; a light chain variable region CDR2 comprising amino acids having the sequence set forth in SEQ ID NO: 135; and a light chain variable region CDR3 comprising amino acids having the sequence set forth in SEQ ID NO: 136; (i) a heavy chain variable region CDR1 comprising amino acids having the sequence set forth in SEQ ID NO: 137; a heavy chain variable region CDR2 comprising amino acids having the sequence set forth in SEQ ID NO: 138; a heavy chain variable region CDR3 comprising amino acids having the sequence set forth in SEQ ID NO: 139; a light chain variable region CDR1 comprising amino acids having the sequence set forth in SEQ ID NO: 140; a light chain variable region CDR2 comprising amino acids having the sequence set forth in SEQ ID NO: 141; and a light chain variable region CDR3 comprising amino acids having the sequence set forth in SEQ ID NO: 142; (j) a heavy chain variable region CDR1 comprising amino acids having the sequence set forth in SEQ ID NO: 143; a heavy chain variable region CDR2 comprising amino acids having the sequence set forth in SEQ ID NO: 144; a heavy chain variable region CDR3 comprising amino acids having the sequence set forth in SEQ ID NO: 145; a light chain variable region CDR1 comprising amino acids having the sequence set forth in SEQ ID NO: 146; a light chain variable region CDR2 comprising amino acids having the sequence set forth in SE ID NO: 147; and a light chain variable region CDR3 comprising amino acids having the sequence set forth in SEQ ID NO: 148; (k) a heavy chain variable region CDR1 comprising amino acids having the sequence set forth in SEQ ID NO: 149; a heavy chain variable region CDR2 comprising amino acids having the sequence set forth in SEQ ID NO: 150; a heavy chain variable region CDR3 comprising amino acids having the sequence set forth in SEQ ID NO: 151; a light chain variable region CDR1 comprising amino acids having the sequence set forth in SEQ ID NO: 152; a light chain variable region CDR2 comprising amino acids having the sequence set forth in SEQ ID NO: 153; and a light chain variable region CDR3 comprising amino acids having the sequence set forth in SEQ ID NO: 154; (l) a heavy chain variable region CDR1 comprising amino acids having the sequence set forth in SEQ ID NO: 155; a heavy chain variable region CDR2 comprising amino acids having the sequence set forth in SEQ ID NO: 156; a heavy chain variable region CDR3 comprising amino acids having the sequence set forth in SEQ ID NO: 157; a light chain variable region CDR1 comprising amino acids having the sequence set forth in SEQ ID NO: 158; a light chain variable region CDR2 comprising amino acids having the sequence set forth in SEQ ID NO: 159; and a light chain variable region CDR3 comprising amino acids having the sequence set forth in SEQ ID NO: 160; (m) a heavy chain variable region CDR1 comprising amino acids having the sequence set forth in SEQ ID NO: 161; a heavy chain variable region CDR2 comprising amino acids having the sequence set forth in SEQ ID NO: 162; a heavy chain variable region CDR3 comprising amino acids having the sequence set forth in SEQ ID NO: 163; a light chain variable region CDR1 comprising amino acids having the sequence set forth in SEQ ID NO: 164; a light chain variable region CDR2 comprising amino acids having the sequence set forth in SEQ ID NO:165; and a light chain variable region CDR3 comprising amino acids having the sequence set forth in SEQ ID NO: 166; (n) a heavy chain variable region CDR1 comprising amino acids having the sequence set forth in SEQ ID NO: 167; a heavy chain variable region CDR2 comprising amino acids having the sequence set forth in SEQ ID NO: 168; a heavy chain variable region CDR3 comprising amino acids having the sequence set forth in SEQ ID NO: 169; a light chain variable region CDR1 comprising amino acids having the sequence set forth in SEQ ID NO: 170; a light chain variable region CDR2 comprising amino acids having the sequence set forth in SEQ ID NO: 171; and a light chain variable region CDR3 comprising amino acids having the sequence set forth in SEQ ID NO: 172; (o) a heavy chain variable region CDR1 comprising amino acids having the sequence set forth in SEQ ID NO: 173; a heavy chain variable region CDR2 comprising amino acids having the sequence set forth in SEQ ID NO: 174; a heavy chain variable region CDR3 comprising amino acids having the sequence set forth in SEQ ID NO: 175; a light chain variable region CDR1 comprising amino acids having the sequence set forth in SEQ ID NO: 176; a light chain variable region CDR2 comprising amino acids having the sequence set forth in SEQ ID NO: 177; and a light chain variable region CDR3 comprising amino acids having the sequence set forth in SEQ ID NO: 178; (p) a heavy chain variable region CDR1 comprising amino acids having the sequence set forth in SEQ ID NO: 179; a heavy chain variable region CDR2 comprising amino acids having the sequence set forth in SEQ ID NO: 180; a heavy chain variable region CDR3 comprising amino acids having the sequence set forth in SEQ ID NO: 181; a light chain variable region CDR1 comprising amino acids having the sequence set forth in SEQ ID NO: 182; a light chain variable region CDR2 comprising amino acids having the sequence set forth in SEQ ID NO: 183; and a light chain variable region CDR3 comprising amino acids having the sequence set forth in SEQ ID NO: 184; or (q) a heavy chain variable region CDR1 comprising amino acids having the sequence set forth in SEQ ID NO: 185; a heavy chain variable region CDR2 comprising amino acids having the sequence set forth in SEQ ID NO: 186; a heavy chain variable region CDR3 comprising amino acids having the sequence set forth in SEQ ID NO: 187; a light chain variable region CDR1 comprising amino acids having the sequence set forth in SEQ ID NO: 188; a light chain variable region CDR2 comprising amino acids having the sequence set forth in SEQ ID NO: 189; and a light chain variable region CDR3 comprising amino acids having the sequence set forth in SEQ ID NO: 190. In certain embodiments, the human scFv comprises: a heavy chain variable region CDR1 comprising amino acids having the sequence set forth in SEQ ID NO: 119; a heavy chain variable region CDR2 comprising amino acids having the sequence set forth in SEQ ID NO: 120; a heavy chain variable region CDR3 comprising amino acids having the sequence set forth in SEQ ID NO: 121; a light chain variable region CDR1 comprising amino acids having the sequence set forth in SEQ ID NO: 122; a light chain variable region CDR2 comprising amino acids having the sequence set forth in SEQ ID NO: 123; and a light chain variable region CDR3 comprising amino acids having the sequence set forth in SEQ ID NO: 124. In certain embodiments, the human scFv comprises: a heavy chain variable region CDR1 comprising amino acids having the sequence set forth in SEQ ID NO: 167; a heavy chain variable region CDR2 comprising amino acids having the sequence set forth in SEQ ID NO: 168; a heavy chain variable region CDR3 comprising amino acids having the sequence set forth in SEQ ID NO: 169; a light chain variable region CDR1 comprising amino acids having the sequence set forth in SEQ ID NO: 170; a light chain variable region CDR2 comprising amino acids having the sequence set forth in SEQ ID NO: 171; and a light chain variable region CDR3 comprising amino acids having the sequence set forth in SEQ ID NO: 172. In certain embodiments, the human scFv comprises: a heavy chain variable region CDR1 comprising amino acids having the sequence set forth in SEQ ID NO: 173; a heavy chain variable region CDR2 comprising amino acids having the sequence set forth in SEQ ID NO: 174; a heavy chain variable region CDR3 comprising amino acids having the sequence set forth in SEQ ID NO: 175; a light chain variable region CDR1 comprising amino acids having the sequence set forth in SEQ ID NO: 176; a light chain variable region CDR2 comprising amino acids having the sequence set forth in SEQ ID NO: 177; and a light chain variable region CDR3 comprising amino acids having the sequence set forth in SEQ ID NO: 178. In certain embodiments, the human scFv comprises: a heavy chain variable region CDR1 comprising amino acids having the sequence set forth in SEQ ID NO: 179; a heavy chain variable region CDR2 comprising amino acids having the sequence set forth in SEQ ID NO: 180; a heavy chain variable region CDR3 comprising amino acids having the sequence set forth in SEQ ID NO: 181; a light chain variable region CDR1 comprising amino acids having the sequence set forth in SEQ ID NO: 182; a light chain variable region CDR2 comprising amino acids having the sequence set forth in SEQ ID NO: 183; and a light chain variable region CDR3 comprising amino acids having the sequence set forth in SEQ ID NO: 184. In certain embodiments, the human scFv comprises: a heavy chain variable region CDR1 comprising amino acids having the sequence set forth in SEQ ID NO: 185; a heavy chain variable region CDR2 comprising amino acids having the sequence set forth in SEQ ID NO: 186; a heavy chain variable region CDR3 comprising amino acids having the sequence set forth in SEQ ID NO: 187; a light chain variable region CDR1 comprising amino acids having the sequence set forth in SEQ ID NO: 188; a light chain variable region CDR2 comprising amino acids having the sequence set forth in SEQ ID NO: 189; and a light chain variable region CDR3 comprising amino acids having the sequence set forth in SEQ ID NO: 190.

In certain embodiments, the BCMA comprises the amino acid sequence set forth in SEQ ID NO:71. In certain embodiments, the human scFv binds to an epitope region comprising amino acids 14-22 of SEQ ID NO:71. In certain embodiments, the human scFv that binds to an epitope region comprising amino acids 14-22 of SEQ ID NO:71 comprises a $V_H$ comprising amino acids having the sequence set forth in SEQ ID NO:21 and a $V_L$ comprising amino acids having the sequence set forth in SEQ ID NO:22, In certain embodiments, the human scFv that binds to an epitope region comprising amino acids 14-22 of SEQ ID NO:71 comprises a $V_H$ CDR1 comprising amino acids having the sequence set forth in SEQ ID NO:119, a $V_H$ CDR2 comprising amino acids having the sequence set forth in SEQ ID NO:120, a $V_H$ CDR3 comprising amino acids having the sequence set forth in SEQ ID NO:121, a $V_L$ CDR1 comprising amino acids having the sequence set forth in SEQ ID NO:122, a $V_L$ CDR2 comprising amino acids having the sequence set forth in SEQ ID NO:123, and a $V_L$ CDR3 comprising amino acids having the sequence set forth in SEQ ID NO:124.

In accordance with the presently disclosed subject matter, the extracellular antigen-binding domain is covalently joined to a transmembrane domain. The extracellular antigen-binding domain can comprise a signal peptide that is covalently joined to the 5' terminus of the extracellular antigen-binding domain. In certain embodiments, the transmembrane domain of the CAR comprises a CD8 polypeptide, a CD28 polypeptide, a CD3ζ polypeptide, a CD4 polypeptide, a 4-1BB polypeptide, an OX40 polypeptide, an ICOS polypeptide, a CTLA-4 polypeptide, a PD-1 polypeptide, a LAG-3 polypeptide, a 2B4 polypeptide, a BTLA polypeptide, a synthetic peptide (not based on a protein associated with the immune response), or a combination thereof. In certain embodiments, the transmembrane domain comprises a CD8 polypeptide. In certain embodiments, the transmembrane domain comprises a CD28 polypeptide.

In accordance with the presently disclosed subject matter, the intracellular domain comprises a CD3ζ polypeptide. In certain embodiments, the intracellular domain further comprises at least one signaling region. In certain embodiments, the at least one signaling region comprises a CD28 polypeptide, a 4-1BB polypeptide, an OX40 polypeptide, an ICOS polypeptide, a DAP-10 polypeptide, a PD-1 polypeptide, a CTLA-4 polypeptide, a LAG-3 polypeptide, a 2B4 polypeptide, a BTLA polypeptide, a synthetic peptide (not based on a protein associated with the immune response), or a combination thereof. In certain embodiments, the signaling region is a co-stimulatory signaling region. In certain embodiments, the co-stimulatory signaling region comprises a CD28 polypeptide, a 4-1BB polypeptide, an OX40 polypeptide, an ICOS polypeptide, a DAP-10 polypeptide, or a combination thereof. In certain embodiments, the at least one co-stimulatory signaling region comprises a CD28 polypeptide. In certain embodiments, the at least one signaling region comprises a 4-1BB polypeptide. In one specific non-limiting embodiment, the transmembrane domain comprises a CD28 polypeptide, the intracellular domain comprises a CD3ζ polypeptide, and the at least one signaling domain comprises a CD28 polypeptide.

In certain embodiments, the CAR is recombinantly expressed. The CAR can be expressed from a vector. In certain embodiments, the vector is a γ-retroviral rector.

The presently disclosed subject matter also provides isolated immunoresponsive cells comprising the above-described CARs. In certain embodiments, the isolated immunoresponsive cell is transduced with the CAR, for example, the CAR is constitutively expressed on the surface of the immunoresponsive cell. In certain embodiments, the isolated immunoresponsive cell is further transduced with at least one co-stimulatory ligand such that the immunoresponsive cell expresses the at least one co-stimulatory ligand. In certain embodiments, the at least one co-stimulatory ligand is selected from the group consisting of 4-1BBL, CD80, CD86, CD70, OX40L, CD48, TNFRSF14, and combinations thereof. In certain embodiments, the isolated immunoresponsive cell is further transduced with at least one cytokine such that the immunoresponsive cell secrets the at least one cytokine. In certain embodiments, the at least one cytokine is selected from the group consisting of IL-2, IL-3, IL-6, IL-7, IL-11, IL-12, IL-15, IL-17, IL-21, and combinations thereof. In certain embodiments, the isolated immunoresponsive cell is selected from the group consisting of a T cell, a Natural Killer (NK) cell, a cytotoxic T lymphocyte (CTL), a regulatory T cell, a human embryonic stem cell, a lymphoid progenitor cell, a T cell-precursor cell, and a pluripotent stem cell from which lymphoid cells may be differentiated. In certain embodiments, the immunoresponsive cell is a T cell.

The presently disclosed subject matter further provides nucleic acid molecules encoding the presently disclosed CARs, vectors comprising the nucleic acid molecules, and host cells expressing such nucleic acid molecules. In certain embodiments, the nucleic acid molecule comprises nucleic acids having the sequence set forth in SEQ ID NO:207 In certain embodiments, the nucleic acid molecule comprises nucleic acids having the sequence set forth in SEQ ID NO:208. In certain embodiments, the nucleic acid molecule comprises nucleic acids having the sequence set forth in SEQ ID NO:209. In certain embodiments, the nucleic acid molecule comprises nucleic acids having the sequence set forth in SEQ ID NO:229. In certain embodiments, the nucleic acid molecule comprises nucleic acids having the sequence set forth in SEQ ID NO:230. In certain embodiments, the nucleic acid molecule comprises nucleic acids having the sequence set forth in SEQ ID NO:231. In certain embodiments, the nucleic acid molecule comprises nucleic acids having the sequence set forth in SEQ ID NO:232. In certain embodiments, the nucleic acid molecule comprises nucleic acids having the sequence set forth in SEQ ID NO:233. In certain embodiments, the nucleic acid molecule comprises nucleic acids having the sequence set forth in SEQ ID NO:234. In certain embodiments, the nucleic acid molecule comprises nucleic acids having the sequence set forth in SEQ ID NO:235. In certain embodiments, the vector is a γ-retroviral vector. In certain embodiments, the host cell is a T cell.

Furthermore, the presently disclosed subject matter provides methods of using the above-described immunoresponsive cell for reducing tumor burden in a subject. For example, the presently disclosed subject matter provides methods of reducing tumor burden in a subject, where the method comprises administering an effective amount of the presently disclosed immunoresponsive cell to the subject, thereby inducing tumor cell death in the subject. In certain embodiments, the method reduces the number of tumor cells. In another embodiment, the method reduces the tumor size. In yet another embodiment, the method eradicates the tumor in the subject. In certain embodiments, the tumor is selected from the group consisting of multiple myeloma, Non-Hodgkin Lymphoma, Hodgkin Lymphoma, Chronic Lymphocytic Leukemia (CLL), glioblastoma, and Waldenstrom's Macroglobulinemia. In certain embodiments, the tumor is multiple myeloma. In certain embodiments, the subject is a human. In certain embodiments, the immunoresponsive cell is a T cell.

Furthermore, the presently disclosed subject matter provides methods of using the above-described immunoresponsive cell for increasing or lengthening survival of a subject having neoplasia. For example, the presently disclosed subject matter provides methods of increasing or lengthening survival of a subject having neoplasia, where the method comprises administering an effective amount of the presently disclosed immunoresponsive cell to the subject, thereby increasing or lengthening survival of the subject. In certain embodiments, the neoplasia is selected from the group consisting of multiple myeloma, Non-Hodgkin Lymphoma, Hodgkin Lymphoma, Chronic Lymphocytic Leukemia (CLL), glioblastoma, and Waldenstrom's Macroglobulinemia. In certain embodiments, the neoplasia is multiple myeloma. In certain embodiments, the method reduces or eradicates tumor burden in the subject.

The presently disclosed subject matter also provides methods for producing an immunoresponsive cell that binds to BCMA. In one non-limiting example, the method comprises introducing into the immunoresponsive cell a nucleic acid sequence that encodes a chimeric antigen receptor (CAR), which comprises an extracellular antigen-binding domain, a transmembrane domain and an intracellular domain, wherein the extracellular antigen-binding domain comprises a human scFv that specifically binds to BCMA.

The presently disclosed subject matter further provides pharmaceutical compositions comprising an effective amount of the presently disclosed immunoresponsive cells and a pharmaceutically acceptable excipient. In certain embodiments, the pharmaceutical compositions are for treating a neoplasia. In certain embodiments, the neoplasia is selected from the group consisting of multiple myeloma, Non-Hodgkin Lymphoma, Hodgkin Lymphoma, Chronic Lymphocytic Leukemia (CLL), glioblastoma, and Waldenstrom's Macroglobulinemia. In certain embodiments, the neoplasia is multiple myeloma.

The presently disclosed subject matter further provides kits for treating a neoplasia, comprising the presently disclosed immunoresponsive cells. In certain embodiments, the kit further include written instructions for using the immunoresponsive cell for treating a neoplasia. In certain embodiments, the neoplasia is selected from the group consisting of multiple myeloma, Non-Hodgkin Lymphoma, Hodgkin Lymphoma, Chronic Lymphocytic Leukemia (CLL), glioblastoma, and Waldenstrom's Macroglobulinemia. In certain embodiments, the neoplasia is multiple myeloma.

BRIEF DESCRIPTION OF THE FIGURES

The following Detailed Description, given by way of example, but not intended to limit the invention to specific embodiments described, may be understood in conjunction with the accompanying drawings.

FIG. 20 depicts epitope mapping of ET140-3, ET140-24, and ET140-54.

DETAILED DESCRIPTION OF THE INVENTION

Figure 1:
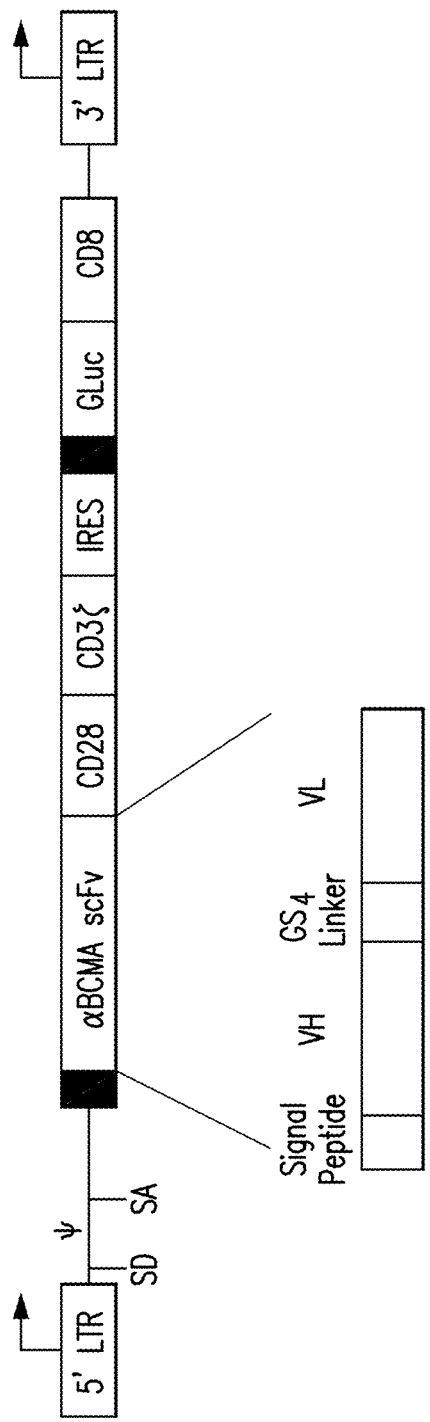
FIG. 1 shows a chimeric antigen receptor targeting BCMA in accordance with one non-limiting embodiment of the presently disclosed subject matter.
Figure 2A:
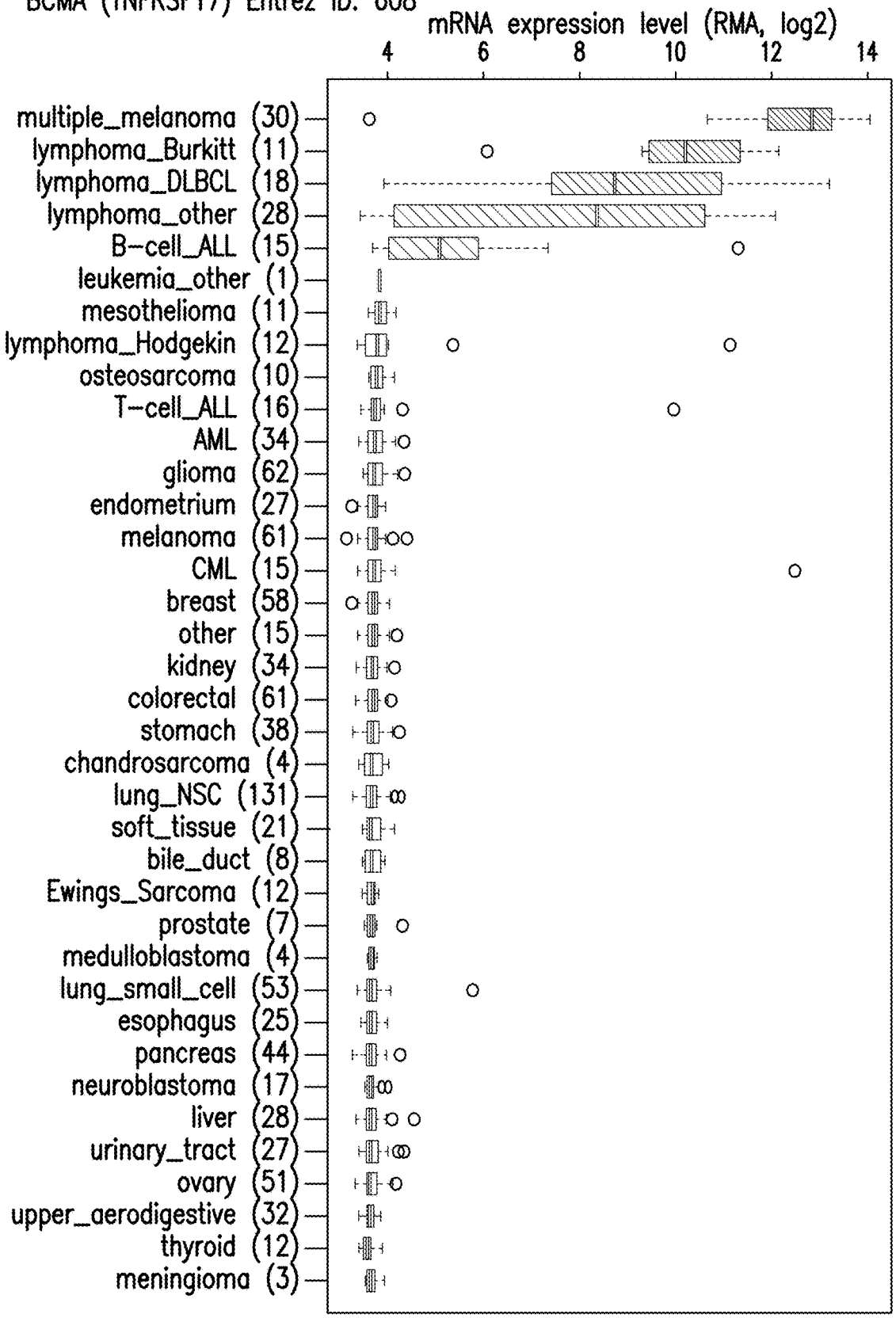
FIGS. 2A-2D depict the human BCMA expression in normal tissues and human cancer cell lines.
Figure 2B:
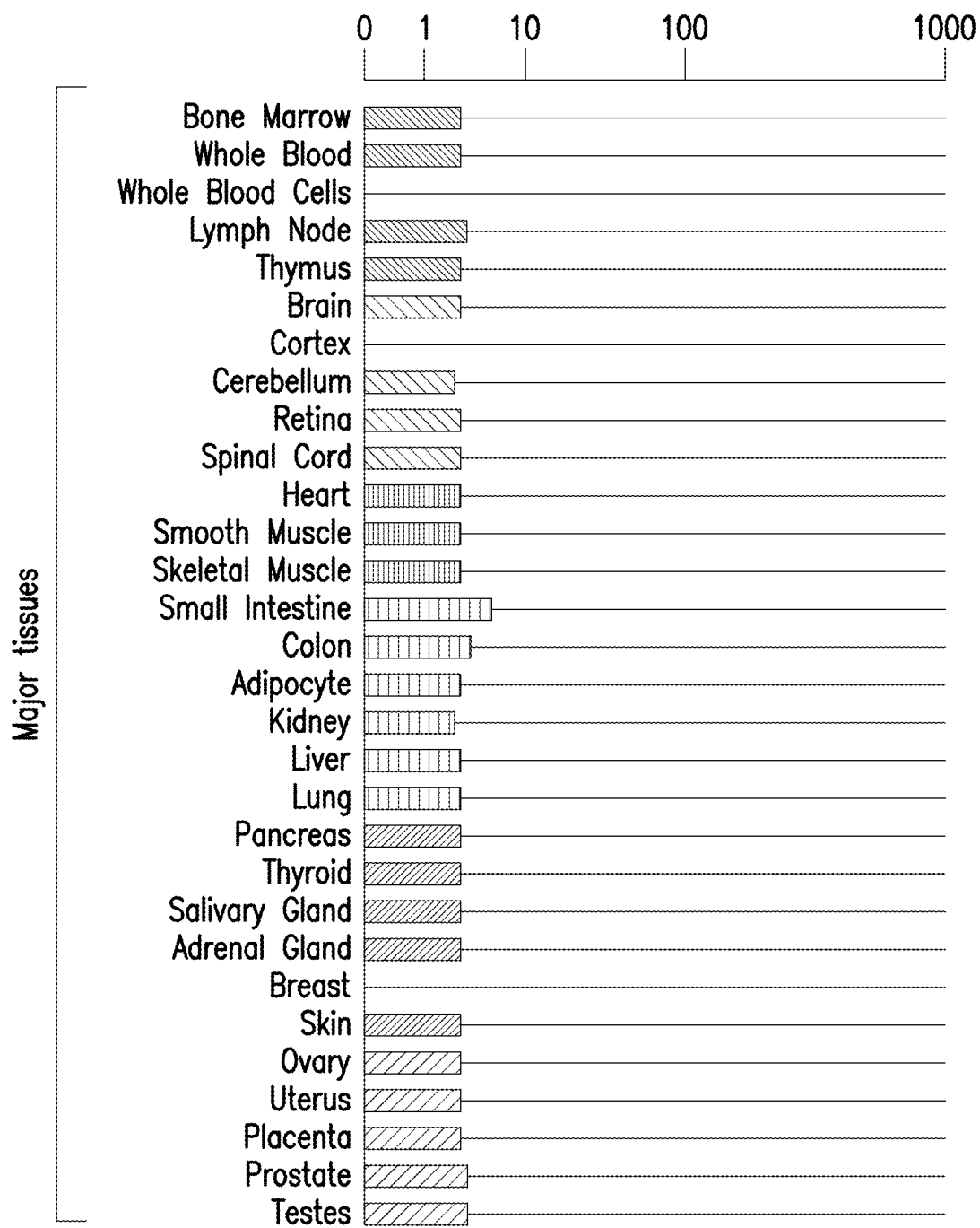
Figure 2C:
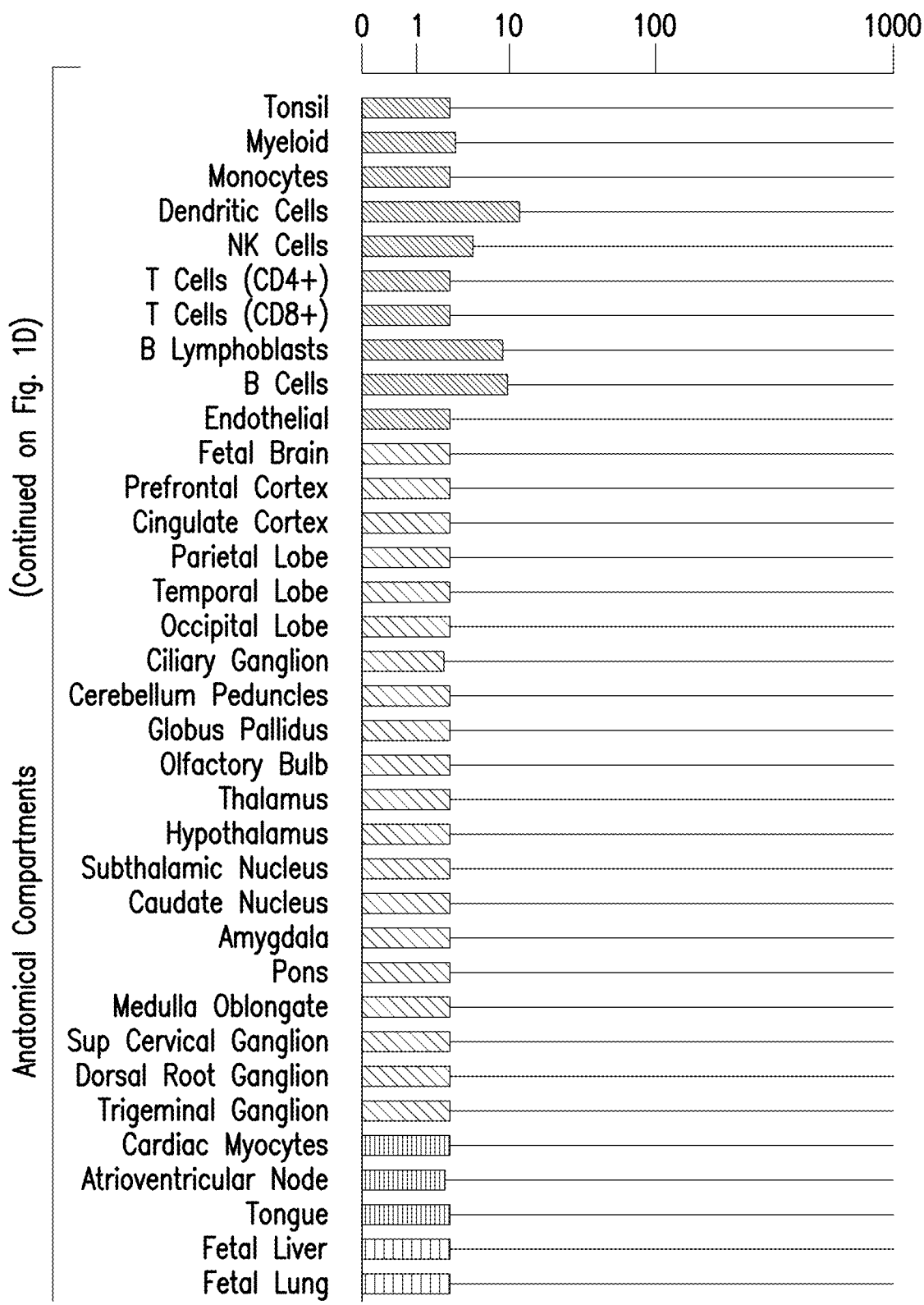
Figure 2D:
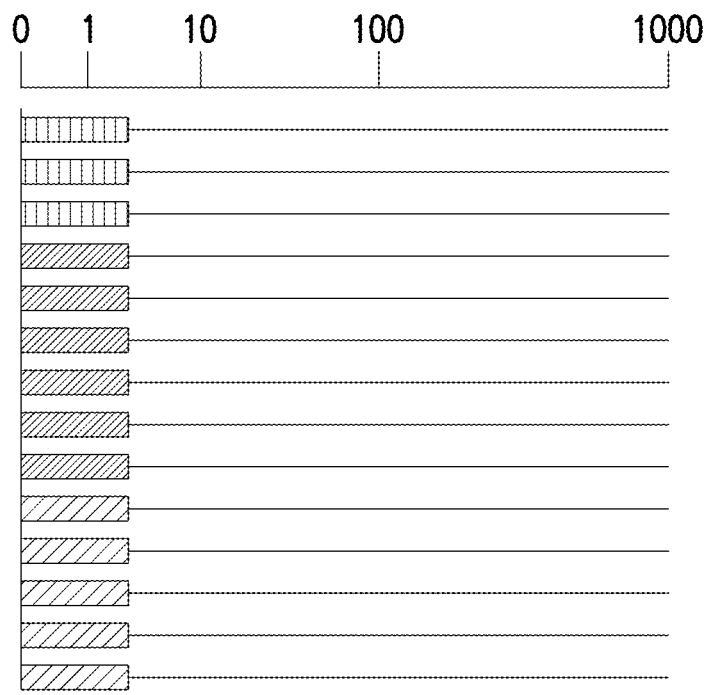

The presently disclosed subject matter generally provides chimeric antigen receptors (CARs) targeting BCMA. In one non-limiting example, the CAR comprises an extracellular antigen-binding domain, a transmembrane domain and an intracellular domain, where the extracellular antigen-binding domain specifically binds to BCMA. The presently disclosed subject matter also provides immunoresponsive cells (e.g., T cell, a Natural Killer (NK) cell, a cytotoxic T lymphocyte (CTL), a regulatory T cell, a human embryonic stem cell, a lymphoid progenitor cell, a T cell-precursor cell, and a pluripotent stem cell from which lymphoid cells may be differentiated) expressing the BCMA-targeted CARs, and methods of using such immunoresponsive cells for treating a tumor, e.g., multiple myeloma.

I. Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used herein, the term "cell population" refers to a group of at least two cells expressing similar or different phenotypes. In non-limiting examples, a cell population can include at least about 10, at least about 100, at least about 200, at least about 300, at least about 400, at least about 500, at least about 600, at least about 700, at least about 800, at least about 900, at least about 1000 cells expressing similar or different phenotypes.

As used herein, the term "antibody" means not only intact antibody molecules, but also fragments of antibody molecules that retain immunogen-binding ability. Such fragments are also well known in the art and are regularly employed both in vitro and in vivo. Accordingly, as used herein, the term "antibody" means not only intact immunoglobulin molecules but also the well-known active fragments F(ab')$_2$, and Fab. F(ab')$_2$, and Fab fragments that lack the Fc fragment of intact antibody, clear more rapidly from the circulation, and may have less non-specific tissue binding of an intact antibody (Wahl et al., *J. Nucl. Med.* 24:316-325 (1983). The antibodies of the invention comprise whole native antibodies, bispecific antibodies; chimeric antibodies; Fab, Fab', single chain V region fragments (scFv), fusion polypeptides, and unconventional antibodies.

As used herein, the term "single-chain variable fragment" or "scFv" is a fusion protein of the variable regions of the heavy ($V_H$) and light chains ($V_L$) of an immunoglobulin (e.g., mouse or human) covalently linked to form a $V_H$::$V_L$ heterodimer. The heavy ($V_H$) and light chains ($V_L$) are either joined directly or joined by a peptide-encoding linker (e.g., 10, 15, 20, 25 amino acids), which connects the N-terminus of the $V_H$ with the C-terminus of the $V_L$, or the C-terminus of the $V_H$ with the N-terminus of the $V_L$. The linker is usually rich in glycine for flexibility, as well as serine or threonine for solubility. The linker can link the heavy chain variable region and the light chain variable region of the extracellular antigen-binding domain. Non-limiting examples of linkers are disclosed in Shen et al., Anal. Chem. 80(6):1910-1917 (2008) and WO 2014/087010, the contents of which are hereby incorporated by reference in their entireties. In certain embodiments, the linker is a G4S linker.

In a non-limiting example, the linker comprises amino acids having the sequence set forth in SEQ ID NO:210 as provided below.

```
                                     [SEQ ID NO: 210]
            GGGGSGGGGSGGGGS.
```

In certain embodiments, the nucleic acid sequence encoding the amino acid sequence of SEQ ID NO:210 is set forth in SEQ ID NO:211, which is provided below:

```
                                     [SEQ ID NO: 211]
GGTGGAGGTGGATCAGGTGGAGGTGGATCTGGTGGAGGTGGATCT.
```

In one non-limiting example, the linker comprises amino acids having the sequence set forth in SEQ ID NO:69 as provided below.

```
                                     [SEQ ID NO: 69]
            SRGGGGSGGGGSGGGGSLEMA
```

In certain embodiments, the nucleic acid sequence encoding the amino acid sequence of SEQ ID NO:69 is set forth in SEQ ID NO:70, which is provided below:

[SEQ ID NO: 70]
tctagaggtggtggtggtagcggcggcggcggctctggtggtggtggatc cctcgagatggcc Despite removal of the constant regions and the introduction of a linker, scFv proteins retain the specificity of the original immunoglobulin. Single chain Fv polypeptide antibodies can be expressed from a nucleic acid comprising $V_H$- and $V_L$-encoding sequences as described by Huston, et al. (Proc. Nat. Acad. Sci. USA, 85:5879-5883, 1988). See, also, U.S. Pat. Nos. 5,091,513, 5,132,405 and 4,956,778; and U.S. Patent Publication Nos. 20050196754 and 20050196754. Antagonistic scFvs having inhibitory activity have been described (see, e.g., Zhao et al., Hyrbidoma (Larchmt) 2008 27(6):455-51; Peter et al., J Cachexia Sarcopenia Muscle 2012 Aug. 12; Shieh et al., J Imunol 2009 183(4):2277-85; Giomarelli et al., Thromb Haemost 2007 97(6):955-63; Fife eta., J Clin Invst 2006 116(8):2252-61; Brocks et al., Immunotechnology 1997 3(3):173-84; Moosmayer et al., Ther Immunol 1995 2(10:31-40). Agonistic scFvs having stimulatory activity have been described (see, e.g., Peter et al., J Bioi Chern 2003 25278(38):36740-7; Xie et al., Nat Biotech 1997 15(8):768-71; Ledbetter et al., Crit Rev Immunol 1997 17(5-6):427-55; Ho et al., BioChim Biophys Acta 2003 1638(3):257-66).

As used herein, "F(ab)" refers to a fragment of an antibody structure that binds to an antigen but is monovalent and does not have a Fc portion, for example, an antibody digested by the enzyme papain yields two F(ab) fragments and an Fc fragment (e.g., a heavy (H) chain constant region; Fc region that does not bind to an antigen).

As used herein, "F(ab')$_2$," refers to an antibody fragment generated by pepsin digestion of whole IgG antibodies, wherein this fragment has two antigen binding (ab') (bivalent) regions, wherein each (ab') region comprises two separate amino acid chains, a part of a H chain and a light (L) chain linked by an S—S bond for binding an antigen and where the remaining H chain portions are linked together. A "F(ab')$_2$," fragment can be split into two individual Fab' fragments.

As used herein, the term "vector" refers to any genetic element, such as a plasmid, phage, transposon, cosmid, chromosome, virus, virion, etc., which is capable of replication when associated with the proper control elements and which can transfer gene sequences into cells. Thus, the term includes cloning and expression vehicles, as well as viral vectors and plasmid vectors.

As used herein, the term "expression vector" refers to a recombinant nucleic acid sequence, i.e. recombinant DNA molecule, containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

As used herein, "CDRs" are defined as the complementarity determining region amino acid sequences of an antibody which are the hypervariable regions of immunoglobulin heavy and light chains. See, e.g., Kabat et al., Sequences of Proteins of Immunological Interest, 4th U. S. Department of Health and Human Services, National Institutes of Health (1987). Generally, antibodies comprise three heavy chain and three light chain CDRs or CDR regions in the variable region. CDRs provide the majority of contact residues for the binding of the antibody to the antigen or epitope. In certain embodiments, the CDRs regions are delineated using the Kabat system (Kabat, E. A., et al. (1991) Sequences of Proteins of Immunological Interest, Fifth Edition, U.S. Department of Health and Human Services, NIH Publication No. 91-3242).

As used herein, the term "affinity" is meant a measure of binding strength. Without being bound to theory, affinity depends on the closeness of stereochemical fit between antibody combining sites and antigen determinants, on the size of the area of contact between them, and on the distribution of charged and hydrophobic groups. Affinity also includes the term "avidity," which refers to the strength of the antigen-antibody bond after formation of reversible complexes. Methods for calculating the affinity of an antibody for an antigen are known in the art, comprising use of binding experiments to calculate affinity. Antibody activity in functional assays (e.g., flow cytometry assay) is also reflective of antibody affinity. Antibodies and affinities can be phenotypically characterized and compared using functional assays (e.g., flow cytometry assay).

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Rogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. In an exemplary approach to determining the degree of identity, a BLAST program may be used, with a probability score between e-3 and e-100 indicating a closely related sequence.

As used herein, the term "analog" refers to a structurally related polypeptide or nucleic acid molecule having the function of a reference polypeptide or nucleic acid molecule.

As used herein, the term "ligand" refers to a molecule that binds to a receptor. In particular, the ligand binds a receptor on another cell, allowing for cell-to-cell recognition and/or interaction.

As used herein, the term "disease" refers to any condition or disorder that damages or interferes with the normal function of a cell, tissue, or organ. Examples of diseases include neoplasia or pathogen infection of cell.

As used herein, the term "effective amount" refers to an amount sufficient to have a therapeutic effect. In certain embodiments, an "effective amount" is an amount sufficient to arrest, ameliorate, or inhibit the continued proliferation, growth, or metastasis (e.g., invasion, or migration) of a neoplasia.

As used herein, the term "heterologous nucleic acid molecule or polypeptide" refers to a nucleic acid molecule (e.g., a cDNA, DNA or RNA molecule) or polypeptide that is not normally present in a cell or sample obtained from a cell. This nucleic acid may be from another organism, or it may be, for example, an mRNA molecule that is not normally expressed in a cell or sample.

As used herein, the term "immunoresponsive cell" refers to a cell that functions in an immune response or a progenitor, or progeny thereof.

As used herein, the term "modulate" refers positively or negatively alter. Exemplary modulations include an about 1%, about 2%, about 5%, about 10%, about 25%, about 50%, about 75%, or about 100% change.

As used herein, the term "increase" refers to alter positively by at least about 5%, including, but not limited to, alter positively by about 5%, by about 10%, by about 25%, by about 30%, by about 50%, by about 75%, or by about 100%.

As used herein, the term "reduce" refers to alter negatively by at least about 5% including, but not limited to, alter negatively by about 5%, by about 10%, by about 25%, by about 30%, by about 50%, by about 75%, or by about 100%.

As used herein, the term "isolated cell" refers to a cell that is separated from the molecular and/or cellular components that naturally accompany the cell.

As used herein, the term "isolated," "purified," or "biologically pure" refers to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

As used herein, the term "secreted" is meant a polypeptide that is released from a cell via the secretory pathway through the endoplasmic reticulum, Golgi apparatus, and as a vesicle that transiently fuses at the cell plasma membrane, releasing the proteins outside of the cell.

As used herein, the term "specifically binds" or "specifically binds to" or "specifically target" is meant a polypeptide or fragment thereof that recognizes and binds a biological molecule of interest (e.g., a polypeptide), but which does not substantially recognize and bind other molecules in a sample, for example, a biological sample, which naturally includes a polypeptide of the invention.

As used herein, the term "treating" or "treatment" refers to clinical intervention in an attempt to alter the disease course of the individual or cell being treated, and can be performed either for prophylaxis or during the course of clinical pathology. Therapeutic effects of treatment include, without limitation, preventing occurrence or recurrence of disease, alleviation of symptoms, diminishment of any direct or indirect pathological consequences of the disease, preventing metastases, decreasing the rate of disease progression, amelioration or palliation of the disease state, and remission or improved prognosis. By preventing progression of a disease or disorder, a treatment can prevent deterioration due to a disorder in an affected or diagnosed subject or a subject suspected of having the disorder, but also a treatment may prevent the onset of the disorder or a symptom of the disorder in a subject at risk for the disorder or suspected of having the disorder.

As used herein, the term "subject" refers to any animal (e.g., a mammal), including, but not limited to, humans, non-human primates, rodents, and the like (e.g., which is to be the recipient of a particular treatment, or from whom cells are harvested).

II. B Cell Maturation Antigen (BCMA)

BCMA is an ideal target for Adoptive T cell therapy (e.g., CAR therapy) as BCMA is involved in B cell differentiation and signaling and is known to be expressed on non-malignant differentiated B cells and plasma cells. While there might be risk of inducing a B cell aplasia, B cell aplasias induced by the CD19 CAR have been remarkably well tolerated. Several groups have confirmed BCMA multiple myeloma (MM) surface expression, with one group finding it as an alternative to CD138 as a FACS marker for malignant plasma cells from fresh or frozen patient bone marrow samples with mean relative mean fluorescence intensity (MFI) between 9-16 (n=35).[1,2]

In certain non-limiting embodiments, BCMA is human BCMA having the amino acid sequence set forth in SEQ ID NO:71, or fragments thereof.

SEQ ID NO:71 is provided below:

[SEQ ID NO: 71]
MLQMAGQCSQNEYFDSLLHACIPCQLRCSSNTPPLTCQRYCNASVTNSVK

GTNAILWTCLGLSLIISLAVEVLMELLRKINSEPLKDEFKNTGSGLLGMA

NIDLEKSRTGDEIILPRGLEYTVEECTCEDCIKSKPKVDSDHCFPLPAME

EGATILVTTKTNDYCKSLPAALSATEIEKSISAR

III. Chimeric Antigen Receptor (CAR)

Chimeric antigen receptors (CARs) are engineered receptors, which graft or confer a specificity of interest onto an immune effector cell. CARs can be used to graft the specificity of a monoclonal antibody onto a T cell; with transfer of their coding sequence facilitated by retroviral vectors.

There are three generations of CARs. "First generation" CARs are typically composed of an extracellular antigen binding domain (e.g., a single-chain variable fragments (scFv)) fused to a transmembrane domain, fused to cytoplasmic/intracellular domain of the T cell receptor chain. "First generation" CARs typically have the intracellular domain from the CD3ξ-chain, which is the primary transmitter of signals from endogenous TCRs. "First generation" CARs can provide de novo antigen recognition and cause activation of both $CD4^+$ and $CD8^+$ T cells through their CD3ζ chain signaling domain in a single fusion molecule, independent of HLA-mediated antigen presentation. "Second generation" CARs add intracellular domains from various co-stimulatory molecules (e.g., CD28, 4-1BB, ICOS, OX40) to the cytoplasmic tail of the CAR to provide additional signals to the T cell. "Second generation" CARs comprise those that provide both co-stimulation (e.g., CD28 or 4-1BB) and activation (CD3ζ). Preclinical studies have indicated that "Second Generation" CARs can improve the anti-tumor activity of T cells. For example, robust efficacy of "Second Generation" CAR modified T cells was demonstrated in clinical trials targeting the CD19 molecule in patients with chronic lymphoblastic leukemia (CLL) and acute lymphoblastic leukemia (ALL). "Third generation" CARs comprise those that provide multiple co-stimulation (e.g., CD28 and 4-1BB) and activation (CD3ζ).

In accordance with the presently disclosed subject matter, the CARs comprise an extracellular antigen-binding domain, a transmembrane domain and an intracellular domain, where the extracellular antigen-binding domain binds to BCMA. In certain embodiments, the extracellular antigen-binding domain is a scFv. In certain embodiments, the extracellular antigen-binding domain is a Fab, which is optionally crosslinked. In a certain embodiments, the extracellular binding domain is a $F(ab)_2$. In certain embodiments, any of the foregoing molecules may be comprised in a fusion protein with a heterologous sequence to form the extracellular antigen-binding domain. In one specific non-limiting embodiment, the extracellular antigen-binding domain comprises a human scFv that binds specifically to human BCMA.

In certain non-limiting embodiments, the extracellular antigen-binding domain of a CAR has a high binding specificity as well as high binding affinity to the BCMA. For example, in such embodiments, the extracellular antigen-binding domain of the CAR (embodied, for example, in a human scFv or an analog thereof) binds to BCMA with a dissociation constant ($K_D$) of about $3\times10^{-6}$ M or less. In certain embodiments, the $K_D$ is about $1\times10^{-6}$ M or less, about $1\times10^{-7}$ M or less, about $1\times10^{-8}$ M or less, or about $1\times10^{-9}$ M or less, about $1\times10^{-10}$ M or less, or about $1\times10^{-11}$ M or less. In certain embodiments, the $K_D$ is about $1\times10^{-8}$ M or less. In certain embodiments, the $K_D$ is from about $1\times10^{-11}$ M to about $3\times10^{-6}$ M, such as from about $1\times10^{-11}$ M to about $1\times10^{-10}$ M, from about $1\times10^{-10}$ M to about $1\times10^{-9}$ M, from about $1\times10^{-9}$ M to about $1\times10^{-8}$ M, from about $1\times10^{-8}$ M to about $1\times10^{-7}$ M, or from about $1\times10^{-7}$ M to about $1\times10^{-6}$ M, or from about $1\times10^{-6}$ M to about $3\times10^{-6}$ M. In certain embodiments, the $K_D$ is from about $1\times10^{-9}$ M to about $1\times10^{-8}$ M. In certain embodiments, the $K_D$ is from about $1\times10^{-9}$ M to about $1.5\times10^{-9}$ M. In certain embodiments, the $K_D$ is about $1.2\times10^{-9}$ M. In certain embodiments, the $K_D$ is from about $4\times10^{-9}$ M to about $5\times10^{-9}$ M. In certain embodiments, the $K_D$ is about $5\times10^{-9}$ M. In certain embodiments, the $K_D$ is about $4.8\times10^{-9}$ M. In certain embodiments, the $K_D$ is from about $8\times10^{-9}$ M to about $9\times10^{-9}$ M. In certain embodiments, the $K_D$ is about $8\times10^{-9}$ M. In certain embodiments, the $K_D$ is about $8.1\times10^{-9}$ M.

Binding of the extracellular antigen-binding domain (embodiment, for example, in a human scFv or an analog thereof) of a presently disclosed CAR to BCMA can be confirmed by, for example, enzyme-linked immunosorbent assay (ELISA), radioimmunoassay (RIA), FACS analysis, bioassay (e.g., growth inhibition), or Western Blot assay. Each of these assays generally detect the presence of protein-antibody complexes of particular interest by employing a labeled reagent (e.g., an antibody, or a scFv) specific for the complex of interest. For example, the scFv can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a γ counter or a scintillation counter or by autoradiography. In certain embodiments, the BCMA-targeted extracellular antigen-binding domain is labeled with a fluorescent marker. Non-limiting examples of fluorescent markers include green fluorescent protein (GFP), blue fluorescent protein (e.g., EBFP, EBFP2, Azurite, and mKalama1), cyan fluorescent protein (e.g., ECFP, Cerulean, and CyPet), and yellow fluorescent protein (e.g., YFP, Citrine, Venus, and YPet). In certain embodiments, the BCMA-targeted human scFv is labeled with GFP.

In certain embodiments, the extracellular antigen-binding domain of a presently disclosed CAR comprises a single-chain variable fragment (scFv). In one specific non-limiting embodiment, the extracellular antigen-binding domain of a presently disclosed CAR comprises a human scFv that specifically binds to human BCMA. In certain embodiments, the scFv are identified by screening scFv phage library with BCMA-Fc fusion protein.

Extracellular Antigen Binding Domain of a CAR

In certain embodiments, the extracellular antigen-binding domain (e.g., human scFv) comprises a heavy chain variable region comprising amino acids having a sequence selected from the group consisting of: SEQ ID NOS:1, 5, 9, 13, 17, 21, 25, 29, 33, 37, 41, 45, 49, 53, 57, 61, and 65. The nucleic acid sequences encoding the amino acid sequence of SEQ ID NOS:1, 5, 9, 13, 17, 21, 25, 29, 33, 37, 41, 45, 49, 53, 57, 61, and 65 are 3, 7, 11, 15, 19, 23, 27, 31, 35, 39, 43, 47, 51, 55, 59, 63, and 67, respectively. In certain embodiments, the extracellular antigen-binding domain (e.g., human scFv) comprises a light chain variable region comprising amino acids having a sequence selected from the group consisting of SEQ ID NOS: 2, 6, 10, 14, 18, 22, 26, 30, 34, 38, 42, 46, 50, 54, 58, 62, and 66. The nucleic acid sequences encoding the amino acid sequence of SEQ ID NOS: 2, 6, 10, 14, 18, 22, 26, 30, 34, 38, 42, 46, 50, 54, 58, 62, and 66 are 4, 8, 12, 16, 20, 24, 28, 32, 36, 40, 44, 48, 52, 56, 60, 64, and 68, respectively. The sequences of SEQ ID NOS:1-68 are described in the following Tables 1-17.

In certain embodiments, the extracellular antigen-binding domain (e.g., scFv) comprises heavy and light chain variable regions comprising amino acid sequences that are homologous to the amino acid sequences described herein and as disclosed in Tables 1-17. For example, and not by way of limitation, the extracellular antigen-binding domain (e.g., scFv) comprises a heavy chain variable region comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to an amino acid sequence selected from the group consisting of SEQ ID NOS: 1, 5, 9, 13, 17, 21, 25, 29, 33, 37, 41, 45, 49, 53, 57, 61, and 65.

In certain embodiments, the extracellular antigen-binding domain (e.g., scFv) comprises a light chain variable region comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to an amino acid sequence selected from the group consisting of SEQ ID NOS: 2, 6, 10, 14, 18, 22, 26, 30, 34, 38, 42, 46, 50, 54, 58, 62, and 66 are 4, 8, 12, 16, 20, 24, 28, 32, 36, 40, 44, 48, 52, 56, 60, 64, and 68.

In certain embodiments, the extracellular antigen-binding domain (e.g., scFv) comprises (a) a heavy chain variable region comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to an amino acid sequence selected from the group consisting of SEQ ID NOS: 1, 5, 9, 13, 17, 21, 25, 29, 33, 37, 41, 45, 49, 53, 57, 61, and 65; and (b) a light chain variable region comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to an amino acid sequence selected from the group consisting of SEQ ID NOS: 2, 6, 10, 14, 18, 22, 26, 30, 34, 38, 42, 46, 50, 54, 58, 62, and 66 are 4, 8, 12, 16, 20, 24, 28, 32, 36, 40, 44, 48, 52, 56, 60, 64, and 68.

The presently disclosed subject matter further provides extracellular antigen-binding domains (e.g., scFv) that comprise heavy chain variable region and light chain variable region CDRs, e.g., CDR1s, CDR2s and CDR3s, as disclosed herein in Tables 1-17. The CDR regions are delineated using the Kabat system (Kabat, E. A., et al. (1991) Sequences of Proteins of Immunological Interest, Fifth Edition, U.S. Department of Health and Human Services, NIH Publication No. 91-3242). The presently disclosed subject matter further provides extracellular antigen-binding domains (e.g., scFv) that comprise conservative modifications of the antibody sequences disclosed herein. For example, and not by way of limitation, an extracellular antigen-binding domains (e.g., scFv) of the presently disclosed subject matter comprises a heavy chain variable region comprising CDR1, CDR2 and CDR3 sequences and a light chain variable region comprising CDR1, CDR2 and CDR3 sequences, wherein one or more of these CDR sequences comprise specified amino acid sequences disclosed herein, or conservative modifications thereof, and wherein the extracellular antigen-binding domains retain the desired functional properties.

In certain embodiments, the presently disclosed subject matter provides an extracellular antigen-binding domain (e.g., scFv) comprising a heavy chain variable region, wherein the heavy chain variable region comprises: (a) a CDR1 comprising an amino acid sequence selected from the group consisting of SEQ ID NOS: 89, 95, 101, 107, 113, 119, 125, 131, 137, 143, 149, 155, 161, 167, 173, 179, and 185, and conservative modifications thereof; (b) a CDR2 comprising an amino acid sequence selected from the group consisting of SEQ ID NOS: 90, 96, 102, 108, 114, 120, 126, 132, 138, 144, 150, 156, 162, 168, 174, 180, and 186, and conservative modifications thereof; and (c) a CDR3 comprising an amino acid sequence selected from the group consisting of SEQ ID NOS: 91, 97, 103, 109, 115, 121, 127, 133, 139, 145, 151, 157, 163, 169, 175, 181, and 187, and conservative modifications thereof.

In certain embodiments, the extracellular antigen-binding domain (e.g., scFv) comprises a light chain variable region, wherein the light chain variable region comprises: (a) a CDR1 comprising an amino acid sequence selected from the group consisting of SEQ ID NOS: 92, 98, 104, 110, 116, 122, 128, 134, 140, 146, 152, 158, 164, 170, 176, 182, and 188, and conservative modifications thereof; (b) a CDR2 comprising an amino acid sequence selected from the group consisting of SEQ ID NOS: 93, 99, 105, 111, 117, 123, 129, 135, 141, 147, 153, 159, 165, 171, 177, 183, and 189, and conservative modifications thereof; and (c) a CDR3 comprising an amino acid sequence selected from the group consisting of SEQ ID NOS: 94, 100, 106, 112, 118, 124, 130, 136, 142, 148, 154, 160, 166, 172, 178, 184, and 190, and conservative modifications thereof.

The presently disclosed subject matter provides an extracellular antigen-binding domain (e.g., scFv) comprising a heavy chain variable region comprising CDR1, CDR2, and CDR3 sequences and a light chain variable region comprising CDR1, CDR2, and CDR3 sequences, wherein: (a) the heavy chain variable region CDR3 comprises an amino acid sequence selected from the group consisting of SEQ ID NOs: 91, 97, 103, 109, 115, 121, 127, 133, 139, 145, 151, 157, 163, 169, 175, 181, and 187, and conservative modifications thereof; and (b) the light chain variable region CDR3 comprises an amino acid sequence selected from the group consisting of SEQ ID NOS: 94, 100, 106, 112, 118, 124, 130, 136, 142, 148, 154, 160, 166, 172, 178, 184, and 190, and conservative modifications thereof; wherein the extracellular antigen-binding domain specifically binds to a BCMA polypeptide (e.g., a human BCMA polypeptide). In certain embodiments, the heavy chain variable region CDR2 comprises an amino acid sequence selected from the group consisting of SEQ ID NOs: 125, 131, 137, 143, 149, 155, 161, 167, 173, 179, 185, 191, 197, 203, 209, 215, 221, 227, 233, 239, 245, 251, 257, 263, 305, 317, 329, 341, 353, 365, 377, and 389, and conservative modifications thereof; and (b) the light chain variable region CDR2 comprises an amino acid sequence selected from the group consisting of SEQ ID NOS: 93, 99, 105, 111, 117, 123, 129, 135, 141, 147, 153, 159, 165, 171, 177, 183, and 189, and conservative modifications thereof; wherein the extracellular antigen-binding domain specifically binds to a BCMA polypeptide (e.g., a human BCMA polypeptide). In certain embodiments, the heavy chain variable region CDR1 comprises an amino acid sequence selected from the group consisting of SEQ ID NOs: 89, 95, 101, 107, 113, 119, 125, 131, 137, 143, 149, 155, 161, 167, 173, 179, and 185, and conservative modifications thereof; and (b) the light chain variable region CDR1 comprises an amino acid sequence selected from the group consisting of SEQ ID NOS: 92, 98, 104, 110, 116, 122, 128, 134, 140, 146, 152, 158, 164, 170, 176, 182, and 188, and conservative modifications thereof; wherein the extracellular antigen-binding domain specifically binds to a BCMA polypeptide (e.g., a human BCMA polypeptide).

In certain embodiments, the extracellular antigen-binding domain is a human scFv, which comprises the amino acid sequence of SEQ ID NO: 72 and specifically binds to a BCMA polypeptide (e.g., a BCMA polypeptide having the amino acid sequence SEQ ID NO:71, or fragments thereof), which is designated as ET140-192 scFv (also referred to as "ET140-42 scFv").

In certain embodiments, the extracellular antigen-binding domain is a human scFv, which comprises a heavy chain variable region comprising amino acids having the sequence set forth in SEQ ID NO:1 and a light chain variable region comprising amino acids having the sequence set forth in SEQ ID NO:2, optionally with (iii) a linker sequence, for example a linker peptide, between the heavy chain variable region and the light chain variable region. In certain embodiments, the linker comprises amino acids having the sequence set forth in SEQ ID NO:69. In certain embodiments, the extracellular antigen-binding domain is a human scFv-Fc fusion protein or full length human IgG with $V_H$ and $V_L$ regions or CDRs selected from Table 1. In certain embodiments, the extracellular antigen-binding domain comprises a $V_H$ comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:1, as shown in Table 1. In certain embodiments, the extracellular antigen-binding domain comprises a $V_H$ comprising amino acids having the sequence set forth in SEQ ID NO:1, as shown in Table 1. In certain embodiments, the extracellular antigen-binding domain comprises a $V_L$ comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:2, as shown in Table 1. In certain embodiments, the extracellular antigen-binding domain comprises a $V_L$ comprising amino acids having the sequence set forth in SEQ ID NO:2, as shown in Table 1. In certain embodiments, the extracellular antigen-binding domain comprises a $V_H$ comprising amino acids having the sequence set forth in SEQ ID NO:1 and a $V_L$ comprising amino acids having the sequence set forth in SEQ ID NO:2, as shown in Table 1. In certain embodiments, the extracellular antigen-binding domain comprises a $V_H$ CDR1 comprising amino acids having the sequence set forth in SEQ ID NO:89 or conservative modifications thereof, a $V_H$ CDR2 comprising amino acids having the sequence set forth in SEQ ID NO:90 or conservative modifications thereof, and a $V_H$ CDR3 comprising amino acids having the sequence set forth in SEQ ID NO:91 or conservative modifications thereof, as shown in Table 1. In certain embodiments, the extracellular antigen-binding domain comprises a $V_L$ CDR1 comprising amino acids having the sequence set forth in SEQ ID NO:92 or conservative modifications thereof, a $V_L$ CDR2 comprising amino acids having the sequence set forth in SEQ ID NO:93 or conservative modifications thereof, and a $V_L$ CDR3 comprising amino acids having the sequence set forth in SEQ ID NO:94 or conservative modifications thereof, as shown in Table 1. In certain embodiments, the extracellular antigen-binding domain comprises a $V_H$ CDR1 comprising amino acids having the sequence set forth in SEQ ID NO:89 or conservative modifications thereof, a $V_H$ CDR2 comprising amino acids having the sequence set forth in SEQ ID NO:90 or conservative modifications thereof, a $V_H$ CDR3 comprising amino acids having the sequence set forth in SEQ ID NO:91 or conservative modifications thereof, a $V_L$ CDR1 comprising amino acids having the sequence set forth in SEQ ID NO:92 or conservative modifications thereof, a $V_L$ CDR2 comprising amino acids having the sequence set forth in SEQ ID NO:93 or conservative modifications thereof, and a $V_L$ CDR3 comprising amino acids having the sequence set forth in SEQ ID NO:94 or conservative modifications thereof, as shown in Table 1. In certain embodiments, the extracellular antigen-binding domain comprises a $V_H$ CDR1 comprising amino acids having the sequence set forth in SEQ ID NO:89, a $V_H$ CDR2 comprising amino acids having the sequence set forth in SEQ ID NO:90, a $V_H$ CDR3 comprising amino acids having the sequence set forth in SEQ ID NO:91, a $V_L$ CDR1 comprising amino acids having the sequence set forth in SEQ ID NO:92, a $V_L$ CDR2 comprising amino acids having the sequence set forth in SEQ ID NO:93, and a $V_L$ CDR3 comprising amino acids having the sequence set forth in SEQ ID NO:94.

TABLE 1

```
Antigen    A BCMA polypeptide having the amino acid sequence of SEQ ID NO: 71
CDRs       1                          2                       3
V_H        VSSNSAAWN [SEQ             YRSKWYN [SEQ ID         ARQGYSYYGYSDV
           ID NO: 89]                 NO: 90]                 [SEQ ID NO: 91]

V_L        SSNIGHND [SEQ ID           FDD [SEQ ID NO: 93]     AAWDGSLNAFV
           NO: 92]                                            [SEQ ID NO: 94]

Full V_H   QVQLQQSGPGLVKPSQTLSLTCAISGDSVSSNSAAWNWIRQSPSRG
           LEWLGRTYYRSKWYNDYAVSVKSRITINPDTSKNQFSLQLNSVTP
           EDTAVYYCARQGYSYYGYSDVWGQGTLVTVSS [SEQ ID NO: 1]

DNA        Caggtacagctgcagcagtcaggtccaggactggtgaagccctcgcagaccctctcactcacctgtgcc
           atctccggggacagtgtctctagcaacagtgctgcttggaactggatcaggcagtccccatcgagaggcc
           ttgagtggctgggaaggacatactacaggtccaagtggtataatgattatgcagtatctgtgaaaagtcga
           ataaccatcaacccagacacatccaagaaccagttctccctgcagctgaactctgtgactcccgaggaca
           cggctgtgtattactgtgcgcgccagggttactcttactacggttactctgatgrnggggtcaaggtactct
           ggtgaccgtctcctca [SEQ ID NO: 3]

Full V_L   QSVLTQPPSVSVAPRQRVTISCSGSSSNIGHNDVSWYQHLPGKAPR
           LLIYFDDLLPSGVSDRFSASKSGTSASLAISGLQSEDEADYYCAAW
           DGSLNAFVFGTGTKVTVLG [SEQ ID NO: 2]

DNA        Cagtctgtgctgactcagccaccctcggtgtctgtagccccaggcagagggtcaccatctcgtgttctg
           gaagcagctccaacatcggacataatgatgtaagctggtaccagcatctcccagggaaggctcccagac
           tcctcatctattttgatgacctgctgccgtcaggggtctctgaccgattctctgcctccaagtctggcacctca
           gcctccctggccatcagtgggctccagtctgaggatgaggctgattattactgtgcagcatgggatggca
           gcctgaatgcctttgtcttcggaactgggaccaaggtcaccgtcctaggt [SEQ ID NO: 4]

scFv       QSVLTQPPSVSVAPRQRVTISCSGSSSNIGHNDVSWYQHLPGKAPR
           LLIYFDDLLPSGVSDRFSASKSGTSASLAISGLQSEDEADYYCAAW
           DGSLNAFVFGTGTKVTVLGSRGGGGSGGGGSGGGGSLEMAQVQL
           QQSGPGLVKPSQTLSLTCAISGDSVSSNSAAWNWIRQSPSRGLEWL
           GRTYYRSKWYNDYAVSVKSRITINPDTSKNQFSLQLNSVTPEDTA
           VYYCARQGYSYYGYSDVWGQGTLVTVSS [SEQ ID NO: 72]
```

In certain embodiments, the extracellular antigen-binding domain is a human scFv, which comprises the amino acid sequence of SEQ ID NO:73 and specifically binds to a BCMA polypeptide (e.g., a BCMA polypeptide having the amino acid sequence SEQ ID NO:71, or fragments thereof), which is designated as ET140-197 scFv (also referred to as "ET140-47 scFv").

In certain embodiments, the extracellular antigen-binding domain is a human scFv, which comprises a heavy chain variable region comprising amino acids having the sequence set forth in SEQ ID NO:5 and a light chain variable region comprising amino acids having the sequence set forth in SEQ ID NO:6, optionally with (iii) a linker sequence, for example a linker peptide, between the heavy chain variable region and the light chain variable region. In certain embodiments, the linker comprises amino acids having the sequence set forth in SEQ ID NO:69. In certain embodiments, the extracellular antigen-binding domain is a human scFv-Fc fusion protein or full length human IgG with $V_H$ and $V_L$ regions or CDRs selected from Table 2. In certain embodiments, the extracellular antigen-binding domain comprises a $V_H$ comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:5, as shown in Table 2. In certain embodiments, the extracellular antigen-binding domain comprises a $V_H$ comprising amino acids having the sequence set forth in SEQ ID NO:5, as shown in Table 2. In certain embodiments, the extracellular antigen-binding domain comprises a $V_L$ comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:6, as shown in Table 2. In certain embodiments, the extracellular antigen-binding domain comprises a $V_L$ comprising amino acids having the sequence set forth in SEQ ID NO:6, as shown in Table 2. In certain embodiments, the extracellular antigen-binding domain comprises a $V_H$ comprising amino acids having the sequence set forth in SEQ ID NO:5 and a $V_L$ comprising amino acids having the sequence set forth in SEQ ID NO:6, as shown in Table 2. In certain embodiments, the extracellular antigen-binding domain comprises a $V_H$ CDR1 comprising amino acids having the sequence set forth in SEQ ID NO:95 or conservative modifications thereof, a $V_H$ CDR2 comprising amino acids having the sequence set forth in SEQ ID NO:96 or conservative modifications thereof, and a $V_H$ CDR3 comprising amino acids having the sequence set forth in SEQ ID NO:97 or conservative modifications thereof, as shown in Table 2. In certain embodiments, the extracellular antigen-binding domain comprises a $V_L$ CDR1 comprising amino acids having the sequence set forth in SEQ ID NO:98 or conservative modifications thereof, a $V_L$ CDR2 comprising amino acids having the sequence set forth in SEQ ID NO:99 or conservative modifications thereof, and a $V_L$ CDR3 comprising amino acids having the sequence set forth in SEQ ID NO:100 or conservative modifications thereof, as shown in Table 2. In certain embodiments, the extracellular antigen-binding domain comprises a $V_H$ CDR1 comprising amino acids having the sequence set forth in SEQ ID NO:95 or conservative modifications thereof, a $V_H$ CDR2 comprising amino acids having the sequence set forth in SEQ ID NO:96 or conservative modifications thereof, a $V_H$ CDR3 comprising amino acids having the sequence set forth in SEQ ID NO:97 or conservative modifications thereof, a $V_L$ CDR1 comprising amino acids having the sequence set forth in SEQ ID NO:98 or conservative modifications thereof, a $V_L$ CDR2 comprising amino acids having the sequence set forth in SEQ ID NO:99 or conservative modifications thereof, and a $V_L$ CDR3 comprising amino acids having the sequence set forth in SEQ ID NO:100 or conservative modifications thereof, as shown in Table 2. In certain embodiments, the extracellular antigen-binding domain comprises a $V_H$ CDR1 comprising amino acids having the sequence set forth in SEQ ID NO:95, a $V_H$ CDR2 comprising amino acids having the sequence set forth in SEQ ID NO:96, a $V_H$ CDR3 comprising amino acids having the sequence set forth in SEQ ID NO:97, a $V_L$ CDR1 comprising amino acids having the sequence set forth in SEQ ID NO:98, a $V_L$ CDR2 comprising amino acids having the sequence set forth in SEQ ID NO:99, and a $V_L$ CDR3 comprising amino acids having the sequence set forth in SEQ ID NO:100.

$V_L$ regions or CDRs selected from Table 3. In certain embodiments, the extracellular antigen-binding domain comprises a $V_H$ comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:9, as shown in Table 3. In certain embodiments, the extracellular antigen-binding domain comprises a $V_H$ comprising amino acids having the sequence set forth in SEQ ID NO:9, as shown in Table 3. In certain embodiments, the extracellular antigen-binding domain comprises a $V_L$ comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID

TABLE 2

```
Antigen  A BCMA polypeptide having the amino acid sequence of SEQ ID NO: 71
CDRs     1                          2                    3
V_H      VSSNSAAWN [SEQ ID          YRSKWYN [SEQ         ARYGFSGSRFYDT
         NO: 95]                    ID NO: 96]           [SEQ ID NO: 97]

V_L      SSNIGNNA [SEQ ID           FDD [SEQ             AAWDDSLNGYV
         NO: 98]                    ID NO: 99]           [SEQ ID NO: 100]

Full V_H  QVQLQQSGPGLVKPSQTLSLTCAISGDSVSSNSAAWNWIRQSPSR
          GLEWLGRTYYRSKWYNDYAVSVKSRITINPDTSKNQFSLQLNSV
          TPEDTAVYYCARYGFSGSRFYDTWGQGTLVTVSS [SEQ ID NO: 5]

DNA       Caggtacagctgcagcagtcaggtccaggactggtgaagccctcgcagaccctctcactcacctgtgc
          catctccggggacagtgtctctagcaacagtgctgcttggaactggatcaggcagtccccatcgagagg
          ccttgagtggctgggaaggacatactacaggtccaagtggtataatgattatgcagtatctgtgaaaagtc
          gaataaccatcaacccagacacatccaagaaccagttctccctgcagctgaactctgtgactcccgagg
          acacggctgtgtattactgtgcgcgctacggtttctctggttctcgtttctacgatacttggggtcaaggtac
          tctggtgaccgtctcctca [SEQ ID NO: 7]

Full V_L  QPVLTQPPSVSEAPRQRVTISCSGSSSNIGNNAVNWYQQLPGKAP
          KLLIYFDDLLSSGVSDRFSGSKSGTSASLAISGLQSEDEADYYCAA
          WDDSLNGYVFGTGTKVTVLG [SEQ ID NO: 6]

DNA       Cagcctgtgctgactcagccaccctcggtgtctgaagcccccaggcagagggtcaccatctcctgttct
          ggaagcagctccaacatcggaaataatgctgtaaactggtaccagcagctcccaggaaaggctcccaa
          actcctcatctatttgatgatctgctgtcctcaggggtctctgaccgattctctggctccaagtctggcacct
          cagcctccctggccatcagtgggctccagtctgaagatgaggctgattattactgtgcagcatgggatga
          cagcctgaatggttatgtcttcggaactgggaccaaggtcaccgtcctaggt [SEQ ID NO: 8]

scFv      QPVLTQPPSVSEAPRQRVTISCSGSSSNIGNNAVNWYQQLPGKAP
          KLLIYFDDLLSSGVSDRFSGSKSGTSASLAISGLQSEDEADYYCAA
          WDDSLNGYVFGTGTKVTVLGSRGGGGSGGGGSGGGGSLEMAQ
          VQLQQSGPGLVKPSQTLSLTCAISGDSVSSNSAAWNWIRQSPSRG
          LEWLGRTYYRSKWYNDYAVSVKSRITINPDTSKNQFSLQLNSVTP
          EDTAVYYCARYGFSGSRFYDTWGQGTLVTVSS [SEQ ID NO: 73]
```

In certain embodiments, the extracellular antigen-binding domain is a human scFv, which comprises the amino acid sequence of SEQ ID NO:74 and specifically binds to a BCMA polypeptide (e.g., a BCMA polypeptide having the amino acid sequence SEQ ID NO:71, or fragments thereof), which is designated as ET140-180 scFv (also referred to as "ET140-30 scFv").

In certain embodiments, the extracellular antigen-binding domain is a human scFv, which comprises a heavy chain variable region comprising amino acids having the sequence set forth in SEQ ID NO:9 and a light chain variable region comprising amino acids having the sequence set forth in SEQ ID NO:10, optionally with (iii) a linker sequence, for example a linker peptide, between the heavy chain variable region and the light chain variable region. In certain embodiments, the linker comprises amino acids having the sequence set forth in SEQ ID NO:69. In certain embodiments, the extracellular antigen-binding domain is a human scFv-Fc fusion protein or full length human IgG with $V_H$ and NO:10, as shown in Table 3. In certain embodiments, the extracellular antigen-binding domain comprises a $V_L$ comprising amino acids having the sequence set forth in SEQ ID NO:10, as shown in Table 3. In certain embodiments, the extracellular antigen-binding domain comprises a $V_H$ comprising amino acids having the sequence set forth in SEQ ID NO:9 and a $V_L$ comprising amino acids having the sequence set forth in SEQ ID NO:10, as shown in Table 3. In certain embodiments, the extracellular antigen-binding domain comprises a $V_H$ CDR1 comprising amino acids having the sequence set forth in SEQ ID NO:101 or conservative modifications thereof, a $V_H$ CDR2 comprising amino acids having the sequence set forth in SEQ ID NO:102 or conservative modifications thereof, and a $V_H$ CDR3 comprising amino acids having the sequence set forth in SEQ ID NO:103 or conservative modifications thereof, as shown in Table 3. In certain embodiments, the extracellular antigen-binding domain comprises a $V_L$ CDR1 comprising amino acids having the sequence set forth in SEQ ID NO:104 or conservative modifications thereof, a $V_L$ CDR2 comprising amino acids having the sequence set forth in SEQ ID NO:105 or conservative modifications thereof, and a $V_L$ CDR3 comprising amino acids having the sequence set forth in SEQ ID NO:106 or conservative modifications thereof, as shown in Table 3. In certain embodiments, the extracellular antigen-binding domain comprises a $V_H$ CDR1 comprising amino acids having the sequence set forth in SEQ ID NO:101 or conservative modifications thereof, a $V_H$ CDR2 comprising amino acids having the sequence set forth in SEQ ID NO:102 or conservative modifications thereof, a $V_H$ CDR3 comprising amino acids having the sequence set forth in SEQ ID NO:103 or conservative modifications thereof, a $V_L$ CDR1 comprising amino acids having the sequence set forth in SEQ ID NO:104 or conservative modifications thereof, a $V_L$ CDR2 comprising amino acids having the sequence set forth in SEQ ID NO:105 or conservative modifications thereof, and a $V_L$ CDR3 comprising amino acids having the sequence set forth in SEQ ID NO:106 or conservative modifications thereof, as shown in Table 3. In certain embodiments, the extracellular antigen-binding domain comprises a $V_H$ CDR1 comprising amino acids having the sequence set forth in SEQ ID NO:101, a $V_H$ CDR2 comprising amino acids having the sequence set forth in SEQ ID NO:102, a $V_H$ CDR3 comprising amino acids having the sequence set forth in SEQ ID NO:103, a $V_L$ CDR1 comprising amino acids having the sequence set forth in SEQ ID NO:104, a $V_L$ CDR2 comprising amino acids having the sequence set forth in SEQ ID NO:105, and a $V_L$ CDR3 comprising amino acids having the sequence set forth in SEQ ID NO:106.

BCMA polypeptide (e.g., a BCMA polypeptide having the amino acid sequence SEQ ID NO:71, or fragments thereof), which is designated as ET140-172 scFv (also referred to as "ET140-22 scFv").

In certain embodiments, the extracellular antigen-binding domain is a human scFv, which comprises a heavy chain variable region comprising amino acids having the sequence set forth in SEQ ID NO:13 and a light chain variable region comprising amino acids having the sequence set forth in SEQ ID NO:14, optionally with (iii) a linker sequence, for example a linker peptide, between the heavy chain variable region and the light chain variable region. In certain embodiments, the linker comprises amino acids having the sequence set forth in SEQ ID NO:69. In certain embodiments, the extracellular antigen-binding domain is a human scFv-Fc fusion protein or full length human IgG with $V_H$ and $V_L$ regions or CDRs selected from Table 4. In certain embodiments, the extracellular antigen-binding domain comprises a $V_H$ comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:13, as shown in Table 4. In certain embodiments, the extracellular antigen-binding domain comprises a $V_H$ comprising amino acids having the sequence set forth in SEQ ID NO:13, as shown in Table 4. In certain embodiments, the extracellular antigen-binding domain comprises a $V_L$ comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID

TABLE 3

```
Antigen   A BCMA polypeptide having the amino acid sequence of SEQ ID NO: 71
CDRs      1                        2                        3
V_H       GGTFSSYA [SEQ ID         IIPILGIA [SEQ ID         ARSGYSKSIVSYMD
          NO: 101]                 NO: 102]                 Y [SEQ ID NO: 103]

V_L       SSNIGSNV [SEQ ID         RNN [SEQ ID              AAWDDSLSGYV
          NO: 104]                 NO: 105]                 [SEQ ID NO: 106]

Full V_H  EVQLVQSGAEVKKPGSSVKVSCKASGGTFSSYAISWVRQAPGQGL
          EWMGRIIPILGIANYAQKFQGRVTMTEDTSTDTAYMELSSLRSEDT
          AVYYCARSGYSKSIVSYMDYWGQGTLVTVSS [SEQ ID NO: 9]

DNA       Gaggtccagctggtgcagtctggagctgaggtgaagaagcctgggtcctcggtgaaggtctcctgcaa
          ggatctggaggcaccttcagcagctatgctatcagctgggtgcgacaggcccctggacaagggcttga
          gtggatgggaaggatcatccctatccttggtatagcaaactacgcacagaagttccagggcagagtcacc
          atgaccgaggacacatctacagacacagcctacatggagctgagcagcctgagatctgaggacacggc
          cgtgtattactgtgcgcgctctggttactctaaatctatcgtttcttacatggattactggggtcaaggtactct
          ggtgaccgtctcctca [SEQ ID NO: 11]

Full V_L  LPVLTQPPSTSGTPGQRVTVSCSGSSSNIGSNVVFWYQQLPGTAPK
          LVIYRNNQRPSGVPDRFSVSKSGTSASLAISGLRSEDEADYYCAAW
          DDSLSGYVFGTGTKVTVLG [SEQ ID NO: 10]

DNA       Ctgcctgtgctgactcagccccctccacgtctgggaccccgggcagagggtcaccgtctcttgttctg
          gaagcagctccaacatcggaagtaatgttgtattctggtaccagcagctcccaggcacggcccccaaact
          tgtcatctataggaataatcaacggcctcaggggtccctgaccgattctctgtctccaagtctggcacctc
          agcctcccggcatcagtgggctccggtccgaggacgaggctgattattattgtgcagatgggatgac
          agcctgagtggttatgtatcggaactgggaccaaggtcaccgtcctaggt [SEQ ID NO: 12]

scFv      LPVLTQPPSTSGTPGQRVTVSCSGSSSNIGSNVVFWYQQLPGTAPK
          LVIYRNNQRPSGVPDRFSVSKSGTSASLAISGLRSEDEADYYCAAW
          DDSLSGYVFGTGTKVTVLGSRGGGGSGGGGSGGGGSLEMAEVQL
          VQSGAEVKKPGSSVKVSCKASGGTFSSYAISWVRQAPGQGLEWM
          GRIIPILGIANYAQKFQGRVTMTEDTSTDTAYMELSSLRSEDTAVY
          YCARSGYSKSIVSYMDYWGQGTLVTVSS [SEQ ID NO: 74]
```

In certain embodiments, the extracellular antigen-binding domain is a human scFv, which comprises the amino acid sequence of SEQ ID NO:75 and specifically binds to a NO:14, as shown in Table 4. In certain embodiments, the extracellular antigen-binding domain comprises a $V_L$ comprising amino acids having the sequence set forth in SEQ ID NO:14, as shown in Table 4. In certain embodiments, the extracellular antigen-binding domain comprises a $V_H$ comprising amino acids having the sequence set forth in SEQ ID NO:13 and a $V_L$ comprising amino acids having the sequence set forth in SEQ ID NO:14, as shown in Table 4. In certain embodiments, the extracellular antigen-binding domain comprises a $V_H$ CDR1 comprising amino acids having the sequence set forth in SEQ ID NO:107 or conservative modifications thereof, a $V_H$ CDR2 comprising amino acids having the sequence set forth in SEQ ID NO:108 or conservative modifications thereof, and a $V_H$ CDR3 comprising amino acids having the sequence set forth in SEQ ID NO:109 or conservative modifications thereof, as shown in Table 4. In certain embodiments, the extracellular antigen-binding domain comprises a $V_L$ CDR1 comprising amino acids having the sequence set forth in SEQ ID NO:110 or conservative modifications thereof, a $V_L$ CDR2 comprising amino acids having the sequence set forth in SEQ ID NO:111 or conservative modifications thereof, and a $V_L$ CDR3 comprising amino acids having the sequence set forth in SEQ ID NO:112 or conservative modifications thereof, as shown in Table 4. In certain embodiments, the extracellular antigen-binding domain comprises a $V_H$ CDR1 comprising amino acids having the sequence set forth in SEQ ID NO:107 or conservative modifications thereof, a $V_H$ CDR2 comprising amino acids having the sequence set forth in SEQ ID NO:108 or conservative modifications thereof, a $V_H$ CDR3 comprising amino acids having the sequence set forth in SEQ ID NO:109 or conservative modifications thereof, a $V_L$ CDR1 comprising amino acids having the sequence set forth in SEQ ID NO:110 or conservative modifications thereof, a $V_L$ CDR2 comprising amino acids having the sequence set forth in SEQ ID NO:111 or conservative modifications thereof, and a $V_L$ CDR3 comprising amino acids having the sequence set forth in SEQ ID NO:112 or conservative modifications thereof, as shown in Table 4. In certain embodiments, the extracellular antigen-binding domain comprises a $V_H$ CDR1 comprising amino acids having the sequence set forth in SEQ ID NO:107, a $V_H$ CDR2 comprising amino acids having the sequence set forth in SEQ ID NO:108, a $V_H$ CDR3 comprising amino acids having the sequence set forth in SEQ ID NO:109, a $V_L$ CDR1 comprising amino acids having the sequence set forth in SEQ ID NO:110, a $V_L$ CDR2 comprising amino acids having the sequence set forth in SEQ ID NO:111, and a $V_L$ CDR3 comprising amino acids having the sequence set forth in SEQ ID NO:112.

TABLE 4

| Antigen | A BCMA polypeptide having the amino acid sequence of SEQ ID NO: 71 | | |
|---|---|---|---|
| CDRs | 1 | 2 | 3 |
| $V_H$ | GYTFTSYY [SEQ ID NO: 107] | INPSGGST [SEQ ID NO: 108] | ARSQWGGVLDY [SEQ ID NO: 109] |
| $V_L$ | SSNIGARYD [SEQ ID NO: 110] | GNN [SEQ ID NO: 111] | QSYDSSLSASV [SEQ ID NO: 112] |
| Full $V_H$ | EVQLVQSGAEVKKPGASVKVSCKASGYTFTSYYMHWVRQAPGQ GLEWMGIINPSGGSTSYAQKFQGRVTMTRDTSTSTVYMELSSLRS EDTAVYYCARSQWGGVLDYWGQGTLVTVSS [SEQ ID NO: 13] | | |
| DNA | Gaggtccagctggtacagtctggggctgaggtgaagaagcctggggcctcagtgaaggtttcctgcaa ggcatctggatacaccttcaccagctactatatgcactgggtgcgacaggcccctggacaagggcttgag tggatgggaataatcaaccctagtggtggtagcacaagctacgcacagaagttccagggcagagtcacc atgaccagggacacgtccacgagcacagtctacatggagctgagcagcctgagatctgaggacacggc cgtgtattactgtgcgcgctctcagtggggtggtgttctggattactggggtcaaggtactctggtgaccgt ctcctca [SEQ ID NO: 15] | | |
| Full $V_L$ | QSVVTQPPSVSGAPGQRVTISCSGSSSNIGARYDVQWYQQLPGTAP KLLIFGNNNRPSGVPDRFSGSKSGTSASLAITGLQAEDEADYYCQS YDSSLSASVFGGGTKLTVLG [SEQ ID NO: 14] | | |
| DNA | Cagtctgtcgtgacgcagccgccctcagtgtctggggcccagggcagagggtcaccatctcctgcag tgggagcagctccaacatcggggcacgttatgatgttcagtggtaccagcagcttccaggaacagcccc caaactcctcatctttggtaacaacaatcggccctcaggggtccctgaccgattctctggctccaagtctgg cacgtcagcctccctggccatcactgggctccaggctgaggatgaggctgattattactgccagtcctatg acagcagcctgagtgcttcggtgttcggcggagggaccaagctgaccgtcctaggt [SEQ ID NO: 16] | | |
| scFv | QSVVTQPPSVSGAPGQRVTISCSGSSSNIGARYDVQWYQQLPGTAP KLLIFGNNNRPSGVPDRFSGSKSGTSASLAITGLQAEDEADYYCQS YDSSLSASVFGGGTKLTVLGSRGGGGSGGGGSGGGGSLEMAEVQ LVQSGAEVKKPGASVKVSCKASGYTFTSYYMHWVRQAPGQGLE WMGIINPSGGSTSYAQKFQGRVTMTRDTSTSTVYMELSSLRSEDT AVYYCARSQWGGVLDYWGQGTLVTVSS [SEQ ID NO: 75] | | |

In certain embodiments, the extracellular antigen-binding domain is a human scFv, which comprises the amino acid sequence of SEQ ID NO:76 and specifically binds to a BCMA polypeptide (e.g., a BCMA polypeptide having the amino acid sequence SEQ ID NO:71, or fragments thereof), which is designated as ET140-157 scFv (also referred to as "ET140-7 scFv").

In certain embodiments, the extracellular antigen-binding domain is a human scFv, which comprises a heavy chain variable region comprising amino acids having the sequence set forth in SEQ ID NO:17 and a light chain variable region comprising amino acids having the sequence set forth in SEQ ID NO:18, optionally with (iii) a linker sequence, for example a linker peptide, between the heavy chain variable region and the light chain variable region. In certain embodiments, the linker comprises amino acids having the sequence set forth in SEQ ID NO:69. In certain embodiments, the extracellular antigen-binding domain is a human scFv-Fc fusion protein or full length human IgG with $V_H$ and $V_L$ regions or CDRs selected from Table 5. In certain embodiments, the extracellular antigen-binding domain comprises a $V_H$ comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:17, as shown in Table 5. In certain embodiments, the extracellular antigen-binding domain comprises a $V_H$ comprising amino acids having the sequence set forth in SEQ ID NO:17, as shown in Table 5. In certain embodiments, the extracellular antigen-binding domain comprises a $V_L$ comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:18, as shown in Table 5. In certain embodiments, the extracellular antigen-binding domain comprises a $V_L$ comprising amino acids having the sequence set forth in SEQ ID NO:18, as shown in Table 5. In certain embodiments, the extracellular antigen-binding domain comprises a $V_H$ comprising amino acids having the sequence set forth in SEQ ID NO:17 and a $V_L$ comprising amino acids having the sequence set forth in SEQ ID NO:18, as shown in Table 5. In certain embodiments, the extracellular antigen-binding domain comprises a $V_H$ CDR1 comprising amino acids having the sequence set forth in SEQ ID NO:113 or conservative modifications thereof, a $V_H$ CDR2 comprising amino acids having the sequence set forth in SEQ ID NO:114 or conservative modifications thereof, and a $V_H$ CDR3 comprising amino acids having the sequence set forth in SEQ ID NO:115 or conservative modifications thereof, as shown in Table 5. In certain embodiments, the extracellular antigen-binding domain comprises a $V_L$ CDR1 comprising amino acids having the sequence set forth in SEQ ID NO:116 or conservative modifications thereof, a $V_L$ CDR2 comprising amino acids having the sequence set forth in SEQ ID NO:117 or conservative modifications thereof, and a $V_L$ CDR3 comprising amino acids having the sequence set forth in SEQ ID NO:118 or conservative modifications thereof, as shown in Table 5. In certain embodiments, the extracellular antigen-binding domain comprises a $V_H$ CDR1 comprising amino acids having the sequence set forth in SEQ ID NO:113 or conservative modifications thereof, a $V_H$ CDR2 comprising amino acids having the sequence set forth in SEQ ID NO:114 or conservative modifications thereof, a $V_H$ CDR3 comprising amino acids having the sequence set forth in SEQ ID NO:115 or conservative modifications thereof, a $V_L$ CDR1 comprising amino acids having the sequence set forth in SEQ ID NO:116 or conservative modifications thereof, a $V_L$ CDR2 comprising amino acids having the sequence set forth in SEQ ID NO:117 or conservative modifications thereof, and a $V_L$ CDR3 comprising amino acids having the sequence set forth in SEQ ID NO:118 or conservative modifications thereof, as shown in Table 5. In certain embodiments, the extracellular antigen-binding domain comprises a $V_H$ CDR1 comprising amino acids having the sequence set forth in SEQ ID NO:113, a $V_H$ CDR2 comprising amino acids having the sequence set forth in SEQ ID NO:114, a $V_H$ CDR3 comprising amino acids having the sequence set forth in SEQ ID NO:115, a $V_L$ CDR1 comprising amino acids having the sequence set forth in SEQ ID NO:116, a $V_L$ CDR2 comprising amino acids having the sequence set forth in SEQ ID NO:117, and a $V_L$ CDR3 comprising amino acids having the sequence set forth in SEQ ID NO:118.

TABLE 5

| Antigen | A BCMA polypeptide having the amino acid sequence of SEQ ID NO: 71 | | |
|---|---|---|---|
| CDRs | 1 | 2 | 3 |
| $V_H$ | GGTFSSYA [SEQ ID NO: 113] | IIPILGIA [SEQ ID NO: 114] | ARTGYESWGSYEVI DR [SEQ ID NO: 115] |
| $V_L$ | SSNIGSNT [SEQ ID NO: 116] | SNN [SEQ ID NO: 117] | AAWDDSLNGVV [SEQ ID NO: 118] |
| Full $V_H$ | QVQLVESGAEVKKPGSSVKVSCKASGGTFSSYAISWVRQAPGQGL EWMGRIIPILGIANYAQKFQGRVTITADESTSTAYMELSSLRSEDTA VYYCARTGYESWGSYEVIDRWGQGTLVTVSS [SEQ ID NO: 17] | | |
| DNA | Caggtgcagctggtggagtctgggctgaggtgaagaagcctgggtcctcggtgaaggtctcctgcaa ggcttctggaggcacctcagcagctatgctatcagctgggtgcgacaggcccctggacaagggcttga gtggatgggaaggatcatccctatccttggtatagcaaactacgcacagaagttccaggcagagtcacg attaccgcggacgaatccacgagcacagcctacatggagctgagcagcctgagatctgaggacacggc cgtatattactgtgcgcgcactggttacgaatcttggggttcttacgaagttatcgatcgttggggtcaaggt actctggtgaccgtctcctca [SEQ ID NO: 19] | | |
| Full $V_L$ | QAVLTQPPSASGTPGQRVTISCSGSSSNIGSNTVNWYRQLPGTAPK LLIYSNNQRPSGVPDRFSGSKSGTSASLAISGLQSEDEADYYCAAW DDSLNGVVFGGGTKLTVLG [SEQ ID NO: 18] | | |
| DNA | Caggctgtgctgactcagccaccctcagcgtctggaccccgggcagagggtcaccatctcttgttct ggaagcagctccaacatcggaagtaatactgtaaactggtaccggcagctcccaggaacggcccccaa actcctcatctatagtaataatcagcggccctcaggggtccctgaccgattctctggctccaagtctgcac ctcagcctccctggccatcagtgggctccagtctgaggatgaggctgattattactgtgcagcatgggatg acagcctgaatggtgtggtattcggcggagggaccaagctgaccgtcctaggt [SEQ ID NO: 20] | | |
| scFv | QAVLTQPPSASGTPGQRVTISCSGSSSNIGSNTVNWYRQLPGTAPK LLIYSNNQRPSGVPDRFSGSKSGTSASLAISGLQSEDEADYYCAAW DDSLNGVVFGGGTKLTVLGSRGGGGSGGGGSGGGGSLEMAQVQ LVESGAEVKKPGSSVKVSCKASGGTFSSYAISWVRQAPGQGLEW MGRIIPILGIANYAQKFQGRVTITADESTSTAYMELSSLRSEDTAVY YCARTGYESWGSYEVIDRWGQGTLVTVSS [SEQ ID NO: 76] | | |

In certain embodiments, the extracellular antigen-binding domain is a human scFv, which comprises the amino acid sequence of SEQ ID NO:77 and specifically binds to a BCMA polypeptide (e.g., a BCMA polypeptide having the amino acid sequence SEQ ID NO:71, or fragments thereof), which is designated as ET140-153 scFv (also referred to as "ET140-3 scFv").

In certain embodiments, the extracellular antigen-binding domain is a human scFv, which comprises a heavy chain variable region comprising amino acids having the sequence set forth in SEQ ID NO:21 and a light chain variable region comprising amino acids having the sequence set forth in SEQ ID NO:22, optionally with (iii) a linker sequence, for example a linker peptide, between the heavy chain variable region and the light chain variable region. In certain embodiments, the linker comprises amino acids having the sequence set forth in SEQ ID NO:69. In certain embodiments, the extracellular antigen-binding domain is a human scFv-Fc fusion protein or full length human IgG with $V_H$ and $V_L$ regions or CDRs selected from Table 6. In certain embodiments, the extracellular antigen-binding domain comprises a $V_H$ comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99%. A homologous to the amino acid sequence set forth in SEQ ID NO:21, as shown in Table 6. In certain embodiments, the extracellular antigen-binding domain comprises a $V_H$ comprising amino acids having the sequence set forth in SEQ ID NO:21, as shown in Table 6. In certain embodiments, the extracellular antigen-binding domain comprises a $V_L$ comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:22, as shown in Table 6. In certain embodiments, the extracellular antigen-binding domain comprises a $V_L$ comprising amino acids having the sequence set forth in SEQ ID NO:22, as shown in Table 6. In certain embodiments, the extracellular antigen-binding domain comprises a $V_H$ comprising amino acids having the sequence set forth in SEQ ID NO:21 and a $V_L$ comprising amino acids having the sequence set forth in SEQ ID NO:22, as shown in Table 6.

In certain embodiments, the extracellular antigen-binding domain comprises a $V_H$ CDR1 comprising amino acids having the sequence set forth in SEQ ID NO:119 or conservative modifications thereof, a $V_H$ CDR2 comprising amino acids having the sequence set forth in SEQ ID NO:120 or conservative modifications thereof, and a $V_H$ CDR3 comprising amino acids having the sequence set forth in SEQ ID NO:121 or conservative modifications thereof, as shown in Table 6. In certain embodiments, the extracellular antigen-binding domain comprises a $V_L$ CDR1 comprising amino acids having the sequence set forth in SEQ ID NO:122 or conservative modifications thereof, a $V_L$ CDR2 comprising amino acids having the sequence set forth in SEQ ID NO:123 or conservative modifications thereof, and a $V_L$ CDR3 comprising amino acids having the sequence set forth in SEQ ID NO:124 or conservative modifications thereof, as shown in Table 6. In certain embodiments, the extracellular antigen-binding domain comprises a $V_H$ CDR1 comprising amino acids having the sequence set forth in SEQ ID NO:119 or conservative modifications thereof, a $V_H$ CDR2 comprising amino acids having the sequence set forth in SEQ ID NO:120 or conservative modifications thereof, a $V_H$ CDR3 comprising amino acids having the sequence set forth in SEQ ID NO:121 or conservative modifications thereof, a $V_L$ CDR1 comprising amino acids having the sequence set forth in SEQ ID NO:122 or conservative modifications thereof, a $V_L$ CDR2 comprising amino acids having the sequence set forth in SEQ ID NO:123 or conservative modifications thereof, and a $V_L$ CDR3 comprising amino acids having the sequence set forth in SEQ ID NO:124 or conservative modifications thereof, as shown in Table 6. In certain embodiments, the extracellular antigen-binding domain comprises a $V_H$ CDR1 comprising amino acids having the sequence set forth in SEQ ID NO:119, a $V_H$ CDR2 comprising amino acids having the sequence set forth in SEQ ID NO:120, a $V_H$ CDR3 comprising amino acids having the sequence set forth in SEQ ID NO:121, a $V_L$ CDR1 comprising amino acids having the sequence set forth in SEQ ID NO:122, a $V_L$ CDR2 comprising amino acids having the sequence set forth in SEQ ID NO:123, and a $V_L$ CDR3 comprising amino acids having the sequence set forth in SEQ ID NO:124.

TABLE 6

| Antigen | A BCMA polypeptide having the amino acid sequence of SEQ ID NO: 71 | | |
|---|---|---|---|
| CDRs | 1 | 2 | 3 |
| $V_H$ | GGTFSSYA [SEQ ID NO: 119] | IIPILGIA [SEQ ID NO: 120] | ARGGYYSHDMWS ED [SEQ ID NO: 121] |
| $V_L$ | SSNIGSNS [SEQ ID NO: 122] | SNN [SEQ ID NO: 123] | ATWDDNLNVHYV [SEQ ID NO: 124] |

Full $V_H$  QVQLVQSGAEVKKPGSSVKVSCKASGGTFSSYAISWVRQAPGQGL
EWMGRIIPILGIANYAQKFQGRVTITADKSTSTAYMELSSLRSEDTA
VYYCARGGYYSHDMWSEDWGQGTLVTVSS [SEQ ID NO: 21]

DNA     Caggtgcagctggtgcagtctggggctgaggtgaagaagcctgggtcctcggtgaaggtctcctgcaag
gcttctggaggcacctttcagcagctatgctatcagctgggtgcgacaggcccctggacaagggcttgagt
ggatgggaaggatcatccctatccttggtatagcaaactacgcacagaagttccagggcagagtcacgatt
accgcggacaaatccacgagcacagcctacatggagctgagcagcctgagatctgaggacacggccgt
gtattactgtgcgcgcggtggttactactctcatgacatgtggtctgaagattggggtcaaggtactctggtg
accgtctcctca [SEQ ID NO: 23]

Full $V_L$  LPVLTQPPSASGTPGQRVTISCSGRSSNIGSNSVNWYRQLPGAAPKL
LIYSNNQRPPGVPVRFSGSKSGTSASLAISGLQSEDEATYYCATWD
DNLNVHYVFGTGTKVTVLG [SEQ ID NO: 22]

TABLE 6-continued

| DNA | Ctgcctgtgctgactcagccaccctcagcgtctgggacccccgggcagagggtcaccatctcttgttctg gacgcagttccaacatcgggagtaattctgttaactggtatcgacaactcccaggagcggcccccaaactc ctcatctatagtaataatcagcggccccaggggtccctgtgcgattctctggctccaagtctggcacctca gcctccctggccatcagtgggctccagtctgaagatgaggccacttattactgtgcaacatgggatgacaa tctgaatgttcactatgtcttcggaactgggaccaaggtcaccgtcctaggt [SEQ ID NO: 24] |
|---|---|
| scFv | LPVLTQPPSASGTPGQRVTISCSGRSSNIGSNSVNWYRQLPGAAPKL LIYSNNQRPPGVPVRFSGSKSGTSASLAISGLQSEDEATYYCATWD DNLNVHYVFGTGTKVTVLGSRGGGGSGGGGSGGGGSLEMAQVQ LVQSGAEVKKPGSSVKVSCKASGGTFSSYAISWVRQAPGQGLEW MGRIIPILGIANYAQKFQGRVTITADKSTSTAYMELSSLRSEDTAVY YCARGGYYSHDMWSEDWGQGTLVTVSS [SEQ ID NO: 77] |

In certain embodiments, the extracellular antigen-binding domain is a human scFv, which comprises the amino acid sequence of SEQ ID NO:78 and specifically binds to a BCMA polypeptide (e.g., a BCMA polypeptide having the amino acid sequence SEQ ID NO:71, or fragments thereof), which is designated as ET140-201 scFv (also referred to as "ET140-51 scFv").

In certain embodiments, the extracellular antigen-binding domain is a human scFv, which comprises a heavy chain variable region comprising amino acids having the sequence set forth in SEQ ID NO:25 and a light chain variable region comprising amino acids having the sequence set forth in SEQ ID NO:26, optionally with (iii) a linker sequence, for example a linker peptide, between the heavy chain variable region and the light chain variable region. In certain embodiments, the linker comprises amino acids having the sequence set forth in SEQ ID NO:69. In certain embodiments, the extracellular antigen-binding domain is a human scFv-Fc fusion protein or full length human IgG with $V_H$ and $V_L$ regions or CDRs selected from Table 7. In certain embodiments, the extracellular antigen-binding domain comprises a $V_H$ comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:25, as shown in Table 7. In certain embodiments, the extracellular antigen-binding domain comprises a $V_H$ comprising amino acids having the sequence set forth in SEQ ID NO:25, as shown in Table 7. In certain embodiments, the extracellular antigen-binding domain comprises a $V_L$ comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:26, as shown in Table 7. In certain embodiments, the extracellular antigen-binding domain comprises a $V_L$ comprising amino acids having the sequence set forth in SEQ ID NO:26, as shown in Table 7. In certain embodiments, the extracellular antigen-binding domain comprises a $V_H$ comprising amino acids having the sequence set forth in SEQ ID NO:25 and a $V_L$ comprising amino acids having the sequence set forth in SEQ ID NO:26, as shown in Table 7.

In certain embodiments, the extracellular antigen-binding domain comprises a $V_H$ CDR1 comprising amino acids having the sequence set forth in SEQ ID NO:125 or conservative modifications thereof, a $V_H$ CDR2 comprising amino acids having the sequence set forth in SEQ ID NO:126 or conservative modifications thereof, and a $V_H$ CDR3 comprising amino acids having the sequence set forth in SEQ ID NO:127 or conservative modifications thereof, as shown in Table 7. In certain embodiments, the extracellular antigen-binding domain comprises a $V_L$ CDR1 comprising amino acids having the sequence set forth in SEQ ID NO:128 or conservative modifications thereof, a $V_L$ CDR2 comprising amino acids having the sequence set forth in SEQ ID NO:129 or conservative modifications thereof, and a $V_L$ CDR3 comprising amino acids having the sequence set forth in SEQ ID NO:130 or conservative modifications thereof, as shown in Table 7. In certain embodiments, the extracellular antigen-binding domain comprises a $V_H$ CDR1 comprising amino acids having the sequence set forth in SEQ ID NO:125 or conservative modifications thereof, a $V_H$ CDR2 comprising amino acids having the sequence set forth in SEQ ID NO:126 or conservative modifications thereof, a $V_H$ CDR3 comprising amino acids having the sequence set forth in SEQ ID NO:127 or conservative modifications thereof, a $V_L$ CDR1 comprising amino acids having the sequence set forth in SEQ ID NO:128 or conservative modifications thereof, a $V_L$ CDR2 comprising amino acids having the sequence set forth in SEQ ID NO:129 or conservative modifications thereof, and a $V_L$ CDR3 comprising amino acids having the sequence set forth in SEQ ID NO:130 or conservative modifications thereof, as shown in Table 7. In certain embodiments, the extracellular antigen-binding domain comprises a $V_H$ CDR1 comprising amino acids having the sequence set forth in SEQ ID NO:125, a $V_H$ CDR2 comprising amino acids having the sequence set forth in SEQ ID NO:126, a $V_H$ CDR3 comprising amino acids having the sequence set forth in SEQ ID NO:127, a $V_L$ CDR1 comprising amino acids having the sequence set forth in SEQ ID NO:128, a $V_L$ CDR2 comprising amino acids having the sequence set forth in SEQ ID NO:129, and a $V_L$ CDR3 comprising amino acids having the sequence set forth in SEQ ID NO:130.

TABLE 7

| Antigen | A BCMA polypeptide having the amino acid sequence of SEQ ID NO: 71 | | |
|---|---|---|---|
| CDRs | 1 | 2 | 3 |
| $V_H$ | GGSISNSNW [SEQ ID NO: 125] | IYHSGST [SEQ ID NO: 126] | ARRDNWKTPTTKID GFDI [SEQ ID NO: 127] |
| $V_L$ | SGYSNYK [SEQ ID NO: 128] | VGTGGIVG [SEQ ID NO: 129] | GADHGSGSNFVYV SEQ ID NO: 130] |

TABLE 7-continued

```
Full V_H   QVQLQESGPGLVKPSGTLSLTCGVSGGSISNSNWWSWVRQPPGKG
           LEWIGEIYHSGSTKYNPSLRSRVTISVDKSKNQFSLKLSSVTAADT
           AVYYCARRDNWKTPTTKIDGFDIWGQGTMVTVSS [SEQ ID
           NO: 25]

DNA        Caggtgcagctgcaggagtcgggcccaggactggtgaagccttcggggaccctgtccctcacctgcg
           gtgtctctggtggctccatcagcaatagtaactggtggagttgggtccgccagcccccgggaaggggc
           tggagtggattggggaaatctatcatagtgggagcaccaagtacaaacccgtccctcaggagtcgagtcac
           catatcagtagacaagtccaagaaccagttctccctaaaattgagctctgtgaccgccgcggacacggcc
           gtatattactgtgcgagacgagataactggaagaccccactaccaaaattgatggttttgatatctggggc
           caagggacaatggtcaccgtctcttca [SEQ ID NO: 27]

Full V_L   QPVLTQPPSASASLGASVTLTCTLSSGYSNYKVDWYQQRPGKGPR
           FVMRVGTGGIVGSKGDGIPDRFSVLGSGLNRYLTIKNIQEEDEGDY
           HCGADHGSGSNFVYVFGTGTKVTVLG [SEQ ID NO: 26]

DNA        Cagcctgtgctgactcagccacctttctgcatcagcctccctgggagcctcggtcacactcacctgcaccc
           tgagcagcggctacagtaattataaagtggactggtaccagcagagaccagggaagggccccggtttg
           tgatgcgagtgggcactggtgggattgtgggatccaaggggatggcatccctgatcgcttctcagtcttg
           ggctcaggcctgaatcggtacctgaccatcaagaacatccaggaagaagatgagggtgactatcactgt
           ggggcagaccatggcagtgggagcaacttcgtgtatgtcttcggaactgggaccaaggtcaccgtccta
           ggt [SEQ ID NO: 28]

scFv       QPVLTQPPSASASLGASVTLTCTLSSGYSNYKVDWYQQRPGKGPR
           FVMRVGTGGIVGSKGDGIPDRFSVLGSGLNRYLTIKNIQEEDEGDY
           HCGADHGSGSNFVYVFGTGTKVTVLGSRGGGSGGGGSGGGGSL
           EMAQVQLQESGPGLVKPSGTLSLTCGVSGGSISNSNWWSWVRQP
           PGKGLEWIGEIYHSGSTKYNPSLRSRVTISVDKSKNQFSLKLSSVTA
           ADTAVYYCARRDNWKTPTTKIDGFDIWGQGTMVTVSS [SEQ ID
           NO: 78]
```

In certain embodiments, the extracellular antigen-binding domain is a human scFv, which comprises the amino acid sequence of SEQ ID NO:79 and specifically binds to a BCMA polypeptide (e.g., a BCMA polypeptide having the amino acid sequence SEQ ID NO:71, or fragments thereof), which is designated as ET140-167 scFv (also referred to as "ET140-17 scFv").

In certain embodiments, the extracellular antigen-binding domain is a human scFv, which comprises a heavy chain variable region comprising amino acids having the sequence set forth in SEQ ID NO:29 and a light chain variable region comprising amino acids having the sequence set forth in SEQ ID NO:30, optionally with (iii) a linker sequence, for example a linker peptide, between the heavy chain variable region and the light chain variable region. In certain embodiments, the linker comprises amino acids having the sequence set forth in SEQ ID NO:69. In certain embodiments, the extracellular antigen-binding domain is a human scFv-Fc fusion protein or full length human IgG with $V_H$ and $V_L$ regions or CDRs selected from Table 8. In certain embodiments, the extracellular antigen-binding domain comprises a $V_H$ comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:29, as shown in Table 8. In certain embodiments, the extracellular antigen-binding domain comprises a $V_H$ comprising amino acids having the sequence set forth in SEQ ID NO:29, as shown in Table 8. In certain embodiments, the extracellular antigen-binding domain comprises a $V_L$ comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:30, as shown in Table 8. In certain embodiments, the extracellular antigen-binding domain comprises a $V_L$ comprising amino acids having the sequence set forth in SEQ ID NO:30, as shown in Table 8. In certain embodiments, the extracellular antigen-binding domain comprises a $V_H$ comprising amino acids having the sequence set forth in SEQ ID NO:29 and a $V_L$ comprising amino acids having the sequence set forth in SEQ ID NO:30, as shown in Table 8. In certain embodiments, the anti-BCMA comprises a $V_H$ CDR1 comprising amino acids having the sequence set forth in SEQ ID NO:131 or conservative modifications thereof, a $V_H$ CDR2 comprising amino acids having the sequence set forth in SEQ ID NO:132 or conservative modifications thereof, and a $V_H$ CDR3 comprising amino acids having the sequence set forth in SEQ ID NO:133 or conservative modifications thereof, as shown in Table 8. In certain embodiments, the extracellular antigen-binding domain comprises a $V_L$ CDR1 comprising amino acids having the sequence set forth in SEQ ID NO:134 or conservative modifications thereof, a $V_L$ CDR2 comprising amino acids having the sequence set forth in SEQ ID NO:135 or conservative modifications thereof, and a $V_L$ CDR3 comprising amino acids having the sequence set forth in SEQ ID NO:136 or conservative modifications thereof, as shown in Table 8. In certain embodiments, the extracellular antigen-binding domain comprises a $V_H$ CDR1 comprising amino acids having the sequence set forth in SEQ ID NO:131 or conservative modifications thereof, a $V_H$ CDR2 comprising amino acids having the sequence set forth in SEQ ID NO:132 or conservative modifications thereof, a $V_H$ CDR3 comprising amino acids having the sequence set forth in SEQ ID NO:133 or conservative modifications thereof, a $V_L$ CDR1 comprising amino acids having the sequence set forth in SEQ ID NO:134 or conservative modifications thereof, a $V_L$ CDR2 comprising amino acids having the sequence set forth in SEQ ID NO:135 or conservative modifications thereof, and a $V_L$ CDR3 comprising amino acids having the sequence set forth in SEQ ID NO:136 or conservative modifications thereof, as shown in Table 8. In certain embodiments, the extracellular antigen-binding domain comprises a $V_H$ CDR1 comprising amino acids having the sequence set forth in SEQ ID NO:131, a $V_H$ CDR2 comprising amino acids having the sequence set forth in SEQ ID NO:132, a V$_H$ CDR3 comprising amino acids having the sequence set forth in SEQ ID NO:133, a V$_L$ CDR1 comprising amino acids having the sequence set forth in SEQ ID NO:134, a V$_L$ CDR2 comprising amino acids having the sequence set forth in SEQ ID NO:135, and a V$_L$ CDR3 comprising amino acids having the sequence set forth in SEQ ID NO:136.

ments, the extracellular antigen-binding domain comprises a V$_H$ comprising amino acids having the sequence set forth in SEQ ID NO:33, as shown in Table 9. In certain embodiments, the extracellular antigen-binding domain comprises a V$_L$ comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID

TABLE 8

| | | | |
|---|---|---|---|
| Antigen | A BCMA polypeptide having the amino acid sequence of SEQ ID NO: 71 | | |
| CDRs | 1 | 2 | 3 |
| V$_H$ | GYTFTGYY [SEQ ID NO: 131] | INPNSGGT [SEQ ID NO: 132] | ARSQWGSSWDY [SEQ ID NO: 133] |
| V$_L$ | QSISSY [SEQ ID NO: 134] | AAS [SEQ ID NO: 135] | QQSYSTPPT [SEQ ID NO: 136] |
| Full V$_H$ | QVQLVQSGAEVKKPGASVKVSCKASGYTFTGYYMHWVRQAPGQ GLEWMGWINPNSGGTNYAQKFQGRVTMTRDTSISTAYMELSRLR SDDTAVYYCARSQWGSSWDYWGQGTLVTVSS [SEQ ID NO: 29] | | |
| DNA | Caggtccagctggtacagtctggggctgaggtgaagaagcctggggcctcagtgaaggtctcctgcaa ggcttctggatacacctt caccggctactatatgcactgggtgcgacaggcccctggacaagggcttgag tggatgggatggatcaaccctaacagtggtggcacaaactatgcacagaagtttcagggcagggtcacc atgaccagggacacgtccatcagcacagcctacatggagctgagcaggctgagatctgacgacacggc cgtgtattactgtgcgcgctctcagtggggttcttcttgggattactggggtcaaggtactctggtgaccgtc tcctca [SEQ ID NO: 31] | | |
| Full V$_L$ | DIQLTQSPSSLSASVGDRVTITCRASQSISSYLNWYQQKPGKAPKL LIYAASSLQSGVPSRFSGSGSGTDFTLTISSLQPEDFATYYCQQSYS TPPTFGQGTKVEIKR [SEQ ID NO: 30] | | |
| DNA | Gacatccagttgacccagtctccatcctccctgtctgcatctgtaggagacagagtcaccatcacttgccg ggcaagtcagagcattagcagctatttaaattggtatcagcagaaaccagggaaagcccctaagctcctg atctatgctgcatccagtttgcaaagtggggtcccatcaaggttcagtggcagtggatctgggacagattc actctcaccatcagcagtctgcaacctgaagattttgcaacttactactgtcaacagagttacagtacccctc cgacgttcggccaagggaccaaggtggagatcaaacgt [SEQ ID NO: 32] | | |
| scFv | DIQLTQSPSSLSASVGDRVTITCRASQSISSYLNWYQQKPGKAPKL LIYAASSLQSGVPSRFSGSGSGTDFTLTISSLQPEDFATYYCQQSYS TPPTFGQGTKVEIKRSRGGGGSGGGGSGGGGSLEMAQVQLVQSG AEVKKPGASVKVSCKASGYTFTGYYMHWVRQAPGQGLEWMGW INPNSGGTNYAQKFQGRVTMTRDTSISTAYMELSRLRSDDTAVYY CARSQWGSSWDYWGQGTLVTVSS [SEQ ID NO: 79] | | |

In certain embodiments, the extracellular antigen-binding domain is a human scFv, which comprises the amino acid sequence of SEQ ID NO:80 and specifically binds to a BCMA polypeptide (e.g., a BCMA polypeptide having the amino acid sequence SEQ ID NO:71, or fragments thereof), which is designated as ET140-163 scFv (also referred to as "ET140-13 scFv").

In certain embodiments, the extracellular antigen-binding domain is a human scFv, which comprises a heavy chain variable region comprising amino acids having the sequence set forth in SEQ ID NO:33 and a light chain variable region comprising amino acids having the sequence set forth in SEQ ID NO:34, optionally with (iii) a linker sequence, for example a linker peptide, between the heavy chain variable region and the light chain variable region. In certain embodiments, the linker comprises amino acids having the sequence set forth in SEQ ID NO:69. In certain embodiments, the extracellular antigen-binding domain is a human scFv-Fc fusion protein or full length human IgG with V$_H$ and V$_L$ regions or CDRs selected from Table 9. In certain embodiments, the extracellular antigen-binding domain comprises a V$_H$ comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:33, as shown in Table 9. In certain embodi- NO:34, as shown in Table 9. In certain embodiments, the extracellular antigen-binding domain comprises a V$_L$ comprising amino acids having the sequence set forth in SEQ ID NO:34, as shown in Table 9. In certain embodiments, the extracellular antigen-binding domain comprises a V$_H$ comprising amino acids having the sequence set forth in SEQ ID NO:33 and a V$_L$ comprising amino acids having the sequence set forth in SEQ ID NO:34, as shown in Table 9. In certain embodiments, the extracellular antigen-binding domain comprises a V$_H$ CDR1 comprising amino acids having the sequence set forth in SEQ ID NO:137 or conservative modifications thereof, a V$_H$ CDR2 comprising amino acids having the sequence set forth in SEQ ID NO:138 or conservative modifications thereof, and a V$_H$ CDR3 comprising amino acids having the sequence set forth in SEQ ID NO:139 or conservative modifications thereof, as shown in Table 9. In certain embodiments, the extracellular antigen-binding domain comprises a V$_L$ CDR1 comprising amino acids having the sequence set forth in SEQ ID NO:140 or conservative modifications thereof, a V$_L$ CDR2 comprising amino acids having the sequence set forth in SEQ ID NO:141 or conservative modifications thereof, and a V$_L$ CDR3 comprising amino acids having the sequence set forth in SEQ ID NO:142 or conservative modifications thereof, as shown in Table 9. In certain embodiments, the extracellular antigen-binding domain comprises a V$_H$ CDR1 comprising amino acids having the sequence set forth in SEQ ID NO:137 or conservative modifications thereof, a V$_H$ CDR2 comprising amino acids having the sequence set forth in SEQ ID NO:138 or conservative modifications thereof, a V$_H$ CDR3 comprising amino acids having the sequence set forth in SEQ ID NO:139 or conservative modifications thereof, a V$_L$ CDR1 comprising amino acids having the sequence set forth in SEQ ID NO:140 or conservative modifications thereof, a V$_L$ CDR2 comprising amino acids having the sequence set forth in SEQ ID NO:141 or conservative modifications thereof, and a V$_L$ CDR3 comprising amino acids having the sequence set forth in SEQ ID NO:142 or conservative modifications thereof, as shown in Table 9. In certain embodiments, the extracellular antigen-binding domain comprises a V$_H$ CDR1 comprising amino acids having the sequence set forth in SEQ ID NO:137, a V$_H$ CDR2 comprising amino acids having the sequence set forth in SEQ ID NO:138, a V$_H$ CDR3 comprising amino acids having the sequence set forth in SEQ ID NO:139, a V$_L$ CDR1 comprising amino acids having the sequence set forth in SEQ ID NO:140, a V$_L$ CDR2 comprising amino acids having the sequence set forth in SEQ ID NO:141, and a V$_L$ CDR3 comprising amino acids having the sequence set forth in SEQ ID NO:142.

variable region comprising amino acids having the sequence set forth in SEQ ID NO:37 and a light chain variable region comprising amino acids having the sequence set forth in SEQ ID NO:38, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the extracellular antigen-binding domain is a human scFv-Fc fusion protein or full length human IgG with V$_H$ and V$_L$ regions or CDRs selected from Table 10. In certain embodiments, the extracellular antigen-binding domain comprises a V$_H$ comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:37, as shown in Table 10. In certain embodiments, the extracellular antigen-binding domain comprises a V$_H$ comprising amino acids having the sequence set forth in SEQ ID NO:37, as shown in Table 10. In certain embodiments, the extracellular antigen-binding domain comprises a V$_L$ comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99%

TABLE 9

| Antigen | A BCMA polypeptide having the amino acid sequence of SEQ ID NO: 71 | | |
|---|---|---|---|
| CDRs | 1 | 2 | 3 |
| V$_H$ | GYTFTGYY [SEQ ID NO: 137] | INPNSGGT [SEQ ID NO: 138] | ARSSYHLYGYDS [SEQ ID NO: 139] |
| V$_L$ | NDYTNYK [SEQ ID NO: 140] | VGPGGIVG [SEQ ID NO: 141] | GADHGTGSNFVYV [SEQ ID NO: 142] |
| Full V$_H$ | EVQLVESGAEVKKPGASVKVSCKASGYTFTGYYMHWVRQAPGQ GLEWMGWINPNSGGTNYAQKFQGRVTMTRDTSISTAYMELSRLR SDDTAVYYCARSSYHLYGYDSWGQGTLVTVSS [SEQ ID NO: 33] | | |
| DNA | Gaggtgcagctggtggagtccggggctgaggtgaagaagcctggggcctcagtgaaggtctcctgca aggcttctggatacacctttcaccggctactatatgcactgggtgcgacaggcccctggacaagggcttga gtggatgggatggatcaaccctaacagtggtggcacaaactatgcacagaagtttcagggcagggtcac catgaccagggacacgtccatcagcacagcctacatggagctgagcaggctgagatctgacgacacgg ccgtatattactgtgcgcgctcttcttaccatctgtacggttacgattcttggggtcaaggtactctggtgacc gtctcctca [SEQ ID NO: 35] | | |
| Full V$_L$ | QPVLTQPPSASASLGASVTLTCTLSNDYTNYKVDWYQQRPGKGPR FVMRVGPGGIVGSKGDGIPDRFSVLGSGLNRYLTIKNIQEEDESDY HCGADHGTGSNFVYVFGGGTKLTVLG [SEQ ID NO: 34] | | |
| DNA | Cagcctgtgctgactcagccacctactgtgcatcagcctcctgggagcctcggtcactctccacctgcacct gagcaacgactacactaattatataaagtggactggtaccagcagagaccagggaagggcccccggtttgt gatgcgagtgggccctggtgggattgtgggatccaaggggggatggcatccctgatcgcttctcagtcttg ggctcaggcctgaatcgatacctgaccatcaagaacatccaggaggaggatgagagtgactaccactgt ggggcggaccatggcaccgggagcaacttcgtgtacgtgttcggcggagggaccaagctgaccgtcct aggt [SEQ ID NO: 36] | | |
| scFv | QPVLTQPPSASASLGASVTLTCTLSNDYTNYKVDWYQQRPGKGPR FVMRVGPGGIVGSKGDGIPDRFSVLGSGLNRYLTIKNIQEEDESDY HCGADHGTGSNFVYVFGGGTKLTVLGSRGGGGSGGGGSGGGGSL EMAEVQLVESGAEVKKPGASVKVSCKASGYTFTGYYMHWVRQA PGQGLEWMGWINPNSGGTNYAQKFQGRVTMTRDTSISTAYMELS RLRSDDTAVYYCARSSYHLYGYDSWGQGTLVTVSS [SEQ ID NO: 80] | | |

In certain embodiments, the extracellular antigen-binding domain is a human scFv, which comprises the amino acid sequence of SEQ ID NO:81 and specifically binds to a BCMA polypeptide (e.g., a BCMA polypeptide having the amino acid sequence SEQ ID NO:71, or fragments thereof), which is designated as ET140-207 scFv (also referred to as "ET140-57 scFv").

In certain embodiment, the extracellular antigen-binding domain is a human scFv, which comprises a heavy chain homologous to the amino acid sequence set forth in SEQ ID NO:38, as shown in Table 10. In certain embodiments, the extracellular antigen-binding domain comprises a V$_L$ comprising amino acids having the sequence set forth in SEQ ID NO:38, as shown in Table 10. In certain embodiments, the extracellular antigen-binding domain comprises a V$_H$ comprising amino acids having the sequence set forth in SEQ ID NO:37 and a V$_L$ comprising amino acids having the sequence set forth in SEQ ID NO:38, as shown in Table 10.

In certain embodiments, the extracellular antigen-binding domain comprises a $V_H$ CDR1 comprising amino acids having the sequence set forth in SEQ ID NO:143 or conservative modifications thereof, a $V_H$ CDR2 comprising amino acids having the sequence set forth in SEQ ID NO:144 or conservative modifications thereof, and a $V_H$ CDR3 comprising amino acids having the sequence set forth in SEQ ID NO:145 or conservative modifications thereof, as shown in Table 10. In certain embodiments, the extracellular antigen-binding domain comprises a $V_L$ CDR1 comprising amino acids having the sequence set forth in SEQ ID NO:146 or conservative modifications thereof, a $V_L$ CDR2 comprising amino acids having the sequence set forth in SEQ ID NO:147 or conservative modifications thereof, and a $V_L$ CDR3 comprising amino acids having the sequence set forth in SEQ ID NO:148 or conservative modifications thereof, as shown in Table 10. In certain embodiments, the extracellular antigen-binding domain comprises a $V_H$ CDR1 comprising amino acids having the sequence set forth in SEQ ID NO:143 or conservative modifications thereof, a $V_H$ CDR2 comprising amino acids having the sequence set forth in SEQ ID NO:144 or conservative modifications thereof, a $V_H$ CDR3 comprising amino acids having the sequence set forth in SEQ ID NO:145 or conservative modifications thereof, a $V_L$ CDR1 comprising amino acids having the sequence set forth in SEQ ID NO:146 or conservative modifications thereof, a $V_L$ CDR2 comprising amino acids having the sequence set forth in SEQ ID NO:147 or conservative modifications thereof, and a $V_L$ CDR3 comprising amino acids having the sequence set forth in SEQ ID NO:148 or conservative modifications thereof, as shown in Table 10. In certain embodiments, the extracellular antigen-binding domain comprises a $V_H$ CDR1 comprising amino acids having the sequence set forth in SEQ ID NO:143, a $V_H$ CDR2 comprising amino acids having the sequence set forth in SEQ ID NO:144, a $V_H$ CDR3 comprising amino acids having the sequence set forth in SEQ ID NO:145, a $V_L$ CDR1 comprising amino acids having the sequence set forth in SEQ ID NO:146, a $V_L$ CDR2 comprising amino acids having the sequence set forth in SEQ ID NO:147, and a $V_L$ CDR3 comprising amino acids having the sequence set forth in SEQ ID NO:148.

TABLE 10

| Antigen | A BCMA polypeptide having the amino acid sequence of SEQ ID NO: 71 | | |
|---|---|---|---|
| CDRs | 1 | 2 | 3 |
| $V_H$ | GGTFSSYA [SEQ ID NO: 143] | IIPIFSTA [SEQ ID NO: 144] | ARQPWTWYSPYDQ [SEQ ID NO: 145] |
| $V_L$ | SGYSNYK [SEQ ID NO: 146] | VDTGGIVG [SEQ ID NO: 147] | GADHGSGSNFVWV [SEQ ID NO: 148] |
| Full $V_H$ | QVQLVQSGAEVKKPGSSVKVSCKASGGTFSSYAISWVRQAPGQG LEWMGGIIPIFSTANYAQKFQGRVTMTTDTSTSTAYMELRSLRSD DTAVYYCARQPWTWYSPYDQWGQGTLVTVSS [SEQ ID NO: 37] | | |
| DNA | Caggtgcagctggtgcagtctggggctgaggtgaagaagcctgggtcctcggtgaaggtctcctgcaa ggcttctggaggcaccttcagcagctatgctatcagctgggtgcgacaggcccctggacaagggcttga gtggatgggagggatcatccctatctttagtacagcaaactacgcacagaagttccagggcagagtcacc atgaccacagacacatccacgagcacagcctacatggagctgaggagcctgagatctgacgacacggc cgtgtattactgtgcgcgccagccgtggacttggtactctccgtacgatcagtggggtcaaggtactctgg tgaccgtctcctca [SEQ ID NO: 39] | | |
| Full $V_L$ | QPVLTQPPSASASLGASVTLTCTLSSGYSNYKVDWYQQRPGKGPR FLMRVDTGGIVGSKGDGIPDRFSVSGSGLNRYLTIKNIQEEDESDY HCGADHGSGSNFVWVFGGGTKLTVLG [SEQ ID NO: 38] | | |
| DNA | Cagcctgtgctgactcagccacccttctgcatcagcctccctgggagcctcggtcacactcacctgcaccc tgagcagcggctacagtaattataaagtggactggtatcaacagagaccagggaagggcccccggtttct gatgcgagtagacaccggtgggattgtgggatccaaggggatggcatccctgatcgcttctcagtctcg ggctcaggtctgaatcggtacctgaccatcaagaacattcaggaagaggatgagagtgactaccactgtg gggcagaccatggcagtgggagcaacttcgtgtgggtgttcggcggagggaccaagctgaccgtccta ggt [SEQ ID NO: 40] |  |  |
| scFv | QPVLTQPPSASASLGASVTLTCTLSSGYSNYKVDWYQQRPGKGPR FLMRVDTGGIVGSKGDGIPDRFSVSGSGLNRYLTIKNIQEEDESDY HCGADHGSGSNFVWVFGGGTKLTVLGSRGGGGSGGGGSGGGGS LEMAQVQLVQSGAEVKKPGSSVKVSCKASGGTFSSYAISWVRQA PGQGLEWMGGIIPIFSTANYAQKFQGRVTMTTDTSTSTAYMELRS LRSDDTAVYYCARQPWTWYSPYDQWGQGTLVTVSS [SEQ ID NO: 81] | | |

In certain embodiments, the extracellular antigen-binding domain is a human scFv, which comprises the amino acid sequence of SEQ ID NO:82 and specifically binds to a BCMA polypeptide (e.g., a BCMA polypeptide having the amino acid sequence SEQ ID NO:71, or fragments thereof), which is designated as ET140-165 scFv (also referred to as "ET140-15 scFv").

In certain embodiments, the extracellular antigen-binding domain is a human scFv, which comprises a heavy chain variable region comprising amino acids having the sequence set forth in SEQ ID NO:41 and a light chain variable region comprising amino acids having the sequence set forth in SEQ ID NO:42, optionally with (iii) a linker sequence, for example a linker peptide, between the heavy chain variable region and the light chain variable region. In certain embodiments, the linker comprises amino acids having the sequence set forth in SEQ ID NO:69. In certain embodiments, the extracellular antigen-binding domain is a human scFv-Fc fusion protein or full length human IgG with $V_H$ and $V_L$ regions or CDRs selected from Table 11. In certain embodiments, the extracellular antigen-binding domain comprises a $V_H$ comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:41, as shown in Table 11. In certain embodiments, the extracellular antigen-binding domain comprises a $V_H$ comprising amino acids having the sequence set forth in SEQ ID NO:41, as shown in Table 11. In certain embodiments, the extracellular antigen-binding domain comprises a $V_L$ comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:42, as shown in Table 11. In certain embodiments, the extracellular antigen-binding domain comprises a $V_L$ comprising amino acids having the sequence set forth in SEQ ID NO:42, as shown in Table 11. In certain embodiments, the extracellular antigen-binding domain comprises a $V_H$ comprising amino acids having the sequence set forth in SEQ ID NO:41 and a $V_L$ comprising amino acids having the sequence set forth in SEQ ID NO:42, as shown in Table 11. In certain embodiments, the extracellular antigen-binding domain comprises a $V_H$ CDR1 comprising amino acids having the sequence set forth in SEQ ID NO:149 or conservative modifications thereof, a $V_H$ CDR2 comprising amino acids having the sequence set forth in SEQ ID NO: 150 or conservative modifications thereof, and a $V_H$ CDR3 comprising amino acids having the sequence set forth in SEQ ID NO: 151 or conservative modifications thereof, as shown in Table 11. In certain embodiments, the extracellular antigen-binding domain comprises a $V_L$ CDR1 comprising amino acids having the sequence set forth in SEQ ID NO: 152 or conservative modifications thereof, a $V_L$ CDR2 comprising amino acids having the sequence set forth in SEQ ID NO: 153 or conservative modifications thereof, and a $V_L$ CDR3 comprising amino acids having the sequence set forth in SEQ ID NO: 154 or conservative modifications thereof, as shown in Table 11. In certain embodiments, the extracellular antigen-binding domain comprises a $V_H$ CDR1 comprising amino acids having the sequence set forth in SEQ ID NO: 147 or conservative modifications thereof, a $V_H$ CDR2 comprising amino acids having the sequence set forth in SEQ ID NO: 150 or conservative modifications thereof, a $V_H$ CDR3 comprising amino acids having the sequence set forth in SEQ ID NO: 151 or conservative modifications thereof, a $V_L$ CDR1 comprising amino acids having the sequence set forth in SEQ ID NO: 152 or conservative modifications thereof, a $V_L$ CDR2 comprising amino acids having the sequence set forth in SEQ ID NO: 153 or conservative modifications thereof, and a $V_L$ CDR3 comprising amino acids having the sequence set forth in SEQ ID NO: 154 or conservative modifications thereof, as shown in Table 11. In certain embodiments, the extracellular antigen-binding domain comprises a $V_H$ CDR1 comprising amino acids having the sequence set forth in SEQ ID NO: 149, a $V_H$ CDR2 comprising amino acids having the sequence set forth in SEQ ID NO: 150, a $V_H$ CDR3 comprising amino acids having the sequence set forth in SEQ ID NO: 151, a $V_L$ CDR1 comprising amino acids having the sequence set forth in SEQ ID NO: 152, a $V_L$ CDR2 comprising amino acids having the sequence set forth in SEQ ID NO: 153, and a $V_L$ CDR3 comprising amino acids having the sequence set forth in SEQ ID NO: 154.

TABLE 11

| | | | |
|---|---|---|---|
| Antigen | A BCMA polypeptide having the amino acid sequence of SEQ ID NO: 71 | | |
| CDRs | 1 | 2 | 3 |
| $V_H$ | GFTFSTYA [SEQ ID NO: 149] | ITPGGDRT [SEQ ID NO: 150] | ARYYGYMIDM [SEQ ID NO: 151] |
| $V_L$ | QSLLHSNGYNY [SEQ ID NO: 152] | LGS [SEQ ID NO: 153] | MQALQTPLT [SEQ ID NO: 154] |
| Full $V_H$ | EVQLVETGGGLVQPGGSLRLSCAASGFTFSTYAMTWVRQAPGKGL EWVSAITPGGDRTYYADSVKGRFTISRDNSRNTLYLQMNSLRAEDT AVYYCARYYGYMIDMWGQGTLVTVSS [SEQ ID NO: 41] | | |
| DNA | Gaggtgcagctggtggagactgggggaggcctggtacagcctggggggtccctgagactctcctgtgct gcctctggattcacctttagcacctatgccatgacctgggtccgccaggctccagggaagggcctggagt gggtctcagctattactcctggtggtgatcgcacatactacgcagactccgtgaagggccgtttcactatctc cagagacaattccaggaacacgctgtatctgcaaatgaacagcctgagagccgaggacacggccgtatat tactgtgcgcgctactacggttacatgatcgatatgtggggtcaaggtactctggtgaccgtctcctca [SEQ ID NO: 43] | | |
| Full $V_L$ | DVVMTQSPLSLPVTPGEPASISCRSSQSLLHSNGYNYLDWYLQKPG QSPQLLIYLGSNRASGVPDRFSGSGSGTDFTLKISRVEAEDVGVYYC MQALQTPLTFGGGTKVEIKR [SEQ ID NO: 42] | | |
| DNA | Gatgttgtgatgactcagtctccactctccctgcccgtcacccctggagagccggcctccatctcctgcag gtctagtcagagcctcctgcatagtaatggatacaactatttggattggtacctgcagaagccagggcagtc tccacagctcctgatctatttgggttctaatcgggcctccggggtccctgacaggttcagtggcagtggatca ggcacagattttacactgaaaatcagcagagtggaggctgaggatgttggggtttattactgcatgcaagct ctacaaactcctctcactttcggcggagggaccaaggtggaaatcaaacgt [SEQ ID NO: 44] | | |
| scFv | DVVMTQSPLSLPVTPGEPASISCRSSQSLLHSNGYNYLDWYLQKPG QSPQLLIYLGSNRASGVPDRFSGSGSGTDFTLKISRVEAEDVGVYYC MQALQTPLTFGGGTKVEIKRSRGGGGSGGGGSGGGGSLEMAEVQL VETGGGLVQPGGSLRLSCAASGFTFSTYAMTWVRQAPGKGLEWV SAITPGGDRTYYADSVKGRFTISRDNSRNTLYLQMNSLRAEDTAVY YCARYYGYMIDMWGQGTLVTVSS [SEQ ID NO: 82] | | |

In certain embodiments, the extracellular antigen-binding domain is a human scFv, which comprises the amino acid sequence of SEQ ID NO:83 and specifically binds to a BCMA polypeptide (e.g., a BCMA polypeptide having the amino acid sequence SEQ ID NO:71, or fragments thereof), which is designated as ET140-188 scFv (also referred to as "ET140-38 scFv").

In certain embodiments, the extracellular antigen-binding domain is a human scFv, which comprises a heavy chain variable region comprising amino acids having the sequence set forth in SEQ ID NO:45 and a light chain variable region comprising amino acids having the sequence set forth in SEQ ID NO:46, optionally with (iii) a linker sequence, for example a linker peptide, between the heavy chain variable region and the light chain variable region. In certain embodiments, the linker comprises amino acids having the sequence set forth in SEQ ID NO:69. In certain embodiments, the extracellular antigen-binding domain is a human scFv-Fc fusion protein or full length human IgG with $V_H$ and $V_L$ regions or CDRs selected from Table 12. In certain embodiments, the extracellular antigen-binding domain comprises a $V_H$ comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:45, as shown in Table 12. In certain embodiments, the extracellular antigen-binding domain comprises a $V_H$ comprising amino acids having the sequence set forth in SEQ ID NO:45, as shown in Table 12. In certain embodiments, the extracellular antigen-binding domain comprises a $V_L$ comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:46, as shown in Table 12. In certain embodiments, the extracellular antigen-binding domain comprises a $V_L$ comprising amino acids having the sequence set forth in SEQ ID NO:46, as shown in Table 12. In certain embodiments, the extracellular antigen-binding domain comprises a $V_H$ comprising amino acids having the sequence set forth in SEQ ID NO:45 and a $V_L$ comprising amino acids having the sequence set forth in SEQ ID NO:46, as shown in Table 12.

In certain embodiments, the extracellular antigen-binding domain comprises a $V_H$ CDR1 comprising amino acids having the sequence set forth in SEQ ID NO:155 or conservative modifications thereof, a $V_H$ CDR2 comprising amino acids having the sequence set forth in SEQ ID NO: 156 or conservative modifications thereof, and a $V_H$ CDR3 comprising amino acids having the sequence set forth in SEQ ID NO: 157 or conservative modifications thereof, as shown in Table 12. In certain embodiments, the extracellular antigen-binding domain comprises a $V_L$ CDR1 comprising amino acids having the sequence set forth in SEQ ID NO: 158 or conservative modifications thereof, a $V_L$ CDR2 comprising amino acids having the sequence set forth in SEQ ID NO: 159 or conservative modifications thereof, and a $V_L$ CDR3 comprising amino acids having the sequence set forth in SEQ ID NO: 160 or conservative modifications thereof, as shown in Table 12. In certain embodiments, the extracellular antigen-binding domain comprises a $V_H$ CDR1 comprising amino acids having the sequence set forth in SEQ ID NO: 155 or conservative modifications thereof, a $V_H$ CDR2 comprising amino acids having the sequence set forth in SEQ ID NO: 156 or conservative modifications thereof, a $V_H$ CDR3 comprising amino acids having the sequence set forth in SEQ ID NO: 157 or conservative modifications thereof, a $V_L$ CDR1 comprising amino acids having the sequence set forth in SEQ ID NO: 158 or conservative modifications thereof, a $V_L$ CDR2 comprising amino acids having the sequence set forth in SEQ ID NO: 159 or conservative modifications thereof, and a $V_L$ CDR3 comprising amino acids having the sequence set forth in SEQ ID NO: 160 or conservative modifications thereof, as shown in Table 12. In certain embodiments, the extracellular antigen-binding domain comprises a $V_H$ CDR1 comprising amino acids having the sequence set forth in SEQ ID NO: 155, a $V_H$ CDR2 comprising amino acids having the sequence set forth in SEQ ID NO: 156, a $V_H$ CDR3 comprising amino acids having the sequence set forth in SEQ ID NO: 157, a $V_L$ CDR1 comprising amino acids having the sequence set forth in SEQ ID NO: 158, a $V_L$ CDR2 comprising amino acids having the sequence set forth in SEQ ID NO: 159, and a $V_L$ CDR3 comprising amino acids having the sequence set forth in SEQ ID NO: 160.

TABLE 12

| Antigen | A BCMA polypeptide having the amino acid sequence of SEQ ID NO: 71 | | |
|---|---|---|---|
| CDRs | 1 | 2 | 3 |
| $V_H$ | GYTFTGYY [SEQ ID NO: 155] | INPNSGGT [SEQ ID NO: 156] | ARSQWGGTYDY [SEQ ID NO: 157] |
| $V_L$ | SSNIGSNT [SEQ ID NO: 158] | SNN [SEQ ID NO: 159] | AAWDDSLNGWV [SEQ ID NO: 160] |
| Full $V_H$ | QMQLVQSGAEVKKPGASVKVSCKASGYTFTGYYVHWLRQAPGQGLEWMGWINPNSGGTNNAQEFQGRITMTRDTSINTAYMELSRLRSDDTAVYYCARSQWGGTYDYWGQGTLVTVSS [SEQ ID NO: 45] | | |
| DNA | Cagatgcagctggtgcagtctggggctgaggtgaagaagcctggggcctcagtgaaggtctcctgcaaggcttctggatacaccttcaccggctattatgtacactggttgcgacaggcccctggacaagggcttgagtggatgggttggatcaaccctaacagtggcggcacaaacaatgcacaggagtttcaaggcaggatcaccatgaccagggacacgtccatcaacacagcctacatggagctgagcaggctgagatctgacgacacggccgtgtattactgtgcgcgctctcagtggggtggtacttacgattactgggtcaaggtactctggtgaccgtctcctca [SEQ ID NO: 47] | | |
| Full $V_L$ | SYVLTQPPSASGTPGQRVTISCSGSSSNIGSNTVNWYQQVPGTAPKLLIYSNNQRPSGVPDRFSGSKSGASASLAISWLQSEDEADYYCAAWDDSLNGWVFGGGTKLTVLG [SEQ ID NO: 46] | | |
| DNA | Tcctatgtgctgactcagccaccctcagcgtctgggaccccgggcagagggtcaccatctcttgttctggaagcagctccaacatcggaagtaatactgtaaactggtaccagcaggtcccaggaacggcccccaaactcctcatctatagtaataatcagcggccctcaggggtccctgaccgattctctggctccaagtctggcgcctca | | |

TABLE 12-continued

```
gcctccctggccatcagttggctccagtctgaggatgaggctgattattactgtgcagcatgggatgacagc
ctgaatggttgggtgttcggcggagggaccaagctgaccgtcctaggt [SEQ ID NO: 48]
``` scFv    SYVLTQPPSASGTPGQRVTISCSGSSSNIGSNTVNWYQQVPGTAPKL
        LIYSNNQRPSGVPDRFSGSKSGASASLAISWLQSEDEADYYCAAWD
        DSLNGWVFGGGTKLTVLGSRGGGGSGGGGSGGGGSLEMAQMQL
        VQSGAEVKKPGASVKVSCKASGYTFTGYYVHWLRQAPGQGLEW
        MGWINPNSGGTNNAQEFQGRITMTRDTSINTAYMELSRLRSDDTA
        VYYCARSQWGGTYDYWGQGTLVTVSS [SEQ ID NO: 83]

In certain embodiments, the extracellular antigen-binding domain is a human scFv, which comprises the amino acid sequence of SEQ ID NO:84 and specifically binds to a BCMA polypeptide (e.g., a BCMA polypeptide having the amino acid sequence SEQ ID NO:71, or fragments thereof), which is designated as ET140-196 scFv (also referred to as "ET140-46 scFv").

In certain embodiments, the extracellular antigen-binding domain is a human scFv, which comprises a heavy chain variable region comprising amino acids having the sequence set forth in SEQ ID NO:49 and a light chain variable region comprising amino acids having the sequence set forth in SEQ ID NO:50, optionally with (iii) a linker sequence, for example a linker peptide, between the heavy chain variable region and the light chain variable region. In certain embodiments, the linker comprises amino acids having the sequence set forth in SEQ ID NO:69. In certain embodiments, the extracellular antigen-binding domain is a human scFv-Fc fusion protein or full length human IgG with $V_H$ and $V_L$ regions or CDRs selected from Table 13. In certain embodiments, the extracellular antigen-binding domain comprises a $V_H$ comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:49, as shown in Table 13. In certain embodiments, the extracellular antigen-binding domain comprises a $V_H$ comprising amino acids having the sequence set forth in SEQ ID NO:49, as shown in Table 13. In certain embodiments, the extracellular antigen-binding domain comprises a $V_L$ comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:50, as shown in Table 13. In certain embodiments, the extracellular antigen-binding domain comprises a $V_L$ comprising amino acids having the sequence set forth in SEQ ID NO:50, as shown in Table 13. In certain embodiments, the extracellular antigen-binding domain comprises a $V_H$ comprising amino acids having the sequence set forth in SEQ ID NO:49 and a $V_L$ comprising amino acids having the sequence set forth in SEQ ID NO:50, as shown in Table 13. In certain embodiments, the extracellular antigen-binding domain comprises a $V_H$ CDR1 comprising amino acids having the sequence set forth in SEQ ID NO:161 or conservative modifications thereof, a $V_H$ CDR2 comprising amino acids having the sequence set forth in SEQ ID NO: 162 or conservative modifications thereof, and a $V_H$ CDR3 comprising amino acids having the sequence set forth in SEQ ID NO: 163 or conservative modifications thereof, as shown in Table 13. In certain embodiments, the extracellular antigen-binding domain comprises a $V_L$ CDR1 comprising amino acids having the sequence set forth in SEQ ID NO: 164 or conservative modifications thereof, a $V_L$ CDR2 comprising amino acids having the sequence set forth in SEQ ID NO:165 or conservative modifications thereof, and a $V_L$ CDR3 comprising amino acids having the sequence set forth in SEQ ID NO:166 or conservative modifications thereof, as shown in Table 13. In certain embodiments, the extracellular antigen-binding domain comprises a $V_H$ CDR1 comprising amino acids having the sequence set forth in SEQ ID NO: 161 or conservative modifications thereof, a $V_H$ CDR2 comprising amino acids having the sequence set forth in SEQ ID NO: 162 or conservative modifications thereof, a $V_H$ CDR3 comprising amino acids having the sequence set forth in SEQ ID NO: 163 or conservative modifications thereof, a $V_L$ CDR1 comprising amino acids having the sequence set forth in SEQ ID NO: 164 or conservative modifications thereof, a $V_L$ CDR2 comprising amino acids having the sequence set forth in SEQ ID NO:165 or conservative modifications thereof, and a $V_L$ CDR3 comprising amino acids having the sequence set forth in SEQ ID NO:166 or conservative modifications thereof, as shown in Table 13. In certain embodiments, the extracellular antigen-binding domain comprises a $V_H$ CDR1 comprising amino acids having the sequence set forth in SEQ ID NO: 161, a $V_H$ CDR2 comprising amino acids having the sequence set forth in SEQ ID NO: 162, a $V_H$ CDR3 comprising amino acids having the sequence set forth in SEQ ID NO: 163, a $V_L$ CDR1 comprising amino acids having the sequence set forth in SEQ ID NO: 164, a $V_L$ CDR2 comprising amino acids having the sequence set forth in SEQ ID NO:165, and a $V_L$ CDR3 comprising amino acids having the sequence set forth in SEQ ID NO:166.

TABLE 13

| Antigen | A BCMA polypeptide having the amino acid sequence of SEQ ID NO: 71 | | |
|---|---|---|---|
| CDRs | 1 | 2 | 3 |
| $V_H$ | GYDFTTYW [SEQ ID NO: 161] | IYPGDSDT [SEQ ID NO: 162] | ARMWTFSQDG [SEQ ID NO: 163] |
| $V_L$ | SSNIGSYT [SEQ ID NO: 164] | SNN [SEQ ID NO: 165] | AAWDDSLNGYV [SEQ ID NO: 166] |

Full $V_H$  EVQLVQSGAEVKKPGESLKISCKGSGYDFTTYWIGWVRQMPGKG
           LEWMGIIYPGDSDTRYSPSVRGRVTISADKSINTAYLQWSSLEASD
           TAMYYCARMWTFSQDGWGQGTLVTVSS [SEQ ID NO: 49]

TABLE 13-continued

```
DNA      gaggtgcagctggtgcagtctggagcagaggtgaaaaagccgggggagtctctgaagatctcctgtaa
         gggttctggatatgactttaccacctactggatcgggtgggtgcgccagatgcccgggaagggcctgga
         gtggatggggatcatctatcctggtgactctgataccagatacagcccgtccgtccgaggccgggtcacc
         atctcagccgacaagtccatcaacaccgcctatttgcagtggagtagcctggaggcctccgacaccgcc
         atgtattactgtgcgcgcatgtggactttctctcaggatggttggggtcaaggtactctggtgaccgtctcct
         ca [SEQ ID NO: 51]

Full V_L QAVLTQPPSASGTPGQRVTISCSGSSSNIGSYTVSWYQQLPGTAPK
         FLIYSNNQRPSGVPDRFSGSKSGTSASLAISGLQSEDEADYYCAAW
         DDSLNGYVFGTGTKVTVLG [SEQ ID NO: 50]

DNA      Caggctgtgctgactcagccaccctcagcgtctgggaccccgggcagagggtcaccatctcttgttct
         ggaagcagctccaacatcggaagttatactgtaagctggtaccagcaactcccaggaacggcccccaaa
         ttcctcatctattctaataatcagcggccctcaggggtccctgaccgattctctggctccaagtctggcacct
         cagcctccctggccatcagtgggctccagtctgaggatgaggctgattattactgtgctgcatgggatgac
         agcctgaatggttatgtcttcggaactgggaccaaggtcaccgtcctaggt [SEQ ID NO: 52]

scFv     QAVLTQPPSASGTPGQRVTISCSGSSSNIGSYTVSWYQQLPGTAPK
         FLIYSNNQRPSGVPDRFSGSKSGTSASLAISGLQSEDEADYYCAAW
         DDSLNGYVFGTGTKVTVLGSRGGGGSGGGGSGGGGSLEMAEVQL
         VQSGAEVKKPGESLKISCKGSGYDFTTYWIGWVRQMPGKGLEW
         MGIIYPGDSDTRYSPSVRGRVTISADKSINTAYLQWSSLEASDTAM
         YYCARMWTFSQDGWGQGTLVTVSS [SEQ ID NO: 84]
```

In certain embodiments, the extracellular antigen-binding domain is a human scFv, which comprises the amino acid sequence of SEQ ID NO:85 and specifically binds to a BCMA polypeptide (e.g., a BCMA polypeptide having the amino acid sequence SEQ ID NO:71, or fragments thereof), which is designated as ET140-204 scFv (also referred to as "ET140-54 scFv").

In certain embodiments, the extracellular antigen-binding domain is a human scFv, which comprises a heavy chain variable region comprising amino acids having the sequence set forth in SEQ ID NO:53 and a light chain variable region comprising amino acids having the sequence set forth in SEQ ID NO:54, optionally with (iii) a linker sequence, for example a linker peptide, between the heavy chain variable region and the light chain variable region. In certain embodiments, the linker comprises amino acids having the sequence set forth in SEQ ID NO:69. In certain embodiments, the extracellular antigen-binding domain is a human scFv-Fc fusion protein or full length human IgG with $V_H$ and $V_L$ regions or CDRs selected from Table 14. In certain embodiments, the extracellular antigen-binding domain comprises a $V_H$ comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:53, as shown in Table 14. In certain embodiments, the extracellular antigen-binding domain comprises a $V_H$ comprising amino acids having the sequence set forth in SEQ ID NO:53, as shown in Table 14. In certain embodiments, the extracellular antigen-binding domain comprises a $V_L$ comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:54, as shown in Table 14. In certain embodiments, the extracellular antigen-binding domain comprises a $V_L$ comprising amino acids having the sequence set forth in SEQ ID NO:54, as shown in Table 14. In certain embodiments, the extracellular antigen-binding domain comprises a $V_H$ comprising amino acids having the sequence set forth in SEQ ID NO:53 and a $V_L$ comprising amino acids having the sequence set forth in SEQ ID NO:54, as shown in Table 14. In certain embodiments, the extracellular antigen-binding domain comprises a $V_H$ CDR1 comprising amino acids having the sequence set forth in SEQ ID NO:167 or conservative modifications thereof, a $V_H$ CDR2 comprising amino acids having the sequence set forth in SEQ ID NO:168 or conservative modifications thereof, and a $V_H$ CDR3 comprising amino acids having the sequence set forth in SEQ ID NO:169 or conservative modifications thereof, as shown in Table 14. In certain embodiments, the extracellular antigen-binding domain comprises a $V_L$ CDR1 comprising amino acids having the sequence set forth in SEQ ID NO: 170 or conservative modifications thereof, a $V_L$ CDR2 comprising amino acids having the sequence set forth in SEQ ID NO: 171 or conservative modifications thereof, and a $V_L$ CDR3 comprising amino acids having the sequence set forth in SEQ ID NO: 172 or conservative modifications thereof, as shown in Table 14. In certain embodiments, the extracellular antigen-binding domain comprises a $V_H$ CDR1 comprising amino acids having the sequence set forth in SEQ ID NO: 167 or conservative modifications thereof, a $V_H$ CDR2 comprising amino acids having the sequence set forth in SEQ ID NO: 168 or conservative modifications thereof, a $V_H$ CDR3 comprising amino acids having the sequence set forth in SEQ ID NO: 169 or conservative modifications thereof, a $V_L$ CDR1 comprising amino acids having the sequence set forth in SEQ ID NO: 170 or conservative modifications thereof, a $V_L$ CDR2 comprising amino acids having the sequence set forth in SEQ ID NO: 171 or conservative modifications thereof, and a $V_L$ CDR3 comprising amino acids having the sequence set forth in SEQ ID NO: 172 or conservative modifications thereof, as shown in Table 14. In certain embodiments, the extracellular antigen-binding domain comprises a $V_H$ CDR1 comprising amino acids having the sequence set forth in SEQ ID NO: 167, a $V_H$ CDR2 comprising amino acids having the sequence set forth in SEQ ID NO: 168, a $V_H$ CDR3 comprising amino acids having the sequence set forth in SEQ ID NO: 169, a $V_L$ CDR1 comprising amino acids having the sequence set forth in SEQ ID NO: 170, a $V_L$ CDR2 comprising amino acids having the sequence set forth in SEQ ID NO: 171, and a $V_L$ CDR3 comprising amino acids having the sequence set forth in SEQ ID NO: 172.

TABLE 14

| | | | |
|---|---|---|---|
| Antigen | A BCMA polypeptide having the amino acid sequence of SEQ ID NO: 71 | | |
| CDRs | 1 | 2 | 3 |
| V$_H$ | GYTFIDYY [SEQ ID NO: 167] | INPNSGGT [SEQ ID NO: 168] | ARSQRDGYMDY [SEQ ID NO: 169] |
| V$_L$ | ISCTGTSSD [SEQ ID NO: 170] | EDS [SEQ ID NO: 171] | SSNTRSSTLV [SEQ ID NO: 172] |
| Full V$_H$ | EVQLVQSGAEMKKPGASLKLSCKASGYTFIDYVVYWMRQAPGQ GLESMGWINPNSGGTNYAQKFQGRVTMTRDTSISTAYMELSRLRS DDTAMYYCARSQRDGYMDYWGQGTLVTVSS [SEQ ID NO: 53] | | |
| DNA | Gaagtgcagctggtgcagtctggggctgagatgaagaagcctggggcctcactgaagctctcctgcaa ggcttctggatacaccttcatcgactactatgtatactggatgcgacaggcccctggacaagggcttgagt ccatgggatggatcaaccctaacagtggtggcacaaactatgcacagaagtttcagggcagggtcacca tgaccagggacacgtccatcagcacagcctacatggagctgagcaggctgagatctgacgacaccgcc atgtattactgtgcgcgctcccagcgtgacggttacatggattactggggtcaaggtactctggtgaccgt ctcctca [SEQ ID NO: 55] | | |
| Full V$_L$ | QSALTQPASVSASPGQSIAISCTGTSSDVGWYQQHPGKAPKLMIYE DSKRPSGVSNRFSGSKSGNTASLTISGLQAEDEADYYCSSNTRSST LVFGGGTKLTVLG [SEQ ID NO: 54] | | |
| DNA | Caatctgccctgactcagcctgcctccgtgtctgcgtctcctggacagtcgatcgccatctcctgcactgg aaccagcagtgacgttggttggtatcaacagcacccaggcaaagccccaaactcatgatttatgagga cagtaagcggcccctcaggggtttctaatcgcttctctggctccaagtctggcaacacggcctccctgacc atctctgggctccaggctgaggacgaggctgattattactgcagctcaaatacaagaagcagctttggt gttcggcggagggaccaagctgaccgtcctaggt [SEQ ID NO: 56] | | |
| scFv | QSALTQPASVSASPGQSIAISCTGTSSDVGWYQQHPGKAPKLMIYE DSKRPSGVSNRFSGSKSGNTASLTISGLQAEDEADYYCSSNTRSST LVFGGGTKLTVLGSRGGGGSGGGGSGGGGSLEMAEVQLVQSGAE MKKPGASLKLSCKASGYTFIDYVYVWMRQAPGQGLESMGWINP NSGGTNYAQKFQGRVTMTRDTSISTAYMELSRLRSDDTAMYYCA RSQRDGYMDYWGQGTLVTVSS [SEQ ID NO: 85] | | |

In certain embodiments, the extracellular antigen-binding domain is a human scFv, which comprises the amino acid sequence of SEQ ID NO:86 and specifically binds to a BCMA polypeptide (e.g., a BCMA polypeptide having the amino acid sequence SEQ ID NO:71, or fragments thereof), which is designated as ET140-190 scFv (also referred to as "ET140-40 scFv").

In certain embodiments, the extracellular antigen-binding domain is a human scFv, which comprises a heavy chain variable region comprising amino acids having the sequence set forth in SEQ ID NO:57 and a light chain variable region comprising amino acids having the sequence set forth in SEQ ID NO:58, optionally with (iii) a linker sequence, for example a linker peptide, between the heavy chain variable region and the light chain variable region. In certain embodiments, the linker comprises amino acids having the sequence set forth in SEQ ID NO:69. In certain embodiments, the extracellular antigen-binding domain is a human scFv-Fc fusion protein or full length human IgG with V$_H$ and V$_L$ regions or CDRs selected from Table 15. In certain embodiments, the extracellular antigen-binding domain comprises a V$_H$ comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:57, as shown in Table 15. In certain embodiments, the extracellular antigen-binding domain comprises a V$_H$ comprising amino acids having the sequence set forth in SEQ ID NO:57, as shown in Table 15. In certain embodiments, the extracellular antigen-binding domain comprises a V$_L$ comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:58, as shown in Table 15. In certain embodiments, the extracellular antigen-binding domain comprises a V$_L$ comprising amino acids having the sequence set forth in SEQ ID NO:58, as shown in Table 15. In certain embodiments, the extracellular antigen-binding domain comprises a V$_H$ comprising amino acids having the sequence set forth in SEQ ID NO:57 and a V$_L$ comprising amino acids having the sequence set forth in SEQ ID NO:58, as shown in Table 15. In certain embodiments, the extracellular antigen-binding domain comprises a V$_H$ CDR1 comprising amino acids having the sequence set forth in SEQ ID NO:173 or conservative modifications thereof, a V$_H$ CDR2 comprising amino acids having the sequence set forth in SEQ ID NO: 174 or conservative modifications thereof, and a V$_H$ CDR3 comprising amino acids having the sequence set forth in SEQ ID NO: 175 or conservative modifications thereof, as shown in Table 15. In certain embodiments, the extracellular antigen-binding domain comprises a V$_L$ CDR1 comprising amino acids having the sequence set forth in SEQ ID NO: 176 or conservative modifications thereof, a V$_L$ CDR2 comprising amino acids having the sequence set forth in SEQ ID NO: 177 or conservative modifications thereof, and a V$_L$ CDR3 comprising amino acids having the sequence set forth in SEQ ID NO: 178 or conservative modifications thereof, as shown in Table 15. In certain embodiments, the extracellular antigen-binding domain comprises a V$_H$ CDR1 comprising amino acids having the sequence set forth in SEQ ID NO: 173 or conservative modifications thereof, a V$_H$ CDR2 comprising amino acids having the sequence set forth in SEQ ID NO: 174 or conservative modifications thereof, a V$_H$ CDR3 comprising amino acids having the sequence set forth in SEQ ID NO: 175 or conservative modifications thereof, a V$_L$ CDR1 comprising amino acids having the sequence set forth in SEQ ID NO: 176 or conservative modifications thereof, a V_L CDR2 comprising amino acids having the sequence set forth in SEQ ID NO: 177 or conservative modifications thereof, and a V_L CDR3 comprising amino acids having the sequence set forth in SEQ ID NO: 178 or conservative modifications thereof, as shown in Table 15. In certain embodiments, the extracellular antigen-binding domain comprises a V_H CDR1 comprising amino acids having the sequence set forth in SEQ ID NO: 173, a V_H CDR2 comprising amino acids having the sequence set forth in SEQ ID NO: 174, a V_H CDR3 comprising amino acids having the sequence set forth in SEQ ID NO: 175, a V_L CDR1 comprising amino acids having the sequence set forth in SEQ ID NO: 176, a V_L CDR2 comprising amino acids having the sequence set forth in SEQ ID NO: 177, and a V_L CDR3 comprising amino acids having the sequence set forth in SEQ ID NO: 178.

scFv-Fc fusion protein or full length human IgG with V_H and V_L regions or CDRs selected from Table 16. In certain embodiments, the extracellular antigen-binding domain comprises a V_H comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:61, as shown in Table 16. In certain embodiments, the extracellular antigen-binding domain comprises a V_H comprising amino acids having the sequence set forth in SEQ ID NO:61, as shown in Table 16. In certain embodiments, the extracellular antigen-binding domain comprises a V_L comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID

TABLE 15

```
Antigen    A BCMA polypeptide having the amino acid sequence of SEQ ID NO: 71
CDRs       1                         2                         3
V_H        GYTFTDYY [SEQ ID          INPNSGGT [SEQ             ARSPYSGVLDK [SEQ
           NO: 173]                  ID NO: 174]               ID NO: 175]

V_L        SSNIGAGFD [SEQ ID         GNS [SEQ ID NO:           QSYDSSLSGYV [SEQ
           NO: 176]                  177]                      ID NO: 178]

Full V_H   QVQLVQSGAEVKKPGASVKVSCKASGYTFTDYYMHWVRQAPGQ
           RLEWMGWINPNSGGTNYAQKFQDRITVTRDTSSNTGYMELTRLRS
           DDTAVYYCARSPYSGVLDKWGQGTLVTVSS [SEQ ID NO: 57]

DNA        Caggtccagctggtacagtctggggctgaggtgaagaagcctgggcctcagtgaaggtctcctgcaag
           gcttctggatacaccttcaccgactactatatgcactgggtgcgacaggcccctggacaacggcttgagtg
           gatgggatggatcaaccctaacagtggtggcacaaactatgcacagaagtttcaggacaggatcaccgtg
           accagggacacctccagcaacacaggctacatggagctgaccaggctgagatctgacgacacggccgt
           gtattactgtgcgcgctctccgtactctggtgttctggataaatgggtcaaggtactctggtgaccgtctcct
           ca [SEQ ID NO: 59]

Full V_L   QSVLTQPPSVSGAPGQRVTISCTGSSSNIGAGFDVHWYQQLPGTAP
           KLLIYGNSNRPSGVPDRFSGSKSGTSASLAITGLQAEDEADYYCQS
           YDSSLSGYVFGTGTKVTVLG [SEQ ID NO: 58]

DNA        Cagtctgtgctgacgcagccgccctcagtgtctggggcccagggcagagggtcaccatctcctgcact
           gggagcagctccaacatcggggcaggttttgatgtacactggtaccagcagcttccaggaacagcccc
           aaactcctcatctatggtaacagcaatcggccctcaggggtccctgaccgattctctggctccaagtctggc
           acctcagcctccctggccatcactgggctccaggctgaggatgaggctgattattactgccagtcctatgac
           agcagcctgagtggttatgtcttcggaactgggaccaaggtcaccgtcctaggt [SEQ ID NO: 60]

scFv       QSVLTQPPSVSGAPGQRVTISCTGSSSNIGAGFDVHWYQQLPGTAP
           KLLIYGNSNRPSGVPDRFSGSKSGTSASLAITGLQAEDEADYYCQS
           YDSSLSGYVFGTGTKVTVLGSRGGGGSGGGGSGGGGSLEMAQVQ
           LVQSGAEVKKPGASVKVSCKASGYTFTDYYMHWVRQAPGQRLE
           WMGWINPNSGGTNYAQKFQDRITVTRDTSSNTGYMELTRLRSDD
           TAVYYCARSPYSGVLDKWGQGTLVTVSS [SEQ ID NO: 86]
```

In certain embodiments, the extracellular antigen-binding domain is a human scFv, which comprises the amino acid sequence of SEQ ID NO: 87 and specifically binds to a BCMA polypeptide (e.g., a BCMA polypeptide having the amino acid sequence SEQ ID NO:71, or fragments thereof), which is designated as ET140-187 scFv (also referred to as "ET140-37 scFv").

In certain embodiments, the extracellular antigen-binding domain is a human scFv, which comprises a heavy chain variable region comprising amino acids having the sequence set forth in SEQ ID NO:61 and a light chain variable region comprising amino acids having the sequence set forth in SEQ ID NO:62, optionally with (iii) a linker sequence, for example a linker peptide, between the heavy chain variable region and the light chain variable region. In certain embodiments, the linker comprises amino acids having the sequence set forth in SEQ ID NO:69. In certain embodiments, the extracellular antigen-binding domain is a human NO:62, as shown in Table 16. In certain embodiments, the extracellular antigen-binding domain comprises a V_L comprising amino acids having the sequence set forth in SEQ ID NO:62, as shown in Table 16. In certain embodiments, the extracellular antigen-binding domain comprises a V_H comprising amino acids having the sequence set forth in SEQ ID NO:61 and a V_L comprising amino acids having the sequence set forth in SEQ ID NO:62, as shown in Table 16. In certain embodiments, the extracellular antigen-binding domain comprises a V_H CDR1 comprising amino acids having the sequence set forth in SEQ ID NO:179 or conservative modifications thereof, a V_H CDR2 comprising amino acids having the sequence set forth in SEQ ID NO: 180 or conservative modifications thereof, and a V_H CDR3 comprising amino acids having the sequence set forth in SEQ ID NO: 181 or conservative modifications thereof, as shown in Table 16. In certain embodiments, the extracellular antigen-binding domain comprises a V_L CDR1 comprising amino acids having the sequence set forth in SEQ ID NO: 182 or conservative modifications thereof, a $V_L$ CDR2 comprising amino acids having the sequence set forth in SEQ ID NO: 183 or conservative modifications thereof, and a $V_L$ CDR3 comprising amino acids having the sequence set forth in SEQ ID NO: 184 or conservative modifications thereof, as shown in Table 16. In certain embodiments, the extracellular antigen-binding domain comprises a $V_H$ CDR1 comprising amino acids having the sequence set forth in SEQ ID NO: 179 or conservative modifications thereof, a $V_H$ CDR2 comprising amino acids having the sequence set forth in SEQ ID NO: 180 or conservative modifications thereof, a $V_H$ CDR3 comprising amino acids having the sequence set forth in SEQ ID NO: 181 or conservative modifications thereof, a $V_L$ CDR1 comprising amino acids having the sequence set forth in SEQ ID NO: 182 or conservative modifications thereof, a $V_L$ CDR2 comprising amino acids having the sequence set forth in SEQ ID NO: 183 or conservative modifications thereof, and a $V_L$ CDR3 comprising amino acids having the sequence set forth in SEQ ID NO: 184 or conservative modifications thereof, as shown in Table 16. In certain embodiments, the extracellular antigen-binding domain comprises a $V_H$ CDR1 comprising amino acids having the sequence set forth in SEQ ID NO: 179, a $V_H$ CDR2 comprising amino acids having the sequence set forth in SEQ ID NO: 180, a $V_H$ CDR3 comprising amino acids having the sequence set forth in SEQ ID NO: 181, a $V_L$ CDR1 comprising amino acids having the sequence set forth in SEQ ID NO: 182, a $V_L$ CDR2 comprising amino acids having the sequence set forth in SEQ ID NO: 183 and a $V_L$ CDR3 comprising amino acids having the sequence set forth in SEQ ID NO: 184.

In certain embodiments, the extracellular antigen-binding domain is a human scFv, which comprises the amino acid sequence of SEQ ID NO:88 and specifically binds to a BCMA polypeptide (e.g., a BCMA polypeptide having the amino acid sequence SEQ ID NO:71, or fragments thereof), which is designated as ET140-174 scFv (also referred to as "ET140-24 scFv").

In certain embodiments, the extracellular antigen-binding domain is a human scFv, which comprises a heavy chain variable region comprising amino acids having the sequence set forth in SEQ ID NO:65 and a light chain variable region comprising amino acids having the sequence set forth in SEQ ID NO:66, optionally with (iii) a linker sequence, for example a linker peptide, between the heavy chain variable region and the light chain variable region. In certain embodiments, the linker comprises amino acids having the sequence set forth in SEQ ID NO:69. In certain embodiments, the extracellular antigen-binding domain is a human scFv-Fc fusion protein or full length human IgG with $V_H$ and $V_L$ regions or CDRs selected from Table 17. In certain embodiments, the extracellular antigen-binding domain comprises a $V_H$ comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:65, as shown in Table 17. In certain embodiments, the extracellular antigen-binding domain comprises a $V_H$ comprising amino acids having the sequence set forth in SEQ ID NO:65, as shown in Table 17. In certain embodiments, the extracellular antigen-binding domain comprises a $V_L$ comprising an amino acid sequence that is at least 80%, 81%, 82%, 83%, 84%, 85%, 86%, 87%, 88%, 89%, 90%,

TABLE 16

| | | | |
|---|---|---|---|
| Antigen | A BCMA polypeptide having the amino acid sequence of SEQ ID NO: 71 | | |
| CDRs | 1 | 2 | 3 |
| $V_H$ | GGTFSSYA [SEQ ID NO: 179] | IIPILGTA [SEQ ID NO: 180] | ARSGYGSYRWEDS [SEQ ID NO: 181] |
| $V_L$ | SSNIGSNY [SEQ ID NO: 182] | SNN [SEQ ID NO: 183] | AAWDDSLSASYV [SEQ ID NO: 184] |
| Full $V_H$ | QVQLVQSGAEVKKPGSSVKVSCKASGGTFSSYAISWVRQAPGQG LEWMGRIIPILGTANYAQKFQGRVTITADESTSTAYMELSSLRSED TAVYYCARSGYGSYRWEDSWGQGTLVTVSS [SEQ ID NO: 61] | | |
| DNA | Caggtgcagctggtgcagtctggggctgaggtgaagaagcctgggtcctcggtgaaggtctcctgcaa ggcttctggaggcaccttcagcagctatgctatcagctgggtgcgacaggcccctggacaagggcttga gtggatgggaaggatcatccctatccttggtacagcaaactacgcacagaagttccagggcagagtcac gattaccgcggacgaatccacgagcacagcctacatggagctgagcagcctgagatctgaggacacgg ccgtgtattactgtgcgcgctctggttacggttcttaccgttgggaagattcttggggtcaaggtactctggt gaccgtctcctca [SEQ ID NO: 63] | | |
| Full $V_L$ | QAVLTQPPSASGTPGQRVTISCSGSSSNIGSNYVFWYQQLPGTAPK LLIYSNNQRPSGVPDRFSGSKSGTSASLAISGLRSEDEADYYCAAW DDSLSASYVFGTGTKVTVLG [SEQ ID NO: 62] | | |
| DNA | Caggctgtgctgactcagccaccctcagcgtctgggaccccgggcagagggtcaccatctcttgttct ggaagcagctccaacatcggaagtaattacgtattctggtaccagcagctcccaggaacggcccccaaa ctcctcatctatagtaataatcagcggcctcaggggtccctgaccgattctctggctccaagtctggcacc tcagcctccctggccatcagtgggctccggtccgaggatgaggctgattattactgtgcagcatgggatg acagcctgagtgcctcttatgttttcggaactgggaccaaggtcaccgtcctaggt [SEQ ID NO: 64] | | |
| scFv | QAVLTQPPSASGTPGQRVTISCSGSSSNIGSNYVFWYQQLPGTAPK LLIYSNNQRPSGVPDRFSGSKSGTSASLAISGLRSEDEADYYCAAW DDSLSASYVFGTGTKVTVLGSRGGGGSGGGGSGGGGSLEMAQVQ LVQSGAEVKKPGSSVKVSCKASGGTFSSYAISWVRQAPGQGLEW MGRIIPILGTANYAQKFQGRVTITADESTSTAYMELSSLRSEDTAV YYCARSGYGSYRWEDSWGQGTLVTVSS [SEQ ID NO: 87] | | |

91%, 92%, 93%, 94%, 95%, 96%, 97%, 98% or 99% homologous to the amino acid sequence set forth in SEQ ID NO:66, as shown in Table 17. In certain embodiments, the extracellular antigen-binding domain comprises a $V_L$ comprising amino acids having the sequence set forth in SEQ ID NO:66, as shown in Table 17. In certain embodiments, the extracellular antigen-binding domain comprises a $V_H$ comprising amino acids having the sequence set forth in SEQ ID NO:65 and a $V_L$ comprising amino acids having the sequence set forth in SEQ ID NO:66, as shown in Table 17. In certain embodiments, the extracellular antigen-binding domain comprises a $V_H$ CDR1 comprising amino acids having the sequence set forth in SEQ ID NO:185 or conservative modifications thereof, a $V_H$ CDR2 comprising amino acids having the sequence set forth in SEQ ID NO: 186 or conservative modifications thereof, and a $V_H$ CDR3 comprising amino acids having the sequence set forth in SEQ ID NO: 187 or conservative modifications thereof, as shown in Table 17. In certain embodiments, the extracellular antigen-binding domain comprises a $V_L$ CDR1 comprising amino acids having the sequence set forth in SEQ ID NO: 188 or conservative modifications thereof, a $V_L$ CDR2 comprising amino acids having the sequence set forth in SEQ ID NO: 189 or conservative modifications thereof, and a $V_L$ CDR3 comprising amino acids having the sequence set forth in SEQ ID NO: 190 or conservative modifications thereof, as shown in Table 17. In certain embodiments, the extracellular antigen-binding domain comprises a $V_H$ CDR1 comprising amino acids having the sequence set forth in SEQ ID NO: 185, a $V_H$ CDR2 comprising amino acids having the sequence set forth in SEQ ID NO: 186, a $V_H$ CDR3 comprising amino acids having the sequence set forth in SEQ ID NO: 187, a $V_L$ CDR1 comprising amino acids having the sequence set forth in SEQ ID NO: 188, a $V_L$ CDR2 comprising amino acids having the sequence set forth in SEQ ID NO: 189, and a $V_L$ CDR3 comprising amino acids having the sequence set forth in SEQ ID NO: 190.

TABLE 17

| Antigen | A BCMA polypeptide having the amino acid sequence of SEQ ID NO: 71 | | |
|---|---|---|---|
| CDRs | 1 | 2 | 3 |
| $V_H$ | GYSFTSYW [SEQ ID NO: 185] | IYPGDSDT [SEQ ID NO: 186] | ARYSGSFDN [SEQ ID NO: 187] |
| $V_L$ | SSNIGSHS [SEQ ID NO: 188] | TNN [SEQ ID NO: 189] | AAWDGSLNGLV [SEQ ID NO: 190] |
| Full $V_H$ | EVQLVQSGAEVKKPGESLKISCKGSGYSFTSYWIGWVRQMPGKG LEWMGIIYPGDSDTRYSPSFQGHVTISADKSISTAYLQWSSLKASD TAMYYCARYSGSFDNWGQGTLVTVSS [SEQ ID NO: 65] | | |
| DNA | Gaggtgcagctggtgcagtctggagcagaggtgaaaaagcccggggagtctctgaagatctcctgta agggttctggatacagctttaccagctactggatcggctgggtgcgccagatgcccgggaaaggcctg gagtggatggggatcatctatcctggtgactctgataccagatacagcccgtccttccaaggccacgtca ccatctcagctgacaagtccatcagcactgcctacctgcagtggagcagcctgaaggcctcggacacc gccatgtattactgtgcgcgctactctggttctttcgataactggggtcaaggtactctggtgaccgtctcct ca [SEQ ID NO: 67] | | |
| Full $V_L$ | SYELTQPPSASGTPGQRVTMSCSGTSSNIGSHSVNWYQQLPGTAP KLLIYTNNQRPSGVPDRFSGSKSGTSASLAISGLQSEDEADYYCA AWDGSLNGLVFGGGTKLTVLG [SEQ ID NO: 66] | | |
| DNA | Tcctatgagctgactcagccaccctcagcgtctgggaccccccgggcagagggtcaccatgtcttgttct ggaaccagctccaacatcggaagtcactctgtaaactggtaccagcagctcccaggaacggcccccaa actcctcatctatactaataatcagcggccctcaggggtccctgaccgattctctggctccaagtctggca cctcagcctccctggccatcagtggcctccagtctgaggatgaggctgattattactgtgcagcatggga tggcagcctgaatggtctggtattcggcggagggaccaagctgaccgtcctaggt [SEQ ID NO: 68] | | |
| scFv | SYELTQPPSASGTPGQRVTMSCSGTSSNIGSHSVNWYQQLPGTAP KLLIYTNNQRPSGVPDRFSGSKSGTSASLAISGLQSEDEADYYCA AWDGSLNGLVFGGGTKLTVLGSRGGGGSGGGGSGGGGSLEMAE VQLVQSGAEVKKPGESLKISCKGSGYSFTSYWIGWVRQMPGKGL EWMGIIYPGDSDTRYSPSFQGHVTISADKSISTAYLQWSSLKASDT AMYYCARYSGSFDNWGQGTLVTVSS [SEQ ID NO: 88] | | | antigen-binding domain comprises a $V_L$ CDR1 comprising amino acids having the sequence set forth in SEQ ID NO: 188 or conservative modifications thereof, a $V_L$ CDR2 comprising amino acids having the sequence set forth in SEQ ID NO: 189 or conservative modifications thereof, and a $V_L$ CDR3 comprising amino acids having the sequence set forth in SEQ ID NO: 190 or conservative modifications thereof, as shown in Table 17. In certain embodiments, the extracellular antigen-binding domain comprises a $V_H$ CDR1 comprising amino acids having the sequence set forth in SEQ ID NO: 185 or conservative modifications thereof, a $V_H$ CDR2 comprising amino acids having the sequence set forth in SEQ ID NO: 186 or conservative modifications thereof, a $V_H$ CDR3 comprising amino acids having the An extracellular antigen-binding domain (e.g., scFv) comprising $V_H$ and/or $V_L$ regions having high (i.e., 80% or greater) homology to the $V_H$ and $V_L$ regions of the sequences set forth above, can be obtained by mutagenesis (e.g., site-directed or PCR-mediated mutagenesis), followed by testing of the encoded altered scFv for retained function (i.e., the binding affinity) using the binding assays described herein. In certain embodiments, a $V_H$ sequence having at least 90%, 91%, 92%, 93%, 94%, 95%, 96%, 97%, 98% or 99% identity contains substitutions (e.g., conservative substitutions to generate conservative modifications of a sequence), insertions or deletions relative to the reference sequence, but an extracellular antigen-binding domain (e.g., scFv) comprising that sequence retains the ability to bind to a BCMA polypeptide. In certain embodiments, a $V_L$ sequence having at least 90%, 91%, 92%, 93%, 94%, 95%, 96%, 97%, 98%, or 99% identity contains substitutions (e.g., conservative substitutions), insertions or deletions relative to the reference sequence, but an extracellular antigen-binding domain (e.g., scFv) comprising that sequence retains the ability to bind to a BCMA polypeptide. In certain embodiments, a total of about 1 to about 10 amino acids have been substituted, inserted and/or deleted in the disclosed sequences. For example, and not by way of limitation, a $V_H$ sequence or a $V_L$ sequence, can have up to about one, up to about two, up to about three, up to about four, up to about five, up to about six, up to about seven, up to about eight, up to about nine or up to about ten amino acid residues that are modified and/or substituted. Non-limiting examples of conservative modifications are provided below, e.g., within Table 18.

As used herein, the term "conservative sequence modifications" refers to amino acid modifications that do not significantly affect or alter the binding characteristics of the presently disclosed CAR (e.g., the extracellular antigen-binding domain) comprising the amino acid sequence. Such conservative modifications include amino acid substitutions, additions and deletions. Modifications can be introduced into the human scFv of the presently disclosed subject matter by standard techniques known in the art, such as site-directed mutagenesis and PCR-mediated mutagenesis. Amino acids can be classified into groups according to their physicochemical properties such as charge and polarity. Conservative amino acid substitutions are ones in which the amino acid residue is replaced with an amino acid within the same group. For example, amino acids can be classified by charge: positively-charged amino acids include lysine, arginine, histidine, negatively-charged amino acids include aspartic acid, glutamic acid, neutral charge amino acids include alanine, asparagine, cysteine, glutamine, glycine, isoleucine, leucine, methionine, phenylalanine, proline, serine, threonine, tryptophan, tyrosine, and valine. In addition, amino acids can be classified by polarity: polar amino acids include arginine (basic polar), asparagine, aspartic acid (acidic polar), glutamic acid (acidic polar), glutamine, histidine (basic polar), lysine (basic polar), serine, threonine, and tyrosine; non-polar amino acids include alanine, cysteine, glycine, isoleucine, leucine, methionine, phenylalanine, proline, tryptophan, and valine. Thus, one or more amino acid residues within a CDR region can be replaced with other amino acid residues from the same group and the altered antibody can be tested for retained function (i.e., the functions set forth in (c) through (l) above) using the functional assays described herein. In certain embodiments, no more than one, no more than two, no more than three, no more than four, no more than five residues within a specified sequence or a CDR region are altered. Exemplary conservative amino acid substitutions are shown in Table 18.

TABLE 18

| Original Residue | Exemplary conservative amino acid Substitutions |
| --- | --- |
| Ala (A) | Val; Leu; Ile |
| Arg (R) | Lys; Gln; Asn |
| Asn (N) | Gln; His; Asp, Lys; Arg |
| Asp (D) | Glu; Asn |
| Cys (C) | Ser; Ala |
| Gln (Q) | Asn; Glu |
| Glu (E) | Asp; Gln |
| Gly (G) | Ala |
| His (H) | Asn; Gln; Lys; Arg |
| Ile (I) | Leu; Val; Met; Ala; Phe |
| Leu (L) | Ile; Val; Met; Ala; Phe |
| Lys (K) | Arg; Gln; Asn |
| Met (M) | Leu; Phe; Ile |

TABLE 18-continued

| Original Residue | Exemplary conservative amino acid Substitutions |
| --- | --- |
| Phe (F) | Trp; Leu; Val; Ile; Ala; Tyr |
| Pro (P) | Ala |
| Ser (S) | Thr |
| Thr (T) | Val; Ser |
| Trp (W) | Tyr; Phe |
| Tyr (Y) | Trp; Phe; Thr; Ser |
| Val (V) | Ile; Leu; Met; Phe; Ala |

In certain non-limiting embodiments, an extracellular antigen-binding domain of the CAR can comprise a linker connecting the heavy chain variable region and light chain variable region of the extracellular antigen-binding domain. As used herein, the term "linker" refers to a functional group (e.g., chemical or polypeptide) that covalently attaches two or more polypeptides or nucleic acids so that they are connected to one another. As used herein, a "peptide linker" refers to one or more amino acids used to couple two proteins together (e.g., to couple $V_H$ and $V_L$ domains). Non-limiting examples of peptide linkers are disclosed in Shen et al., Anal. Chem. 80(6):1910-1917 (2008) and WO 2014/087010.

In one non-limiting example, the linker comprises amino acids having the sequence set forth in SEQ ID NO:69. In certain embodiments, the nucleotide sequence encoding the amino acid sequence of SEQ ID NO:69 is set forth in SEQ ID NO:70. In one non-limiting example, the linker is a G4S linker that comprises amino acids having the sequence set forth in SEQ ID NO:210. In certain embodiments, the nucleotide sequence encoding the amino acid sequence of SEQ ID NO:98 is set forth in SEQ ID NO:211.

In certain embodiments, the linker comprises amino acids having the sequence set forth in SEQ ID NO:212 as provided below.

```
                                              8 SEQ ID NO: 212]
      GGGGS.
```

In certain embodiments, the linker comprises amino acids having the sequence set forth in SEQ ID NO:213 as provided below.

```
                                              [SEQ ID NO: 213]
      SGGSGGS.
```

In certain embodiments, the linker comprises amino acids having the sequence set forth in SEQ ID NO:214 as provided below.

```
                                              [SEQ ID NO: 214]
      GGGGSGGGS.
```

In certain embodiments, the linker comprises amino acids having the sequence set forth in SEQ ID NO:215 as provided below.

```
                                              [SEQ ID NO: 215]
      GGGGSGGGGS.
```

In certain embodiments, the linker comprises amino acids having the sequence set forth in SEQ ID NO:216 as provided below.

```
                                              [SEQ ID NO: 216]
      GGGGSGGGGSGGGGGGS.
```

In certain embodiments, the linker comprises amino acids having the sequence set forth in SEQ ID NO:217 as provided below.

[SEQ ID NO: 217]
GGGGSGGGGSGGGGSGGGGS.

In certain embodiments, the linker comprises amino acids having the sequence set forth in SEQ ID NO:218 as provided below.

[SEQ ID NO: 218]
GGGGSGGGGSGGGGSGGGGSGGGGS.

In certain embodiments, the linker comprises amino acids having the sequence set forth in SEQ ID NO:219 as provided below.

[SEQ ID NO: 219]
GGGGSGGGGSGGGGSGGGGSGGGGSGGGGS.

In certain embodiments, the linker comprises amino acids having the sequence set forth in SEQ ID NO:220 as provided below.

[SEQ ID NO: 220]
GGGGSGGGGSGGGGSGGGGSGGGGSGGGGSGGGGS.

In certain embodiments, the linker comprises amino acids having the sequence set forth in SEQ ID NO:220 as provided below.

[SEQ ID NO: 220]
EPKSCDKTHTCPPCP.

In certain embodiments, the linker comprises amino acids having the sequence set forth in SEQ ID NO:221 as provided below.

[SEQ ID NO: 222]
GGGGSGGGSEPKSCDKTHTCPPCP.

In certain embodiments, the linker comprises amino acids having the sequence set forth in SEQ ID NO:223 as provided below.

[SEQ ID NO: 223]
ELKTPLGDTTHTCPRCPEPKSCDTPPPCPRCPEPKSCDTPPPCPRCPEPKSCDTPPPCPRCP.

In certain embodiments, the linker comprises amino acids having the sequence set forth in SEQ ID NO:224 as provided below.

[SEQ ID NO: 224]
GSGSGS.

In certain embodiments, the linker comprises amino acids having the sequence set forth in SEQ ID NO:225 as provided below.

[SEQ ID NO: 225]
AAA.

In addition, the extracellular antigen-binding domain can comprise a leader or a signal peptide that directs the nascent protein into the endoplasmic reticulum. Signal peptide or leader can be essential if the CAR is to be glycosylated and anchored in the cell membrane. The signal sequence or leader can be a peptide sequence (about 5, about 10, about 15, about 20, about 25, or about 30 amino acids long) present at the N-terminus of newly synthesized proteins that directs their entry to the secretory pathway. In non-limiting examples, the signal peptide is covalently joined to the 5' terminus of the extracellular antigen-binding domain. In certain embodiments, the signal peptide comprises a CD8 polypeptide comprising amino acids having the sequence set forth in SEQ ID NO:191 as provided below.

[SEQ ID NO: 191]
MALPVTALLLPLALLLHAAR

The nucleotide sequence encoding the amino acid sequence of SEQ ID NO:191 is set forth in SEQ ID NO:192, which is provided below:

[SEQ ID NO: 192]
ATGGCTCTCCCAGTGACTGCCCTACTGCTTCCCCTAGCGCTTCTCCTGCA

TGCAGCTCGT

In another embodiment, the signal peptide comprises amino acids having the sequence set forth in SEQ ID NO:205 as provided below.

[SEQ ID NO: 205]
METDTLLLWVLLLWVPGSTG

The nucleotide sequence encoding the amino acid sequence of SEQ ID NO:205 is set forth in SEQ ID NO:206, which is provided below:

[SEQ ID NO: 206]
ATGGAAACCGACACCCTGCTGCTGTGGGTGCTGCTGCTGTGGGTGCCAGG

ATCCACAGGA

In certain embodiments, the human scFv comprises a heavy chain variable region, a light chain variable region, a linker peptide between the heavy chain variable region and the light chain variable region, and an His-tag and an HA-tag. In certain embodiments, the amino acid sequence of the His-tag and HA-tag comprises the amino acid sequence of SEQ ID NO:275, which is provided below:

[SEQ ID NO: 275]
TSGQAGQHHHHHHGAYPYDVPDYAS

The nucleotide sequence encoding SEQ ID NO: 275 is SEQ ID NO: 276, which is provided below:

[SEQ ID NO: 276]
ACTAGTGGCCAGGCCGGCCAGCACCATCACCATCACCATGGCGCATACCC

GTACGACGTTCCGGACTACGCTTCT

In certain embodiments, the extracellular antigen-binding domain (e.g., a human scFv) binds to a human BCMA polypeptide comprising the amino acid sequence set forth in SEQ ID NO: 71. In certain embodiments, the extracellular antigen-binding domain (e.g., a human scFv) binds to one or more portion of the amino acid sequence set forth in SEQ ID NO: 71. In certain embodiments, the extracellular antigen-binding domain (e.g., a human scFv) binds to an epitope region comprising amino acids 14-22 of SEQ ID NO: 71. In certain embodiments, the extracellular antigen-binding domain (e.g., a human scFv) binds to one, two, three, four, five, six, or seven epitope region selected from the group consisting of amino acids 8-22, 9-23, 10-24, 11-25, 12-26, 13-27, 14-28 and 8-28 of SEQ ID NO: 71. In certain embodiments, the extracellular antigen-binding domain (e.g., a human scFv) that binds to an epitope region comprising amino acids 14-22 of SEQ ID NO: 71 comprises a heavy chain variable region comprising amino acids having the sequence set forth in SEQ ID NO:9 and a light chain variable region comprising amino acids having the sequence set forth in SEQ ID NO:10, optionally with (iii) a linker sequence, for example a linker peptide, between the heavy chain variable region and the light chain variable region. In certain embodiments, the linker comprises amino acids having the sequence set forth in SEQ ID NO:69. In certain embodiments, the extracellular antigen-binding domain that binds to an epitope region comprising amino acids 14-22 of SEQ ID NO: 71 is a human scFv with $V_H$ and $V_L$ regions or CDRs selected from Table 6. In certain embodiments, the extracellular antigen-binding domain that binds to amino acids 14-22 of SEQ ID NO: 71 comprises is a human scFv-Fc fusion protein or full length human IgG with $V_H$ and $V_L$ regions or CDRs selected from Table 6. In certain embodiments, the extracellular antigen-binding domain (e.g., a human scFv) that binds to an epitope region comprising amino acids 14-22 of SEQ ID NO: 71 comprises a $V_H$ comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:21. In certain embodiments, the extracellular antigen-binding domain (e.g., a human scFv) that binds to an epitope region comprising amino acids 14-22 of SEQ ID NO: 71 comprises a $V_H$ comprising amino acids having the sequence set forth in SEQ ID NO:21. In certain embodiments, the extracellular antigen-binding domain (e.g., a human scFv) that binds to an epitope region comprising amino acids 14-22 of SEQ ID NO: 71 comprises a $V_L$ comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:22. In certain embodiments, the extracellular antigen-binding domain (e.g., a human scFv) that binds to an epitope region comprising amino acids 14-22 of SEQ ID NO: 71 comprises a $V_L$ comprising amino acids having the sequence set forth in SEQ ID NO:22. In certain embodiments, the extracellular antigen-binding domain (e.g., a human scFv) that binds to an epitope region comprising amino acids 14-22 of SEQ ID NO: 71 comprises a $V_H$ comprising amino acids having the sequence set forth in SEQ ID NO:21 and a $V_L$ comprising amino acids having the sequence set forth in SEQ ID NO:22. In certain embodiments, the extracellular antigen-binding domain (e.g., a human scFv) that binds to an epitope region comprising amino acids 14-22 of SEQ ID NO: 71 comprises a $V_H$ CDR1 comprising amino acids having the sequence set forth in SEQ ID NO:119 or conservative modifications thereof, a $V_H$ CDR2 comprising amino acids having the sequence set forth in SEQ ID NO:120 or conservative modifications thereof, and a $V_H$ CDR3 comprising amino acids having the sequence set forth in SEQ ID NO:121 or conservative modifications thereof. In certain embodiments, the extracellular antigen-binding domain (e.g., a human scFv) that binds to an epitope region comprising amino acids 14-22 of SEQ ID NO: 71 comprises a $V_L$ CDR1 comprising amino acids having the sequence set forth in SEQ ID NO:122 or conservative modifications thereof, a $V_L$ CDR2 comprising amino acids having the sequence set forth in SEQ ID NO:123 or conservative modifications thereof, and a $V_L$ CDR3 comprising amino acids having the sequence set forth in SEQ ID NO:124 or conservative modifications thereof. In certain embodiments, the extracellular antigen-binding domain (e.g., a human scFv) that binds to an epitope region comprising amino acids 14-22 of SEQ ID NO: 71 comprises a $V_H$ CDR1 comprising amino acids having the sequence set forth in SEQ ID NO:119 or conservative modifications thereof, a $V_H$ CDR2 comprising amino acids having the sequence set forth in SEQ ID NO:120 or conservative modifications thereof, a $V_H$ CDR3 comprising amino acids having the sequence set forth in SEQ ID NO:121 or conservative modifications thereof, a $V_L$ CDR1 comprising amino acids having the sequence set forth in SEQ ID NO:122 or conservative modifications thereof, a $V_L$ CDR2 comprising amino acids having the sequence set forth in SEQ ID NO:123 or conservative modifications thereof, and a $V_L$ CDR3 comprising amino acids having the sequence set forth in SEQ ID NO:124 or conservative modifications thereof. In certain embodiments, the extracellular antigen-binding domain (e.g., a human scFv) that binds to an epitope region comprising amino acids 14-22 of SEQ ID NO: 71 comprises a $V_H$ CDR1 comprising amino acids having the sequence set forth in SEQ ID NO:119, a $V_H$ CDR2 comprising amino acids having the sequence set forth in SEQ ID NO:120, a $V_H$ CDR3 comprising amino acids having the sequence set forth in SEQ ID NO:121, a $V_L$ CDR1 comprising amino acids having the sequence set forth in SEQ ID NO:122, a $V_L$ CDR2 comprising amino acids having the sequence set forth in SEQ ID NO:123, and a $V_L$ CDR3 comprising amino acids having the sequence set forth in SEQ ID NO:124. In certain embodiments, the extracellular antigen-binding domain is ET140-3 (or "ET140-153") scFv.

Transmembrane Domain of a CAR

In certain non-limiting embodiments, the transmembrane domain of the CAR comprises a hydrophobic alpha helix that spans at least a portion of the membrane. Different transmembrane domains result in different receptor stability. After antigen recognition, receptors cluster and a signal is transmitted to the cell. In accordance with the presently disclosed subject matter, the transmembrane domain of the CAR can comprise a CD8 polypeptide, a CD28 polypeptide, a CD3ζ polypeptide, a CD4 polypeptide, a 4-1BB polypeptide, an OX40 polypeptide, an ICOS polypeptide, a CTLA-4 polypeptide, a PD-1 polypeptide, a LAG-3 polypeptide, a 2B4 polypeptide, a BTLA polypeptide, a synthetic peptide (not based on a protein associated with the immune response), or a combination thereof.

In certain embodiments, the transmembrane domain of a presently disclosed CAR comprises a CD28 polypeptide. The CD28 polypeptide can have an amino acid sequence that is at least about 85%, about 90%, about 95%, about 96%, about 97%, about 98%, about 99% or 100% homologous to the sequence having a NCBI Reference No: P10747 or NP_006130 (SEQ ID No:193), or fragments thereof, and/or may optionally comprise up to one or up to two or up to three conservative amino acid substitutions. In certain embodiments, the CD28 polypeptide can have an amino acid sequence that is a consecutive portion of SEQ ID NO: 193 which is at least 20, or at least 30, or at least 40, or at least 50, and up to 220 amino acids in length. Alternatively or additionally, in non-limiting various embodiments, the CD28 polypeptide has an amino acid sequence of amino acids 1 to 220, 1 to 50, 50 to 100, 100 to 150, 150 to 200, or 200 to 220 of SEQ ID NO: 193. In certain embodiments, the CAR of the presently disclosed comprises a transmembrane domain comprising a CD28 polypeptide, and an intracellular domain comprising a co-stimulatory signaling region that comprises a CD28 polypeptide. In certain embodiments, the CD28 polypeptide comprised in the transmembrane domain and the intracellular domain has an amino acid sequence of amino acids 114 to 220 of SEQ ID NO: 193.

SEQ ID NO: 193 is provided below:

```
                                                                      [SEQ ID NO: 193]
  1 MLRLLLALNL FPSIQVTGNK ILVKQSPMLV AYDNAVNLSC KYSYNLFSRE FRASLHKGLD

61 SAVEVCVVYG NYSQQLQVYS KTGFNCDGKL GNESVTFYLQ NLYVNQTDIY FCKIEVMYPP

121 PYLDNEKSNG TIIHVKGKHL CPSPLFPGPS KPFWVLVVVG GVLACYSLLV TVAFIIFWVR

181 SKRSRLLHSD YMNMTPRRPG PTRKHYQPYA PPRDFAAYRS
```

In accordance with the presently disclosed subject matter, a "CD28 nucleic acid molecule" refers to a polynucleotide encoding a CD28 polypeptide. In certain embodiments, the CD28 nucleic acid molecule encoding the CD28 polypeptide comprised in the transmembrane domain and the intracellular domain (e.g., the co-stimulatory signaling region) of the presently disclosed CAR (amino acids 114 to 220 of SEQ ID NO: 193) comprises nucleic acids having the sequence set forth in SEQ ID NO: 194 as provided below.

```
                                         [SEQ ID NO: 194]
ATTGAAGTTATGTATCCTCCTCCTTACCTAGACAATGAGAAGAGCAATGG

AACCATTATCCATGTGAAAGGGAAACACCTTTGTCCAAGTCCCCTATTTC

CCGGACCTTCTAAGCCCTTTTGGGTGCTGGTGGTGGTTGGTGGAGTCCTG

GCTTGCTATAGCTTGCTAGTAACAGTGGCCTTTATTATTTTCTGGGTGAG

GAGTAAGAGGAGCAGGCTCCTGCACAGTGACTACATGAACATGACTCCCC

GCCGCCCCGGGCCCACCCGCAAGCATTACCAGCCCTATGCCCCACCACGC

GACTTCGCAGCCTATCGCTCC
```

In certain embodiments, the transmembrane domain of a presently disclosed CAR comprises a CD8 polypeptide. The CD8 polypeptide can have an amino acid sequence that is at least about 85%, about 90%, about 95%, about 96%, about 97%, about 98%, about 99% or 100% homologous to the sequence having a NCBI Reference No: AAH25715 (SEQ ID No:226), or fragments thereof, and/or may optionally comprise up to one or up to two or up to three conservative amino acid substitutions. In non-limiting embodiments, the CD8 polypeptide can have an amino acid sequence that is a consecutive portion of SEQ ID NO: 226 which is at least 20, or at least 30, or at least 40, or at least 50, or at least 70, or at least 100, or at least 150, or at least 200 and up to 235 amino acids in length. Alternatively or additionally, in non-limiting various embodiments, the CD28 polypeptide has an amino acid sequence of amino acids 1 to 235, 1 to 50, 50 to 100, 100 to 150, 150 to 200, 130 to 210, or 200 to 235 of SEQ ID NO: 226. In certain embodiments, the CD8 polypeptide comprised in the transmembrane domain has an amino acid sequence of amino acids 137 to 207 of SEQ ID NO: 226.

SEQ ID NO: 226 is provided below:

```
                                                                      [SEQ ID NO: 226]
  1 MALPVTALLL PLALLLHAAR PSQFRVSPLD RTWNLGETVE LKCQVLLSNP TSGCSWLFQP

61 RGAAASPTFL LYLSQNKPKA AEGLDTQRFS GKRLGDTFVL TLSDFRRENE GCYFCSALSN

121 SIMYFSHFVP VFLPAKPTTT PAPRPPTPAP TIASQPLSLR PEACRPAAGG AVHTRGLDFA

181 CDIYIWAPLA GTCGVLLLSL VITLYCNHRN RRRVCKCPRP VVKSGDKPSL SARYV.
```

In accordance with the presently disclosed subject matter, a "CD8 nucleic acid molecule" refers to a polynucleotide encoding a CD8 polypeptide. In certain embodiments, the CD8 nucleic acid molecule encoding the CD8 polypeptide comprised in the transmembrane domain of the presently disclosed CAR (amino acids 137 to 207 of SEQ ID NO: 226) comprises nucleic acids having the sequence set forth in SEQ ID NO: 227 as provided below.

```
                                                      [SEQ ID NO: 227]
CCCACCACGACGCCAGCGCCGCGACCACCAACCCCGGCGCCCACGATCGC

GTCGCAGCCCCTGTCCCTGCGCCCAGAGGCGTGCCGGCCAGCGGCGGGGG

GCGCAGTGCACACGAGGGGGCTGGACTTCGCCTGTGATATCTACATCTGG

GCGCCCCTGGCCGGGACTTGTGGGGTCCTTCTCCTGTCACTGGTTATCAC

CCTTTACTGCAAC
```

In certain non-limiting embodiments, a CAR can also comprise a spacer region that links the extracellular antigen-binding domain to the transmembrane domain. The spacer region can be flexible enough to allow the antigen binding domain to orient in different directions to facilitate antigen recognition. The spacer region can be the hinge region from IgG1, or the $CH_2CH_3$ region of immunoglobulin and portions of CD3.

Intracellular Domain of a CAR

In certain non-limiting embodiments, an intracellular domain of the CAR can comprise a CD3ζ polypeptide, which can activate or stimulate a cell (e.g., a cell of the lymphoid lineage, e.g., a T cell). CD3ζ comprises three ITAMs, and transmits an activation signal to the cell (e.g., a cell of the lymphoid lineage, e.g., a T cell) after antigen is bound. The CD3ζ polypeptide can have an amino acid sequence that is at least about 85%, about 90%, about 95%, about 96%, about 97%, about 98%, about 99% or about 100% homologous to the sequence set forth in SEQ ID NO: 195, or fragments thereof, and/or may optionally comprise up to one or up to two or up to three conservative amino acid substitutions. In non-limiting embodiments, the CD3ζ polypeptide can have an amino acid sequence that is a consecutive portion of SEQ ID NO: 195 which is at least 20, or at least 30, or at least 40, or at least 50, and up to 163 amino acids in length. Alternatively or additionally, in non-limiting various embodiments, the CD3ζ polypeptide has an amino acid sequence of amino acids 1 to 163, 1 to 50, 50 to 100, 100 to 150, or 150 to 163 of SEQ ID NO: 195. In certain embodiments, the CD3ζ polypeptide comprised in the intracellular domain of a presently disclosed CAR has an amino acid sequence of amino acids 52 to 163 of SEQ ID NO: 195.

SEQ ID NO: 195 is provided below:

```
                                                           [SEQ ID NO: 195]
  1 MKWKALFTAA ILQAQLPITE AQSFGLLDPK LCYLLDGILF IYGVILTALF LRVKFSRSAD

61 APAYQQGQNQ LYNELNLGRR EEYDVLDKRR GRDPEMGGKP RRKNPQEGLY NELQKDKMAE

121 AYSEIGMKGE RRRGKGHDGL YQGLSTATKD TYDALHMQAL PPR
```

In accordance with the presently disclosed subject matter, a "CD3ζ nucleic acid molecule" refers to a polynucleotide encoding a CD3ζ polypeptide. In certain embodiments, the CD3ζ nucleic acid molecule encoding the CD3ζ polypeptide comprised in the intracellular domain of a presently disclosed CARs (amino acid sequence of amino acids 52 to 163 of SEQ ID NO: 195) comprises nucleic acids having the sequence set forth in SEQ ID NO:196 as provided below.

```
[SEQ ID NO: 196]
AGAGTGAAGTTCAGCAGGAGCGCAGACGCCCCCGCGTACCAGCAGGGCCA

GAACCAGCTCTATAACGAGCTCAATCTAGGACGAAGAGAGGAGTACGATG

TTTTGGACAAGAGACGTGGCCGGGACCCTGAGATGGGGGGAAAGCCGAGA

AGGAAGAACCCTCAGGAAGGCCTGTACAATGAACTGCAGAAAGATAAGAT

GGCGGAGGCCTACAGTGAGATTGGGATGAAAGGCGAGCGCCGGAGGGGCA

AGGGGCACGATGGCCTTTACCAGGGTCTCAGTACAGCCACCAAGGACACC

TACGACGCCCTTCACATGCAGGCCCTGCCCCCTCGCTAA
```

In certain non-limiting embodiments, an intracellular domain of the CAR further comprises at least one signaling region. The at least one signaling region can include a CD28 polypeptide, a 4-1BB polypeptide, an OX40 polypeptide, an ICOS polypeptide, a DAP-10 polypeptide, a PD-1 polypeptide, a CTLA-4 polypeptide, a LAG-3 polypeptide, a 2B4 polypeptide, a BTLA polypeptide, a synthetic peptide (not based on a protein associated with the immune response), or a combination thereof.

In certain embodiments, the signaling region is a co-stimulatory signaling region. In certain embodiments, the co-stimulatory region comprises at least one co-stimulatory molecule, which can provide optimal lymphocyte activation. As used herein, "co-stimulatory molecules" refer to cell surface molecules other than antigen receptors or their ligands that are required for an efficient response of lymphocytes to antigen. The at least one co-stimulatory signaling region can include a CD28 polypeptide, a 4-1BB polypeptide, an OX40 polypeptide, an ICOS polypeptide, a DAP-10 polypeptide, or a combination thereof. The co-stimulatory molecule can bind to a co-stimulatory ligand, which is a protein expressed on cell surface that upon binding to its receptor produces a co-stimulatory response, i.e., an intracellular response that effects the stimulation provided when an antigen binds to its CAR molecule. Co-stimulatory ligands, include, but are not limited to CD80, CD86, CD70, OX40L, 4-1BBL, CD48, TNFRSF14, and PD-L1. As one example, a 4-1BB ligand (i.e., 4-1BBL) may bind to 4-1BB (also known as "CD137") for providing an intracellular signal that in combination with a CAR signal induces an effector cell function of the CAR+ T cell. CARs comprising an intracellular domain that comprises a co-stimulatory signaling region comprising 4-1BB, ICOS or DAP-10 are disclosed in U.S. Pat. No. 7,446,190 (e.g., the nucleotide sequence encoding 4-1BB is set forth in SEQ ID NO:15, the nucleotide sequence encoding ICOS is set forth in SEQ ID NO:16, and the nucleotide sequence encoding DAP-10 is set forth in SEQ ID NO:17 in U.S. Pat. No. 7,446,190), which is herein incorporated by reference in its entirety. In certain embodiments, the intracellular domain of the CAR comprises a co-stimulatory signaling region that comprises a CD28 polypeptide. In certain embodiments, the intracellular domain of the CAR comprises a co-stimulatory signaling region that comprises two co-stimulatory molecules:CD28 and 4-1BB or CD28 and OX40.

4-1BB can act as a tumor necrosis factor (TNF) ligand and have stimulatory activity. The 4-1BB polypeptide can have an amino acid sequence that is at least about 85%, about 90%, about 95%, about 96%, about 97%, about 98%, about 99% or 100% homologous to the sequence having a NCBI Reference No: P41273 or NP_001552 (SEQ ID NO:197) or fragments thereof, and/or may optionally comprise up to one or up to two or up to three conservative amino acid substitutions. In certain embodiments, the 4-1BB polypeptide comprised in the intracellular domain of a presently disclosed CAR has an amino acid sequence of amino acids 214-255 of SEQ ID NO: 197.

SEQ ID NO: 197 is provided below:

```
                                                           [SEQ ID NO: 197]
  1 MGNSCYNIVA TLLLVLNFER TRSLQDPCSN CPAGTFCDNN RNQICSPCPP NSFSSAGGQR

61 TCDICRQCKG VFRTRKECSS TSNAECDCTP GFHCLGAGCS MCEQDCKQGQ ELTKKGCKDC

121 CFGTFNDQKR GICRPWTNCS LDGKSVLVNG TKERDVVCGP SPADLSPGAS SVTPPAPARE

181 PGHSPQIISF FLALTSTALL FLLFFLTLRF SVVKRGRKKL LYIFKQPFMR PVQTTQEEDG

241 CSCRFPEEEE GGCEL
```

In accordance with the presently disclosed subject matter, a "4-1BB nucleic acid molecule" refers to a polynucleotide encoding a 4-1BB polypeptide. In certain embodiments, the 4-1BB nucleic acid molecule encoding the 4-1BB polypeptide comprised in the intracellular domain of a presently disclosed CARs (amino acids 214-255 of SEQ ID NO: 197) comprises nucleic acids having the sequence set forth in SEQ ID NO: 228 as provided below.

[SEQ ID NO: 228]
```
aaacggggcagaaagaagctcctgtatatattcaaacaaccatttatgag accagtacaaactactcaagaggaagatggctgtagctgccgatttccag aagaagaagaaggaggatgtgaactg
```

An OX40 polypeptide can have an amino acid sequence that is at least about 85%, about 90%, about 95%, about 96%, about 97%, about 98%, about 99% or 100% homologous to the sequence having a NCBI Reference No: P43489 or NP_003318 (SEQ ID NO: 198), or fragments thereof, and/or may optionally comprise up to one or up to two or up to three conservative amino acid substitutions.

SEQ ID NO: 198 is provided below:

[SEQ ID NO: 198]
```
  1 MCVGARRLGR GPCAALLLLG LGLSTVTGLH CVGDTYPSND RCCHECRPGN GMVSRCSRSQ

61 NTVCRPCGPG FYNDVVSSKP CKPCTWCNLR SGSERKQLCT ATQDTVCRCR AGTQPLDSYK

121 PGVDCAPCPP GHFSPGDNQA CKPWTNCTLA GKHTLQPASN SSDAICEDRD PPATQPQETQ

181 GPPARPITVQ PTEAWPRTSQ GPSTRPVEVP GGRAVAAILG LGLVLGLLGP LAILLALYLL

241 RRDQRLPPDA HKPPGGGSFR TPIQEEQADA HSTLAKI
```

In accordance with the presently disclosed subject matter, an "OX40 nucleic acid molecule" refers to a polynucleotide encoding an OX40 polypeptide.

An ICOS polypeptide can have an amino acid sequence that is at least about 85%, about 90%, about 95%, about 96%, about 97%, about 98%, about 99% or 100% homologous to the sequence having a NCBI Reference No: NP_036224 (SEQ ID NO: 199) or fragments thereof, and/or may optionally comprise up to one or up to two or up to three conservative amino acid substitutions.

SEQ ID NO: 199 is provided below:

[SEQ ID NO: 199]
```
  1 MKSGLWYFFL FCLRIKVLTG EINGSANYEM FIFHNGGVQI LCKYPDIVQQ FKMQLLKGGQ

61 ILCDLTKTKG SGNTVSIKSL KFCHSQLSNN SVSFFLYNLD HSHANYYFCN LSIFDPPPFK

121 VTLTGGYLHI YESQLCCQLK FWLPIGCAAF VVVCILGCIL ICWLTKKKYS SSVHDPNGEY

181 MFMRAVNTAK KSRLTDVTL
```

In accordance with the presently disclosed subject matter, an "ICOS nucleic acid molecule" refers to a polynucleotide encoding an ICOS polypeptide.

CTLA-4 is an inhibitory receptor expressed by activated T cells, which when engaged by its corresponding ligands (CD80 and CD86; B7-1 and B7-2, respectively), mediates activated T cell inhibition or anergy. In both preclinical and clinical studies, CTLA-4 blockade by systemic antibody infusion, enhanced the endogenous anti-tumor response albeit, in the clinical setting, with significant unforeseen toxicities.

CTLA-4 contains an extracellular V domain, a transmembrane domain, and a cytoplasmic tail. Alternate splice variants, encoding different isoforms, have been characterized. The membrane-bound isoform functions as a homodimer interconnected by a disulfide bond, while the soluble isoform functions as a monomer. The intracellular domain is similar to that of CD28, in that it has no intrinsic catalytic activity and contains one YVKM motif able to bind PI3K, PP2A and SHP-2 and one proline-rich motif able to bind SH3 containing proteins. One role of CTLA-4 in inhibiting T cell responses seem to be directly via SHP-2 and PP2A dephosphorylation of TCR-proximal signaling proteins such as CD3 and LAT. CTLA-4 can also affect signaling indirectly via competing with CD28 for CD80/86 binding. CTLA-4 has also been shown to bind and/or interact with PI3K, CD80, AP2M1, and PPP2R5A.

In accordance with the presently disclosed subject matter, a CTLA-4 polypeptide can have an amino acid sequence that is at least about 85%, about 90%, about 95%, about 96%, about 97%, about 98%, about 99% or about 100% homologous to UniProtKB/Swiss-Prot Ref. No.: P16410.3 (SEQ ID NO: 200) (homology herein may be determined using standard software such as BLAST or FASTA) or fragments thereof, and/or may optionally comprise up to one or up to two or up to three conservative amino acid substitutions.

SEQ ID NO: 200 is provided below:

[SEQ ID NO: 200]
```
  1 MACLGFQRHK AQLNLATRTW PCTLLFFLLF IPVFCKAMHV AQPAVVLASS RGIASFVCEY

61 ASPGKATEVR VTVLRQADSQ VTEVCAATYM MGNELTFLDD SICTGTSSGN QVNLTIQGLR

121 AMDTGLYICK VELMYPPPYY LGIGNGTQIY VIDPEPCPDS DFLLWILAAV SSGLFFYSFL

181 LTAVSLSKML KKRSPLTTGV YVKMPPTEPE CEKQFQPYFI PIN
```

In accordance with the presently disclosed subject matter, a "CTLA-4 nucleic acid molecule" refers to a polynucleotide encoding a CTLA-4 polypeptide.

PD-1 is a negative immune regulator of activated T cells upon engagement with its corresponding ligands PD-L1 and PD-L2 expressed on endogenous macrophages and dendritic cells. PD-1 is a type I membrane protein of 268 amino acids. PD-1 has two ligands, PD-L1 and PD-L2, which are members of the B7 family. The protein's structure comprises an extracellular IgV domain followed by a transmembrane region and an intracellular tail. The intracellular tail contains two phosphorylation sites located in an immunoreceptor tyrosine-based inhibitory motif and an immunoreceptor tyrosine-based switch motif, that PD-1 negatively regulates TCR signals. SHP-I and SHP-2 phosphatases bind to the cytoplasmic tail of PD-1 upon ligand binding. Upregulation of PD-L1 is one mechanism tumor cells may evade the host immune system. In pre-clinical and clinical trials, PD-1 blockade by antagonistic antibodies induced anti-tumor responses mediated through the host endogenous immune system.

In accordance with the presently disclosed subject matter, a PD-1 polypeptide can have an amino acid sequence that is at least about 85%, about 90%, about 95%, about 96%, about 97%, about 98%, about 99% or about 100% homologous to NCBI Reference No: NP_005009.2 (SEQ ID NO: 201) or fragments thereof, and/or may optionally comprise up to one or up to two or up to three conservative amino acid substitutions.

SEQ ID NO: 201 is provided below:

[SEQ ID NO: 201]
```
  1 MQIPQAPWPV VWAVLQLGWR PGWFLDSPDR PWNPPTFSPA LLVVTEGDNA TFTCSFSNTS

61 ESFVLNWYRM SPSNQTDKLA AFPEDRSQPG QDCRFRVTQL PNGRDFHMSV VRARRNDSGT

121 YLCGAISLAP KAQIKESLRA ELRVTERRAE VPTAHPSPSP RPAGQFQTLV VGVVGGLLGS

181 LVLLVWVLAV ICSRAARGTI GARRTGQPLK EDPSAVPVFS VDYGELDFQW REKTPEPPVP

241 CVPEQTEYAT IVFPSGMGTS SPARRGSADG PRSAQPLRPE DGHCSWPL
```

In accordance with the presently disclosed subject matter, a "PD-1 nucleic acid molecule" refers to a polynucleotide encoding a PD-1 polypeptide.

Lymphocyte-activation protein 3 (LAG-3) is a negative immune regulator of immune cells. LAG-3 belongs to the immunoglobulin (1 g) superfamily and contains 4 extracellular Ig-like domains. The LAG3 gene contains 8 exons. The sequence data, exon/intron organization, and chromosomal localization all indicate a close relationship of LAG3 to CD4. LAG3 has also been designated CD223 (cluster of differentiation 223).

In accordance with the presently disclosed subject matter, a LAG-3 polypeptide can have an amino acid sequence that is at least about 85%, about 90%, about 95%, about 96%, about 97%, about 98%, about 99% or about 100% homologous to UniProtKB/Swiss-Prot Ref. No.: P18627.5 (SEQ ID NO: 202) or fragments thereof, and/or may optionally comprise up to one or up to two or up to three conservative amino acid substitutions.

SEQ ID NO: 202 is provided below:

[SEQ ID NO: 202]
```
  1 MWEAQFLGLL FLQPLWVAPV KPLQPGAEVP VVWAQEGAPA QLPCSPTIPL QDLSLLRRAG

61 VTWQHQPDSG PPAAAPGHPL APGPHPAAPS SWGPRPRRYT VLSVGPGGLR SGRLPLQPRV

121 QLDERGRQRG DFSLWLRPAR RADAGEYRAA VHLRDRALSC RLRLRLGQAS MTASPPGSLR

181 ASDWVILNCS FSRPDRPASV HWFRNRGQGR VPVRESPHHH LAESFLFLPQ VSPMDSGPWG

241 CILTYRDGFN VSIMYNLTVL GLEPPTPLTV YAGAGSRVGL PCRLPAGVGT RSFLTAKWTP

301 PGGGPDLLVT GDNGDFTLRL EDVSQAQAGT YTCHIHLQEQ QLNATVTLAI ITVTPKSFGS

361 PGSLGKLLCE VTPVSGQERF VWSSLDTPSQ RSFSGPWLEA QEAQLLSQPW QCQLYQGERL

421 LGAAVYFTEL SSPGAQRSGR APGALPAGHL LLFLILGVLS LLLLVTGAFG FHLWRRQWRP

481 RRFSALEQGI HPPQAQSKIE ELEQEPEPEP EPEPEPEPEP EPEQL
```

In accordance with the presently disclosed subject matter, a "LAG-3 nucleic acid molecule" refers to a polynucleotide encoding a LAG-3 polypeptide.

Natural Killer Cell Receptor 2B4 (2B4) mediates non-MHC restricted cell killing on NK cells and subsets of T cells. To date, the function of 2B4 is still under investigation, with the 2B4-S isoform believed to be an activating receptor, and the 2B4-L isoform believed to be a negative immune regulator of immune cells. 2B4 becomes engaged upon binding its high-affinity ligand, CD48. 2B4 contains a tyrosine-based switch motif, a molecular switch that allows the protein to associate with various phosphatases. 2B4 has also been designated CD244 (cluster of differentiation 244).

In accordance with the presently disclosed subject matter, a 2B4 polypeptide can have an amino acid sequence that is at least about 85%, about 90%, about 95%, about 96%, about 97%, about 98%, about 99% or about 100% homologous to UniProtKB/Swiss-Prot Ref. No.: Q9BZW8.2 (SEQ ID NO: 203) or fragments thereof, and/or may optionally comprise up to one or up to two or up to three conservative amino acid substitutions.

SEQ ID NO: 203 is provided below:

[SEQ ID NO: 203]
```
  1 MLGQVVTLIL LLLLKVYQGK GCQGSADHVV SISGVPLQLQ PNSIQTKVDS IAWKKLLPSQ
 61 NGFHHILKWE NGSLPSNTSN DRFSFIVKNL SLLIKAAQQQ DSGLYCLEVT SISGKVQTAT
121 FQVFVFESLL PDKVEKPRLQ GQGKILDRGR CQVALSCLVS RDGNVSYAWY RGSKLIQTAG
181 NLTYLDEEVD INGTHTYTCN VSNPVSWESH TLNLTQDCQN AHQEFRFWPF LVIIVILSAL
241 FLGTLACFCV WRRKRKEKQS ETSPKEFLTI YEDVKDLKTR RNHEQEQTFP GGGSTIYSMI
301 QSQSSAPTSQ EPAYTLYSLI QPSRKSGSRK RNHSPSFNST IYEVIGKSQP KAQNPARLSR
361 KELENFDVYS
```

In accordance with the presently disclosed subject matter, a "2B4 nucleic acid molecule" refers to a polynucleotide encoding a 2B4 polypeptide.

B- and T-lymphocyte attenuator (BTLA) expression is induced during activation of T cells, and BTLA remains expressed on Th1 cells but not Th2 cells. Like PD1 and CTLA4, BTLA interacts with a B7 homolog, B7H4. However, unlike PD-1 and CTLA-4, BTLA displays T-Cell inhibition via interaction with tumor necrosis family receptors (TNF-R), not just the B7 family of cell surface receptors. BTLA is a ligand for tumor necrosis factor (receptor) superfamily, member 14 (TNFRSF14), also known as herpes virus entry mediator (HVEM). BTLA-HVEM complexes negatively regulate T-cell immune responses. BTLA activation has been shown to inhibit the function of human CD8$^+$ cancer-specific T cells. BTLA has also been designated as CD272 (cluster of differentiation 272).

In accordance with the presently disclosed subject matter, a BTLA polypeptide can have an amino acid sequence that is at least about 85%, about 90%, about 95%, about 96%, about 97%, about 98%, about 99% or about 100% homologous to UniProtKB/Swiss-Prot Ref. No.: Q7Z6A9.3 (SEQ ID NO: 204) or fragments thereof, and/or may optionally comprise up to one or up to two or up to three conservative amino acid substitutions.

SEQ ID NO: 204 is provided below:

[SEQ ID NO: 204]
```
  1 MKTLPAMLGT GKLFWVFFLI PYLDIWNIHG KESCDVQLYI KRQSEHSILA GDPFELECPV
 61 KYCANRPHVT WCKLNGTTCV KLEDRQTSWK EEKNISFFIL HFEPVLPNDN GSYRCSANFQ
121 SNLIESHSTT LYVTDVKSAS ERPSKDEMAS RPWLLYRLLP LGGLPLLITT CFCLFCCLRR
181 HQGKQNELSD TAGREINLVD AHLKSEQTEA STRQNSQVLL SETGIYDNDP DLCFRMQEGS
241 EVYSNPCLEE NKPGIVYASL NHSVIGPNSR LARNVKEAPT EYASICVRS
```

In accordance with the presently disclosed subject matter, a "BTLA nucleic acid molecule" refers to a polynucleotide encoding a BTLA polypeptide.

In certain embodiments, the CAR comprises an extracellular antigen-binding region that comprises a human scFv that specifically binds to human BCMA, a transmembrane domain comprising a CD28 polypeptide, and an intracellular domain comprising a CD3ζ polypeptide and a co-stimulatory signaling region that comprises a CD28 polypeptide, as shown in FIG. 1. As shown in FIG. 1, the CAR also comprises a signal peptide or a leader covalently joined to the 5' terminus of the extracellular antigen-binding domain. In certain embodiments, the signal peptide comprises amino acids having the sequence set forth in SEQ ID NO:205.

Figure 7:
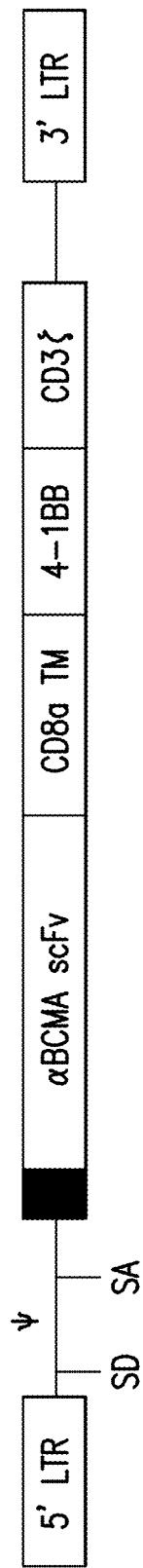
FIG. 7 shows a chimeric antigen receptor targeting BCMA in accordance with one non-limiting embodiment of the presently disclosed subject matter.
Figure 8:
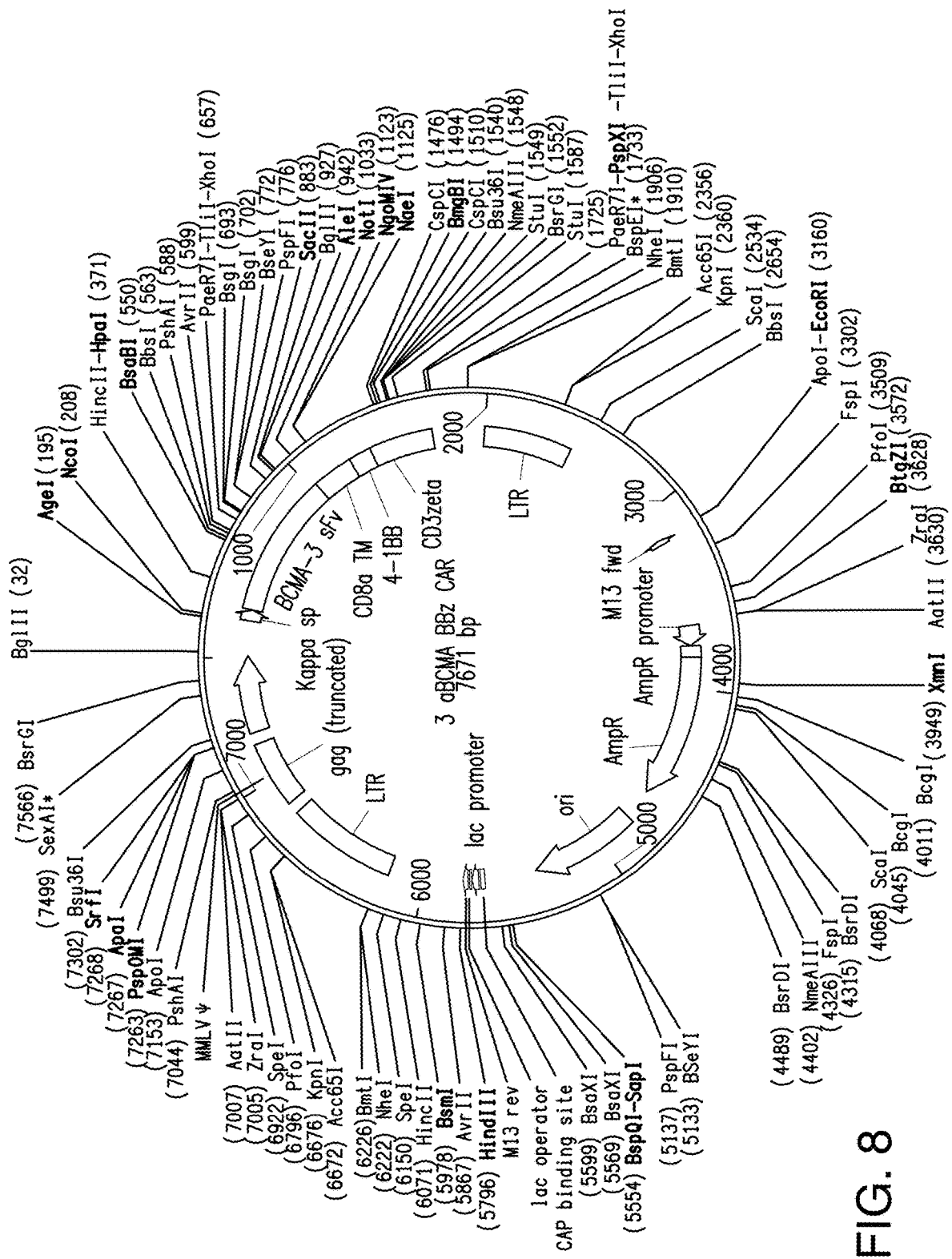
FIG. 8 depicts a nucleic acid molecule that encodes a BCMA-targeted CAR in accordance with one non-limiting embodiment of the presently disclosed subject matter.
Figure 9:
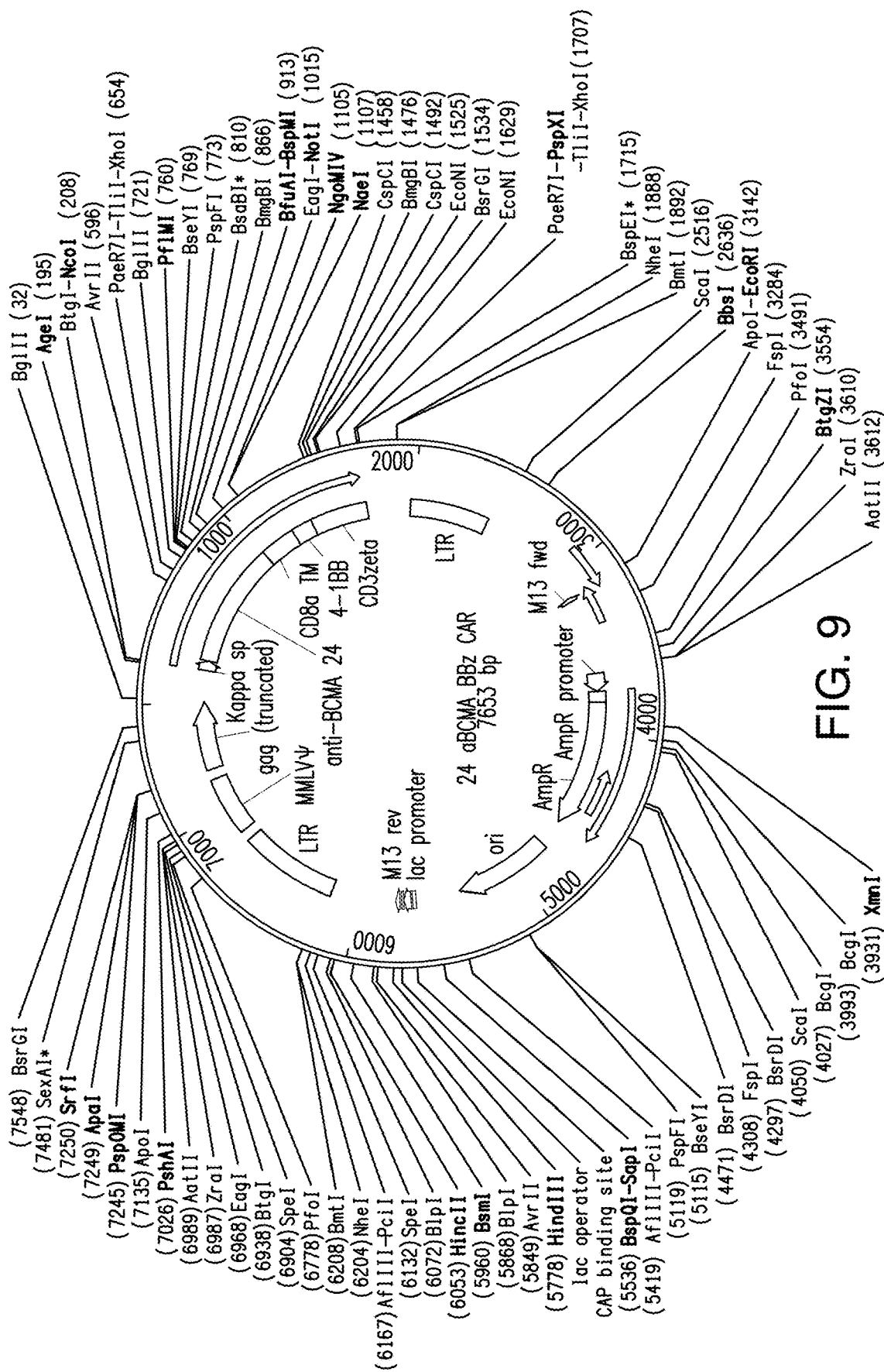
FIG. 9 depicts a nucleic acid molecule that encodes a BCMA-targeted CAR in accordance with one non-limiting embodiment of the presently disclosed subject matter.
Figure 10:
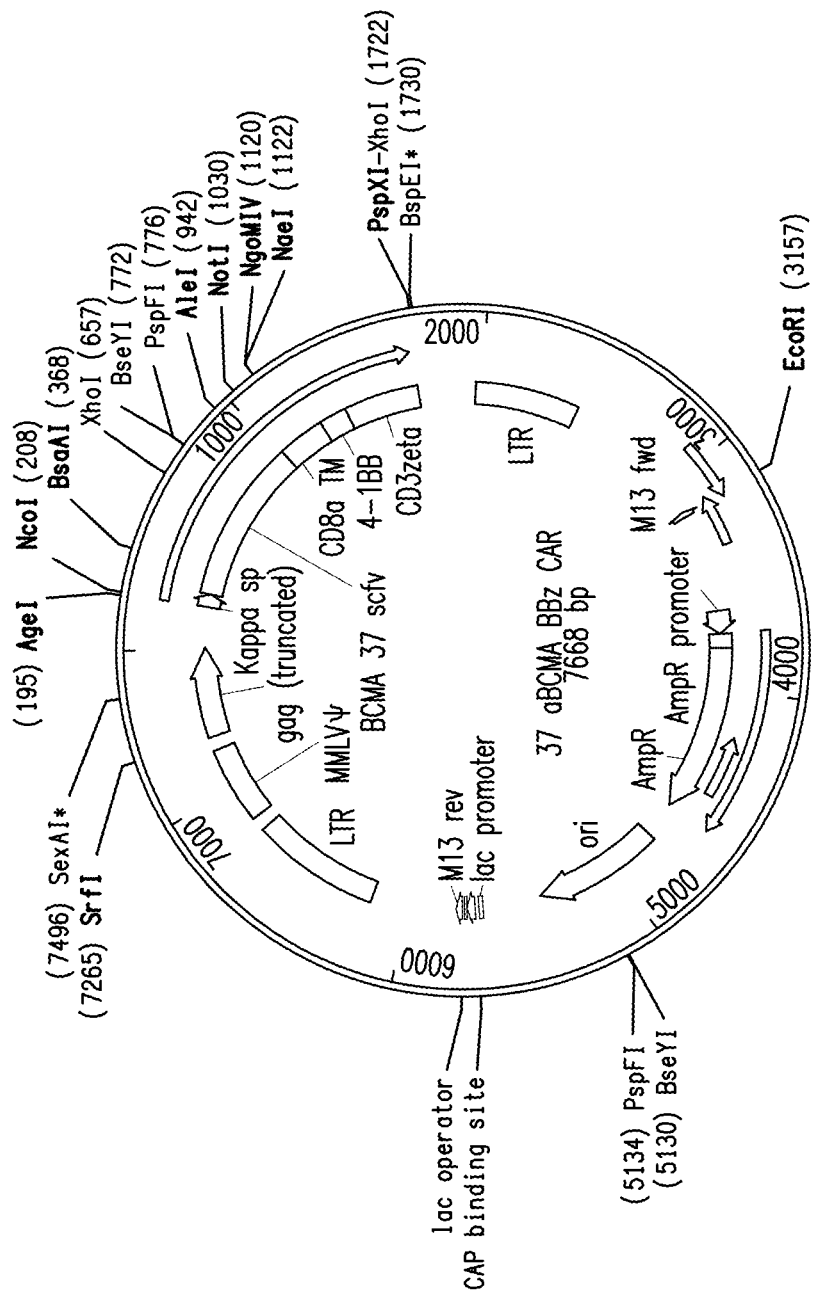
FIG. 10 depicts a nucleic acid molecule that encodes a BCMA-targeted CAR in accordance with one non-limiting embodiment of the presently disclosed subject matter.
Figure 11:
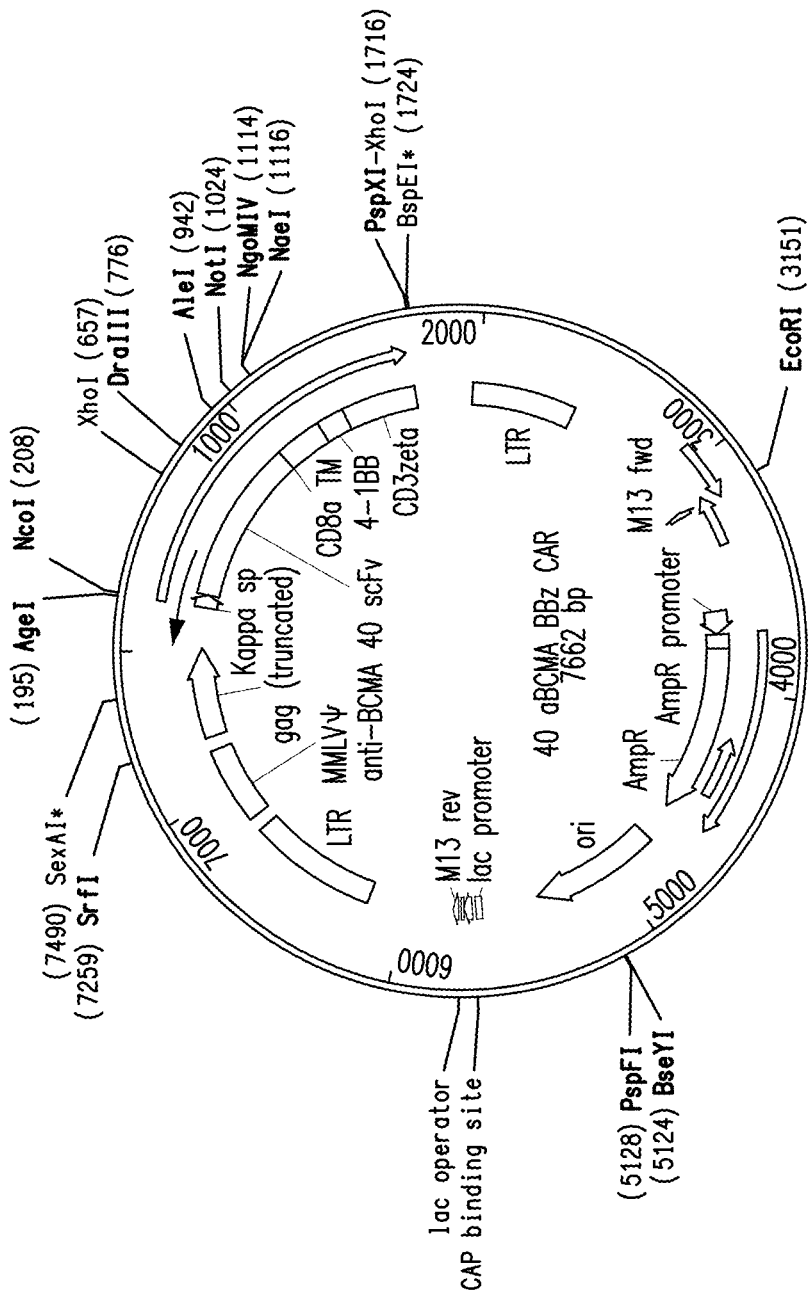
FIG. 11 depicts a nucleic acid molecule that encodes a BCMA-targeted CAR in accordance with one non-limiting embodiment of the presently disclosed subject matter.
Figure 12:
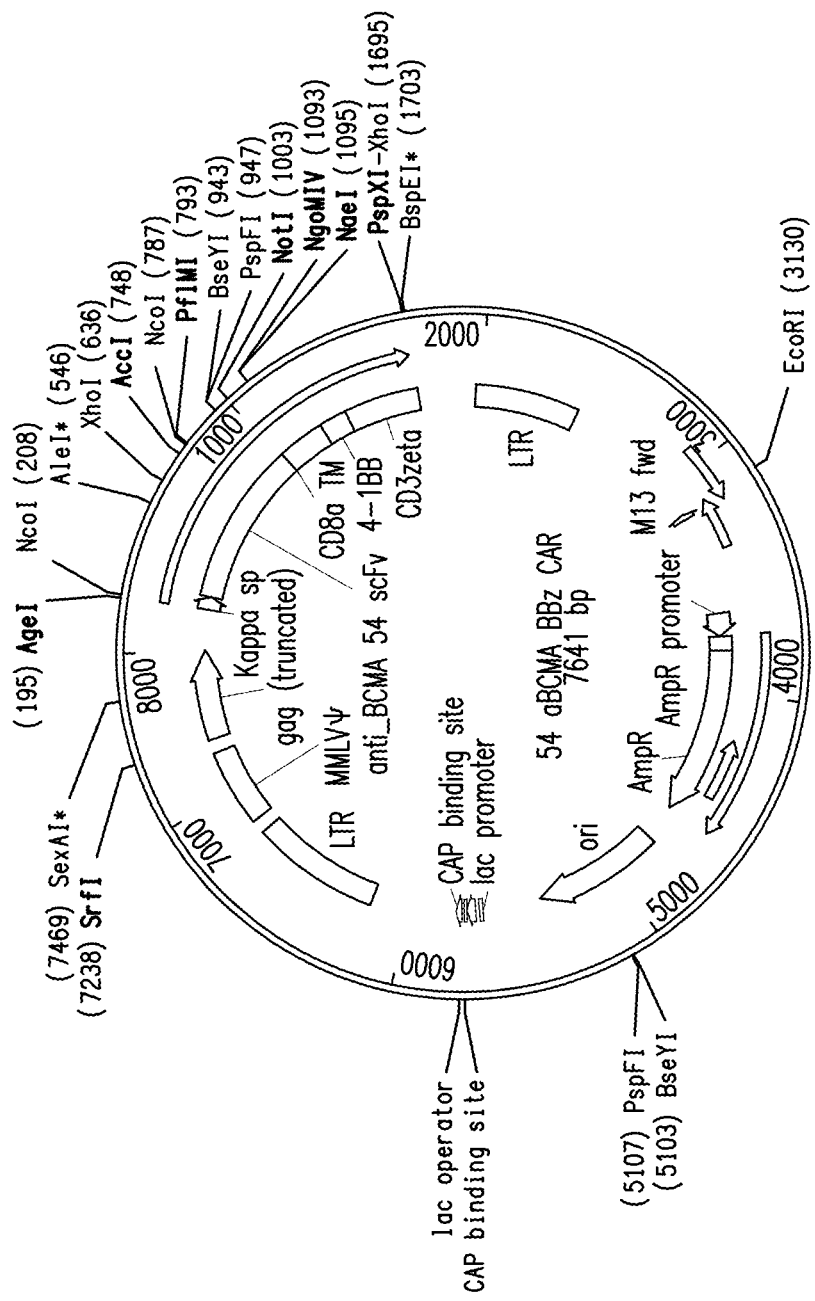
FIG. 12 depicts a nucleic acid molecule that encodes a BCMA-targeted CAR in accordance with one non-limiting embodiment of the presently disclosed subject matter.

In certain embodiments, the CAR comprises an extracellular antigen-binding region that comprises a human scFv that specifically binds to human BCMA, a transmembrane domain comprising a CD8 polypeptide, and an intracellular domain comprising a CD3ζ polypeptide and a co-stimulatory signaling region that comprises a 4-1BB polypeptide, as shown in FIG. 7. As shown in FIG. 7, the CAR also comprises a signal peptide or a leader covalently joined to the 5' terminus of the extracellular antigen-binding domain. In certain embodiments, the signal peptide comprises amino acids having the sequence set forth in SEQ ID NO:205.

In certain embodiments, the CAR of the presently disclosed subject matter can further comprise an inducible promoter, for expressing nucleic acid sequences in human cells. Promoters for use in expressing CAR genes can be a constitutive promoter, such as ubiquitin C (UbiC) promoter.

The presently disclosed subject matter also provides isolated nucleic acid molecule encoding the BCMA-targeted CAR described herein or a functional portion thereof. In certain embodiments, the isolated nucleic acid molecule encodes a presently disclosed BCMA-targeted CAR comprising a human scFv that specifically binds to human BCMA, a transmembrane domain comprising a CD28 polypeptide, and an intracellular domain comprising a CD3ξ polypeptide and a co-stimulatory signaling region comprising a CD28 polypeptide. In one specific non-limiting example, the isolated nucleic acid molecule comprises nucleic acids having the sequence set forth in SEQ ID NO:207 provided below:

[SEQ ID NO: 207]
caatctgccctgactcagcctgcctccgtgtctgcgtctcctggacagtc gatcgccatctcctgcactggaaccagcagtgacgttggttggtatcaac agcacccaggcaaagcccccaaactcatgatttatgaggacagtaagcgg ccctcaggggtttctaatcgcttctctggctccaagtctggcaacacggc ctccctgaccatctctgggctccaggctgaggacgaggctgattattact gcagctcaaatacaagaagcagcactttggtgttcggcggagggaccaag ctgaccgtcctaggttctagaggtggtggtggtagcggcggcggcggctc tggtggtggtggatccctcgagatggccgaagtgcagctggtgcagtctg gggctgagatgaagaagcctggggcctcactgaagctctcctgcaaggct tctggatacaccttcatcgactactatgtatactggatgcgacaggcccc tggacaagggcttgagtccatgggatggatcaaccctaacagtggtggca caaactatgcacagaagtttcagggcagggtcaccatgaccagggacacg tccatcagcacagcctacatggagctgagcaggctgagatctgacgacac cgccatgtattactgtgcgcgctcccagcgtgacggttacatggattact ggggtcaaggtactctggtgaccgtctcctcagcggccgcaattgaagtt atgtatcctcctccttacctagacaatgagaagagcaatggaaccattat ccatgtgaaagggaaacacctttgtccaagtcccctatttcccggacctt ctaagccttttgggtgctggtggtggttggtggagtcctggcttgctat agcttgctagtaacagtggcctttattattttctgggtgaggagtaagag gagcaggctcctgcacagtgactacatgaacatgactccccgccgccccg ggcccacccgcaagcattaccagccctatgccccaccacgcgacttcgca gcctatcgctccagagtgaagttcagcaggagcgcagacgcccccgcgta ccagcagggccagaaccagctctataacgagctcaatctaggacgaagag aggagtacgatgtttggacaagagacgtggccgggaccctgagatgggg ggaaagccgagaaggaagaaccctcaggaaggcctgtacaatgaactgca gaaagataagatggcggaggcctacagtgagattgggatgaaaggcgagc gccggaggggcaagggcacgatggcctttaccagggtctcagtacagcc accaaggacacctacgacgcccttcacatgcaggccctgccccctcgc In one specific non-limiting example, the isolated nucleic acid molecule comprises nucleic acids having the sequence set forth in SEQ ID NO:208 provided below:

[SEQ ID NO: 208]
cagtctgtgctgacgcagccgccctcagtgtctggggcccagggcagag ggtcaccatctcctgcactgggagcagctccaacatcggggcaggttttg atgtacactggtaccagcagcttccaggaacagcccccaaactcctcatc tatggtaacagcaatcggccctcaggggtccctgaccgattctctggctc caagtctggcacctcagcctccctggccatcactgggctccaggctgagg atgaggctgattattactgccagtcctatgacagcagcctgagtggttat gtcttcggaactgggaccaaggtcaccgtcctaggttctagaggtggtgg tggtagcggcggcggcggctctggtggtggtggatccctcgagatggccc aggtccagctggtacagtctggggctgaggtgaagaagcctggggcctca gtgaaggtctcctgcaaggcttctggatacaccttcaccgactactatat gcactgggtgcgacaggcccctggacaacggcttgagtggatgggatgga tcaaccctaacagtggtggcacaaactatgcacagaagtttcaggacagg atcaccgtgaccagggacacctccagcaacacaggctacatggagctgac caggctgagatctgacgacacggccgtgtattactgtgcgcgctctccgt actctggtgttctggataaatggggtcaaggtactctggtgaccgtctcc tcagcggccgcaattgaagttatgtatcctcctccttacctagacaatga gaagagcaatggaaccattatccatgtgaaagggaaacacctttgtccaa gtcccctatttcccggaccttctaagccttttgggtgctggtggtggtt ggtggagtcctggcttgctatagcttgctagtaacagtggcctttattat tttctgggtgaggagtaagaggagcaggctcctgcacagtgactacatga acatgactccccgccgccccgggcccacccgcaagcattaccagccctat gccccaccacgcgacttcgcagcctatcgctccagagtgaagttcagcag gagcgcagacgcccccgcgtaccagcagggccagaaccagctctataacg agctcaatctaggacgaagagaggagtacgatgtttttggacaagagacgt ggccgggaccctgagatgggggggaaagccgagaaggaagaaccctcagga aggcctgtacaatgaactgcagaaagataagatggcggaggcctacagtg agattgggatgaaaggcgagcgccggaggggcaaggggcacgatggcctt taccagggtctcagtacagccaccaaggacacctacgacgcccttcacat gcaggccctgccccctcgc In one specific non-limiting example, the isolated nucleic acid molecule comprises nucleic acids having the sequence set forth in SEQ ID NO:209 provided below:

[SEQ ID NO: 209]
tcctatgagctgactcagccaccctcagcgtctgggaccccggcagag ggtcaccatgtcttgttctggaaccagctccaacatcggaagtcactctg taaactggtaccagcagctcccaggaacggcccccaaactcctcatctat actaataatcagcggccctcaggggtccctgaccgattctctggctccaa gtctggcacctcagcctccctggccatcagtggcctccagtctgaggatg aggctgattattactgtgcagcatgggatggcagcctgaatggtctggta ttcggcggagggaccaagctgaccgtcctaggttctagaggtggtggtgg tagcggcggcggcggctctggtggtggtggatccctcgagatggccgagg tgcagctggtgcagtctggagcagaggtgaaaaagcccggggagtctctg aagatctcctgtaagggttctggatacagctttaccagctactggatcgg ctgggtgcgccagatgcccgggaaaggcctggagtggatggggatcatct atcctggtgactctgataccagatacagcccgtccttccaaggccacgtc accatctcagctgacaagtccatcagcactgcctacctgcagtggagcag cctgaaggcctcggacaccgccatgtattactgtgcgcgctactctggtt cttttcgataactggggtcaaggtactctggtgaccgtctcctcagcggcc gcaattgaagttatgtatcctcctccttacctagacaatgagaagagcaa tggaaccattatccatgtgaaagggaaacacctttgtccaagtcccctat ttcccggaccttctaagccctttttgggtgctggtggtggttggtggagtc ctggcttgctatagcttgctagtaacagtggcctttattattttctgggt gaggagtaagaggagcaggctcctgcacagtgactacatgaacatgactc cccgccgcccgggcccacccgcaagcattaccagccctatgccccacca cgcgacttcgcagcctatcgctccagagtgaagttcagcaggagcgcaga cgcccccgcgtaccagcagggccagaaccagctctataacgagctcaatc taggacgaagagaggagtacgatgtttttggacaagagacgtggccgggac cctgagatggggggaaagccgagaaggaagaaccctcaggaaggcctgta caatgaactgcagaaagataagatggcggaggcctacagtgagattggga tgaaaggcgagcgccggaggggcaaggggcacgatggcctttaccagggt ctcagtacagccaccaaggacacctacgacgcccttcacatgcaggccct gccccctcgc In one specific non-limiting example, the isolated nucleic acid molecule comprises nucleic acids having the sequence set forth in SEQ ID NO:229 provided below:

[SEQ ID NO: 229]
CCTTCTCTAGGCGCCCCCATATGGCCATATGAGATCTTATATGGGGCACCCCCGCCCCTTGTAAACTTCCCTGACCCTGA

CATGACAAGAGTTACTAACAGCCCCTCTCTCCAAGCTCACTTACAGGCTCTCTACTTAGTCCAGCACGAAGTCTGGAGAC

CTCTGGCGGCAGCCTACCAAGAACAACTGGACCGACCGGTGCCGCCACCATGGAAACCGACACCCTGCTGCTGTGGGTGC

TGCTGCTGTGGGTGCCAGGATCCACAGGACTGCCTGTGCTGACTCAGCCACCCTCAGCGTCTGGGACCCCCGGGCAGAGG

GTCACCATCTCTTGTTCTGGACGCAGTTCCAACATCGGGAGTAATTCTGTTAACTGGTATCGACAACTCCCAGGAGCGGC

CCCCAAACTCCTCATCTATAGTAATAATCAGCGGCCCCCAGGGGTCCCTGTGCGATTCTCTGGCTCCAAGTCTGGCACCT

CAGCCTCCCTGGCCATCAGTGGGCTCCAGTCTGAAGATGAGGCCACTTATTACTGTGCAACATGGGATGACAATCTGAAT

GTTCACTATGTCTTCGGAACTGGGACCAAGGTCACCGTCCTAGGTTCTAGAGGTGGTGGTGGTAGCGGCGGCGGCGGCTC

TGGTGGTGGTGGATCCCTCGAGATGGCCCAGGTGCAGCTGGTGCAGTCTGGGGCTGAGGTGAAGAAGCCTGGGTCCTCGG

TGAAGGTCTCCTGCAAGGCTTCTGGAGGCACCTTCAGCAGCTATGCTATCAGCTGGGTGCGACAGGCCCCTGGACAAGGG

CTTGAGTGGATGGGAAGGATCATCCCTATCCTTGGTATAGCAAACTACGCACAGAAGTTCCAGGGCAGAGTCACGATTAC

CGCGGACAAATCCACGAGCACAGCCTACATGGAGCTGAGCAGCCTGAGATCTGAGGACACGGCCGTGTATTACTGTGCGC

GCGGTGGTTACTACTCTCATGACATGTGGTCTGAAGATTGGGGTCAAGGTACTCTGGTGACCGTCTCCTCAGCggccgca cccaccacgacgccagcgccgcgaccaccaacccgcgcccacgatcgcgtcgcagcccctgtccctgcgcccagaggc gtgccggccagcggcgggggggcgcagtgcacacgagggggctggacttcgcctgtgatatctacatctgggcgcccctgg ccgggacttgtggggtccttctcctgtcactggttatcacccttactgcaacaaacggggcagaaagaagctcctgtat atattcaaacaaccatttatgagaccagtacaaactactcaagaggaagatggctgtagctgccgatttccagaagaaga agaaggaggatgtgaactgagagtgaagttgagcaggagcgcagagccccccgcgtaccagcagggccagaaccagctct -continued ataacgagctcaatctaggacgaagagaggagtacgatgttttggacaagagacgtggccgggaccctgagatgggggga
aagccgagaaggaagaaccctcaggaaggcctgtacaatgaactgcagaaagataagatggcggaggcctacagtgagat
tgggatgaaaggcgagcgccggaggggcaaggggcacgatggcctttaccagggtctcagtacagccaccaaggacacct
acgacgcccttcacatgcaggccctgcccccctcgctaacagccactcgaggatccggattagtccaatttgttaaagaca
ggatatcagtggtccaggctctagttttgactcaacaatatcaccagctgaagcctatagagtacgagccatagataaaa
taaaagattttatttagtctccagaaaaagggggaatgaaagaccccacctgtaggtttggcaagctagcttaagtaac
gccattttgcaaggcatggaaaaatacataactgagaatagagaagttcagatcaaggtcaggaacagatggaacagctg
aatatgggccaaacaggatatctgtggtaagcagttcctgccccggctcagggcaagaacagatggaacagctgaatat
gggccaaacaggatatctgtggtaagcagttcctgccccggctcagggccaagaacagatggtccccagatgcggtccag
ccctcagcagtttctagagaaccatcagatgtttccagggtgccccaaggacctgaaatgaccctgtgccttatttgaac
taaccaatcagttcgcttctcgcttctgttcgcgcgcttctgctccccgagctcaataaaagagcccacaacccctcact
cggggcgccagtcctccgattgactgagtcgcccgggtacccgtgtatccaataaaccctcttgcagttgcatccgactt
gtggtctcgctgttccttgggagggtctcctctgagtgattgactacccgtcagcggggtctttcacacatgcagcatg
tatcaaaattaatttggttttttttcttaagtatttacattaaatggccatagtacttaaagttacattggcttccttga
aataaacatggagtattcagaatgtgtcataaatatttctaattttaagatagtatctccattggctttctacttttttct
tttatttttttttgtcctctgtcttccatttgttgttgttgttgtttgtttgtttgttggttggttggttaatttt
tttttaaagatcctacactatagttcaagctagactattagctactctgtaacccagggtgaccttgaagtcatgggtag
cctgctgttttagccttcccacatctaagattacaggtatgagctatcattttggtatattgattgattgattgattga
tgtgtgtgtgtgtgattgtgtttgtgtgtgtgactgtgaaaatgtgtgatgggtgtgtgtgaatgtgtgtatgtatgtg
tgtgtgagtgtgtgtgtgtgtgtgcatgtgtgtgtgtgtgactgtgtctatgtgtatgactgtgtgtgtgtgtgtg
tgtgtgtgtgtgtgtgtgtgtgtgtgttgtgaaaaaatattctatggtagtgagagccaacgctccggctcaggtg
tcaggttggttttttgagacagagtctttcacttagcttggAATTCACTGGCCGTCGTTTTACAACGTCGTGACTGGGAAA
ACCCTGGCGTTACCCAACTTAATCGCCTTGCAGCACATCCCCCTTTCGCCAGCTGGCGTAATAGCGAAGAGGCCCGCACC
GATCGCCCTTCCCAACAGTTGCGCAGCCTGAATGGCGAATGGCGCCTGATGCGGTATTTTCTCCTTACGCATCTGTGCGG
TATTTCACACCGCATATGGTGCACTCTCAGTACAATCTGCTCTGATGCCGCATAGTTAAGCCAGCCCCGACACCCGCCAA
CACCCGCTGACGCGCCCTGACGGGCTTGTCTGCTCCCGGCATCCGCTTACAGACAAGCTGTGACCGTCTCCGGGAGCTGC
ATGTGTCAGAGGTTTTCACCGTCATCACCGAAACGCGCGATGACGAAAGGGCCTCGTGATACGCCTATTTTTATAGGTTA
ATGTCATGATAATAATGGTTTCTTAGACGTCAGGTGGCACTTTTCGGGGAAATGTGCGCGGAACCCCTATTTGTTTATTT
TTCTAAATACATTCAAATATGTATCCGCTCATGAGACAATAACCCTGATAAATGCTTCAATAATATTGAAAAAGGAAGAG
TATGAGTATTCAACATTTCCGTGTCGCCCTTATTCCCTTTTTTGCGGCATTTTGCCTTCCTGTTTTTGCTCACCCAGAAA
CGCTGGTGAAAGTAAAAGATGCTGAAGATCAGTTGGGTGCACGAGTGGGTTACATCGAACTGGATCTCAACAGCGGTAAG
ATCCTTGAGAGTTTTCGCCCCGAAGAACGTTTTCCAATGATGAGCACTTTTAAAGTTCTGCTATGTGGCGCGGTATTATC
CCGTATTGACGCCGGGCAAGAGCAACTCGGTCGCCGCATACACTATTCTCAGAATGACTTGGTTGAGTACTCACCAGTCA
CAGAAAAGCATCTTACGGATGGCATGACAGTAAGAGAATTATGCAGTGCTGCCATAACCATGAGTGATAACACTGCGGCC
AACTTACTTCTGACAACGATCGGAGGACCGAAGGAGCTAACCGCTTTTTTGCACAACATGGGGGATCATGTAACTCGCCT
TGATCGTTGGGAACCGGAGCTGAATGAAGCCATACCAAACGACGAGCGTGACACCACGATGCCTGTAGCAATGGCAACAA
CGTTGCGCAAACTATTAACTGGCGAACTACTTACTCTAGCTTCCCGGCAACAATTAATAGACTGGATGGAGGCGGATAAA
GTTGCAGGACCACTTCTGCGCTCGGCCCTTCCGGCTGGCTGGTTTATTGCTGATAAATCTGGAGCCGGTGAGCGTGGGTC
TCGCGGTATCATTGCAGCACTGGGGCCAGATGGTAAGCCCTCCCGTATCGTAGTTATCTACACGACGGGGAGTCAGGCAA
CTATGGATGAACGAAATAGACAGATCGCTGAGATAGGTGCCTCACTGATTAAGCATTGGTAACTGTCAGACCAAGTTTAC -continued

```
TCATATATACTTTAGATTGATTTAAAACTTCATTTTTAATTTAAAAGGATCTAGGTGAAGATCCTTTTTGATAATCTCAT
GACCAAAATCCCTTAACGTGAGTTTTCGTTCCACTGAGCGTCAGACCCCGTAGAAAAGATCAAAGGATCTTCTTGAGATC
CTTTTTTTCTGCGCGTAATCTGCTGCTTGCAAACAAAAAAACCACCGCTACCAGCGGTGGTTTGTTTGCCGGATCAAGAG
CTACCAACTCTTTTTCCGAAGGTAACTGGCTTCAGCAGAGCGCAGATACCAAATACTGTCCTTCTAGTGTAGCCGTAGTT
AGGCCACCACTTCAAGAACTCTGTAGCACCGCCTACATACCTCGCTCTGCTAATCCTGTTACCAGTGGCTGCTGCCAGTG
GCGATAAGTCGTGTCTTACCGGGTTGGACTCAAGACGATAGTTACCGGATAAGGCGCAGCGGTCGGGCTGAACGGGGGGT
TCGTGCACACAGCCCAGCTTGGAGCGAACGACCTACACCGAACTGAGATACCTACAGCGTGAGCATTGAGAAAGCGCCAC
GCTTCCCGAAGGGAGAAAGGCGGACAGGTATCCGGTAAGCGGCAGGGTCGGAACAGGAGAGCGCACGAGGGAGCTTCCAG
GGGGAAACGCCTGGTATCTTTATAGTCCTGTCGGGTTTCGCCACCTCTGACTTGAGCGTCGATTTTTGTGATGCTCGTCA
GGGGGGCGGAGCCTATGGAAAAACGCCAGCAACGCGGCCTTTTTACGGTTCCTGGCCTTTTGCTGGCCTTTTGCTCACAT
GTTCTTTCCTGCGTTATCCCCTGATTCTGTGGATAACCGTATTACCGCCTTTGAGTGAGCTGATACCGCTCGCCGCAGCC
GAACGACCGAGCGCAGCGAGTCAGTGAGCGAGGAAGCGGAAGAGCGCCCAATACGCAAACCGCCTCTCCCCGCGCGTTGG
CCGATTCATTAATGCAGCTGGCACGACAGGTTTCCCGACTGGAAAGCGGGCAGTGAGCGCAACGCAATTAATGTGAGTTA
GCTCACTCATTAGGCACCCCAGGCTTTACACTTTATGCTTCCGGCTCGTATGTTGTGTGGAATTGTGAGCGGATAACAAT
TTCACACAGGAAACAGCTATGACCATGATTACGCCAAGCTTTGCTCTTAGGAGTTTCCTAATACATCCCAAACTCAAATA
TATAAAGCATTTGACTTGTTCTATGCCCTAGGGGGCGGGGGGAAGCTAAGCCAGCTTTTTTTAACATTTAAAATGTTAAT
TCCATTTTAAATGCACAGATGTTTTTATTTCATAAGGGTTTCAATGTGCATGAATGCTGCAATATTCCTGTTACCAAAGC
TAGTATAAATAAAAATAGATAAACGTGGAAATTACTTAGAGTTTCTGTCATTAACGTTTCCTTCCTCAGTTGACAACATA
AATGCGCTGCTGAGCAAGCCAGTTTGCATCTGTCAGGATCAATTTCCCATTATGCCAGTCATATTAATTACTAGTCAATT
AGTTGATTTTTATTTTTGACATATACATGTGAATGAAAGACCCCACCTGTAGGTTTGGCAAGCTAGCTTAAGTAACGCCA
TTTTGCAAGGCATGGAAAAATACATAACTGAGAATAGAAAAGTTCAGATCAAGGTCAGGAACAGATGGAACAGCTGAATA
TGGGCCAAACAGGATATCTGTGGTAAGCAGTTCCTGCCCCGGCTCAGGGCCAAGAACAGATGGAACAGCTGAATATGGGC
CAAACAGGATATCTGTGGTAAGCAGTTCCTGCCCCGGCTCAGGGCCAAGAACAGATGGTCCCCAGATGCGGTCCAGCCCT
CAGCAGTTTCTAGAGAACCATCAGATGTTTCCAGGGTGCCCCAAGGACCTGAAATGACCCTGTGCCTTATTTGAACTAAC
CAATCAGTTCGCTTCTCGCTTCTGTTCGCGCGCTTATGCTCCCCGAGCTCAATAAAAGAGCCCACAACCCCTCACTCGGG
GCGCCAGTCCTCCGATTGACTGAGTCGCCCGGGTACCCGTGTATCCAATAAACCCTCTTGCAGTTGCATCCGACTTGTGG
TCTCGCTGTTCCTTGGGAGGGTCTCCTCTGAGTGATTGACTACCCGTCAGCGGGGGTCTTTCATTTGGGGGCTCGTCCGG
GATCGGGAGACCCCTGCCCAGGGACCACCGACCCACCACCGGGAGGTAAGCTGGCCAGCAACTTATCTGTGTCTGTCCGA
TTGTCTAGTGTCTATGACTGATTTTATGCGCCTGCGTCGGTACTAGTTAGCTAACTAGCTCTGTATCGGCGGACCCGTG
GTGGAACTGACGAGTTCGGAACACCCGGCCGCAACCCTGGGAGACGTCCCAGGGACTTCGGGGGCCGTTTTTGTGGCCCG
ACCTGAGTCCTAAAATCCCGATCGTTTAGGACTCTTTGGTGCACCCCCCTTAGAGGAGGGATATGTGGTTCTGGTAGGAG
ACGAGAACCTAAAACAGTTCCCGCCTCCGTCTGAATTTTTGCTTTCGGTTTGGGACCGAAGCCGCGCCGCGCGTCTTGTC
TGCTGCAGCATCGTTCTGTGTTGTCTCTGTCTGACTGTGTTTCTGTATTTGTCTGAAAATATGGGCCCGGGCTAGACTGT
TACCACTCCCTTAAGTTTGACCTTAGGTCACTGGAAAGATGTCGAGCGGATCGCTCACAACCAGTCGGTAGATGTCAAGA
AGAGACGTTGGGTTACCTTCTGCTCTGCAGAATGGCCAACCTTTAACGTCGGATGGCCGCGAGACGGCACCTTTAACCGA
GACCTCATCACCCAGGTTAAGATCAAGGTCTTTTCACCTGGCCCGCATGGACACCCAGACCAGGTCCCCTACATCGTGAC
CTGGGAAGCCTTGGCTTTTGACCCCCCTCCCTGGGTCAAGCCCTTTGTACACCCTAAGCCTCCGCCTCCTCTTCCTCCAT
CCGCCCCGTCTCTCCCCCTTGAACCTCCTCGTTCGACCCCGCCTCGATCCTCCCTTTATCCAGCCCTCACT
```

In one specific non-limiting example, the isolated nucleic acid molecule comprises nucleic acids having the sequence set forth in SEQ ID NO:230 provided below:

[SEQ ID NO: 230]
GGCCCTCTAGGCGCCCCCATATGGCCATATGAGATCTTATATGGGGCACCCCCGCCCCTTGTAAACTTCCCTGACCCTGA

CATGACAAGAGTTACTAACAGCCCCTCTCTCCAAGCTCACTTACAGGCTCTCTACTTAGTCCAGCACGAAGTCTGGAGAC

CTCTGGCGGCAGCCTACCAAGAACAACTGGACCGACCGGTGCCGCCACCATGGAAACCGACACCCTGCTGCTGTGGGTGC

TGCTGCTGTGGGTGCCAGGATCCACAGGAtcctatgagctgactcagccaccctcagcgtctgggaccccgggcagagg gtcaccatgtcttgttctggaaccagctccaacatcggaagtcactctgtaaactggtaccagcagctcccaggaacggc ccccaaactcctcatctatactaataatcagcggccctcaggggtccctgaccgattctctggctccaagtctggcacct cagcctccctggccatcagtggcctccagtctgaggatgaggctgattattactgtgcagcatgggatggcagcctgaat ggtctggtattcggcggagggaccaagctgaccgtcctaggttctagaggtggtggtggtagcggcggcggcggctctgg tggtggtggatccctcgagatggccgaggtgcagctggtgcagtctggagcagaggtgaaaaagcccggggagtctctga agatctcctgtaagggttctggatacagctttaccagctactggatcggctgggtgcgccagatgcccgggaaaggcctg gagtggatggggatcatctatcctggtgactctgataccagatacagcccgtccttccaaggccacgtcaccatctcagc tgacaagtccatcagcactgcctacctgcagtggagcagcctgaaggcctcggacaccgccatgtattactgtgcgcgct actctggttcttcttcgataactggggtcaaggtactctggtgaccgtctcctcagcggccgcacccaccacgacgccagcg ccgcgaccaccaacccggcgcccacgatcgcgtcgcagcccctgtcctgcgcccagaggcgtgccggccagcggcggg gggcgcagtgcacacgaggggctggacttcgcctgtgatatctacatctgggcgcccctggccgggacttgtggggtcc ttctcctgtcactggttatcacccctttactgcaacaaacggggcagaaagaagctcctgtatatattcaaacaaccattt atgagaccagtacaaactactcaagaggaagatggctgtagctgccgatttccagaagaagaagaaggaggatgtgaact gagagtgaagttcaggaggagcgcagagcccccgcgtaccaggagggccagaaccagctctataacgagctcaatctag gacgaagagaggagtacgatgttttggacaagagacgtggccgggaccctgagatggggggaaagccgagaaggaagaac cctcaggaaggcctgtacaatgaactgcagaaagataagatggcggaggcctacagtgagattgggatgaaaggcgagcg ccggaggggcaaggggcacgatggcctttaccagggtctcagtacagccaccaaggacacctacgacgcccttcacatgc aggccctgccccctcgctaacagccactcgaggatccggattagtccaatttgttaaagacaggatatcagtggtccagg ctctagttttgactcaacaatatcaccagctgaagcctatagagtacgagccatagataaaataaaagattttattagt ctccagaaaaaggggggaatgaaagaccccacctgtaggtttggcaagctagcttaagtaacgccattttgcaaggcatg gaaaaatacataactgagaatagagaagttcagatcaaggtcaggaacagatggaacagctgaatatgggccaaacagga tatctgtggtaagcagttcctgccccggctcagggccaagaacagatggaacagctgaatatgggccaaacaggatatct gtggtaaggagttcctgccccggctcagggccaagaacagatggtccccagatgcggtccagccctcaggagtttctaga gaaccatcagatgtttccagggtgccccaaggacctgaaatgaccctgtgccttatttgaactaaccaatcagttcgctt ctcgcttctgttcgcgcgcttctgctccccgagctcaataaaagagcccacaacccctcactcggggcgccagtcctccg attgactgagtcgcccgggtacccgtgtatccaataaaccctcttgcagttgcatccgacttgtggtctcgctgttcctt gggagggtctcctctgagtgattgactacccgtcagcgggggtctttcacacatgcagcatgtatcaaaattaatttggt ttttttcttaagtatttacattaaatggccatagtacttaaagttacattggcttccttgaaataaacatggagtattc agaatgtgtcataaatatttctaattttaagatagtatctccattggctttctacttttctttttttttttgtcct ctgtcttccatttgttgttgttgttgtttgtttgtttgttggttggttggttaatttttttttaaagatcctacac tatagttcaagctagactattagctactctgtaacccagggtgaccttgaagtcatgggtagcctgctgttttagccttc ccacatctaagattacaggtatgagctatcattttggtatattgattgattgattgattgatgtgtgtgtgtgtgattg tgtttgtgtgtgtgactgtgaaaatgtgtgtatgggtgtgtgtgaatgtgtgtatgtatgtgtgtgtgtgagtgtgtgtg tgtgtgtgtgcatgtgtgtgtgtgactgtgtctatgtgtatgactgtgtgtgtgtgtgtgtgtgtgtgtgtgtgtg -continued

```
tgtgtgtgtgtgttgtgaaaaaatattctatggtagtgagagccaacgctccggctcaggtgtcaggttggtttttgaga cagagtctttcacttagcttggAATTCACTGGCCGTCGTTTTACAACGTCGTGACTGGGAAAACCCTGGCGTTACCCAAC

TTAATCGCCTTGCAGCACATCCCCCTTTCGCCAGCTGGCGTAATAGCGAAGAGGCCCGCACCGATCGCCCTTCCCAACAG

TTGCGCAGCCTGAATGGCGAATGGCGCCTGATGCGGTATTTTCTCCTTACGCATCTGTGCGGTATTTCACACCGCATATG

GTGCACTCTCAGTACAATCTGCTCTGATGCCGCATAGTTAAGCCAGCCCCGACACCCGCCAACACCCGCTGACGCGCCCT

GACGGGCTTGTCTGCTCCCGGCATCCGCTTACAGACAAGCTGTGACCGTCTCCGGGAGCTGCATGTGTCAGAGGTTTTCA

CCGTCATCACCGAAACGCGCGATGACGAAAGGGCCTCGTGATACGCCTATTTTTATAGGTTAATGTCATGATAATAATGG

TTTCTTAGACGTCAGGTGGCACTTTTCGGGGAAATGTGCGCGGAACCCCTATTTGTTTATTTTTCTAAATACATTCAAAT

ATGTATCCGCTCATGAGACAATAACCCTGATAAATGCTTCAATAATATTGAAAAAGGAAGAGTATGAGTATTCAACATTT

CCGTGTCGCCCTTATTCCCTTTTTTGCGGCATTTTGCCTTCCTGTTTTTGCTCACCCAGAAACGCTGGTGAAAGTAAAAG

ATGCTGAAGATCAGTTGGGTGCACGAGTGGGTTACATCGAACTGGATCTCAACAGCGGTAAGATCCTTGAGAGTTTTCGC

CCCGAAGAACGTTTTCCAATGATGAGCACTTTTAAAGTTCTGCTATGTGGCGCGGTATTATCCCGTATTGACGCCGGGCA

AGAGCAACTCGGTCGCCGCATACACTATTCTCAGAATGACTTGGTTGAGTACTCACCAGTCACAGAAAAGCATCTTACGG

ATGGCATGACAGTAAGAGAATTATGCAGTGCTGCCATAACCATGAGTGATAACACTGCGGCCAACTTACTTCTGACAACG

ATCGGAGGACCGAAGGAGCTAACCGCTTTTTTGCACAACATGGGGGATCATGTAACTCGCCTTGATCGTTGGGAACCGGA

GCTGAATGAAGCCATACCAAACGACGAGCGTGACACCACGATGCCTGTAGCAATGGCAACAACGTTGCGCAAACTATTAA

CTGGCGAACTACTTACTCTAGCTTCCCGGCAACAATTAATAGACTGGATGGAGGCGGATAAAGTTGCAGGACCACTTCTG

CGCTCGGCCCTTCCGGCTGGCTGGTTTATTGCTGATAAATCTGGAGCCGGTGAGCGTGGGTCTCGCGGTATCATTGCAGC

ACTGGGGCCAGATGGTAAGCCCTCCCGTATCGTAGTTATCTACACGACGGGGAGTCAGGCAACTATGGATGAACGAAATA

GACAGATCGCTGAGATAGGTGCCTCACTGATTAAGCATTGGTAACTGTCAGACCAAGTTTACTCATATATACTTTAGATT

GATTTAAAACTTCATTTTTAATTTAAAAGGATCTAGGTGAAGATCCTTTTTGATAATCTCATGACCAAAATCCCTTAACG

TGAGTTTTCGTTCCACTGAGCGTCAGACCCCGTAGAAAAGATCAAAGGATCTTCTTGAGATCCTTTTTTTCTGCGCGTAA

TCTGCTGCTTGCAAACAAAAAAACCACCGCTACCAGCGGTGGTTTGTTTGCCGGATCAAGAGCTACCAACTCTTTTTCCG

AAGGTAACTGGCTTCAGCAGAGCGCAGATACCAAATACTGTCCTTCTAGTGTAGCCGTAGTTAGGCCACCACTTCAAGAA

CTCTGTAGCACCGCCTACATACCTCGCTCTGCTAATCCTGTTACCAGTGGCTGCTGCCAGTGGCGATAAGTCGTGTCTTA

CCGGGTTGGACTCAAGACGATAGTTACCGGATAAGGCGCAGCGGTCGGGCTGAACGGGGGGTTCGTGCACACAGCCCAGC

TTGGAGCGAACGACCTACACCGAACTGAGATACCTACAGCGTGAGCATTGAGAAAGCGCCACGCTTCCCGAAGGGAGAAA

GGCGGACAGGTATCCGGTAAGCGGCAGGGTCGGAACAGGAGAGCGCACGAGGGAGCTTCCAGGGGGAAACGCCTGGTATC

TTTATAGTCCTGTCGGGTTTCGCCACCTCTGACTTGAGCGTCGATTTTTGTGATGCTCGTCAGGGGGCGGAGCCTATGG

AAAAACGCCAGCAACGCGGCCTTTTTACGGTTCCTGGCCTTTTGCTGGCCTTTTGCTCACATGTTCTTTCCTGCGTTATC

CCCTGATTCTGTGGATAACCGTATTACCGCCTTTGAGTGAGCTGATACCGCTCGCCGCAGCCGAACGACCGAGCGCAGCG

AGTCAGTGAGCGAGGAAGCGGAAGAGCGCCCAATACGCAAACCGCCTCTCCCCGCGCGTTGGCCGATTCATTAATGCAGC

TGGCACGACAGGTTTCCCGACTGGAAAGCGGGCAGTGAGCGCAACGCAATTAATGTGAGTTAGCTCACTCATTAGGCACC

CCAGGCTTTACACTTTATGCTTCCGGCTCGTATGTTGTGTGGAATTGTGAGCGGATAACAATTTCACACAGGAAACAGCT

ATGACCATGATTACGCCAAGCTTTGCTCTTAGGAGTTTCCTAATACATCCCAAACTCAAATATATAAAGCATTTGACTTG

TTCTATGCCCTAGGGGCGGGGGAAGCTAAGCCAGCTTTTTTAACATTTAAAATGTTAATTCCATTTTAAATGCACAG

ATGTTTTATTTCATAAGGGTTTCAATGTGCATGAATGCTGCAATATTCCTGTTACCAAAGCTAGTATAAATAAAAATAG

ATAAACGTGGAAATTACTTAGAGTTTCTGTCATTAACGTTTCCTTCCTCAGTTGACAACATAAATGCGCTGCTGAGCAAG

CCAGTTTGCATCTGTCAGGATCAATTTCCCATTATGCCAGTCATATTAATTACTAGTCAATTAGTTGATTTTTATTTTTG

ACATATACATGTGAATGAAAGACCCCACCTGTAGGTTTGGCAAGCTAGCTTAAGTAACGCCATTTTGCAAGGCATGGAAA
```

-continued

```
AATACATAACTGAGAATAGAAAAGTTCAGATCAAGGTCAGGAACAGATGGAACAGCTGAATATGGGCCAAACAGGATATC
TGTGGTAAGCAGTTCCTGCCCCGGCTCAGGGCCAAGAACAGATGGAACAGCTGAATATGGGCCAAACAGGATATCTGTGG
TAAGCAGTTCCTGCCCCGGCTCAGGGCCAAGAACAGATGGTCCCCAGATGCGGTCCAGCCCTCAGCAGTTTCTAGAGAAC
CATCAGATGTTTCCAGGGTGCCCCAAGGACCTGAAATGACCCTGTGCCTTATTTGAACTAACCAATCAGTTCGCTTCTCG
CTTCTGTTCGCGCGCTTATGCTCCCCGAGCTCAATAAAAGAGCCCACAACCCCTCACTCGGGGCGCCAGTCCTCCGATTG
ACTGAGTCGCCCGGGTACCCGTGTATCCAATAAACCCTCTTGCAGTTGCATCCGACTTGTGGTCTCGCTGTTCCTTGGGA
GGGTCTCCTCTGAGTGATTGACTACCCGTCAGCGGGGGTCTTTCATTTGGGGGCTCGTCCGGGATCGGGAGACCCCTGCC
CAGGGACCACCGACCCACCACCGGGAGGTAAGCTGGCCAGCAACTTATCTGTGTCTGTCCGATTGTCTAGTGTCTATGAC
TGATTTTATGCGCCTGCGTCGGTACTAGTTAGCTAACTAGCTCTGTATCTGGCGGACCCGTGGTGGAACTGACGAGTTCG
GAACACCCGGCCGCAACCCTGGGAGACGTCCCAGGGACTTCGGGGGCCGTTTTTGTGGCCCGACCTGAGTCCTAAAATCC
CGATCGTTTAGGACTCTTTGGTGCACCCCCCTTAGAGGAGGGATATGTGGTTCTGGTAGGAGACGAGAACCTAAACAGT
TCCCGCCTCCGTCTGAATTTTTGCTTTCGGTTTGGGACCGAAGCCGCGCCGCGCGTCTTGTCTGCTGCAGCATCGTTCTG
TGTTGTCTCTGTCTGACTGTGTTTCTGTATTTGTCTGAAAATATGGGCCCGGGCTAGACTGTTACCACTCCCTTAAGTTT
GACCTTAGGTCACTGGAAAGATGTCGAGCGGATCGCTCACAACCAGTCGGTAGATGTCAAGAAGAGACGTTGGGTTACCT
TCTGCTCTGCAGAATGGCCAACCTTTAACGTCGGATGGCCGCGAGACGGCACCTTTAACCGAGACCTCATCACCCAGGTT
AAGATCAAGGTCTTTTCACCTGGCCCGCATGGACACCCAGACCAGGTCCCCTACATCGTGACCTGGGAAGCCTTGGCTTT
TGACCCCCCTCCCTGGGTCAAGCCCTTTGTACACCCTAAGCCTCCGCCTCCTCTTCCTCCATCCGCCCCGTCTCTCCCCC
TTGAACCTCCTCGTTCGACCCCGCCTCGATCCTCCCTTTATCCAGCCCTCACT
```

In one specific non-limiting example, the isolated nucleic acid molecule comprises nucleic acids having the sequence set forth in SEQ ID NO:231 provided below:

[SEQ ID NO: 231]
```
CCTTCTCTAGGCGCCCCCATATGGCCATATGAGATCTTATATGGGGCACCCCCGCCCCTTGTAAACTTCCCTGACCCTGA
CATGACAAGAGTTACTAACAGCCCCTCTCTCCAAGCTCACTTACAGGCTCTCTACTTAGTCCAGCACGAAGTCTGGAGAC
CTCTGGCGGCAGCCTACCAAGAACAACTGGACCGACCGGTGCCGCCACCATGGAAACCGACACCCTGCTGCTGTGGGTGC
TGCTGCTGTGGGTGCCAGGATCCACAGGACAGGCTGTGCTGACTCAGCCACCCTCAGCGTCTGGGACCCCCGGGCAGAGG
GTCACCATCTCTTGTTCTGGAAGCAGCTCCAACATCGGAAGTAATTACGTATTCTGGTACCAGCAGCTCCCAGGAACGGC
CCCCAAACTCCTCATCTATAGTAATAATCAGCGGCCCTCAGGGGTCCCTGACCGATTCTCTGGCTCCAAGTCTGGCACCT
CAGCCTCCCTGGCCATCAGTGGGCTCCGGTCCGAGGATGAGGCTGATTATTACTGTGCAGCATGGGATGACAGCCTGAGT
GCCTCTTATGTTTTCGGAACTGGGACCAAGGTCACCGTCCTAGGTTCTAGAGGTGGTGGTGGTAGCGGCGGCGGCGGCTC
TGGTGGTGGTGGATCCCTCGAGATGGCCCAGGTGCAGCTGGTGCAGTCTGGGGCTGAGGTGAAGAAGCCTGGGTCCTCGG
TGAAGGTCTCCTGCAAGGCTTCTGGAGGCACCTTCAGCAGCTATGCTATCAGCTGGGTGCGACAGGCCCCTGGACAAGGG
CTTGAGTGGATGGGAAGGATCATCCCTATCCTTGGTACAGCAAACTACGCACAGAAGTTCCAGGGCAGAGTCACGATTAC
CGCGGACGAATCCACGAGCACAGCCTACATGGAGCTGAGCAGCCTGAGATCTGAGGACACGGCCGTGTATTACTGTGCGC
GCTCTGGTTACGGTTCTTACCGTTGGGAAGATTCTTGGGGTCAAGGTACTCTGGTGACCGTCTCCTCAGggccgcaccc
accacgacgccagcgccgcgaccaccaacccggcgcccacgatcgcgtcgcagcccctgtccctgcgcccagaggcgtg
ccggccagcggcgggggcgcagtgcacacgaggggctggacttcgcctgtgatatctacatctgggcgccctggccg
ggacttgtggggtccttctcctgtcactggttatcacccttactgcaacaaacggggcagaaagaagctcctgtatata
ttcaaacaaccatttatgagaccagtacaaactactcaagaggaagatggctgtagctgccgatttccagaagaagaaga
aggaggatgtgaactgagagtgaagttcaggaggagcgcagagcccccgcgtaccaggagggccagaaccagctctata
acgagctcaatctaggacgaagagaggagtacgatgttttggacaagagacgtggccgggaccctgagatgggggaaag
```

-continued

```
ccgagaaggaagaaccctcaggaaggcctgtacaatgaactgcagaaagataagatggcggaggcctacagtgagattgg
gatgaaaggcgagcgccggaggggcaaggggcacgatggcctttaccagggtctcagtacagccaccaaggacacctacg
acgcccttcacatgcaggccctgcccctcgctaacagccactcgaggatccggattagtccaatttgttaaagacagga
tatcagtggtccaggctctagttttgactcaacaatatcaccagctgaagcctatagagtacgagccatagataaaataa
aagattttatttagtctccagaaaagggggaatgaaagaccccacctgtaggtttggcaagctagcttaagtaacgcc
attttgcaaggcatggaaaaatacataactgagaatagagaagttcagatcaaggtcaggaacagatggaacagctgaat
atgggccaaacaggatatctgtggtaagcagttcctgccccggctcagggccaagaacagatggaacagctgaatatggg
ccaaacaggatatctgtggtaagcagttcctgccccggctcagggccaagaacagatggtccccagatgcggtccagccc
tcagcagtttctagagaaccatcagatgtttccagggtgccccaaggacctgaaatgaccctgtgccttatttgaactaa
ccaatcagttcgcttctcgcttctgttcgcgcgcttctgctccccgagctcaataaaagagcccacaaccctcactcgg
ggcgccagtcctccgattgactgagtcgcccgggtacccgtgtatccaataaaccctcttgcagttgcatccgacttgtg
gtctcgctgttccttgggagggtctcctctgagtgattgactaccgtcagcgggggtctttcacacatgcagcatgtat
caaaattaatttggtttttttcttaagtatttacattaaatggccatagtacttaaagttacattggcttccttgaaat
aaacatggagtattcagaatgtgtcataaatatttctaattttaagatagtatctccattggcttttctacttttttcttt
attttttttgtcctctgtcttccatttgttgttgttgtttgtttgtttgttggttggttggttaatttttttt
ttaaagatcctacactatagttcaagctagactattagctactctgtaacccagggtgaccttgaagtcatgggtagcct
gctgttttagccttcccacatctaagattacaggtatgagctatcattttggtatattgattgattgattgattgatgt
gtgtgtgtgtgattgtgtttgtgtgtgtgactgtgaaatgtgtgtatgggtgtgtgtgaatgtgtgtatgtatgtgtgt
gtgtgagtgtgtgtgtgtgtgtgtgcatgtgtgtgtgtgactgtgtctatgtgtatgactgtgtgtgtgtgtgtgt
gtgtgtgtgtgtgtgtgtgtgtgtgtgttgtgaaaaaatattctatggtagtgagagccaacgctccggctcaggtgtca
ggttggttttgagacagagtctttcacttagcttggAATTCACTGGCCGTCGTTTTACAACGTCGTGACTGGGAAAACC
CTGGCGTTACCCAACTTAATCGCCTTGCAGCACATCCCCCTTTCGCCAGCTGGCGTAATAGCGAAGAGGCCCGCACCGAT
CGCCCTTCCCAACAGTTGCGCAGCCTGAATGGCGAATGGCGCCTGATGCGGTATTTTCTCCTTACGCATCTGTGCGGTAT
TTCACACCGCATATGGTGCACTCTCAGTACAATCTGCTCTGATGCCGCATAGTTAAGCCAGCCCCGACACCCGCCAACAC
CCGCTGACGCGCCCTGACGGGCTTGTCTGCTCCCGGCATCCGCTTACAGACAAGCTGTGACCGTCTCCGGGAGCTGCATG
TGTCAGAGGTTTTCACCGTCATCACCGAAACGCGCGATGACGAAAGGGCCTCGTGATACGCCTATTTTTATAGGTTAATG
TCATGATAATAATGGTTTCTTAGACGTCAGGTGGCACTTTTCGGGGAAATGTGCGCGGAACCCCTATTTGTTTATTTTTC
TAAATACATTCAAATATGTATCCGCTCATGAGACAATAACCCTGATAAATGCTTCAATAATATTGAAAAAGGAAGAGTAT
GAGTATTCAACATTTCCGTGTCGCCCTTATTCCCTTTTTTGCGGCATTTTGCCTTCCTGTTTTTGCTCACCCAGAAACGC
TGGTGAAAGTAAAAGATGCTGAAGATCAGTTGGGTGCACGAGTGGGTTACATCGAACTGGATCTCAACAGCGGTAAGATC
CTTGAGAGTTTTCGCCCCGAAGAACGTTTTCCAATGATGAGCACTTTTAAAGTTCTGCTATGTGGCGCGGTATTATCCCG
TATTGACGCCGGGCAAGAGCAACTCGGTCGCCGCATACACTATTCTCAGAATGACTTGGTTGAGTACTCACCAGTCACAG
AAAAGCATCTTACGGATGGCATGACAGTAAGAGAATTATGCAGTGCTGCCATAACCATGAGTGATAACACTGCGGCCAAC
TTACTTCTGACAACGATCGGAGGACCGAAGGAGCTAACCGCTTTTTTGCACAACATGGGGGATCATGTAACTCGCCTTGA
TCGTTGGGAACCGGAGCTGAATGAAGCCATACCAAACGACGAGCGTGACACCACGATGCCTGTAGCAATGGCAACAACGT
TGCGCAAACTATTAACTGGCGAACTACTTACTCTAGCTTCCCGGCAACAATTAATAGACTGGATGGAGGCGGATAAAGTT
GCAGGACCACTTCTGCGCTCGGCCCTTCCGGCTGGCTGGTTTATTGCTGATAAATCTGGAGCCGGTGAGCGTGGGTCTCG
CGGTATCATTGCAGCACTGGGGCCAGATGGTAAGCCCTCCCGTATCGTAGTTATCTACACGACGGGGAGTCAGGCAACTA
TGGATGAACGAAATAGACAGATCGCTGAGATAGGTGCCTCACTGATTAAGCATTGGTAACTGTCAGACCAAGTTTACTCA
TATATACTTTAGATTGATTTAAAACTTCATTTTTAATTTAAAAGGATCTAGGTGAAGATCCTTTTTGATAATCTCATGAC
```

-continued

```
CAAAATCCCTTAACGTGAGTTTTCGTTCCACTGAGCGTCAGACCCCGTAGAAAAGATCAAAGGATCTTCTTGAGATCCTT
TTTTTCTGCGCGTAATCTGCTGCTTGCAAACAAAAAAACCACCGCTACCAGCGGTGGTTTGTTTGCCGGATCAAGAGCTA
CCAACTCTTTTTCCGAAGGTAACTGGCTTCAGCAGAGCGCAGATACCAAATACTGTCCTTCTAGTGTAGCCGTAGTTAGG
CCACCACTTCAAGAACTCTGTAGCACCGCCTACATACCTCGCTCTGCTAATCCTGTTACCAGTGGCTGCTGCCAGTGGCG
ATAAGTCGTGTCTTACCGGGTTGGACTCAAGACGATAGTTACCGGATAAGGCGCAGCGGTCGGGCTGAACGGGGGGTTCG
TGCACACAGCCCAGCTTGGAGCGAACGACCTACACCGAACTGAGATACCTACAGCGTGAGCATTGAGAAAGCGCCACGCT
TCCCGAAGGGAGAAAGGCGGACAGGTATCCGGTAAGCGGCAGGGTCGGAACAGGAGAGCGCACGAGGGAGCTTCCAGGGG
GAAACGCCTGGTATCTTTATAGTCCTGTCGGGTTTCGCCACCTCTGACTTGAGCGTCGATTTTTGTGATGCTCGTCAGGG
GGGCGGAGCCTATGGAAAAACGCCAGCAACGCGGCCTTTTTACGGTTCCTGGCCTTTTGCTGGCCTTTTGCTCACATGTT
CTTTCCTGCGTTATCCCCTGATTCTGTGGATAACCGTATTACCGCCTTTGAGTGAGCTGATACCGCTCGCCGCAGCCGAA
CGACCGAGCGCAGCGAGTCAGTGAGCGAGGAAGCGGAAGAGCGCCCAATACGCAAACCGCCTCTCCCCGCGCGTTGGCCG
ATTCATTAATGCAGCTGGCACGACAGGTTTCCCGACTGGAAAGCGGGCAGTGAGCGCAACGCAATTAATGTGAGTTAGCT
CACTCATTAGGCACCCCAGGCTTTACACTTTATGCTTCCGGCTCGTATGTTGTGTGGAATTGTGAGCGGATAACAATTTC
ACACAGGAAACAGCTATGACCATGATTACGCCAAGCTTTGCTCTTAGGAGTTTCCTAATACATCCCAAACTCAAATATAT
AAAGCATTTGACTTGTTCTATGCCCTAGGGGGCGGGGGAAGCTAAGCCAGCTTTTTTTAACATTTAAAATGTTAATTCC
ATTTTAAATGCACAGATGTTTTTATTTCATAAGGGTTTCAATGTGCATGAATGCTGCAATATTCCTGTTACCAAAGCTAG
TATAAATAAAAATAGATAAACGTGGAAATTACTTAGAGTTTCTGTCATTAACGTTTCCTTCCTCAGTTGACAACATAAAT
GCGCTGCTGAGCAAGCCAGTTTGCATCTGTCAGGATCAATTTCCCATTATGCCAGTCATATTAATTACTAGTCAATTAGT
TGATTTTTATTTTTGACATATACATGTGAATGAAAGACCCCACCTGTAGGTTTGGCAAGCTAGCTTAAGTAACGCCATTT
TGCAAGGCATGGAAAAATACATAACTGAGAATAGAAAAGTTCAGATCAAGGTCAGGAACAGATGGAACAGCTGAATATGG
GCCAAACAGGATATCTGTGGTAAGCAGTTCCTGCCCCGGCTCAGGGCCAAGAACAGATGGAACAGCTGAATATGGGCCAA
ACAGGATATCTGTGGTAAGCAGTTCCTGCCCCGGCTCAGGGCCAAGAACAGATGGTCCCCAGATGCGGTCCAGCCCTCAG
CAGTTTCTAGAGAACCATCAGATGTTTCCAGGGTGCCCCAAGGACCTGAAATGACCCTGTGCCTTATTTGAACTAACCAA
TCAGTTCGCTTCTCGCTTCTGTTCGCGCGCTTATGCTCCCCGAGCTCAATAAAAGAGCCCACAACCCCTCACTCGGGGCG
CCAGTCCTCCGATTGACTGAGTCGCCCGGGTACCCGTGTATCCAATAAACCCTCTTGCAGTTGCATCCGACTTGTGGTCT
CGCTGTTCCTTGGGAGGGTCTCCTCTGAGTGATTGACTACCCGTCAGCGGGGGTCTTTCATTTGGGGGCTCGTCCGGGAT
CGGGAGACCCCTGCCCAGGGACCACCGACCCACCACCGGGAGGTAAGCTGGCCAGCAACTTATCTGTGTCTGTCCGATTG
TCTAGTGTCTATGACTGATTTTATGCGCCTGCGTCGGTACTAGTTAGCTAACTAGCTCTGTATCTGGCGGACCCGTGGTG
GAACTGACGAGTTCGGAACACCCGGCCGCAACCCTGGGAGACGTCCCAGGGACTTCGGGGGCCGTTTTTGTGGCCCGACC
TGAGTCCTAAAATCCCGATCGTTTAGGACTCTTTGGTGCACCCCCCTTAGAGGAGGGATATGTGGTTCTGGTAGGAGACG
AGAACCTAAAACAGTTCCCGCCTCCGTCTGAATTTTTGCTTTCGGTTTGGGACCGAAGCCGCGCCGCGCGTCTTGTCTGC
TGCAGCATCGTTCTGTGTTGTCTCTGTCTGACTGTGTTTCTGTATTTGTCTGAAAATATGGGCCCGGGCTAGACTGTTAC
CACTCCCTTAAGTTTGACCTTAGGTCACTGGAAAGATGTCGAGCGGATCGCTCACAACCAGTCGGTAGATGTCAAGAAGA
GACGTTGGGTTACCTTCTGCTCTGCAGAATGGCCAACCTTTAACGTCGGATGGCCGCGAGACGGCACCTTTAACCGAGAC
CTCATCACCCAGGTTAAGATCAAGGTCTTTTCACCTGGCCCGCATGGACACCCAGACCAGGTCCCCTACATCGTGACCTG
GGAAGCCTTGGCTTTTGACCCCCCTCCCTGGGTCAAGCCCTTTGTACACCCTAAGCCTCCGCCTCCTCTTCCTCCATCCG
CCCCGTCTCTCCCCCTTGAACCTCCTCGTTCGACCCCGCCTCGATCCTCCCTTTATCCAGCCCTCACT
```

In one specific non-limiting example, the isolated nucleic acid molecule comprises nucleic acids having the sequence set forth in SEQ ID NO:232 provided below:

[SEQ ID NO: 232]
CCTTCTCTAGGCGCCCCCATATGGCCATATGAGATCTTATATGGGGCACCCCCGCCCCTTGTAAACTTCCCTGACCCTGA

CATGACAAGAGTTACTAACAGCCCCTCTCTCCAAGCTCACTTACAGGCTCTCTACTTAGTCCAGCACGAAGTCTGGAGAC

CTCTGGCGGCAGCCTACCAAGAACAACTGGACCGACCGGTGCCGCCACCATGGAAACCGACACCCTGCTGCTGTGGGTGC

TGCTGCTGTGGGTGCCAGGATCCACAGGAcagtctgtgctgacgcagccgccctcagtgtctggggcccagggcagagg gtcaccatctcctgcactgggaggagctccaacatcggggcaggttttgatgtacactggtaccaggagcttccaggaac agcccccaaactcctcatctatggtaacagcaatcggccctcaggggtccctgaccgattctctggctccaagtctggca cctcagcctcctggccatcactgggctccaggctgaggatgaggctgattattactgccagtcctatgacagcagcctg agtggttatgtcttcggaactgggaccaaggtcaccgtcctaggttctagaggtggtggtggtagcggcggcggcggctc tggtggtggtggatccctcgagatgggcccaggtccagctggtacagtctgggggctgaggtgaagaagcctggggcctcag tgaaggtctcctgcaaggcttctggatacaccttcaccgactactatatgcactgggtgcgacaggcccctggacaacgg cttgagtggatgggatggatcaaccctaacagtggtggcacaaactatgcacagaagtttcaggacaggatcaccgtgac cagggacacctccagcaacacaggctacatggagctgaccaggctgagatctgacgacacggccgtgtattactgtgcgc gctctccgtactctggtgttctggataaatggggtcaaggtactctggtgaccgtctcctcagcggccgcacccaccacg acgccagcgccgcgaccaccaaccccggcgcccacgatcgcgtcgcagcccctgtccctgcgcccagaggcgtgccggcc agcggcggggggcgcagtgcacacgaggggggctggacttcgcctgtgatatctacatctgggcgcccctggccgggactt gtggggtccttctcctgtcactggttatcacccctttactgcaacaaacggggcagaaagaagctcctgtatatattcaaa caaccatttatgagaccagtacaaactactcaagaggaagatggctgtagctgccgatttccagaagaagaagaaggagg atgtgaactgagagtgaagttcaggaggagcgcagagccccccgcgtaccaggagggccagaaccagctctataacgagc tcaatctaggacgaagagaggagtacgatgttttggacaagagacgtggccgggaccctgagatgggggggaaagccgaga aggaagaaccctcaggaaggcctgtacaatgaactgcagaaagataagatggcggaggcctacagtgagattgggatgaa aggcgagcgccggaggggcaaggggcacgatggcctttaccagggtctcagtacagccaccaaggacacctacgacgccc ttcacatgcaggccctgccccctcgctaacagccactcgaggatccggattagtccaatttgttaaagacaggatatcag tggtccaggctctagttttgactcaacaatatcaccagctgaagcctatagagtacgagccatagataaaataaaagatt ttatttagtctccagaaaaaggggggaatgaaagaccccacctgtaggtttggcaagctagcttaagtaacgccattttg caaggcatggaaaaatacataactgagaatagagaagttcagatcaaggtcaggaacagatggaacagctgaatatgggc caaacaggatatctgtggtaagcagttcctgccccggctcagggccaagaacagatggaacagctgaatatgggccaaac aggatatctgtggtaagcagttcctgccccggctcagggccaagaacagatggtccccagatgcggtccagccctcagca gtttctagagaaccatcagatgtttccagggtgccccaaggacctgaaatgaccctgtgccttatttgaactaaccaatc agttcgcttctcgcttctgttcgcgcgcttctgctccccgagctcaataaaagagcccacaacccctcactcggggcgcc agtcctccgattgactgagtcgcccgggtacccgtgtatccaataaaccctcttgcagttgcatccgacttgtggtctcg ctgttccttgggagggtctcctctgagtgattgactaccgtcagcgggggtctttcacacatgcagcatgtatcaaaat taatttggttttttttcttaagtatttacattaaatggccatagtacttaaagttacattggcttccttgaaataaacat ggagtattcagaatgtgtcataaatatttctaattttaagatagtatctccattggctttctactttttcttttattttt ttttgtcctctgtcttccatttgttgttgttgttgtttgtttgtttgttggttggttggttaattttttttttaaag atcctacactatagttcaagctagactattagctactctgtaacccagggtgaccttgaagtcatgggtagcctgctgtt ttagccttcccacatctaagattacaggtatgagctatcattttggtatattgattgattgattgattgatgtgtgtgt gtgtgattgtgtttgtgtgtgtgactgtgaaatgtgtgtatgggtgtgtgtgaatgtgtgtatgtatgtgtgtgtgtga gtgtgtgtgtgtgtgtgtgcatgtgtgtgtgtgtgactgtgtctatgtgtatgactgtgtgtgtgtgtgtgtgtgtgt -continued

```
gtgtgtgtgtgtgtgtgtgttgtgaaaaaatattctatggtagtgagagccaacgctccggctcaggtgtcaggttgg
tttttgagacagagtctttcacttagcttggAATTCACTGGCCGTCGTTTTACAACGTCGTGACTGGGAAAACCCTGGCG
TTACCCAACTTAATCGCCTTGCAGCACATCCCCCTTTCGCCAGCTGGCGTAATAGCGAAGAGGCCCGCACCGATCGCCCT
TCCCAACAGTTGCGCAGCCTGAATGGCGAATGGCGCCTGATGCGGTATTTTCTCCTTACGCATCTGTGCGGTATTTCACA
CCGCATATGGTGCACTCTCAGTACAATCTGCTCTGATGCCGCATAGTTAAGCCAGCCCCGACACCCGCCAACACCCGCTG
ACGCGCCCTGACGGGCTTGTCTGCTCCCGGCATCCGCTTACAGACAAGCTGTGACCGTCTCCGGGAGCTGCATGTGTCAG
AGGTTTTCACCGTCATCACCGAAACGCGCGATGACGAAAGGGCCTCGTGATACGCCTATTTTTATAGGTTAATGTCATGA
TAATAATGGTTTCTTAGACGTCAGGTGGCACTTTTCGGGGAAATGTGCGCGGAACCCCTATTTGTTTATTTTTCTAAATA
CATTCAAATATGTATCCGCTCATGAGACAATAACCCTGATAAATGCTTCAATAATATTGAAAAGGAAGAGTATGAGTAT
TCAACATTTCCGTGTCGCCCTTATTCCCTTTTTTGCGGCATTTTGCCTTCCTGTTTTTGCTCACCCAGAAACGCTGGTGA
AAGTAAAAGATGCTGAAGATCAGTTGGGTGCACGAGTGGGTTACATCGAACTGGATCTCAACAGCGGTAAGATCCTTGAG
AGTTTTCGCCCCGAAGAACGTTTTCCAATGATGAGCACTTTTAAAGTTCTGCTATGTGGCGCGGTATTATCCCGTATTGA
CGCCGGGCAAGAGCAACTCGGTCGCCGCATACACTATTCTCAGAATGACTTGGTTGAGTACTCACCAGTCACAGAAAAGC
ATCTTACGGATGGCATGACAGTAAGAGAATTATGCAGTGCTGCCATAACCATGAGTGATAACACTGCGGCCAACTTACTT
CTGACAACGATCGGAGGACCGAAGGAGCTAACCGCTTTTTTGCACAACATGGGGGATCATGTAACTCGCCTTGATCGTTG
GGAACCGGAGCTGAATGAAGCCATACCAAACGACGAGCGTGACACCACGATGCCTGTAGCAATGGCAACAACGTTGCGCA
AACTATTAACTGGCGAACTACTTACTCTAGCTTCCCGGCAACAATTAATAGACTGGATGGAGGCGGATAAAGTTGCAGGA
CCACTTCTGCGCTCGGCCCTTCCGGCTGGCTGGTTTATTGCTGATAAATCTGGAGCCGGTGAGCGTGGGTCTCGCGGTAT
CATTGCAGCACTGGGGCCAGATGGTAAGCCCTCCCGTATCGTAGTTATCTACACGACGGGGAGTCAGGCAACTATGGATG
AACGAAATAGACAGATCGCTGAGATAGGTGCCTCACTGATTAAGCATTGGTAACTGTCAGACCAAGTTTACTCATATATA
CTTTAGATTGATTTAAAACTTCATTTTTAATTTAAAAGGATCTAGGTGAAGATCCTTTTTGATAATCTCATGACCAAAAT
CCCTTAACGTGAGTTTTCGTTCCACTGAGCGTCAGACCCCGTAGAAAAGATCAAAGGATCTTCTTGAGATCCTTTTTTTC
TGCGCGTAATCTGCTGCTTGCAAACAAAAAAACCACCGCTACCAGCGGTGGTTTGTTTGCCGGATCAAGAGCTACCAACT
CTTTTTCCGAAGGTAACTGGCTTCAGCAGAGCGCAGATACCAAATACTGTCCTTCTAGTGTAGCCGTAGTTAGGCCACCA
CTTCAAGAACTCTGTAGCACCGCCTACATACCTCGCTCTGCTAATCCTGTTACCAGTGGCTGCTGCCAGTGGCGATAAGT
CGTGTCTTACCGGGTTGGACTCAAGACGATAGTTACCGGATAAGGCGCAGCGGTCGGGCTGAACGGGGGGTTCGTGCACA
CAGCCCAGCTTGGAGCGAACGACCTACACCGAACTGAGATACCTACAGCGTGAGCATTGAGAAAGCGCCACGCTTCCCGA
AGGGAGAAAGGCGGACAGGTATCCGGTAAGCGGCAGGGTCGGAACAGGAGAGCGCACGAGGGAGCTTCCAGGGGGAAACG
CCTGGTATCTTTATAGTCCTGTCGGGTTTCGCCACCTCTGACTTGAGCGTCGATTTTTGTGATGCTCGTCAGGGGGCGG
AGCCTATGGAAAAACGCCAGCAACGCGGCCTTTTTACGGTTCCTGGCCTTTTGCTGGCCTTTTGCTCACATGTTCTTTCC
TGCGTTATCCCCTGATTCTGTGGATAACCGTATTACCGCCTTTGAGTGAGCTGATACCGCTCGCCGCAGCCGAACGACCG
AGCGCAGCGAGTCAGTGAGCGAGGAAGCGGAAGAGCGCCCAATACGCAAACCGCCTCTCCCCGCGCGTTGGCCGATTCAT
TAATGCAGCTGGCACGACAGGTTTCCCGACTGGAAAGCGGGCAGTGAGCGCAACGCAATTAATGTGAGTTAGCTCACTCA
TTAGGCACCCCAGGCTTTACACTTTATGCTTCCGGCTCGTATGTTGTGTGGAATTGTGAGCGGATAACAATTTCACACAG
GAAACAGCTATGACCATGATTACGCCAAGCTTTGCTCTTAGGAGTTTCCTAATACATCCCAAACTCAAATATATAAAGCA
TTTGACTTGTTCTATGCCCTAGGGGCGGGGGGAAGCTAAGCCAGCTTTTTTAACATTTAAAATGTTAATTCCATTTTA
AATGCACAGATGTTTTTATTTCATAAGGGTTTCAATGTGCATGAATGCTGCAATATTCCTGTTACCAAAGCTAGTATAAA
TAAAAATAGATAAACGTGGAAATTACTTAGAGTTTCTGTCATTAACGTTTCCTTCCTCAGTTGACAACATAAATGCGCTG
CTGAGCAAGCCAGTTTGCATCTGTCAGGATCAATTTCCCATTATGCCAGTCATATTAATTACTAGTCAATTAGTTGATTT
TTATTTTTGACATATACATGTGAATGAAAGACCCCACCTGTAGGTTTGGCAAGCTAGCTTAAGTAACGCCATTTTGCAAG
```

-continued

```
GCATGGAAAAATACATAACTGAGAATAGAAAAGTTCAGATCAAGGTCAGGAACAGATGGAACAGCTGAATATGGGCCAAA
CAGGATATCTGTGGTAAGCAGTTCCTGCCCCGGCTCAGGGCCAAGAACAGATGGAACAGCTGAATATGGGCCAAACAGGA
TATCTGTGGTAAGCAGTTCCTGCCCCGGCTCAGGGCCAAGAACAGATGGTCCCCAGATGCGGTCCAGCCCTCAGCAGTTT
CTAGAGAACCATCAGATGTTTCCAGGGTGCCCCAAGGACCTGAAATGACCCTGTGCCTTATTTGAACTAACCAATCAGTT
CGCTTCTCGCTTCTGTTCGCGCGCTTATGCTCCCCGAGCTCAATAAAAGAGCCCACAACCCCTCACTCGGGGCGCCAGTC
CTCCGATTGACTGAGTCGCCCGGGTACCCGTGTATCCAATAAACCCTCTTGCAGTTGCATCCGACTTGTGGTCTCGCTGT
TCCTTGGGAGGGTCTCCTCTGAGTGATTGACTACCCGTCAGCGGGGTCTTTCATTTGGGGGCTCGTCCGGGATCGGGAG
ACCCCTGCCCAGGGACCACCGACCCACCACCGGGAGGTAAGCTGGCCAGCAACTTATCTGTGTCTGTCCGATTGTCTAGT
GTCTATGACTGATTTTATGCGCCTGCGTCGGTACTAGTTAGCTAACTAGCTCTGTATCTGGCGGACCCGTGGTGGAACTG
ACGAGTTCGGAACACCCGGCCGCAACCCTGGGAGACGTCCCAGGGACTTCGGGGGCCGTTTTTGTGGCCCGACCTGAGTC
CTAAAATCCCGATCGTTTAGGACTCTTTGGTGCACCCCCCTTAGAGGAGGGATATGTGGTTCTGGTAGGAGACGAGAACC
TAAAACAGTTCCCGCCTCCGTCTGAATTTTTGCTTTCGGTTTGGGACCGAAGCCGCGCCGCGCGTCTTGTCTGCTGCAGC
ATCGTTCTGTGTTGTCTCTGTCTGACTGTGTTTCTGTATTTGTCTGAAAATATGGGCCCGGGCTAGACTGTTACCACTCC
CTTAAGTTTGACCTTAGGTCACTGGAAAGATGTCGAGCGGATCGCTCACAACCAGTCGGTAGATGTCAAGAAGAGACGTT
GGGTTACCTTCTGCTCTGCAGAATGGCCAACCTTTAACGTCGGATGGCCGCGAGACGGCACCTTTAACCGAGACCTCATC
ACCCAGGTTAAGATCAAGGTCTTTTCACCTGGCCCGCATGGACACCCAGACCAGGTCCCCTACATCGTGACCTGGGAAGC
CTTGGCTTTTGACCCCCCTCCCTGGGTCAAGCCCTTTGTACACCCTAAGCCTCCGCCTCCTCTTCCTCCATCCGCCCCGT
CTCTCCCCCTTGAACCTCCTCGTTCGACCCCGCCTCGATCCTCCCTTTATCCAGCCCTCACT
```

In one specific non-limiting example, the isolated nucleic acid molecule comprises nucleic acids having the sequence set forth in SEQ ID NO:233 provided below:

[SEQ ID NO: 233]
```
CCTTCTCTAGGCGCCCCCATATGGCCATATGAGATCTTATATGGGGCACCCCCGCCCCTTGTAAACTTCCCTGACCCTGA
CATGACAAGAGTTACTAACAGCCCCTCTCTCCAAGCTCACTTACAGGCTCTCTACTTAGTCCAGCACGAAGTCTGGAGAC
CTCTGGCGGCAGCCTACCAAGAACAACTGGACCGACCGGTGCCGCCACCATGGAAACCGACACCCTGCTGCTGTGGGTGC
TGCTGCTGTGGGTGCCAGGATCCACAGGAcaatctgccctgactcagcctgcctccgtgtctgcgtctcctggacagtcg
atcgccatctcctgcactggaaccagcagtgacgttggttggtatcaacagcacccaggcaaagcccccaaactcatgat
ttatgaggacagtaagcggccctcaggggtttctaatcgcttctctggctccaagtctggcaacacggcctccctgacca
tctctgggctccaggctgaggacgaggctgattattactgcagctcaaatacaagaagcagcactttggtgttcggcgga
gggaccaagctgaccgtcctaggttctagaggtggtggtggtagcggcggcggcggctctggtggtggtggatccctcga
gatggccgaagtgcagctggtgcagtctggggctgagatgaagaagcctggggcctcactgaagctctcctgcaaggctt
ctggatacaccttcatcgactactatgtatactggatgcgacaggcccctggacaagggcttgagtccatgggatggatc
aaccctaacagtggtggcacaaaactatgcacagaagtttcagggcagggtcaccatgaccagggacacgtccatcagcac
agcctacatggagctgagcaggctgagatctgacgacaccgccatgtattactgtgcgcgctcccagcgtgacggttaca
tggattactggggtcaaggtactctggtgaccgtctcctcagcggccgcacccaccacgacgccagcgccgcgaccacca
accccggcgcccacgatcgcgtcgcagcccctgtcctgcgcccagaggcgtgccggccagcggcgggggcgcagtgca
cacgaggggctggacttcgcctgtgatatctacatctgggcgccctggccgggacttgtgggtccttctcctgtcac
tggttatcacccttactgcaacaaacggggcagaaagaagctcctgtatatattcaaacaaccatttatgagaccagta
caaactactcaagaggaagatggctgtagctgccgatttccagaagaagaagaaggaggatgtgaactgagagtgaagtt
caggaggagcgcagagccccccgcgtaccaggagggccagaaccagctctataacgagctcaatctaggacgaagagagg
agtacgatgttttggacaagagacgtggccgggaccctgagatgggggggaaagccgagaaggaagaaccctcaggaaggc
```

-continued ctgtacaatgaactgcagaaagataagatggcggaggcctacagtgagattgggatgaaaggcgagcgccggaggggcaa ggggcacgatggcctttaccagggtctcagtacagccaccaaggacacctacgacgcccttcacatgcaggccctgcccc ctcgctaacagccactcgaggatccggattagtccaatttgttaaagacaggatatcagtggtccaggctctagttttga ctcaacaatatcaccagctgaagcctatagagtacgagccatagataaaataaaagattttatttagtctccagaaaaag gggggaatgaaagaccccacctgtaggtttggcaagctagcttaagtaacgccattttgcaaggcatggaaaaatacata actgagaatagagaagttcagatcaaggtcaggaacagatggaacagctgaatatgggccaaacaggatatctgtggtaa gcagttcctgccccggctcagggccaagaacagatggaacagctgaatatgggccaaacaggatatctgtggtaagcagt tcctgccccggctcagggccaagaacagatggtccccagatgcggtccagccctcagcagtttctagagaaccatcagat gtttccagggtgccccaaggacctgaaatgaccctgtgccttatttgaactaaccaatcagttcgcttctcgcttctgtt cgcgcgcttctgctccccgagctcaataaaagagcccacaacccctcactcggggcgccagtcctccgattgactgagtc gcccgggtacccgtgtatccaataaaccctcttgcagttgcatccgacttgtggtctcgctgttccttgggagggtctcc tctgagtgattgactacccgtcagcgggggtctttcacacatgcagcatgtatcaaaattaatttggtttttttttcttaa gtatttacattaaatggccatagtacttaaagttacattggcttccttgaaataaacatggagtattcagaatgtgtcat aaatatttctaattttaagatagtatctccattggctttctacttttctctttattttttttgtcctctgtcttccatt tgttgttgttgttgtttgtttgtttgtttgttggttggttggttaattttttttaaagatcctacactatagttcaagc tagactattagctactctgtaacccagggtgaccttgaagtcatgggtagcctgctgttttagccttcccacatctaaga ttacaggtatgagctatcattttggtatattgattgattgattgattgatgtgtgtgtgtgtgattgtgtttgtgtgtg tgactgtgaaaatgtgtgtatgggtgtgtgtgaatgtgtgtatgtatgtgtgtgtgtgagtgtgtgtgtgtgtgtgtgca tgtgtgtgtgtgtgactgtgtctatgtgtatgactgtgtgtgtgtgtgtgtgtgtgtgtgtgtgtgtgtgtgtgtgtgtg ttgtgaaaaaatattctatggtagtgagagccaacgctccggctcaggtgtcaggttggttttttgagacagagtctttca cttagcttggAATTCACTGGCCGTCGTTTTACAACGTCGTGACTGGGAAAACCCTGGCGTTACCCAACTTAATCGCCTTG

CAGCACATCCCCCTTTCGCCAGCTGGCGTAATAGCGAAGAGGCCCGCACCGATCGCCCTTCCCAACAGTTGCGCAGCCTG

AATGGCGAATGGCGCCTGATGCGGTATTTTCTCCTTACGCATCTGTGCGGTATTTCACACCGCATATGGTGCACTCTCAG

TACAATCTGCTCTGATGCCGCATAGTTAAGCCAGCCCCGACACCCGCCAACACCCGCTGACGCGCCCTGACGGGCTTGTC

TGCTCCCGGCATCCGCTTACAGACAAGCTGTGACCGTCTCCGGGAGCTGCATGTGTCAGAGGTTTTCACCGTCATCACCG

AAACGCGCGATGACGAAAGGGCCTCGTGATACGCCTATTTTTATAGGTTAATGTCATGATAATAATGGTTTCTTAGACGT

CAGGTGGCACTTTTCGGGGAAATGTGCGCGGAACCCCTATTTGTTTATTTTTCTAAATACATTCAAATATGTATCCGCTC

ATGAGACAATAACCCTGATAAATGCTTCAATAATATTGAAAAAGGAAGAGTATGAGTATTCAACATTTCCGTGTCGCCCT

TATTCCCTTTTTTGCGGCATTTTGCCTTCCTGTTTTTGCTCACCCAGAAACGCTGGTGAAAGTAAAAGATGCTGAAGATC

AGTTGGGTGCACGAGTGGGTTACATCGAACTGGATCTCAACAGCGGTAAGATCCTTGAGAGTTTTCGCCCCGAAGAACGT

TTTCCAATGATGAGCACTTTTAAAGTTCTGCTATGTGGCGCGGTATTATCCCGTATTGACGCCGGGCAAGAGCAACTCGG

TCGCCGCATACACTATTCTCAGAATGACTTGGTTGAGTACTCACCAGTCACAGAAAAGCATCTTACGGATGGCATGACAG

TAAGAGAATTATGCAGTGCTGCCATAACCATGAGTGATAACACTGCGGCCAACTTACTTCTGACAACGATCGGAGGACCG

AAGGAGCTAACCGCTTTTTTGCACAACATGGGGGATCATGTAACTCGCCTTGATCGTTGGGAACCGGAGCTGAATGAAGC

CATACCAAACGACGAGCGTGACACCACGATGCCTGTAGCAATGGCAACAACGTTGCGCAAACTATTAACTGGCGAACTAC

TTACTCTAGCTTCCCGGCAACAATTAATAGACTGGATGGAGGCGGATAAAGTTGCAGGACCACTTCTGCGCTCGGCCCTT

CCGGCTGGCTGGTTTATTGCTGATAAATCTGGAGCCGGTGAGCGTGGGTCTCGCGGTATCATTGCAGCACTGGGGCCAGA

TGGTAAGCCCTCCCGTATCGTAGTTATCTACACGACGGGGAGTCAGGCAACTATGGATGAACGAAATAGACAGATCGCTG

AGATAGGTGCCTCACTGATTAAGCATTGGTAACTGTCAGACCAAGTTTACTCATATATACTTTAGATTGATTTAAAACTT

CATTTTTAATTTAAAAGGATCTAGGTGAAGATCCTTTTTGATAATCTCATGACCAAAATCCCTTAACGTGAGTTTTCGTT

-continued
```
CCACTGAGCGTCAGACCCCGTAGAAAAGATCAAAGGATCTTCTTGAGATCCTTTTTTTCTGCGCGTAATCTGCTGCTTGC

AAACAAAAAAACCACCGCTACCAGCGGTGGTTTGTTTGCCGGATCAAGAGCTACCAACTCTTTTTCCGAAGGTAACTGGC

TTCAGCAGAGCGCAGATACCAAATACTGTCCTTCTAGTGTAGCCGTAGTTAGGCCACCACTTCAAGAACTCTGTAGCACC

GCCTACATACCTCGCTCTGCTAATCCTGTTACCAGTGGCTGCTGCCAGTGGCGATAAGTCGTGTCTTACCGGGTTGGACT

CAAGACGATAGTTACCGGATAAGGCGCAGCGGTCGGGCTGAACGGGGGGTTCGTGCACACAGCCCAGCTTGGAGCGAACG

ACCTACACCGAACTGAGATACCTACAGCGTGAGCATTGAGAAAGCGCCACGCTTCCCGAAGGGAGAAAGGCGGACAGGTA

TCCGGTAAGCGGCAGGGTCGGAACAGGAGAGCGCACGAGGGAGCTTCCAGGGGGAAACGCCTGGTATCTTTATAGTCCTG

TCGGGTTTCGCCACCTCTGACTTGAGCGTCGATTTTTGTGATGCTCGTCAGGGGGCGGAGCCTATGGAAAAACGCCAGC

AACGCGGCCTTTTTACGGTTCCTGGCCTTTTGCTGGCCTTTTGCTCACATGTTCTTTCCTGCGTTATCCCCTGATTCTGT

GGATAACCGTATTACCGCCTTTGAGTGAGCTGATACCGCTCGCCGCAGCCGAACGACCGAGCGCAGCGAGTCAGTGAGCG

AGGAAGCGGAAGAGCGCCCAATACGCAAACCGCCTCTCCCCGCGCGTTGGCCGATTCATTAATGCAGCTGGCACGACAGG

TTTCCCGACTGGAAAGCGGGCAGTGAGCGCAACGCAATTAATGTGAGTTAGCTCACTCATTAGGCACCCCAGGCTTTACA

CTTTATGCTTCCGGCTCGTATGTTGTGTGGAATTGTGAGCGGATAACAATTTCACACAGGAAACAGCTATGACCATGATT

ACGCCAAGCTTTGCTCTTAGGAGTTTCCTAATACATCCCAAACTCAAATATATAAAGCATTTGACTTGTTCTATGCCCTA

GGGGGCGGGGGAAGCTAAGCCAGCTTTTTTTAACATTTAAAATGTTAATTCCATTTTAAATGCACAGATGTTTTTATTT

CATAAGGGTTTCAATGTGCATGAATGCTGCAATATTCCTGTTACCAAAGCTAGTATAAATAAAAATAGATAAACGTGGAA

ATTACTTAGAGTTTCTGTCATTAACGTTTCCTTCCTCAGTTGACAACATAAATGCGCTGCTGAGCAAGCCAGTTTGCATC

TGTCAGGATCAATTTCCCATTATGCCAGTCATATTAATTACTAGTCAATTAGTTGATTTTTATTTTTGACATATACATGT

GAATGAAAGACCCCACCTGTAGGTTTGGCAAGCTAGCTTAAGTAACGCCATTTTGCAAGGCATGGAAAAATACATAACTG

AGAATAGAAAAGTTCAGATCAAGGTCAGGAACAGATGGAACAGCTGAATATGGGCCAAACAGGATATCTGTGGTAAGCAG

TTCCTGCCCCGGCTCAGGGCCAAGAACAGATGGAACAGCTGAATATGGGCCAAACAGGATATCTGTGGTAAGCAGTTCCT

GCCCCGGCTCAGGGCCAAGAACAGATGGTCCCCAGATGCGGTCCAGCCCTCAGCAGTTTCTAGAGAACCATCAGATGTTT

CCAGGGTGCCCCAAGGACCTGAAATGACCCTGTGCCTTATTTGAACTAACCAATCAGTTCGCTTCTCGCTTCTGTTCGCG

CGCTTATGCTCCCCGAGCTCAATAAAAGAGCCCACAACCCCTCACTCGGGGCGCCAGTCCTCCGATTGACTGAGTCGCCC

GGGTACCCGTGTATCCAATAAACCCTCTTGCAGTTGCATCCGACTTGTGGTCTCGCTGTTCCTTGGGAGGGTCTCCTCTG

AGTGATTGACTACCCGTCAGCGGGGGTCTTTCATTTGGGGGCTCGTCCGGGATCGGGAGACCCCTGCCCAGGGACCACCG

ACCCACCACCGGGAGGTAAGCTGGCCAGCAACTTATCTGTGTCTGTCCGATTGTCTAGTGTCTATGACTGATTTTATGCG

CCTGCGTCGGTACTAGTTAGCTAACTAGCTCTGTATCTGGCGGACCCGTGGTGGAACTGACGAGTTCGGAACACCCGGCC

GCAACCCTGGGAGACGTCCCAGGGACTTCGGGGGCCGTTTTTGTGGCCCGACCTGAGTCCTAAAATCCCGATCGTTTAGG

ACTCTTTGGTGCACCCCCCTTAGAGGAGGGATATGTGGTTCTGGTAGGAGACGAGAACCTAAAACAGTTCCCGCCTCCGT

CTGAATTTTTGCTTTCGGTTTGGGACCGAAGCCGCGCCGCGCGTCTTGTCTGCTGCAGCATCGTTCTGTGTTGTCTCTGT

CTGACTGTGTTTCTGTATTTGTCTGAAAATATGGGCCCGGGCTAGACTGTTACCACTCCCTTAAGTTTGACCTTAGGTCA

CTGGAAAGATGTCGAGCGGATCGCTCACAACCAGTCGGTAGATGTCAAGAAGAGACGTTGGGTTACCTTCTGCTCTGCAG

AATGGCCAACCTTTAACGTCGGATGGCCGCGAGACGGCACCTTTAACCGAGACCTCATCACCCAGGTTAAGATCAAGGTC

TTTTCACCTGGCCCGCATGGACACCCAGACCAGGTCCCCTACATCGTGACCTGGGAAGCCTTGGCTTTTGACCCCCCTCC

CTGGGTCAAGCCCTTTGTACACCCTAAGCCTCCGCCTCCTCTTCCTCCATCCGCCCCGTCTCTCCCCCTTGAACCTCCTC

GTTCGACCCCGCCTCGATCCTCCCTTTATCCAGCCCTCACT
```

In one specific non-limiting example, the isolated nucleic acid molecule comprises nucleic acids having the sequence set forth in SEQ ID NO:234 provided below:

[SEQ ID NO: 234]
atggaaaccgacaccctgctgctgtgggtgctgctgctgtgggtgccagg
atccacaggactgcctgtgctgactcagccaccctcagcgtctgggaccc
ccgggcagagggtcaccatctcttgttctggacgcagttccaacatcggg
agtaattctgttaactggtatcgacaactcccaggagcggcccccaaact
cctcatctatagtaataatcagcggccccagggctccctgtgcgattct
ctggctccaagtctggcacctcagcctccctggccatcagtgggctccag
tctgaagatgaggccacttattactgtgcaacatgggatgacaatctgaa
tgttcactatgtcttcggaactgggaccaaggtcaccgtcctaggttcta
gaggtggtggtggtagcggcggcggcggctctggtggtggtggatccctc
gagatggcccaggtgcagctggtgcagtctggggctgaggtgaagaagcc
tgggtcctcggtgaaggtctcctgcaaggcttctggaggcaccttcagca
gctatgctatcagctgggtgcgacaggcccctggacaagggcttgagtgg
atgggaaggatcatccctatccttggtatagcaaactacgcacagaagtt
ccagggcagagtcacgattaccgcggacaaatccacgagcacagcctaca
tggagctgagcagcctgagatctgaggacacggccgtgtattactgtgcg
cgcggtggttactactctcatgacatgtggtctgaagattgggtcaaggt
tactctggtgaccgtctcctcagcggccgcaattgaagttatgtatcctc
ctccttacctagacaatgagaagagcaatggaaccattatccatgtgaaa
gggaaacacctttgtccaagtcccctatttccggaccttctaagcccttt
tgggtgctggtggtggttggtggagtcctggcttgctatagcttgctag
taacagtggcctttattattttctgggtgaggagtaagaggagcaggctc
ctgcacagtgactacatgaacatgactccccgccgccccgggcccacccg
caagcattaccagccctatgccccaccacgcgacttcgcagcctatcgct
ccagagtgaagttcagcaggagcgcagacgccccgcgtaccagcagggc
cagaaccagctctataacgagctcaatctaggacgaagagaggagtacga
tgttttggacaagagacgtggccgggaccctgagatggggggaaagccga
gaaggaagaaccctcaggaaggcctgtacaatgaactgcagaaagataag
atggcggaggcctacagtgagattgggatgaaaggcgagcgccggagggg
caaggggcacgatggcctttaccagggtctcagtacagccaccaaggaca
cctacgacgccttcacatgcaggccctgcccctcgctaa In one specific non-limiting example, the isolated nucleic acid molecule comprises nucleic acids having the sequence set forth in SEQ ID NO:235 provided below:

[SEQ ID NO: 235]
atggaaaccgacaccctgctgctgtgggtgctgctgctgtgggtgccagg
atccacaggacaggctgtgctgactcagccaccctcagcgtctgggaccc
ccgggcagagggtcaccatctcttgttctggaagcagctccaacatcgga
agtaattacgtattctggtaccagcagctcccaggaacggcccccaaact
cctcatctatagtaataatcagcggccctcagggtccctgaccgattct
ctggctccaagtctggcacctcagcctccctggccatcagtgggctccgg
tccgaggatgaggctgattattactgtgcagcatgggatgacagcctgag
tgcctcttatgttttcggaactgggaccaaggtcaccgtcctaggttcta
gaggtggtggtggtagcggcggcggcggctctggtggtggtggatccctc
gagatggcccaggtgcagctggtgcagtctggggctgaggtgaagaagcc
tgggtcctcggtgaaggtctcctgcaaggcttctggaggcaccttcagca
gctatgctatcagctgggtgcgacaggcccctggacaagggcttgagtgg
atgggaaggatcatccctatccttggtacagcaaactacgcacagaagtt
ccagggcagagtcacgattaccgcggacgaatccacgagcacagcctaca
tggagctgagcagcctgagatctgaggacacggccgtgtattactgtgcg
cgctctggttacggttcttaccgttgggaagattcttgggtcaaggtac
tctggtgaccgtctcctcagcggccgcaattgaagttatgtatcctcctc
cttacctagacaatgagaagagcaatggaaccattatccatgtgaaaggg
aaacacctttgtccaagtcccctatttccggaccttctaagcccttttg
ggtgctggtggtggttggtggagtcctggcttgctatagcttgctagtaa
cagtggcctttattattttctgggtgaggagtaagaggagcaggctcctg
cacagtgactacatgaacatgactccccgccgccccgggcccacccgcaa
gcattaccagccctatgccccaccacgcgacttcgcagcctatcgctcca
gagtgaagttcagcaggagcgcagacgccccgcgtaccagcagggccag
aaccagctctataacgagctcaatctaggacgaagagaggagtacgatgt
tttggacaagagacgtggccgggaccctgagatggggggaaagccgagaa
ggaagaaccctcaggaaggcctgtacaatgaactgcagaaagataagatg
gcggaggcctacagtgagattgggatgaaaggcgagcgccggaggggcaa
ggggcacgatggcctttaccagggtctcagtacagccaccaaggacacct
acgacgccttcacatgcaggccctgcccctcgctaa The isolated nucleic acid molecule having the nucleotide sequence of SEQ ID NO:207 encodes a BCMA-targeted CAR (designated as BCMA-targeted 28z CAR54) comprising a human scFv that comprises a heavy chain variable region comprising amino acids having the sequence set forth in SEQ ID NO:53, a light chain variable region comprising amino acids having the sequence set forth in SEQ ID NO:54, and a linker having an amino acid sequence of SEQ ID NO:69 positioned between the heavy chain variable region and the light chain variable region, a transmembrane domain comprising a CD28 polypeptide, and an intracellular domain comprising a CD3ξ polypeptide comprising amino acid sequence of amino acids 52 to 163 of SEQ ID NO: 195, and a co-stimulatory signaling region comprising a CD28 polypeptide, wherein the CD28 region comprising the transmembrane domain and the co-stimulatory signaling region comprises amino acids 114 to 220 of SEQ ID NO:193.

The isolated nucleic acid molecule having the nucleotide sequence of SEQ ID NO:208 encodes a BCMA-targeted CAR (designated as BCMA-targeted 28z CAR40) comprising a human scFv that comprises a heavy chain variable region comprising amino acids having the sequence set forth in SEQ ID NO:57, a light chain variable region comprising amino acids having the sequence set forth in SEQ ID NO:58, and a linker having an amino acid sequence of SEQ ID NO:69 positioned between the heavy chain variable region and the light chain variable region, a transmembrane domain comprising a CD28 polypeptide, and an intracellular domain comprising a CD3ξ polypeptide comprising amino acid sequence of amino acids 52 to 163 of SEQ ID NO: 195, and a co-stimulatory signaling region comprising a CD28 polypeptide, wherein the CD28 region comprising the transmembrance domain and the co-stimulatory signaling region comprises amino acids 114 to 220 of SEQ ID NO:193.

The isolated nucleic acid molecule having the nucleotide sequence of SEQ ID NO:209 encodes a BCMA-targeted CAR (designated as BCMA-targeted 28z CAR24) comprising a human scFv that comprises a heavy chain variable region comprising amino acids having the sequence set forth in SEQ ID NO:65, a light chain variable region comprising amino acids having the sequence set forth in SEQ ID NO:66, and a linker having an amino acid sequence of SEQ ID NO:69 positioned between the heavy chain variable region and the light chain variable region, a transmembrane domain comprising a CD28 polypeptide, and an intracellular domain comprising a CD3ξ polypeptide comprising amino acid sequence of amino acids 52 to 163 of SEQ ID NO: 195, and a co-stimulatory signaling region comprising a CD28 polypeptide, wherein the CD28 region comprising the transmembrance domain and the co-stimulatory signaling region comprises amino acids 114 to 220 of SEQ ID NO:193.

The isolated nucleic acid molecule having the nucleotide sequence of SEQ ID NO:234 encodes a BCMA-targeted CAR (designated as BCMA-targeted 28z CAR3) comprising a human scFv that comprises a heavy chain variable region comprising amino acids having the sequence set forth in SEQ ID NO:21, a light chain variable region comprising amino acids having the sequence set forth in SEQ ID NO:22, and a linker having an amino acid sequence of SEQ ID NO:69 positioned between the heavy chain variable region and the light chain variable region, a transmembrane domain comprising a CD28 polypeptide, and an intracellular domain comprising a CD3ξ polypeptide comprising amino acid sequence of amino acids 52 to 163 of SEQ ID NO: 195, and a co-stimulatory signaling region comprising a CD28 polypeptide, wherein the CD28 region comprising the transmembrance domain and the co-stimulatory signaling region comprises amino acids 114 to 220 of SEQ ID NO:193.

The isolated nucleic acid molecule having the nucleotide sequence of SEQ ID NO:235 encodes a BCMA-targeted CAR (designated as BCMA-targeted 28z CAR37) comprising a human scFv that comprises a heavy chain variable region comprising amino acids having the sequence set forth in SEQ ID NO:61, a light chain variable region comprising amino acids having the sequence set forth in SEQ ID NO:62, and a linker having an amino acid sequence of SEQ ID NO:69 positioned between the heavy chain variable region and the light chain variable region, a transmembrane domain comprising a CD28 polypeptide, and an intracellular domain comprising a CD3ξ polypeptide comprising amino acid sequence of amino acids 52 to 163 of SEQ ID NO: 195, and a co-stimulatory signaling region comprising a CD28 polypeptide, wherein the CD28 region comprising the transmembrance domain and the co-stimulatory signaling region comprises amino acids 114 to 220 of SEQ ID NO:193.

The isolated nucleic acid molecule having the nucleotide sequence of SEQ ID NO:229 encodes a BCMA-targeted CAR (designated as BCMA-targeted BBz CAR3) comprising a human scFv that comprises a heavy chain variable region comprising amino acids having the sequence set forth in SEQ ID NO:21, a light chain variable region comprising amino acids having the sequence set forth in SEQ ID NO:22, and a linker having an amino acid sequence of SEQ ID NO:69 positioned between the heavy chain variable region and the light chain variable region, a transmembrane domain comprising a CD8 polypeptide having amino acids 137 to 207 of SEQ ID NO: 226, and an intracellular domain comprising a CD3ξ polypeptide comprising amino acid sequence of amino acids 52 to 163 of SEQ ID NO: 195, and a co-stimulatory signaling region comprising a 4-1BB polypeptide having the amino acids 214-255 of SEQ ID NO: 197. Nucleotide sequences 270-1031 of SEQ ID NO: 229 encodes the human scFv. Nucleotide sequences 1041-1253 of SEQ ID NO: 229 encodes the CD8 polypeptide comprised in the transmembrane domain. Nucleotide sequences 1254-1379 of SEQ ID NO: 229 encodes the 4-1BB polypeptide comprised in the intracellular domain. Nucleotide sequences 1380-1718 of SEQ ID NO: 229 encodes the CD3zeta polypeptide comprised in the intracellular domain. Other portions of SEQ ID NO: 229 are shown in Table 19.

TABLE 19

| Portions | nucleotide Sequence positions of SEQ ID NO: 229 | number of nucleotides |
| --- | --- | --- |
| Kappa sp | 210 . . . 269 | 60 |
| LTR | 1998 . . . 2467 | 470 |
| M13 fwd | 3166 . . . 3182 | 17 |
| AmpR promoter | 3657 . . . 3761 | 105 |
| AmpR | 3762 . . . 4622 | 861 |
| ori | 4793 . . . 5381 | 589 |
| CAP binding site | 5669 . . . 5690 | 22 |
| lac promoter | 5705 . . . 5735 | 31 |
| lac operator | 5743 . . . 5759 | 17 |
| M13 rev | 5767 . . . 5783 | 17 |
| LTR | 6192 . . . 6785 | 594 |
| MMLV Psi | 6848 . . . 7205 | 358 |
| gag (truncated) | 7270 . . . 15 | 417 |

The isolated nucleic acid molecule having the nucleotide sequence of SEQ ID NO:230 encodes a BCMA-targeted CAR (designated as BCMA-targeted BBz CAR24) comprising a human scFv that comprises a heavy chain variable region comprising amino acids having the sequence set forth in SEQ ID NO:65, a light chain variable region comprising amino acids having the sequence set forth in SEQ ID NO:66, and a linker having an amino acid sequence of SEQ ID NO:69 positioned between the heavy chain variable region and the light chain variable region, a transmembrane domain comprising a CD8 polypeptide having amino acids 137 to 207 of SEQ ID NO: 226, and an intracellular domain comprising a CD3ξ polypeptide comprising amino acid sequence of amino acids 52 to 163 of SEQ ID NO: 195, and a co-stimulatory signaling region comprising a 4-1BB polypeptide having the amino acids 214-255 of SEQ ID NO: 197. Nucleotide sequences 270-1015 of SEQ ID NO: 230 encodes the human scFv. Nucleotide sequences 1023-1235 of SEQ ID NO: 230 encodes the CD8 polypeptide comprised in the transmembrane domain. Nucleotide sequences 1236-1361 of SEQ ID NO: 230 encodes the 4-1BB polypeptide comprised in the intracellular domain. Nucleotide sequences 1362-1700 of SEQ ID NO: 230 encodes the CD3zeta polypeptide comprised in the intracellular domain. Other portions of SEQ ID NO: 230 are shown in Table 20.

TABLE 20

| Portions | nucleotide Sequence positions of SEQ ID NO: 230 | number of nucleotides |
|---|---|---|
| Kappa sp | 210 ... 269 | 60 |
| LTR | 1980 ... 2449 | 470 |
| M13 fwd | 3148 ... 3164 | 17 |
| AmpR promoter | 3639 ... 3743 | 105 |
| AmpR | 3744 ... 4604 | 861 |
| ori | 4775 ... 5363 | 589 |
| CAP binding site | 5651 ... 5672 | 22 |
| lac promoter | 5687 ... 5717 | 31 |
| lac operator | 5725 ... 5741 | 17 |
| M13 rev | 5749 ... 5765 | 17 |
| LTR | 6174 ... 6767 | 594 |
| MMLV Psi | 6830 ... 7187 | 358 |
| gag (truncated) | 7252 ... 15 | 417 |

The isolated nucleic acid molecule having the nucleotide sequence of SEQ ID NO:231 encodes a BCMA-targeted CAR (designated as BCMA-targeted BBz CAR37) comprising a human scFv that comprises a heavy chain variable region comprising amino acids having the sequence set forth in SEQ ID NO:61, a light chain variable region comprising amino acids having the sequence set forth in SEQ ID NO:62, and a linker having an amino acid sequence of SEQ ID NO:69 positioned between the heavy chain variable region and the light chain variable region, a transmembrane domain comprising a CD8 polypeptide having amino acids 137 to 207 of SEQ ID NO: 226, and an intracellular domain comprising a CD3ξ polypeptide comprising amino acid sequence of amino acids 52 to 163 of SEQ ID NO: 195, and a co-stimulatory signaling region comprising a 4-1BB polypeptide having the amino acids 214-255 of SEQ ID NO: 197. Nucleotide sequences 270-1028 of SEQ ID NO: 231 encodes the human scFv. Nucleotide sequences 1038-1250 of SEQ ID NO: 231 encodes the CD8 polypeptide comprised in the transmembrane domain. Nucleotide sequences 1251-1376 of SEQ ID NO: 231 encodes the 4-1BB polypeptide comprised in the intracellular domain. Nucleotide sequences 1377-1715 of SEQ ID NO: 231 encodes the CD3zeta polypeptide comprised in the intracellular domain. Other portions of SEQ ID NO: 231 are shown in Table 21.

TABLE 21

| Portions | nucleotide Sequence positions of SEQ ID NO: 231 | number of nucleotides |
|---|---|---|
| Kappa sp | 210 ... 269 | 60 |
| LTR | 1995 ... 2464 | 470 |
| M13 fwd | 3163 ... 3179 | 17 |
| AmpR promoter | 3654 ... 3758 | 105 |
| AmpR | 3759 ... 4619 | 861 |
| ori | 4790 ... 5378 | 589 |
| CAP binding site | 5666 ... 5687 | 22 |
| lac promoter | 5702 ... 5732 | 31 |
| lac operator | 5740 ... 5756 | 17 |
| M13 rev | 5764 ... 5780 | 17 |
| LTR | 6189 ... 6782 | 594 |
| MMLV Psi | 6845 ... 7202 | 358 |
| gag (truncated) | 7267 ... 15 | 417 |

The isolated nucleic acid molecule having the nucleotide sequence of SEQ ID NO:232 encodes a BCMA-targeted CAR (designated as BCMA-targeted BBz CAR40) comprising a human scFv that comprises a heavy chain variable region comprising amino acids having the sequence set forth in SEQ ID NO:57, a light chain variable region comprising amino acids having the sequence set forth in SEQ ID NO:58, and a linker having an amino acid sequence of SEQ ID NO:69 positioned between the heavy chain variable region and the light chain variable region, a transmembrane domain comprising a CD8 polypeptide having amino acids 137 to 207 of SEQ ID NO: 226, and an intracellular domain comprising a CD3ξ polypeptide comprising amino acid sequence of amino acids 52 to 163 of SEQ ID NO: 195, and a co-stimulatory signaling region comprising a 4-1BB polypeptide having the amino acids 214-255 of SEQ ID NO: 197. Nucleotide sequences 270-1024 of SEQ ID NO: 232 encodes the human scFv. Nucleotide sequences 1032-1244 of SEQ ID NO: 232 encodes the CD8 polypeptide comprised in the transmembrane domain. Nucleotide sequences 1245-1370 of SEQ ID NO: 232 encodes the 4-1BB polypeptide comprised in the intracellular domain. Nucleotide sequences 1371-1709 of SEQ ID NO: 232 encodes the CD3zeta polypeptide comprised in the intracellular domain. Other portions of SEQ ID NO: 232 are shown in Table 22.

TABLE 22

| Portions | nucleotide Sequence positions of SEQ ID NO: 232 | number of nucleotides |
|---|---|---|
| Kappa sp | 210 ... 269 | 60 |
| LTR | 1989 ... 2458 | 470 |
| M13 fwd | 3157 ... 3173 | 17 |
| AmpR promoter | 3648 ... 3752 | 105 |
| AmpR | 3753 ... 4613 | 861 |
| ori | 4784 ... 5372 | 589 |
| CAP binding site | 5660 ... 5681 | 22 |
| lac promoter | 5696 ... 5726 | 31 |
| lac operator | 5734 ... 5750 | 17 |
| M13 rev | 5758 ... 5774 | 17 |
| LTR | 6183 ... 6776 | 594 |
| MMLV Psi | 6839 ... 7196 | 358 |
| gag (truncated) | 7261 ... 15 | 417 |

The isolated nucleic acid molecule having the nucleotide sequence of SEQ ID NO:233 encodes a BCMA-targeted CAR (designated as BCMA-targeted BBz CAR54) comprising a human scFv that comprises a heavy chain variable region comprising amino acids having the sequence set forth in SEQ ID NO:53, a light chain variable region comprising amino acids having the sequence set forth in SEQ ID NO:54, and a linker having an amino acid sequence of SEQ ID NO:69 positioned between the heavy chain variable region and the light chain variable region, a transmembrane domain comprising a CD8 polypeptide having amino acids 137 to 207 of SEQ ID NO: 226, and an intracellular domain comprising a CD3ξ polypeptide comprising amino acid sequence of amino acids 52 to 163 of SEQ ID NO: 195, and a co-stimulatory signaling region comprising a 4-1BB polypeptide having the amino acids 214-255 of SEQ ID NO: 197. Nucleotide sequences 270-1003 of SEQ ID NO: 233 encodes the human scFv. Nucleotide sequences 1011-1223 of SEQ ID NO: 233 encodes the CD8 polypeptide comprised in the transmembrane domain. Nucleotide sequences 1224-1349 of SEQ ID NO: 233 encodes the 4-1BB polypeptide comprised in the intracellular domain. Nucleotide sequences 1350-1688 of SEQ ID NO: 233 encodes the CD3zeta polypeptide comprised in the intracellular domain. Other portions of SEQ ID NO: 233 are shown in Table 23.

TABLE 23

| Portions | nucleotide Sequence positions of SEQ ID NO: 233 | number of nucleotides |
|---|---|---|
| Kappa sp | 210 ... 269 | 60 |
| LTR | 1968 ... 2437 | 470 |

TABLE 23-continued

| Portions | nucleotide Sequence positions of SEQ ID NO: 233 | number of nucleotides |
|---|---|---|
| M13 fwd | 3136 ... 3152 | 17 |
| AmpR promoter | 3627 ... 3731 | 105 |
| AmpR | 3732 ... 4592 | 861 |
| ori | 4763 ... 5351 | 589 |
| CAP binding site | 5639 ... 5660 | 22 |
| lac promoter | 5675 ... 5705 | 31 |
| lac operator | 5713 ... 5729 | 17 |
| M13 rev | 5737 ... 5753 | 17 |
| LTR | 6162 ... 6755 | 594 |
| MMLV Psi | 6818 ... 7175 | 358 |
| gag (truncated) | 7240 ... 15 | 417 |

In certain embodiments, the isolated nucleic acid molecule encodes a functional portion of a presently disclosed BCMA-targeted CAR. As used herein, the term "functional portion" refers to any portion, part or fragment of a presently disclosed BCMA-targeted CAR, which portion, part or fragment retains the biological activity of the BCMA-targeted CAR (the parent CAR). For example, functional portions encompass the portions, parts or fragments of a presently disclosed BCMA-targeted CAR that retains the ability to recognize a target cell, to treat a disease, e.g., multiple myeloma, to a similar, same, or even a higher extent as the parent CAR. In certain embodiments, an isolated nucleic acid molecule encoding a functional portion of a presently disclosed BCMA-targeted CAR can encode a protein comprising, e.g., about 10%, 20%, 25%, 30%, 35%, 40%, 45%, 50%, 55%, 60%, 65%, 70%, 75%, 80%, 85%, 90%, and 95%, or more of the parent CAR.

One Phase I clinical trial (NCT02215967) operated by National Cancer Institute (NCI) used anti-BCMA CAR-transduced T cells for treating multiple myeloma.[33,34] The anti-BCMA CAR applied in the NCI's clinical trial comprises a murine scFv binding to human BCMA. Using a mouse antibody or a mouse scFv for treating humans can lead to anti-mouse antibody (HAMA) response, which may be life-threatening. Unlike NCI clinical trial, in certain embodiments, the presently disclosed BCMA-targeted CAR comprises a human scFv, and thus, affords a much decreased risk of immunogenicity, compared with CARs comprising murine antibodies (see Maus et al., *Cancer Immunol Res* (2003); 1(1):26-31), which reports that the potential immunogenicity of CARs derived from murine antibodies may be a safety issue for mRNA CARs).

III. Immunoresponsive Cells

The presently disclosed subject matter provides immunoresponsive cells expressing a CAR that comprises an extracellular antigen-binding domain, a transmembrane domain and an intracellular domain, where the extracellular antigen-binding domain specifically binds to BCMA (e.g., human BCMA) as described above. The immunoresponsive cells can be transduced with a presently disclosed CAR such that the cells express the CAR. The presently disclosed subject matter also provides methods of using such cells for the treatment of a tumor, e.g., multiple myeloma (MM). The immunoresponsive cells of the presently disclosed subject matter can be cells of the lymphoid lineage. The lymphoid lineage, comprising B, T and natural killer (NK) cells, provides for the production of antibodies, regulation of the cellular immune system, detection of foreign agents in the blood, detection of cells foreign to the host, and the like. Non-limiting examples of immunoresponsive cells of the lymphoid lineage include T cells, Natural Killer (NK) cells, cytotoxic T lymphocytes (CTLs), regulatory T cells, embryonic stem cells, and pluripotent stem cells (e.g., those from which lymphoid cells may be differentiated). T cells can be lymphocytes that mature in the thymus and are chiefly responsible for cell-mediated immunity. T cells are involved in the adaptive immune system. The T cells of the presently disclosed subject matter can be any type of T cells, including, but not limited to, T helper cells, cytotoxic T cells, memory T cells (including central memory T cells, stem-cell-like memory T cells (or stem-like memory T cells), and two types of effector memory T cells: e.g., TEM cells and $T_{EMRA}$ cells), Regulatory T cells (also known as suppressor T cells), Natural killer T cells, Mucosal associated invariant T cells, and γδ T cells. In certain embodiments, the CAR-expressing T cells express Foxp3 to achieve and maintain a T regulatory phenotype. Natural killer (NK) cells can be lymphocytes that are part of cell-mediated immunity and act during the innate immune response. NK cells do not require prior activation in order to perform their cytotoxic effect on target cells. Cytotoxic T cells (CTL or killer T cells) are a subset of T lymphocytes capable of inducing the death of infected somatic or tumor cells.

The immunoresponsive cells of the presently disclosed subject matter can express an extracellular antigen-binding domain (e.g., a human scFV, a Fab that is optionally cross-linked, or a F(ab)$_2$) that specifically binds to BCMA (e.g., human BCMA), for the treatment of multiple myeloma. Such immunoresponsive cells can be administered to a subject (e.g., a human subject) in need thereof for the treatment of multiple myeloma. In certain embodiments, the immunoresponsive cell is a T cell. The T cell can be a CD4$^+$ T cell or a CD8$^+$ T cell. In certain embodiments, the T cell is a CD4$^+$ T cell. In another embodiment, the T cell is a CD8$^+$ T cell.

A presently disclosed immunoresponsive cell can be further transduced with at least one co-stimulatory ligand, such that the immunoresponsive cell co-expresses or is induced to co-express the BCMA-targeted CAR and the at least one co-stimulatory ligand. The interaction between the BCMA-targeted CAR and at least one co-stimulatory ligand provides a non-antigen-specific signal important for full activation of an immunoresponsive cell (e.g., T cell). Co-stimulatory ligands include, but are not limited to, members of the tumor necrosis factor (TNF) superfamily, and immunoglobulin (Ig) superfamily ligands. TNF is a cytokine involved in systemic inflammation and stimulates the acute phase reaction. Its primary role is in the regulation of immune cells. Members of TNF superfamily share a number of common features. The majority of TNF superfamily members are synthesized as type II transmembrane proteins (extracellular C-terminus) containing a short cytoplasmic segment and a relatively long extracellular region. TNF superfamily members include, without limitation, nerve growth factor (NGF), CD40L (CD40L)/CD154, CD137L/4-1BBL, TNF-α, CD134L/OX40L/CD252, CD27L/CD70, Fas ligand (FasL), CD30L/CD153, tumor necrosis factor beta (TNFβ)/lymphotoxin-alpha (LTα), lymphotoxin-beta (LTβ), CD257/B cell-activating factor (BAFF)/Blys/THANK/Tall-1, glucocorticoid-induced TNF Receptor ligand (GITRL), and TNF-related apoptosis-inducing ligand (TRAIL), LIGHT (TNFSF14). The immunoglobulin (Ig) superfamily is a large group of cell surface and soluble proteins that are involved in the recognition, binding, or adhesion processes of cells. These proteins share structural features with immunoglobulins—they possess an immunoglobulin domain (fold). Immunoglobulin superfamily ligands include, but are not limited to, CD80 and CD86, both ligands for CD28, PD-L1/(B7-H1) that ligands for PD-1. In certain embodiments, the at least one co-stimulatory ligand is selected from the group consisting of 4-1BBL, CD80, CD86, CD70, OX40L, CD48, TNFRSF14, PD-L1, and combinations thereof. In certain embodiments, the immunoresponsive cell is transduced with one co-stimulatory ligand that is 4-1BBL. In certain embodiments, the immunoresponsive cell is transduced with two co-stimulatory ligands that are 4-1BBL and CD80. CARs transduced with at least one co-stimulatory ligand are described in U.S. Pat. No. 8,389,282, which is incorporated by reference in its entirety.

Furthermore, a presently disclosed immunoresponsive cell can be further transduced with at least one cytokine, such that the immunoresponsive cell secretes the at least one cytokine as well as expresses the BCMA-targeted CAR. In certain embodiments, the at least one cytokine is selected from the group consisting of IL-2, IL-3, IL-6, IL-7, IL-11, IL-12, IL-15, IL-17, and IL-21. In certain embodiments, the cytokine is IL-12.

The BCMA-specific or BCMA-targeted human lymphocytes that can be used in peripheral donor lymphocytes, e.g., those disclosed in Sadelain, M., et al. 2003 *Nat Rev Cancer* 3:35-45 (disclosing peripheral donor lymphocytes genetically modified to express CARs), in Morgan, R. A., et al. 2006 *Science* 314:126-129 (disclosing peripheral donor lymphocytes genetically modified to express a full-length tumor antigen-recognizing T cell receptor complex comprising the α and β heterodimer), in Panelli, M. C., et al. 2000 *J Immunol* 164:495-504; Panelli, M. C., et al. 2000 *J Immunol* 164:4382-4392 (disclosing lymphocyte cultures derived from tumor infiltrating lymphocytes (TILs) in tumor biopsies), and in Dupont, J., et al. 2005 *Cancer Res* 65:5417-5427; Papanicolaou, G. A., et al. 2003 *Blood* 102:2498-2505 (disclosing selectively in vitro-expanded antigen-specific peripheral blood leukocytes employing artificial antigen-presenting cells (AAPCs) or pulsed dendritic cells). The immunoresponsive cells (e.g., T cells) can be autologous, non-autologous (e.g., allogeneic), or derived in vitro from engineered progenitor or stem cells.

In certain embodiments, a presently disclosed immunoresponsive cell (e.g., T cell) expresses from about 1 to about 4, from about 2 to about 4, from about 3 to about 4, from about 1 to about 2, from about 1 to about 3, or from about 2 to about 3 vector copy numbers/cell of a presently disclosed BCMA-targeted CAR.

The unpurified source of CTLs may be any known in the art, such as the bone marrow, fetal, neonate or adult or other hematopoietic cell source, e.g., fetal liver, peripheral blood or umbilical cord blood. Various techniques can be employed to separate the cells. For instance, negative selection methods can remove non-CTLs initially. Monoclonal antibodies are particularly useful for identifying markers associated with particular cell lineages and/or stages of differentiation for both positive and negative selections.

A large proportion of terminally differentiated cells can be initially removed by a relatively crude separation. For example, magnetic bead separations can be used initially to remove large numbers of irrelevant cells. Preferably, at least about 80%, usually at least 70% of the total hematopoietic cells will be removed prior to cell isolation.

Procedures for separation include, but are not limited to, density gradient centrifugation; resetting; coupling to particles that modify cell density; magnetic separation with antibody-coated magnetic beads; affinity chromatography; cytotoxic agents joined to or used in conjunction with a mAb, including, but not limited to, complement and cytotoxins; and panning with antibody attached to a solid matrix, e.g. plate, chip, elutriation or any other convenient technique.

Techniques for separation and analysis include, but are not limited to, flow cytometry, which can have varying degrees of sophistication, e.g., a plurality of color channels, low angle and obtuse light scattering detecting channels, impedance channels.

The cells can be selected against dead cells, by employing dyes associated with dead cells such as propidium iodide (PI). Preferably, the cells are collected in a medium comprising 2% fetal calf serum (FCS) or 0.2% bovine serum albumin (BSA) or any other suitable, preferably sterile, isotonic medium.

IV. Vectors

Genetic modification of immunoresponsive cells (e.g., T cells, CTL cells, NK cells) can be accomplished by transducing a substantially homogeneous cell composition with a recombinant DNA or RNA construct. The vector can be a retroviral vector (e.g., gamma retroviral), which is employed for the introduction of the DNA or RNA construct into the host cell genome. For example, a polynucleotide encoding the BCMA-targeted CAR can be cloned into a retroviral vector and expression can be driven from its endogenous promoter, from the retroviral long terminal repeat, or from an alternative internal promoter.

Non-viral vectors or RNA may be used as well. Random chromosomal integration, or targeted integration (e.g., using a nuclease, transcription activator-like effector nucleases (TALENs), Zinc-finger nucleases (ZFNs), and/or clustered regularly interspaced short palindromic repeats (CRISPRs), or transgene expression (e.g., using a natural or chemically modified RNA) can be used.

For initial genetic modification of the cells to provide BCMA-targeted CAR expressing cells, a retroviral vector is generally employed for transduction, however any other suitable viral vector or non-viral delivery system can be used. For subsequent genetic modification of the cells to provide cells comprising an antigen presenting complex comprising at least two co-stimulatory ligands, retroviral gene transfer (transduction) likewise proves effective. Combinations of retroviral vector and an appropriate packaging line are also suitable, where the capsid proteins will be functional for infecting human cells. Various amphotropic virus-producing cell lines are known, including, but not limited to, PA12 (Miller, et al. (1985) *Mol. Cell. Biol.* 5:431-437); PA317 (Miller, et al. (1986) *Mol. Cell. Biol.* 6:2895-2902); and CRIP (Danos, et al. (1988) *Proc. Natl. Acad. Sci. USA* 85:6460-6464). Non-amphotropic particles are suitable too, e.g., particles pseudotyped with VSVG, RD114 or GALV envelope and any other known in the art. Possible methods of transduction also include direct co-culture of the cells with producer cells, e.g., by the method of Bregni, et al. (1992) *Blood* 80:1418-1422, or culturing with viral supernatant alone or concentrated vector stocks with or without appropriate growth factors and polycations, e.g., by the method of Xu, et al. (1994) *Exp. Hemat.* 22:223-230; and Hughes, et al. (1992) *J. Clin. Invest.* 89:1817.

Transducing viral vectors can be used to express a co-stimulatory ligand (e.g., 4-1BBL and IL-12) in an immunoresponsive cell. Preferably, the chosen vector exhibits high efficiency of infection and stable integration and expression (see, e.g., Cayouette et al., Human Gene Therapy 8:423-430, 1997; Kido et al., Current Eye Research 15:833-844, 1996; Bloomer et al., Journal of Virology 71:6641-6649, 1997; Naldini et al., Science 272:263 267, 1996; and Miyoshi et al., Proc. Natl. Acad. Sci. U.S.A. 94:10319, 1997). Other viral vectors that can be used include, for example, adenoviral, lentiviral, and adeno-associated viral vectors, vaccinia virus, a bovine papilloma virus, or a herpes virus, such as Epstein-Barr Virus (also see, for example, the vectors of Miller, Human Gene Therapy 15-14, 1990; Friedman, Science 244:1275-1281, 1989; Eglitis et al., BioTechniques 6:608-614, 1988; Tolstoshev et al., Current Opinion in Biotechnology 1:55-61, 1990; Sharp, The Lancet 337:1277-1278, 1991; Cornetta et al., Nucleic Acid Research and Molecular Biology 36:311-322, 1987; Anderson, Science 226:401-409, 1984; Moen, Blood Cells 17:407-416, 1991; Miller et al., Biotechnology 7:980-990, 1989; Le Gal La Salle et al., Science 259:988-990, 1993; and Johnson, Chest 107:77S-83S, 1995). Retroviral vectors are particularly well developed and have been used in clinical settings (Rosenberg et al., N. Engl. J. Med 323:370, 1990; Anderson et al., U.S. Pat. No. 5,399,346).

In certain non-limiting embodiments, the vector expressing a presently disclosed BCMA-targeted CAR is a retroviral vector, e.g., a 293galv9 retroviral vector.

Non-viral approaches can also be employed for the expression of a protein in cell. For example, a nucleic acid molecule can be introduced into a cell by administering the nucleic acid in the presence of lipofection (Feigner et al., Proc. Nat'l. Acad. Sci. U.S.A. 84:7413, 1987; Ono et al., Neuroscience Letters 17:259, 1990; Brigham et al., Am. J. Med. Sci. 298:278, 1989; Staubinger et al., Methods in Enzymology 101:512, 1983), asialoorosomucoid-polylysine conjugation (Wu et al., Journal of Biological Chemistry 263:14621, 1988; Wu et al., Journal of Biological Chemistry 264:16985, 1989), or by micro-injection under surgical conditions (Wolff et al., Science 247:1465, 1990). Other non-viral means for gene transfer include transfection in vitro using calcium phosphate, DEAE dextran, electroporation, and protoplast fusion. Liposomes can also be potentially beneficial for delivery of DNA into a cell. Transplantation of normal genes into the affected tissues of a subject can also be accomplished by transferring a normal nucleic acid into a cultivatable cell type ex vivo (e.g., an autologous or heterologous primary cell or progeny thereof), after which the cell (or its descendants) are injected into a targeted tissue or are injected systemically. Recombinant receptors can also be derived or obtained using transposases or targeted nucleases (e.g. Zinc finger nucleases, meganucleases, or TALE nucleases). Transient expression may be obtained by RNA electroporation.

cDNA expression for use in polynucleotide therapy methods can be directed from any suitable promoter (e.g., the human cytomegalovirus (CMV), simian virus 40 (SV40), or metallothionein promoters), and regulated by any appropriate mammalian regulatory element or intron (e.g. the elongation factor 1α enhancer/promoter/intron structure). For example, if desired, enhancers known to preferentially direct gene expression in specific cell types can be used to direct the expression of a nucleic acid. The enhancers used can include, without limitation, those that are characterized as tissue- or cell-specific enhancers. Alternatively, if a genomic clone is used as a therapeutic construct, regulation can be mediated by the cognate regulatory sequences or, if desired, by regulatory sequences derived from a heterologous source, including any of the promoters or regulatory elements described above.

The resulting cells can be grown under conditions similar to those for unmodified cells, whereby the modified cells can be expanded and used for a variety of purposes.

V. Polypeptides and Analogs and Polynucleotides

Also included in the presently disclosed subject matter are extracellular antigen-binding domains that specifically binds to a BCMA (e.g., human BCMA) (e.g., an scFv (e.g., a human scFv), a Fab, or a (Fab)$_2$), CD3ζ, CD8, CD28, etc. polypeptides or fragments thereof, and polynucleotides encoding thereof that are modified in ways that enhance their anti-tumor activity when expressed in an immunoresponsive cell. The presently disclosed subject matter provides methods for optimizing an amino acid sequence or a nucleic acid sequence by producing an alteration in the sequence. Such alterations may comprise certain mutations, deletions, insertions, or post-translational modifications. The presently disclosed subject matter further comprises analogs of any naturally-occurring polypeptide of the presently disclosed subject matter. Analogs can differ from a naturally-occurring polypeptide of the presently disclosed subject matter by amino acid sequence differences, by post-translational modifications, or by both. Analogs of the presently disclosed subject matter can generally exhibit at least about 85%, about 90%, about 91%, about 92%, about 93%, about 94%, about 95%, about 96%, about 97%, about 98%, about 99% or more identity with all or part of a naturally-occurring amino, acid sequence of the presently disclosed subject matter. The length of sequence comparison is at least 5, 10, 15, 20, 25, 50, 75, 100 or more amino acid residues. Again, in an exemplary approach to determining the degree of identity, a BLAST program may be used, with a probability score between $e^{-3}$ and $e^{-100}$ indicating a closely related sequence. Modifications comprise in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring polypeptides of the presently disclosed subject matter by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, Molecular Cloning: A Laboratory Manual (2d ed.), CSH Press, 1989, or Ausubel et al., supra). Also included are cyclized peptides, molecules, and analogs which contain residues other than L-amina acids, e.g., D-amino acids or non-naturally occurring or synthetic amino acids, e.g., beta (β) or gamma (γ) amino acids.

In addition to full-length polypeptides, the presently disclosed subject matter also provides fragments of any one of the polypeptides or peptide domains of the presently disclosed subject matter. A fragment can be at least 5, 10, 13, or 15 amino acids. In certain embodiments, a fragment is at least 20 contiguous amino acids, at least 30 contiguous amino acids, or at least 50 contiguous amino acids. In certain embodiments, a fragment is at least 60 to 80, 100, 200, 300 or more contiguous amino acids. Fragments of the presently disclosed subject matter can be generated by methods known to those of ordinary skill in the art or may result from normal protein processing (e.g., removal of amino acids from the nascent polypeptide that are not required for biological activity or removal of amino acids by alternative mRNA splicing or alternative protein processing events).

Non-protein analogs have a chemical structure designed to mimic the functional activity of a protein of the invention. Such analogs are administered according to methods of the presently disclosed subject matter. Such analogs may exceed the physiological activity of the original polypeptide. Methods of analog design are well known in the art, and synthesis of analogs can be carried out according to such methods by modifying the chemical structures such that the resultant analogs increase the anti-neoplastic activity of the original polypeptide when expressed in an immunoresponsive cell. These chemical modifications include, but are not limited to, substituting alternative R groups and varying the degree of saturation at specific carbon atoms of a reference polypeptide. The protein analogs can be relatively resistant to in vivo degradation, resulting in a more prolonged therapeutic effect upon administration. Assays for measuring functional activity include, but are not limited to, those described in the Examples below.

In accordance with the presently disclosed subject matter, the polynucleotides encoding an extracellular antigen-binding domain that specifically binds to BCMA (e.g., human BCMA) (e.g., an scFv (e.g., a human scFv), a Fab, or a $(Fab)_2$), CD3ζ, CD8, CD28) can be modified by codon optimization. Codon optimization can alter both naturally occurring and recombinant gene sequences to achieve the highest possible levels of productivity in any given expression system. Factors that are involved in different stages of protein expression include codon adaptability, mRNA structure, and various cis-elements in transcription and translation. Any suitable codon optimization methods or technologies that are known to ones skilled in the art can be used to modify the polynucleotids of the presently disclosed subject matter, including, but not limited to, OptimumGene™, Encor optimization, and Blue Heron.

VI. Administration

BCMA-targeted CARs and immunoresponsive cells expressing thereof of the presently disclosed subject matter can be provided systemically or directly to a subject for treating or preventing a neoplasia. In certain embodiments, the BCMA-targeted CARs and immunoresponsive cells expressing thereof are directly injected into an organ of interest (e.g., an organ affected by a neoplasia). Alternatively or additionally, the BCMA-targeted CARs and immunoresponsive cells expressing thereof are provided indirectly to the organ of interest, for example, by administration into the circulatory system (e.g., the tumor vasculature). Expansion and differentiation agents can be provided prior to, during or after administration of cells and compositions to increase production of T cells in vitro or in vivo.

BCMA-targeted CARs and immunoresponsive cells expressing thereof of the presently disclosed subject matter can be administered in any physiologically acceptable vehicle, normally intravascularly, although they may also be introduced into bone or other convenient site where the cells may find an appropriate site for regeneration and differentiation (e.g., thymus). Usually, at least $1 \times 10^5$ cells can be administered, eventually reaching $1 \times 10^{10}$ or more. A cell population comprising immunoresponsive cells expressing a BCMA-targeted CAR can comprise a purified population of cells. Those skilled in the art can readily determine the percentage of immunoresponsive cells in a cell population using various well-known methods, such as fluorescence activated cell sorting (FACS). The ranges of purity in cell populations comprising genetically modified immunoresponsive cells expressing a BCMA-specific CAR can be from about 50% to about 55%, from about 55% to about 60%, from about 65% to about 70%, from about 70% to about 75%, from about 75% to about 80%, from about 80% to about 85%; from about 85% to about 90%, from about 90% to about 95%, or from about 95 to about 100%. Dosages can be readily adjusted by those skilled in the art (e.g., a decrease in purity may require an increase in dosage). The immunoresponsive cells can be introduced by injection, catheter, or the like. If desired, factors can also be included, including, but not limited to, interleukins, e.g. IL-2, IL-3, IL 6, IL-11, IL-7, IL-12, IL-15, IL-21, as well as the other interleukins, the colony stimulating factors, such as G-, M- and GM-CSF, interferons, e.g., γ-interferon.

Compositions of the presently disclosed subject matter comprise pharmaceutical compositions comprising immunoresponsive cells expressing a BCMA-targeted CAR and a pharmaceutically acceptable carrier. Administration can be autologous or non-autologous. For example, immunoresponsive cells expressing a BCMA-targeted CAR and compositions comprising thereof can be obtained from one subject, and administered to the same subject or a different, compatible subject. Peripheral blood derived T cells of the presently disclosed subject matter or their progeny (e.g., in vivo, ex vivo or in vitro derived) can be administered via localized injection, including catheter administration, systemic injection, localized injection, intravenous injection, or parenteral administration. When administering a pharmaceutical composition of the presently disclosed subject matter (e.g., a pharmaceutical composition comprising immunoresponsive cells expressing a BCMA-targeted CAR), it can be formulated in a unit dosage injectable form (solution, suspension, emulsion).

VII. Formulations

Immunoresponsive cells expressing a generally BCMA-targeted CAR and compositions comprising thereof of the presently disclosed subject matter can be conveniently provided as sterile liquid preparations, e.g., isotonic aqueous solutions, suspensions, emulsions, dispersions, or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof.

Sterile injectable solutions can be prepared by incorporating the compositions comprising immunoresponsive cells expressing a generally BCMA-targeted CAR of the presently disclosed subject matter in the required amount of the appropriate solvent with various amounts of the other ingredients, as desired. Such compositions may be in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired.

Standard texts, such as "REMINGTON'S PHARMACEUTICAL SCIENCE", 17th edition, 1985, incorporated herein by reference, may be consulted to prepare suitable preparations, without undue experimentation.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, alum inum monostearate and gelatin. According to the present invention, however, any vehicle, diluent, or additive used would have to be compatible with the immunoresponsive cells expressing a generally BCMA-targeted CAR of the presently disclosed subject matter.

The compositions can be isotonic, i.e., they can have the same osmotic pressure as blood and lacrimal fluid. The desired isotonicity of the compositions of the presently disclosed subject matter may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions, if desired, can be maintained at the selected level using a pharmaceutically acceptable thickening agent. Methylcellulose can be used because it is readily and economically available and is easy to work with. Other suitable thickening agents include, for example, xanthan gum, carboxymethyl cellulose, hydroxypropyl cellulose, carbomer, and the like. The concentration of the thickener can depend upon the agent selected. The important point is to use an amount that will achieve the selected viscosity. Obviously, the choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

Those skilled in the art will recognize that the components of the compositions should be selected to be chemically inert and will not affect the viability or efficacy of the immunoresponsive cells as describe in the presently disclosed subject matter. This will present no problem to those skilled in chemical and pharmaceutical principles, or problems can be readily avoided by reference to standard texts or by simple experiments (not involving undue experimentation), from this disclosure and the documents cited herein.

One consideration concerning the therapeutic use of the immunoresponsive cells of the presently disclosed subject matter is the quantity of cells necessary to achieve an optimal effect. The quantity of cells to be administered will vary for the subject being treated. In certain embodiments, from about $10^4$ to about $10^{10}$, from about $10^5$ to about $10^9$, or from about $10^6$ to about $10^8$ immunoresponsive cells of the presently disclosed subject matter are administered to a subject. More effective cells may be administered in even smaller numbers. In certain embodiments, at least about $1 \times 10^8$, about $2 \times 10^8$, about $3 \times 10^8$, about $4 \times 10^8$, and about $5 \times 10^8$ immunoresponsive cells of the presently disclosed subject matter are administered to a human subject. The precise determination of what would be considered an effective dose may be based on factors individual to each subject, including their size, age, sex, weight, and condition of the particular subject. Dosages can be readily ascertained by those skilled in the art from this disclosure and the knowledge in the art.

The skilled artisan can readily determine the amount of cells and optional additives, vehicles, and/or carrier in compositions and to be administered in methods of the presently disclosed subject matter. Typically, any additives (in addition to the active cell(s) and/or agent(s)) are present in an amount of from about 0.001% to about 50% by weight) solution in phosphate buffered saline, and the active ingredient is present in the order of micrograms to milligrams, such as from about 0.0001 wt % to about 5 wt %, from about 0.0001 wt % to about 1 wt %, from about 0.0001 wt % to about 0.05 wt %, from about 0.001 wt % to about 20 wt %, from about 0.01 wt % to about 10 wt %, or from about 0.05 wt % to about 5 wt %. For any composition to be administered to an animal or human, and for any particular method of administration, toxicity should be determined, such as by determining the lethal dose (LD) and LD50 in a suitable animal model e.g., rodent such as mouse; and, the dosage of the composition(s), concentration of components therein and timing of administering the composition(s), which elicit a suitable response. Such determinations do not require undue experimentation from the knowledge of the skilled artisan, this disclosure and the documents cited herein. And, the time for sequential administrations can be ascertained without undue experimentation.

VIII. Methods of Treatment

Tumor Microenvironment.

Tumors have a microenvironment that is hostile to the host immune response involving a series of mechanisms by malignant cells to protect themselves from immune recognition and elimination. This "hostile tumor microenvironment" comprises a variety of immune suppressive factors including infiltrating regulatory $CD4^+$ T cells (Tregs), myeloid derived suppressor cells (MDSCs), tumor associated macrophages (TAMs), immune suppressive cytokines including IL-10 and TGF-β, and expression of ligands targeted to immune suppressive receptors expressed by activated T cells (CTLA-4 and PD-1). These mechanisms of immune suppression play a role in the maintenance of tolerance and suppressing inappropriate immune responses, however within the tumor microenvironment these mechanisms prevent an effective anti-tumor immune response. Collectively these immune suppressive factors can induce either marked anergy or apoptosis of adoptively transferred CAR modified T cells upon encounter with targeted tumor cells.

Challenges in Tumor Immunology.

Effective tumor immunity requires recognition of tumor antigens and unopposed tumor elimination by immune effector cells. Tumor antigens must contain peptide epitopes that are presented by the tumor and can be recognized by specific cytotoxic T lymphocytes (CTLs). The primed CTLs must expand to a sufficient number and migrate to tumor sites, wherein they mature into effectors to perform their functions, which are enhanced by helper T cells and dampened by Tregs and inhibitory macrophages.

Targeted T Cell Therapy with Engineered T Lymphocytes.

T cell engineering is a groundbreaking strategy to potentially resolve many previously observed shortcomings of earlier immunotherapeutic approaches. Within the past year, researchers have reported dramatic complete remissions in relapsed[16,17], chemorefractory leukemia and metastatic melanoma[18-20], obtained with autologous peripheral blood T cells targeted to a defined antigen (CD19 and NY-ESO-1, respectively).

Rationale for a Genetic Approach:

Cell engineering can be used to redirect T cells toward tumor antigens and to enhance T cell function. One impetus for genetic T cell modification is the potential to enhance T cell survival and expansion and to offset T cell death, anergy, and immune suppression. The genetic targeting of T cells can also be refined to prevent undesired destruction of normal tissues.

Chimeric Antigen Receptors (CARs):

Tumor-specific T cells can be generated by the transfer of genes that encode CARs[21-26]. Second-generation CARs comprise a tumor antigen-binding domain fused to an intracellular signaling domain capable of activating T cells and a co-stimulatory domain designed to augment T cell potency and persistence[27]. CAR design can therefore reconcile antigen recognition with signal transduction, two functions that are physiologically borne by two separate complexes, the TCR heterodimer and the CD3 complex. The CAR's extracellular antigen-binding domain is usually derived from a murine monoclonal antibody (mAb) or from receptors or their ligands. Antigen recognition is therefore not MHC-restricted[28,29] and is therefore applicable to any patient expressing the target antigen, using the same CAR. Antigen binding by the CARs triggers phosphorylation of immunoreceptor tyrosine-based activation motifs (ITAMs) in the intracellular domain, initiating a signaling cascade required for cytolysis induction, cytokine secretion, and proliferation. Because MHC restriction of antigen recognition is bypassed, the function of CAR-targeted T cells is not affected by HLA downregulation or defects in the antigen-processing machinery.

T Cell Requirements for Expansion and Survival:

Proliferation of tumor-specific T cells is needed ex vivo and is arguably desirable in vivo. T cell proliferation must be accompanied by T cell survival to permit absolute T cell expansion and persistence. To proliferate in response to antigen, T cells must receive two signals. One is provided by TCR recognition of antigenic peptide/MHC complexes displayed on the surface of antigen-presenting cells (APCs)[25]. The other is provided by a T cell co-stimulatory receptor, such as the CD28 or 4-1BB receptors. Whereas the cytolytic activity of T cells does not require concomitant co-stimulation, there is a critical need for the provision of co-stimulatory signals to sustain the antitumor functions of adoptively transferred T cells, as previously demonstrated[23,27,30-32].

Immune Monitoring:

Lymphocytes are multifunctional "drugs" that exhibit dynamically evolving effects after infusion. Upon antigen encounter, tumor-specific T cells activate and/or release a variety of proteins that can trigger tumor killing, T cell proliferation, and recruitment or immunomodulation of other immune cells. Thus, measuring which proteins are secreted from which cells, in what quantity, and at what time point yields profound insights into why a particular patient is or is not responding and provides critical feedback for designing more-effective trials. These assay systems will permit direct and meaningful comparisons of clinical approaches and thus help design rational, next-generation therapeutic strategies.

For treatment, the amount administered is an amount effective in producing the desired effect. An effective amount can be provided in one or a series of administrations. An effective amount can be provided in a bolus or by continuous perfusion.

An "effective amount" (or, "therapeutically effective amount") is an amount sufficient to affect a beneficial or desired clinical result upon treatment. An effective amount can be administered to a subject in one or more doses. In terms of treatment, an effective amount is an amount that is sufficient to palliate, ameliorate, stabilize, reverse or slow the progression of the disease, or otherwise reduce the pathological consequences of the disease. The effective amount is generally determined by the physician on a case-by-case basis and is within the skill of one in the art. Several factors are typically taken into account when determining an appropriate dosage to achieve an effective amount. These factors include age, sex and weight of the subject, the condition being treated, the severity of the condition and the form and effective concentration of the immunoresponsive cells administered.

For adoptive immunotherapy using antigen-specific T cells, cell doses in the range of about $10^6$ to about $10^{10}$ (e.g., about $10^9$) are typically infused. Upon administration of the immunoresponsive cells into the subject and subsequent differentiation, the immunoresponsive cells are induced that are specifically directed against one specific antigen (e.g., BCMA). "Induction" of T cells can include inactivation of antigen-specific T cells such as by deletion or anergy. Inactivation is particularly useful to establish or reestablish tolerance such as in autoimmune disorders. The immunoresponsive cells of the presently disclosed subject matter can be administered by any methods known in the art, including, but not limited to, pleural administration, intravenous administration, subcutaneous administration, intranodal administration, intratumoral administration, intrathecal administration, intrapleural administration, intraperitoneal administration, and direct administration to the thymus. In certain embodiments, the immunoresponsive cells and the compositions comprising thereof are intravenously administered to the subject in need.

The presently disclosed subject matter provides various methods of using the immunoresponsive cells (e.g., T cells) expressing a BCMA-targeted CAR. For example, the presently disclosed subject matter provides methods of reducing tumor burden in a subject. In one non-limiting example, the method of reducing tumor burden comprises administering an effective amount of the presently disclosed immunoresponsive cell to the subject, thereby inducing tumor cell death in the subject. The presently disclosed immunoresponsive cell can reduce the number of tumor cells, reduce tumor size, and/or eradicate the tumor in the subject. Non-limiting examples of suitable tumor include multiple myeloma, Non-Hodgkin Lymphoma, Hodgkin Lymphoma, Chronic Lymphocytic Leukemia (CLL), glioblastoma, and Waldenstrom's Macroglobulinemia. In certain embodiments, the tumor is multiple myeloma.

The presently disclosed subject matter also provides methods of increasing or lengthening survival of a subject having a neoplasia. In one non-limiting example, the method of increasing or lengthening survival of a subject having neoplasia comprises administering an effective amount of the presently disclosed immunoresponsive cell to the subject, thereby increasing or lengthening survival of the subject. The method can reduce or eradicate tumor burden in the subject. The presently disclosed subject matter further provides methods for treating or preventing a neoplasia in a subject, comprising administering the presently disclosed immunoresponsive cell to the subject.

As used herein, the term "neoplasia" refers to a disease characterized by the pathological proliferation of a cell or tissue and its subsequent migration to or invasion of other tissues or organs. Neoplasia growth is typically uncontrolled and progressive, and occurs under conditions that would not elicit, or would cause cessation of, multiplication of normal cells. Neoplasias can affect a variety of cell types, tissues, or organs, including but not limited to an organ selected from the group consisting of bladder, colon, bone, brain, breast, cartilage, glia, esophagus, fallopian tube, gallbladder, heart, intestines, kidney, liver, lung, lymph node, nervous tissue, ovaries, pleura, pancreas, prostate, skeletal muscle, skin, spinal cord, spleen, stomach, testes, thymus, thyroid, trachea, urogenital tract, ureter, urethra, uterus, and vagina, or a tissue or cell type thereof. Neoplasias include cancers, such as sarcomas, carcinomas, or plasmacytomas (malignant tumor of the plasma cells).

Cancers whose growth may be inhibited using the immunoresponsive cells of the presently disclosed subject matter comprise cancers typically responsive to immunotherapy. Non-limiting examples of cancers for treatment include multiple myeloma, Non-Hodgkin Lymphoma, Hodgkin Lymphoma, Chronic Lymphocytic Leukemia (CLL), glioblastoma, and Waldenstrom's Macroglobulinemia. In certain embodiments, the cancer is multiple myeloma.

Additionally, the presently disclosed subject matter provides methods of increasing immune-activating cytokine production in response to a cancer cell in a subject. In one non-limiting example, the method comprises administering the presently disclosed immunoresponsive cell to the subject. The immune-activating cytokine can be granulocyte macrophage colony stimulating factor (GM-CSF), IFN-α, IFN-β, IFN-γ, TNF-α, IL-2, IL-3, IL-6, IL-11, IL-7, IL-12, IL-15, IL-21, interferon regulatory factor 7 (IRF7), and combinations thereof. In certain embodiments, the immunoresponsive cells including a BCMA-specific CAR of the presently disclosed subject matter increase the production of GM-CSF, IFN-γ, and/or TNF-α.

Suitable human subjects for therapy typically comprise two treatment groups that can be distinguished by clinical criteria. Subjects with "advanced disease" or "high tumor burden" are those who bear a clinically measurable tumor (e.g., multiple myeloma). A clinically measurable tumor is one that can be detected on the basis of tumor mass (e.g., by palpation, CAT scan, sonogram, mammogram or X-ray; positive biochemical or histopathologic markers on their own are insufficient to identify this population). A pharmaceutical composition embodied in the presently disclosed subject matter is administered to these subjects to elicit an anti-tumor response, with the objective of palliating their condition. Ideally, reduction in tumor mass occurs as a result, but any clinical improvement constitutes a benefit. Clinical improvement comprises decreased risk or rate of progression or reduction in pathological consequences of the tumor (e.g., multiple myeloma).

A second group of suitable subjects is known in the art as the "adjuvant group." These are individuals who have had a history of neoplasia (e.g., multiple myeloma), but have been responsive to another mode of therapy. The prior therapy can have included, but is not restricted to, surgical resection, radiotherapy, and traditional chemotherapy. As a result, these individuals have no clinically measurable tumor. However, they are suspected of being at risk for progression of the disease, either near the original tumor site, or by metastases. This group can be further subdivided into high-risk and low-risk individuals. The subdivision is made on the basis of features observed before or after the initial treatment. These features are known in the clinical arts, and are suitably defined for each different neoplasia. Features typical of high-risk subgroups are those in which the tumor (e.g., multiple myeloma) has invaded neighboring tissues, or who show involvement of lymph nodes. Another group has a genetic predisposition to neoplasia (e.g., multiple myeloma) but has not yet evidenced clinical signs of neoplasia (e.g., multiple myeloma). For instance, women testing positive for a genetic mutation associated with breast cancer, but still of childbearing age, can wish to receive one or more of the antigen-binding fragments described herein in treatment prophylactically to prevent the occurrence of neoplasia until it is suitable to perform preventive surgery.

The subjects can have an advanced form of disease (e.g., multiple myeloma), in which case the treatment objective can include mitigation or reversal of disease progression, and/or amelioration of side effects. The subjects can have a history of the condition, for which they have already been treated, in which case the therapeutic objective will typically include a decrease or delay in the risk of recurrence.

Further modification can be introduced to the BCMA-targeted CAR-expressing immunoresponsive cells (e.g., T cells) to avert or minimize the risks of immunological complications (known as "malignant T-cell transformation"), e.g., graft versus-host disease (GvHD), or when healthy tissues express the same target antigens as the tumor cells, leading to outcomes similar to GvHD. A potential solution to this problem is engineering a suicide gene into the CAR-expressing T cells. Suitable suicide genes include, but are not limited to, Herpes simplex virus thymidine kinase (hsv-tk), inducible Caspase 9 Suicide gene (iCasp-9), and a truncated human epidermal growth factor receptor (EGFRt) polypeptide. In certain embodiments, the suicide gene is an EGFRt polypeptide. The EGFRt polypeptide can enable T cell elimination by administering anti-EGFR monoclonal antibody (e.g., cetuximab). EGFRt can be covalently joined to the 3' terminus of the intracellular domain of the BCMA-targeted CAR. The suicide gene can be included within the vector comprising nucleic acids encoding the presently disclosed BCMA-targeted CARs. In this way, administration of a prodrug designed to activate the suicide gene (e.g., a prodrug (e.g., AP1903 that can activates iCasp-9) during malignant T-cell transformation (e.g., GVHD) triggers apoptosis in the suicide gene-activated CAR-expressing T cells.

IX. Kits

The presently disclosed subject matter provides kits for the treatment or prevention of a neoplasia (e.g., multiple myeloma). In certain embodiments, the kit comprises a therapeutic or prophylactic composition containing an effective amount of an immunoresponsive cell comprising a BCMA-targeted CAR in unit dosage form. In particular embodiments, the cells further expresses at least one co-stimulatory ligand. In certain embodiments, the kit comprises a sterile container which contains a therapeutic or prophylactic vaccine; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

If desired, the immunoresponsive cell is provided together with instructions for administering the cell to a subject having or at risk of developing a neoplasia (e.g., multiple myeloma). The instructions will generally include information about the use of the composition for the treatment or prevention of a neoplasia (e.g., multiple myeloma). In other embodiments, the instructions include at least one of the following: description of the therapeutic agent; dosage schedule and administration for treatment or prevention of a neoplasia (e.g., multiple myeloma) or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

EXAMPLES

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

Example 1—BCMA Expression in Various Tissues

The Expression of human BCMA was evaluated in various malignant and normal tissues by investigating gene expression profiles in databases such as the cancer cell line encyclopedia and BioGPS. As shown in FIGS. 2A-2D, human BCMA was highly expressed in lymphoma and multiple myeloma, but not in other malignant tissues. Normal expression appeared limited to B-cells and plasma cells. Potential BCMA targeted CAR T cell eradication of these normal cell types may not have significant adverse effects based on inventors' patient experience with CD19 targeted CAR T cells. Any lack of physiologic antibody production can be addressed with intravenous immunoglobulin treatment.

Example 2—Construct of BCMA-Specific 28z CARs

Multiple unique fully human scFv's to BCMA were generated, and CARs based on these scFv's were generated. Multiple scFv's were identified by screening a fully human scFv phage library (>6×10$^{10}$ scFv's) with BCMA-Fc fusion protein and then 3T3 cells expressing human BCMA. After sequencing, 57 unique and BCMA-Fc positive clones were found out of 79 sequenced positive clones; the unique clone rate was 72%. FACS analysis of phage antibody clones against BCMA-3T3 and parental 3T3 cell lines resulted in confirming 25 unique positive clones.

ET140-153 scFv (or "ET140-3 scFv"), ET140-174 scFv (or "ET140-24 scFv"), ET140-187 scFv (or "ET140-37 scFv"), ET140-190 scFv (or "ET140-40 scFv"), and ET140-204 scFv (or "ET140-54 scFv") were used to generate BCMA-targeted 28z CARs 3, 24, 37, 40, and 54, respectively. These BCMA-targeted 28z CARs have similar structure, e.g., each has a transmembrane domain comprising a CD28 polypeptide, and an intracellular domain comprising a CD3ξ polypeptide and a co-stimulatory signaling region that comprises a CD28 polypeptide, as shown in FIG. 1. Each of these BCMA-targeted CARs were cloned into a retroviral vector. These viral vectors were then transduced into HEK 293galv9 viral packaging cells in order to generate a stable packaging line for generation of CAR$^+$ T cells.

Figure 3:
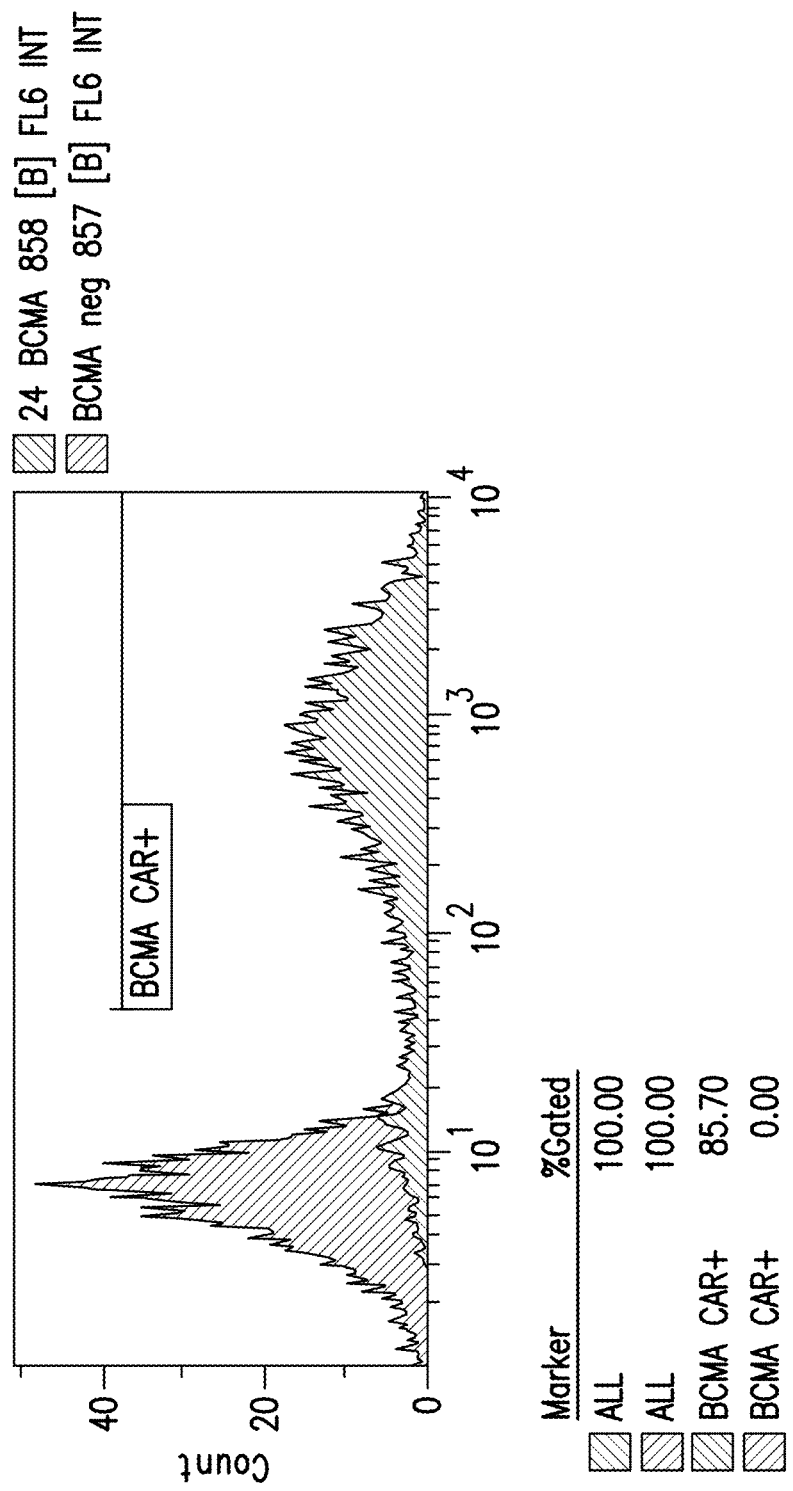
FIG. 3 depicts expression of the presently disclosed BCMA CAR on human T cells.

Human T cells (unselected (CD4 and CD8) human T cells from a healthy donor) were transduced with retrovirus in order to express each of these BCMA-targeted CARs such that the T cells expressed these BCMA-targeted 28z CARs. The cell surface expression of BCMA-targeted CARs on human T cells was determined via binding A647 conjugated BCMA-Fc fusion protein. The cell surface expression of BCMA-targeted 28z CAR24 was assessed, and cell surface detection was valided by flow cytometry, as shown in FIG. 3.

Figure 4:
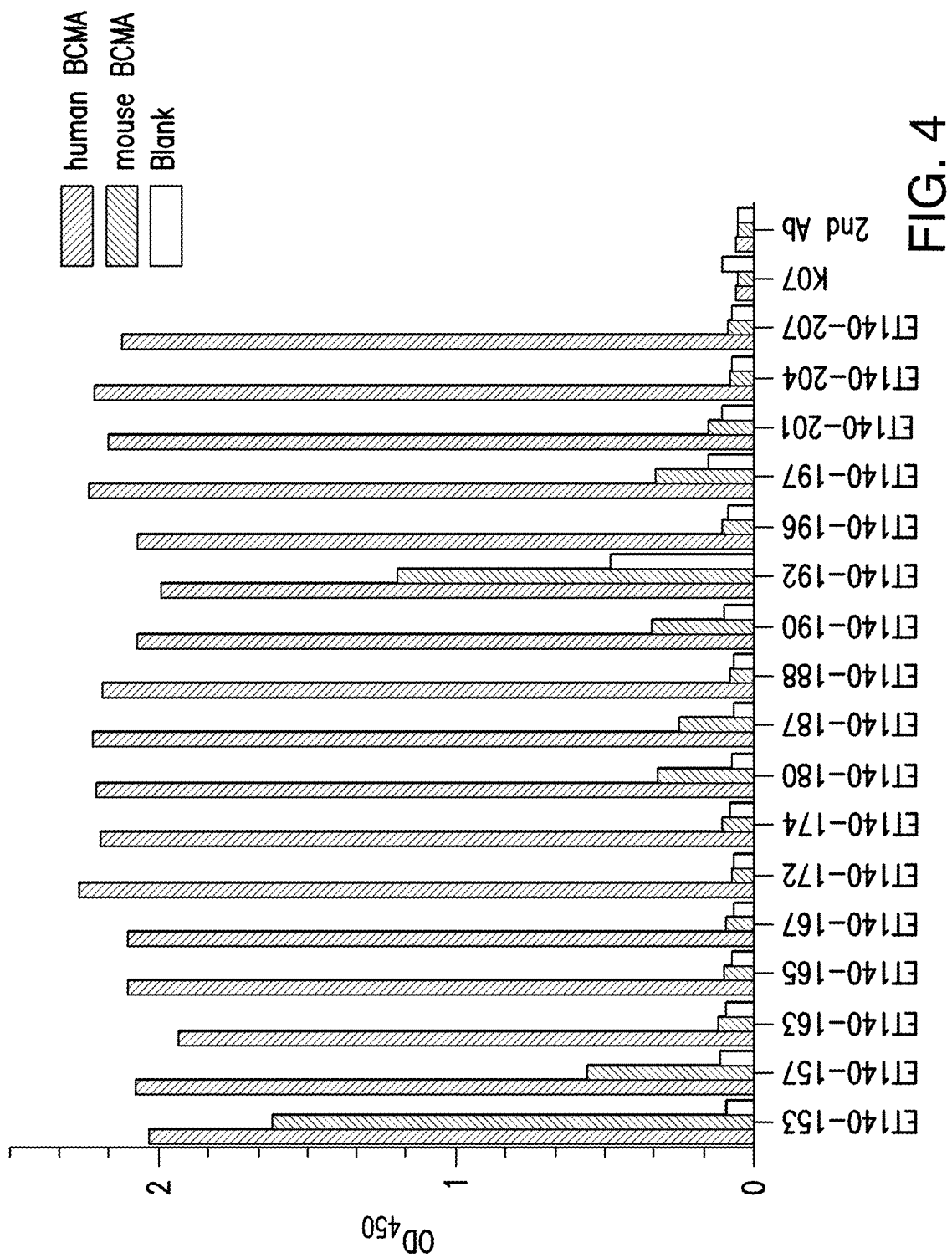
FIG. 4 depicts the cross-reacting activity of human scFv's targeting human BCMA with mouse BCMA.

The cross-reacting activity of seventeen human scFv's between human BCMA and mouse BCMA was assessed. As shown in FIG. 4, certain scFv's, e.g., ET140-153 scFv (or "ET140-3 scFv") and ET140-192 scFv (or "ET140-42 scFv") cross-reacted with mouse BCMA, thus, this scFv can be used for syngeneic mouse studies.

Example 3—Activity of BCMA-Specific CARs

Figure 5:
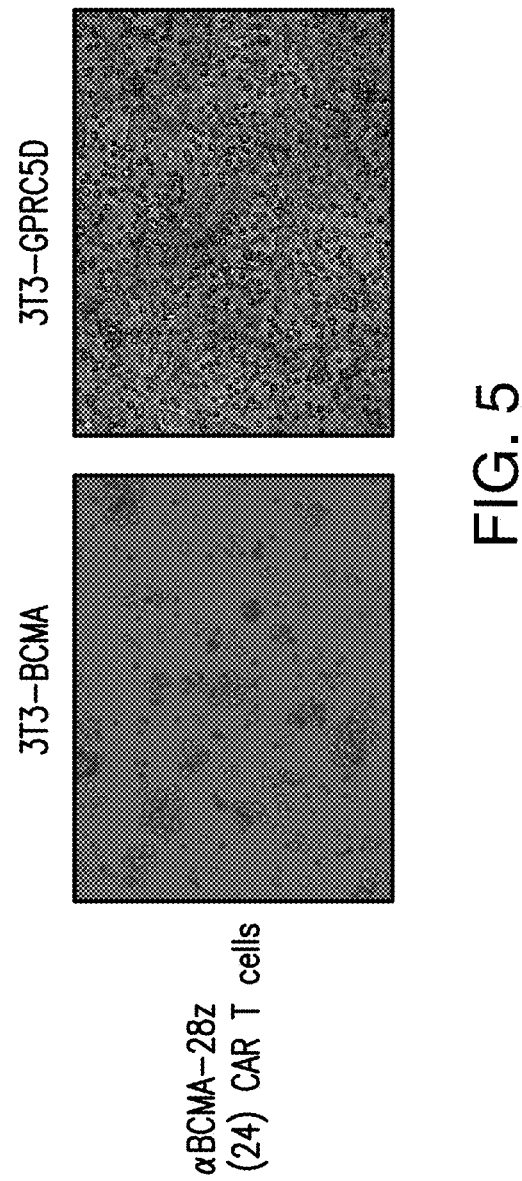
FIG. 5 depicts the killing activity of the presently disclosed BCMA for 3T3 cells overexpressing BCMA.
Figure 6:
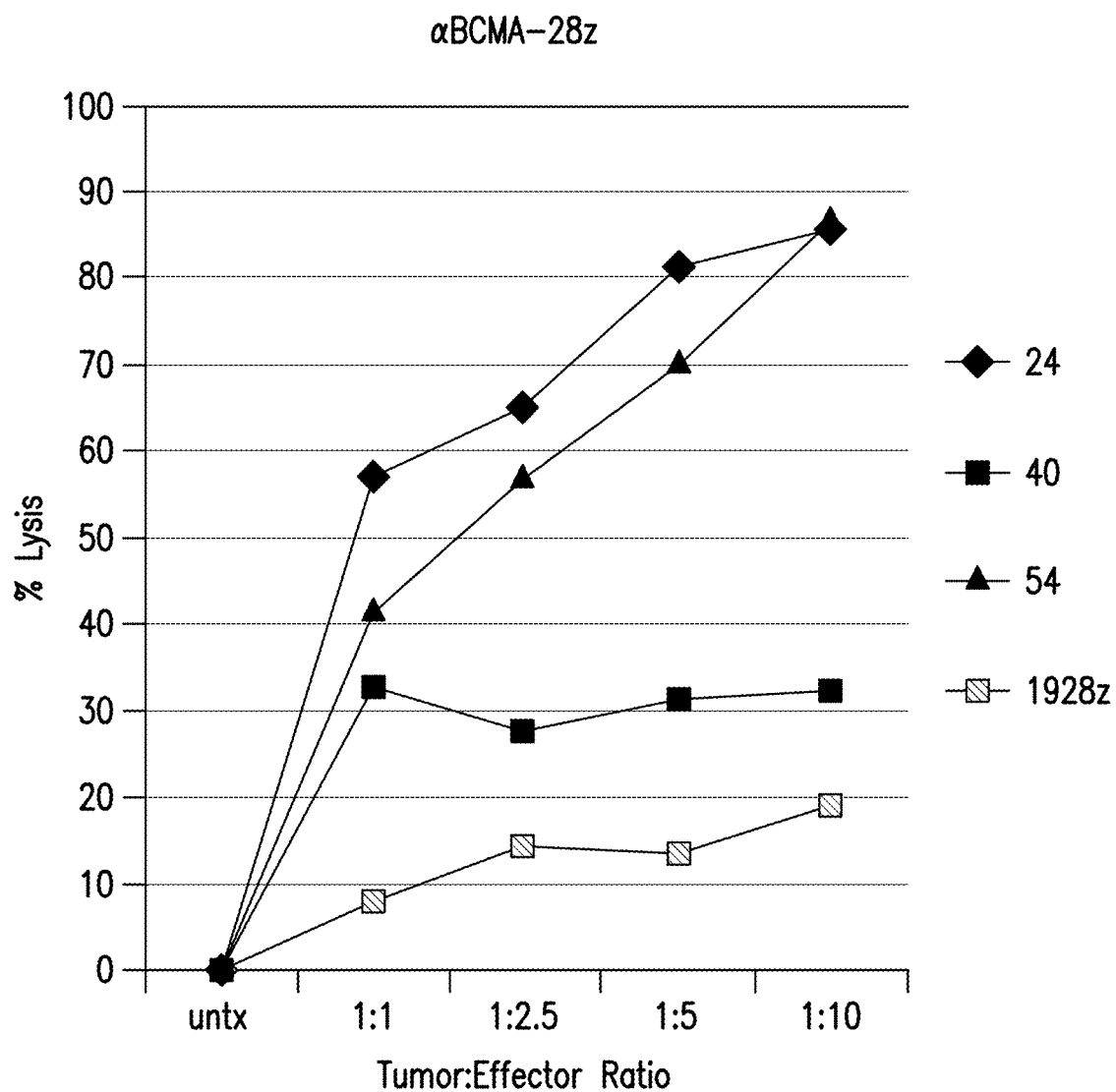
FIG. 6 depicts the killing activity of the presently disclosed BCMA for a human multiple myeloma cell line.

The anti-tumor activity of the presently disclosed BCMA-specific 28z CARs was evaluated. The in vitro data showed that the BCMA-specific CARs specifically killed BCMA presenting cells, including MINI cell lines. For example, as shown in FIG. 5, the T cells expressing the BCMA-specific 28z CAR24 killed 3T3 cells overexpressing BCMA (but not control 3T3s overexpressing an irrelevant antigen). As shown in FIG. 6, the T cells expressing the BCMA-specific 28z CARs 24, 40, and 54 killed human MM cell lines.

Example 4—Screening Data for Anti-BCMA Antibodies

Figure 21:
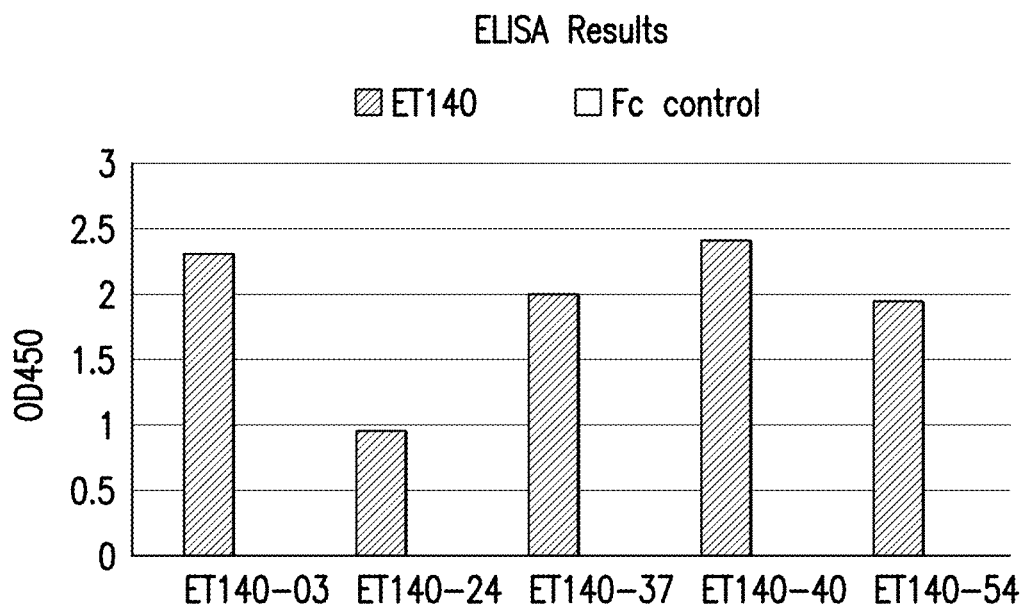
FIG. 21 depicts ELISA screening data of ET140-3, ET140-24, ET140-37, ET140-40, and ET140-54.
Figure 22A:
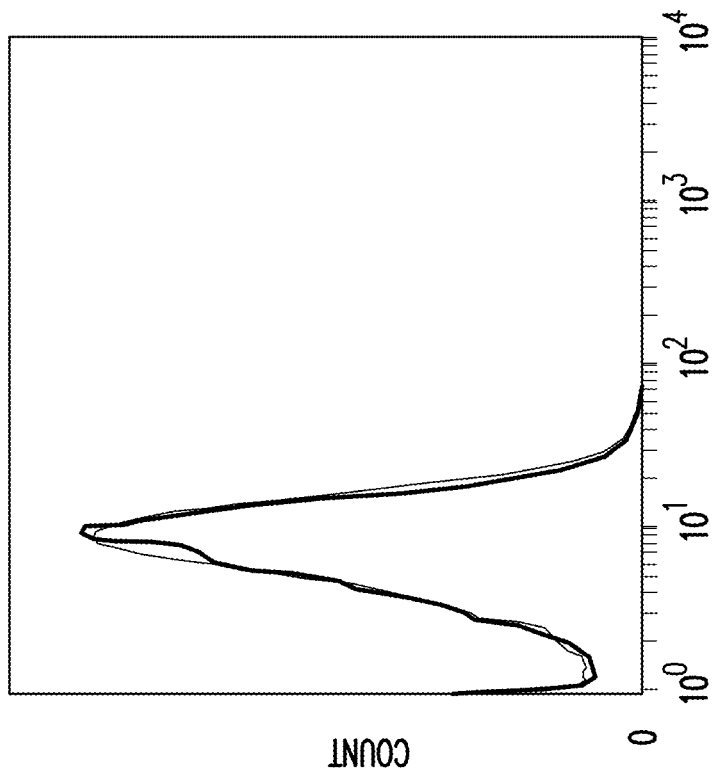
FIGS. 22A-22D depict FCAS screening data of ET140-3 (FIG. 22B), ET140-24 (FIG. 22C), ET140-37 (FIG. 22C), ET140-40 (FIG. 22D), and ET140-54 (FIG. 22D).
Figure 22A:
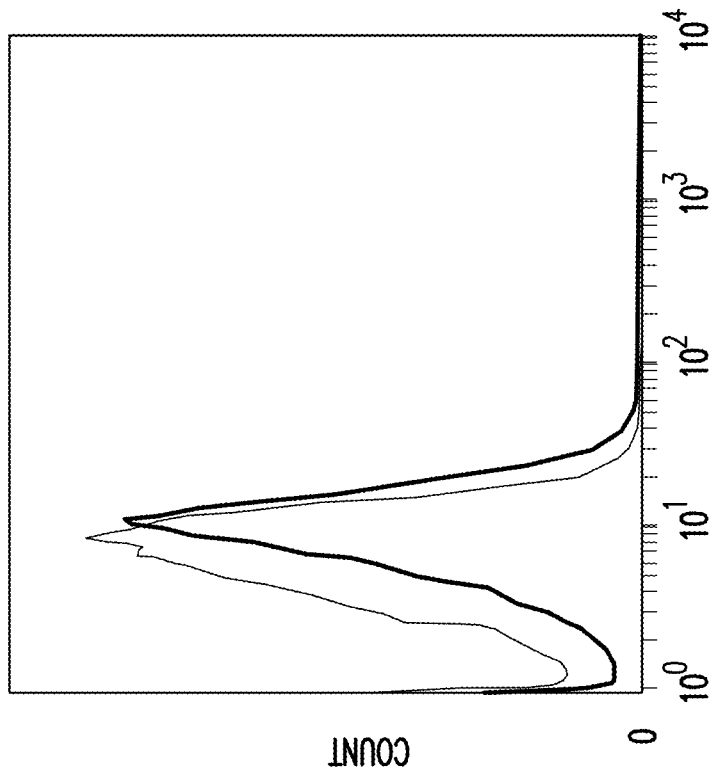
Figure 22B:
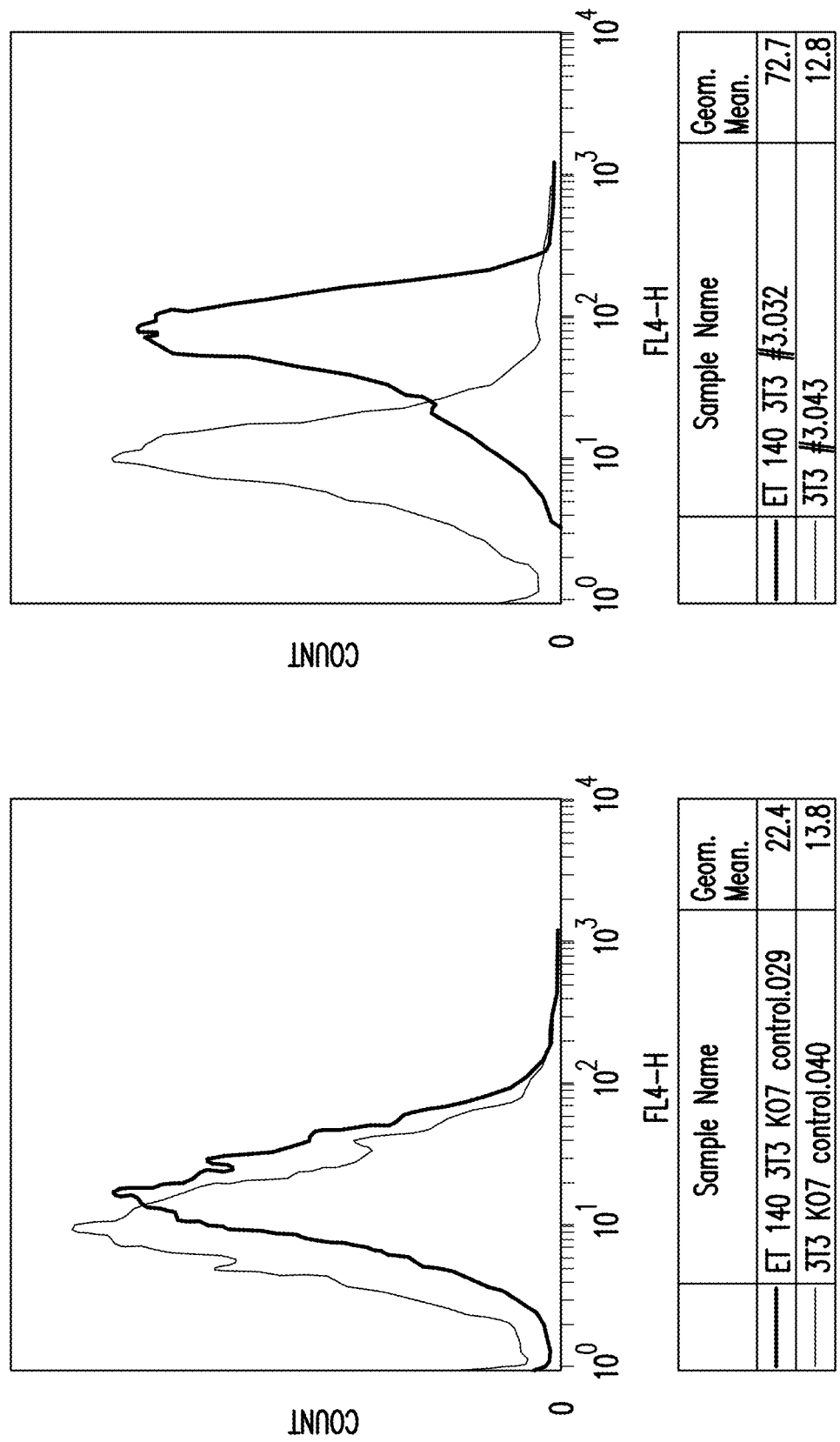
Figure 22C:
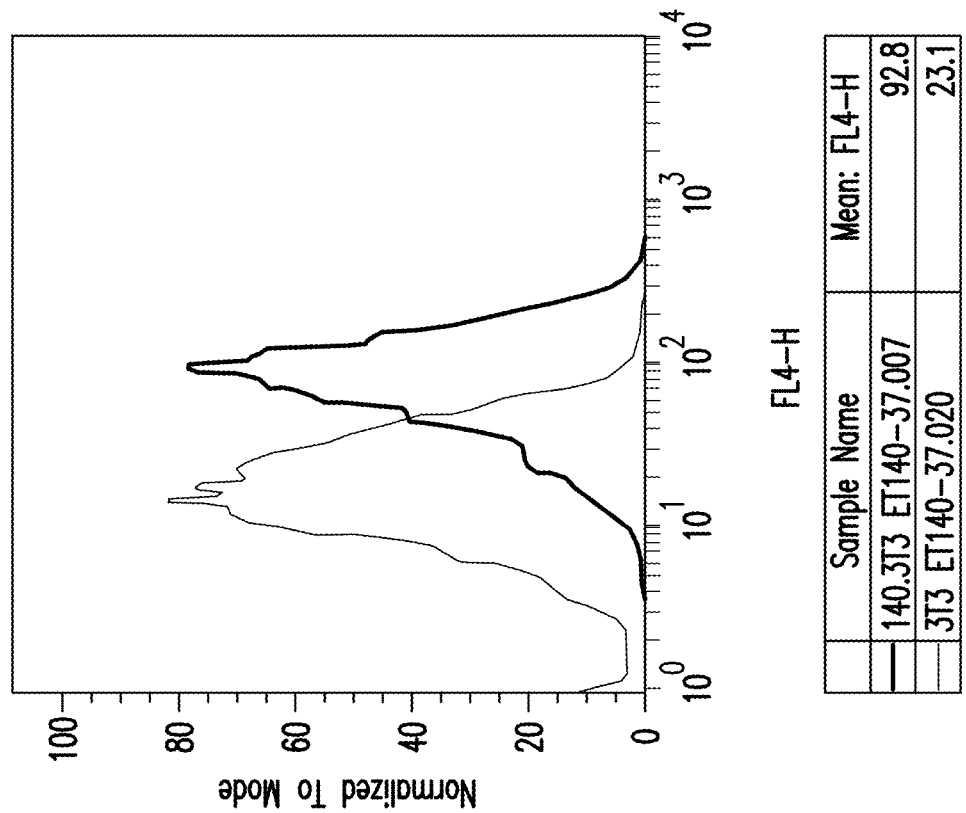
Figure 22C:
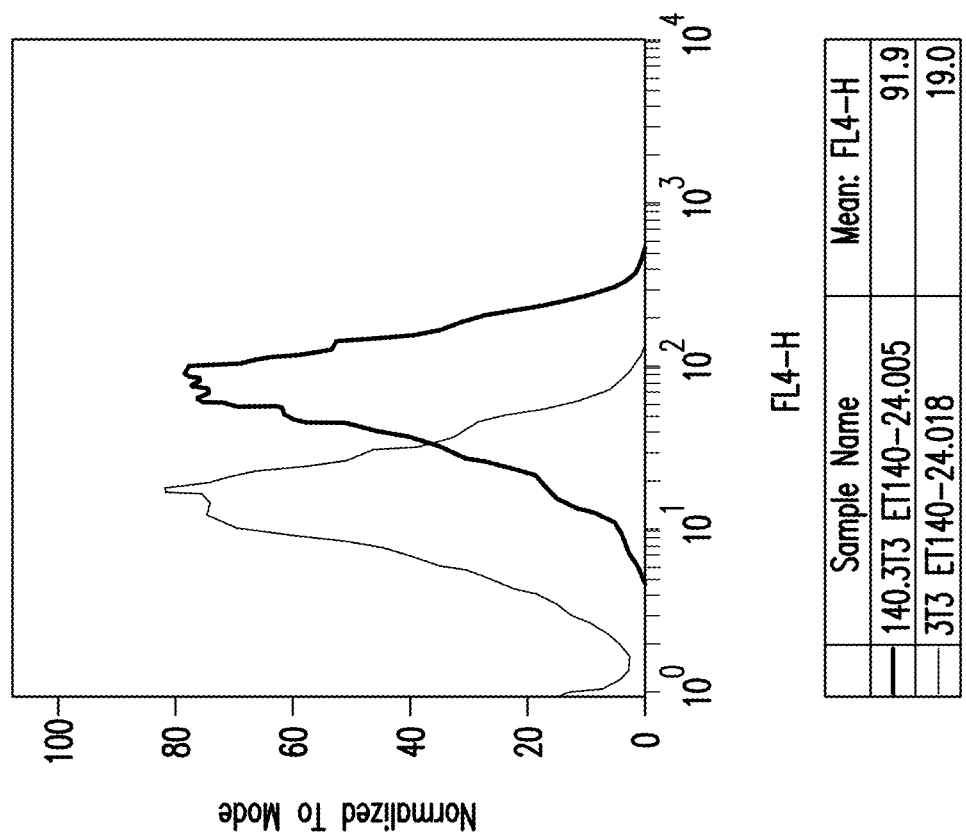
Figure 22D:
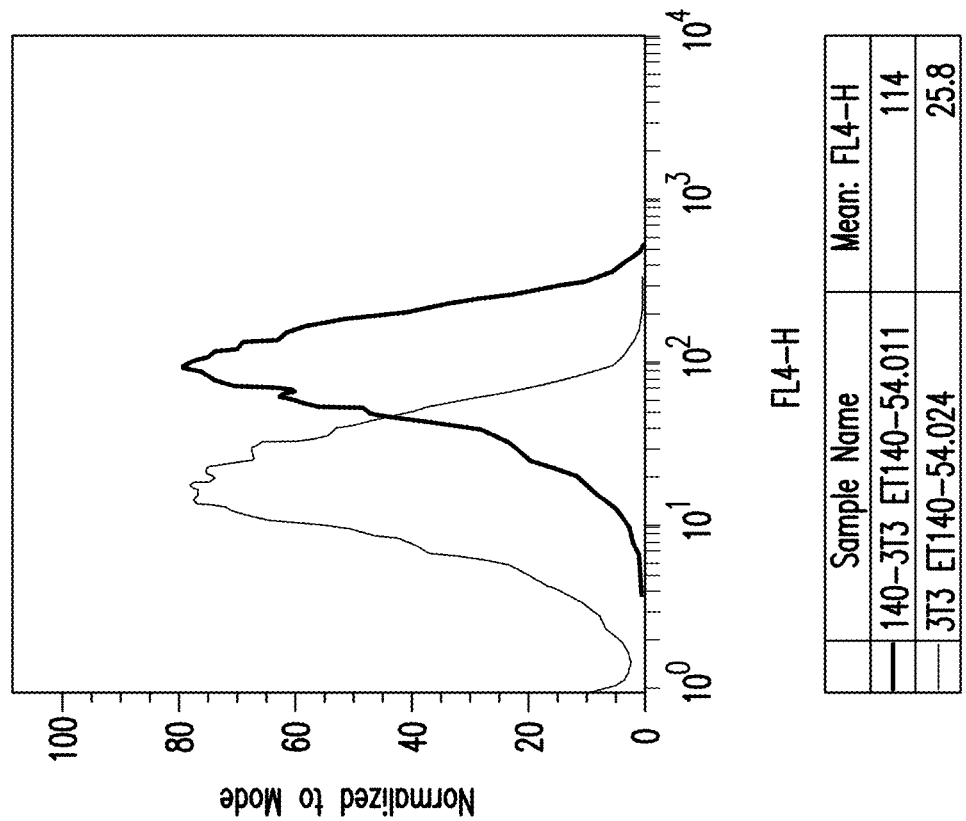
Figure 22D:
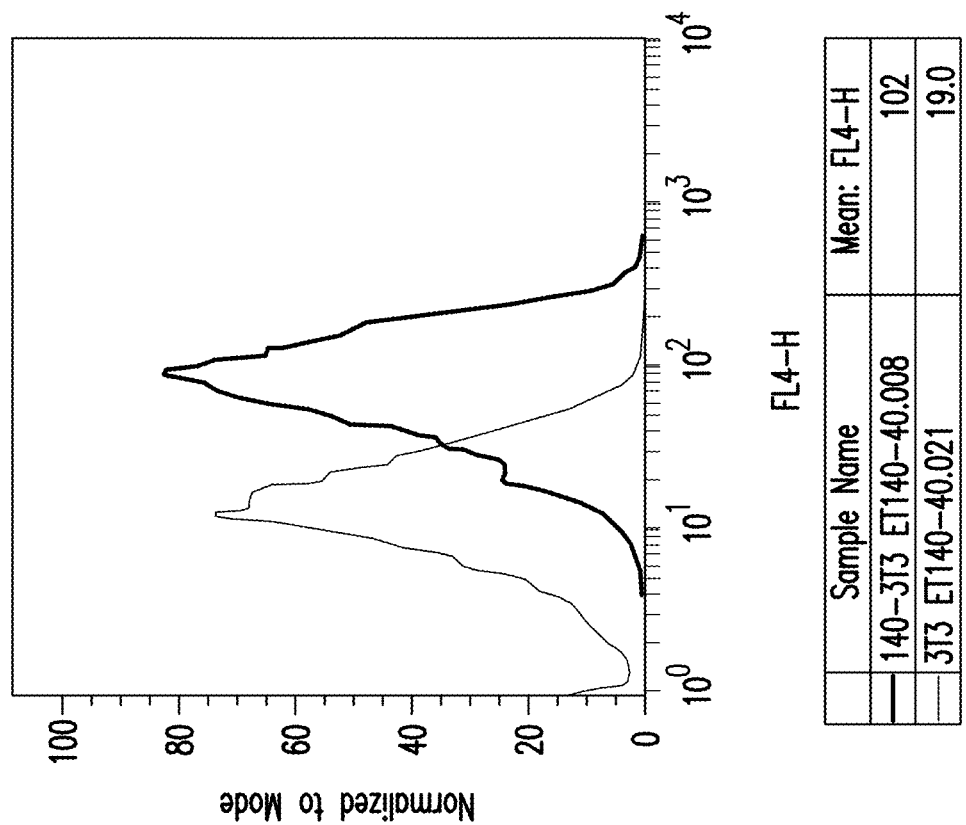

ELISA Screening:
FIG. 21 shows the representative results of protein ELISA screening against BCMA antigen using specific scFv phage antibody clones (ET140-3, ET140-24, ET140-37, ET140-40 and ET140-54). ELISA plates were coated with human BCMA ECD-Fc fusion protein, control-Fc fusion protein, or PBS alone as blank control, respectively. Individual phage clones from enriched phage display panning pools against BCMA ECD-Fc fusion protein were incubated in the coated plates. Binding of the phage clones was detected by HRP-conjugated anti-M13 antibodies and developed using TMB substrate. The absorbance was read at 450 nm.

FACS Screening:
FIGS. 22A-22D show a representative figure of a FACS analysis of the BCMA-specific phage antibody clones ET140-3, ET140-24, ET140-37, ET140-40 and ET140-54. Phage clones were incubated with 3T3-BCMA cell line, then with anti-M13 mouse antibody. Finally APC-labeled anti-mouse IgG 2nd antibody was added to the reaction after washing again. The binding was measured by FACS and expressed as mean fluorescence intensity (MFI). Cells incubated with 2nd antibody alone, M13 K07 helper phage and cells only were used as negative controls.

Example 5—Construct of BCMA-Specific BBz CARs

Multiple unique fully human scFv's to BCMA were generated as described in Example 2. ET140-153 scFv (or "ET140-3 scFv"), ET140-174 scFv (or "ET140-24 scFv"), ET140-187 scFv (or "ET140-37 scFv"), ET140-190 scFv (or "ET140-40 scFv"), and ET140-204 scFv (or "ET140-54 scFv") were used to generate BCMA-targeted BBz CARs 3, 24, 37, 40, and 54, respectively. Each of these BCMA-targeted BBz CARs has a transmembrane domain comprising a CD8 polypeptide, and an intracellular domain comprising a CD3ξ polypeptide and a co-stimulatory signaling region that comprises a 4-1BB polypeptide, as shown in FIG. 7. Each of these BCMA-targeted CARs were cloned into an SFG retroviral vector, as an example the 4-1BB containing CAR vectors are shown in FIGS. 8-12.

Example 6—Activity of BCMA-Targeted CAR T Cells

Figure 13:
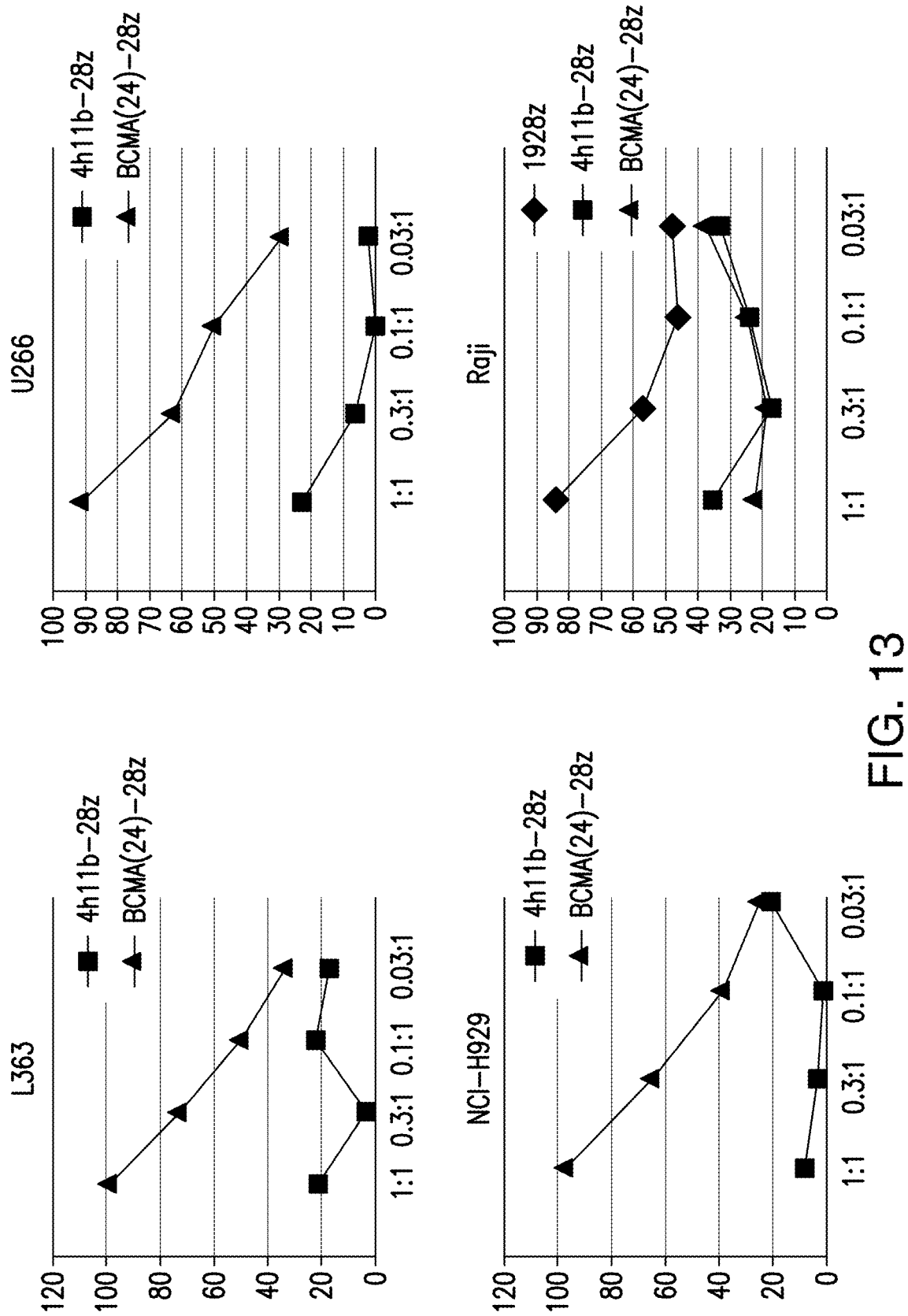
FIG. 13 depicts the cytotoxicity of BCMA targeted CAR T cells for human multiple myeloma cell lines.

As shown in FIG. 13, BCMA-specific 28z CAR24 lysed human MM cell lines L363, NCL-H929, and U266, compared to irrelevantly targeted 4h11-28z MUC16 targeted CAR T cells. The cytotoxicity exhibited by observed BCMA-specific 28z CAR24 was specific to BCMA, as it did not lyse BCMA negative CD19 positive Raji Burkett lymphoma cell line, as shown in FIG. 13.

Example 7—Induction of Cytokine Secretion by BCMA-Targeted CAR T Cells

Figure 14:
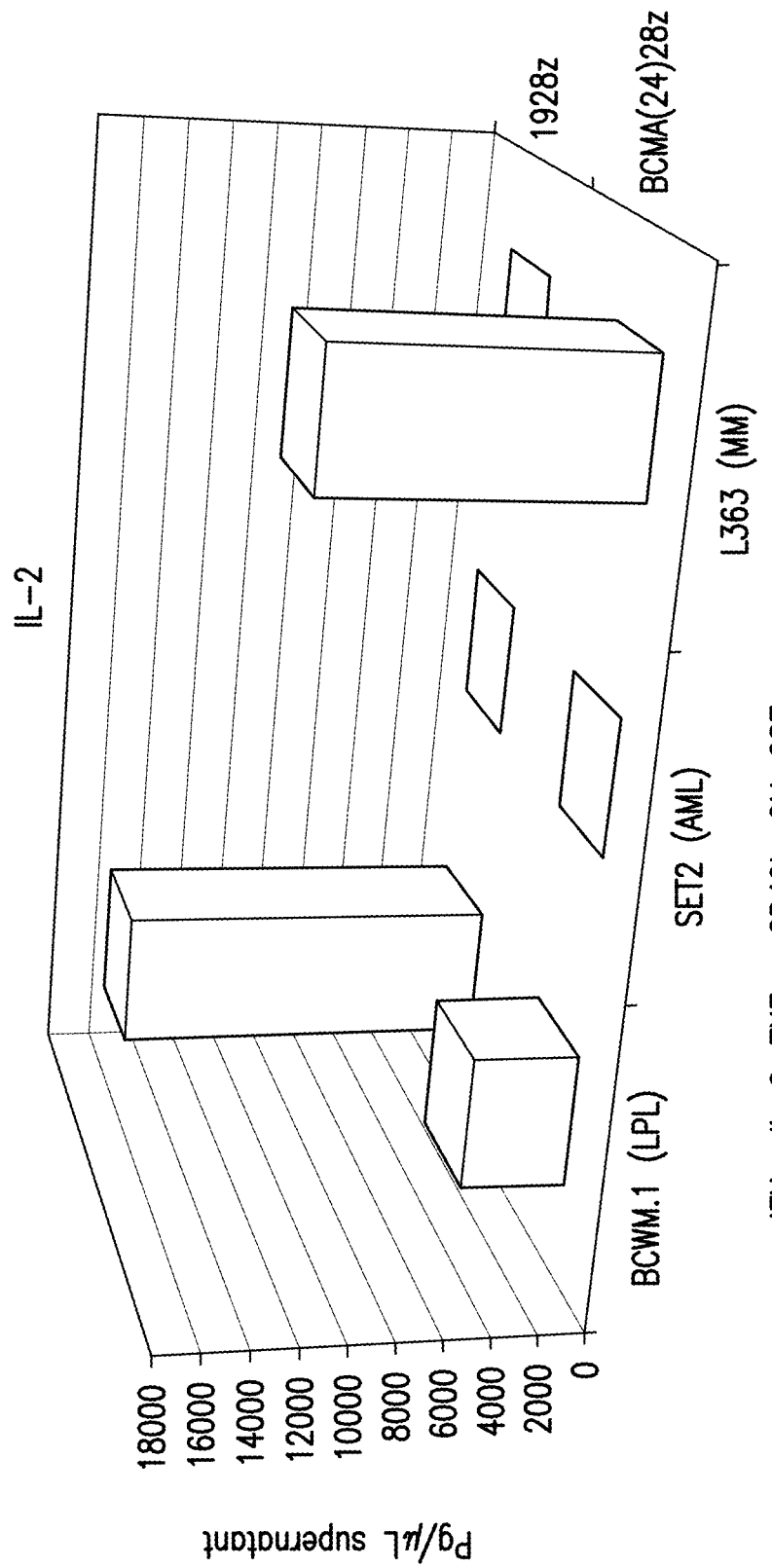
FIG. 14 depicts induction of cytokine secretion of BCMA targeted CAR T cells.

Co-culture of BCMA targeted 28z CAR24 T cells specifically with MM cell line induced cytokine secretion profile consistent with T cell activation. FIG. 14 shows the IL-2 secretion after 24 h co-culture of CAR T cells with human tumor cell lines (E:T ratio 1:1). The lymphoplasmacytic lymphoma (CD19$^+$) with CD19 targeted CAR T cells (positive control) and the MM cell line with the BCMA targeted 28z CAR24 T cells displayed increased cytokine production. IFNg, IL-6, TNFa, sCD40L, GM-CSF all had similar secretion profiles (data not shown).

Example 8—Anti-Tumor Activity of BCMA-Targeted CAR T Cells

Figure 15:
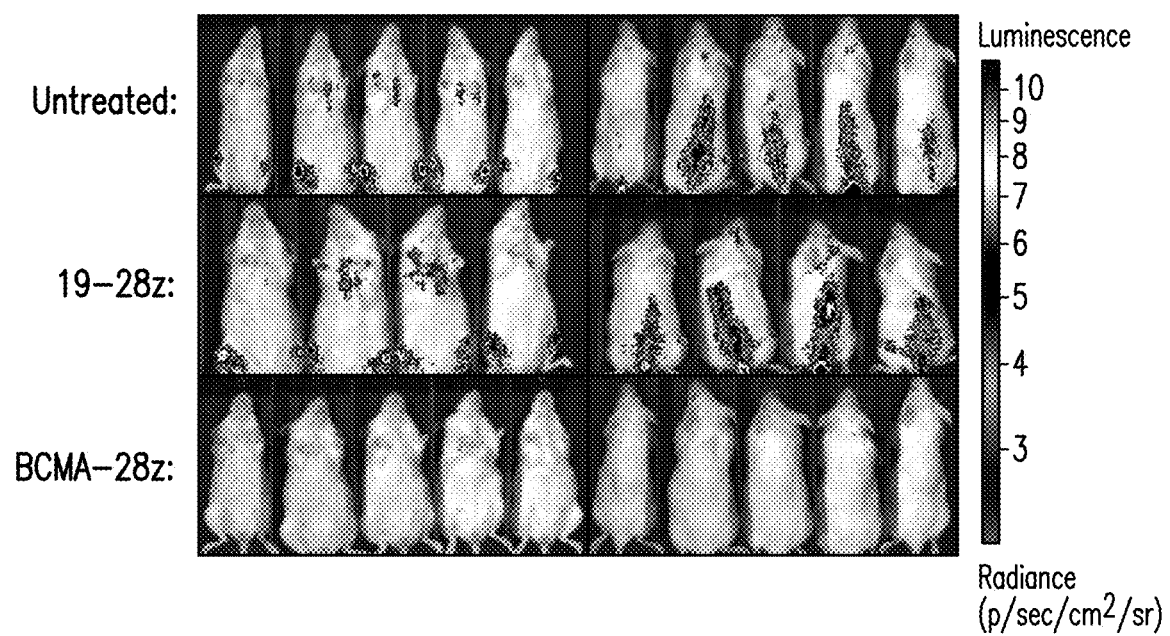
FIG. 15 depicts anti-tumor activity of BCMA targeted CAR T cells.

BCMA targeted 28z CAR54 T cells mediated an anti-myeloma immune response. $1 \times 10^7$ U266 human myeloma cell line cells were injected IV into NSG mice on day 0. On day 4 $1 \times 10^6$ BCMA targeted or CD19 targeted second generation CAR T cells were injected IV. Imaging on day 11 (day 7 s/p CAR T cell injection) shows that, unlike irrelevant (CD19) targeted CAR T cells; BCMA targeted 28z CAR54 T cells can mediate an anti-tumor response. See FIG. 15.

Example 9—Activity of BCMA-Targeted CAR T Cells

Figure 16A:
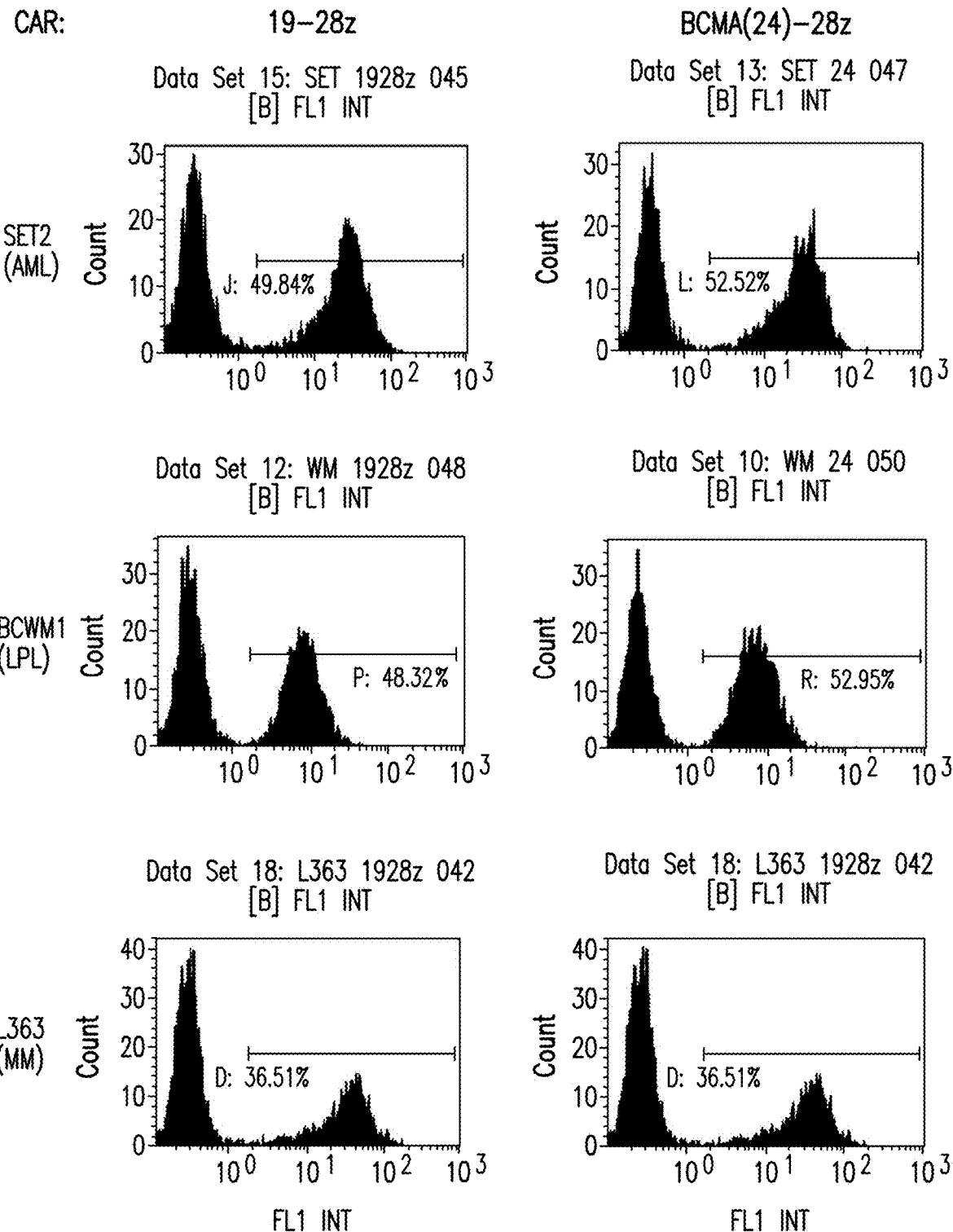
FIGS. 16A and 16B depict the killing activity of BCMA targeted CAR T cells. (A) Shows the percent of GFP+ tumor line at time 0. (B) Shows the killing the percent of GFP+ tumor line at time 36 hours.
Figure 16B:
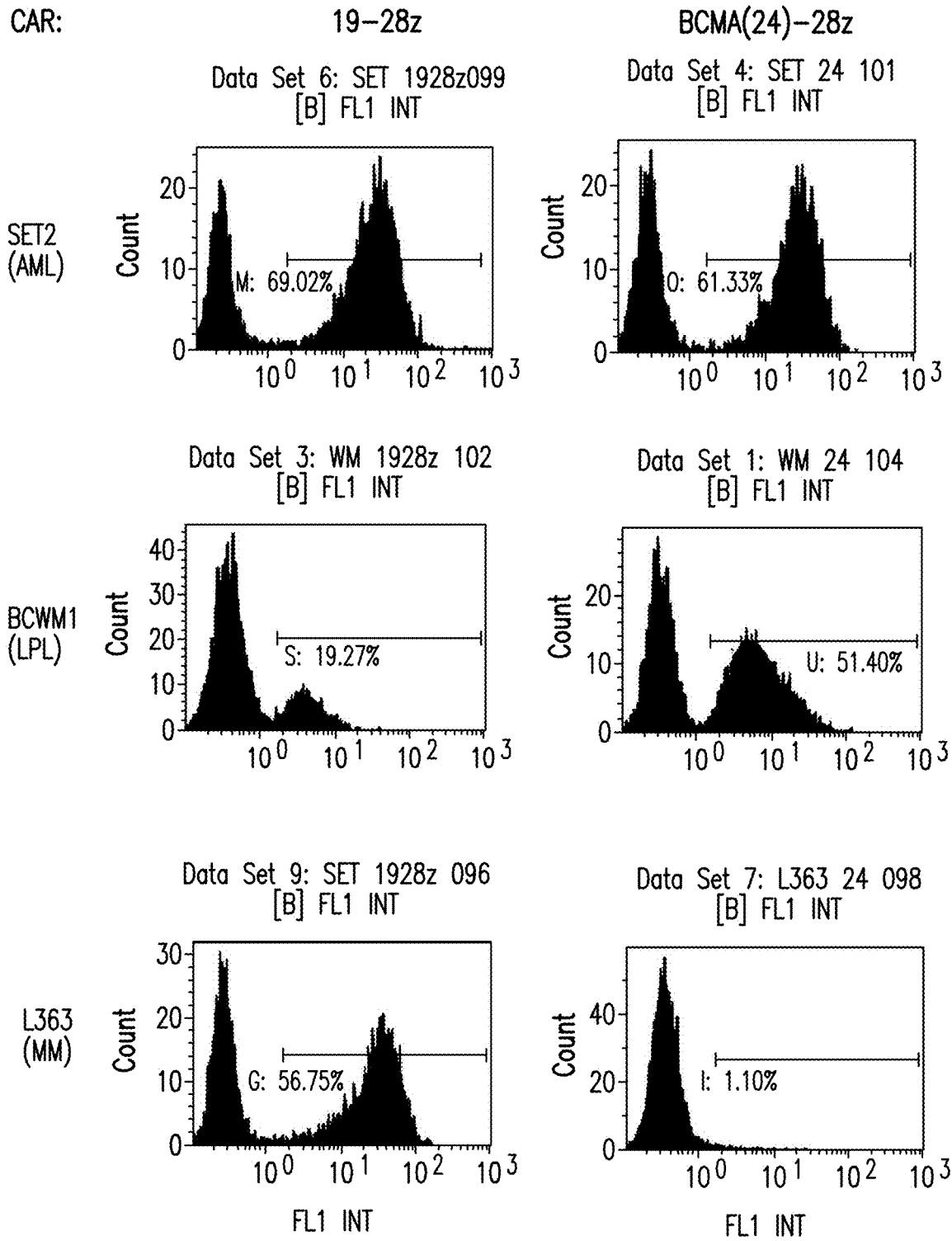

The ability of BCMA targeted CAR T cells to specifically lyse human myeloma cell line (HMCL) was tested. CD19 targeted CAR T cells or BCMA targeted 28z CAR24 T cells were incubated with GFP expressing tumor cell lines SET2 (Acute myeloid leukemia (AML), CD19$^-$BCMA$^-$); BCWM1 (Lymphoplasmacytic Lymphoma (LPL), CD19$^-$BCMA$^-$); L363 (Multiple Myeloma (MM), CD19$^-$BCMA$^+$). At time 0, the percent of GFP$^+$ tumor line is shown in FIG. 16A. At 36 h the positive control CD19 targeted CAR T cells have specifically killed the GFP$^+$ LPL line, and similarly the BCMA targeted 28z CAR24 T cells have specifically killed the GFP$^+$ MM line. See FIG. 16B.

Example 10—Epitope Mapping of Anti-BCMA Antibodies

BCMA peptides were ordered based on the ECD sequence with N-terminal Biotin+SGSG linker+15 amino acids with 1 amino acid space. The peptide library is shown in Table 24.

TABLE 24

| | | |
|---|---|---|
| ET140-p1 | SGSGLQMAGQCSQNEYFDS | [SEQ ID NO: 236] |
| ET140-p2 | SGSGQMAGQCSQNEYFDSL | [SEQ ID NO: 237] |
| ET140-p3 | SGSGMAGQCSQNEYFDSLL | [SEQ ID NO: 238] |
| ET140-p4 | SGSGAGQCSQNEYFDSLLH | [SEQ ID NO: 239] |
| ET140-p5 | SGSGGQCSQNEYFDSLLHA | [SEQ ID NO: 240] |
| ET140-p6 | SGSGQCSQNEYFDSLLHAC | [SEQ ID NO: 241] |
| ET140-p7 | SGSGCSQNEYFDSLLHACI | [SEQ ID NO: 242] |
| ET140-p8 | SGSGSQNEYFDSLLHACIP | [SEQ ID NO: 243] |
| ET140-p9 | SGSGQNEYFDSLLHACIPC | [SEQ ID NO: 244] |
| ET140-p10 | SGSGNEYFDSLLHACIPCQ | [SEQ ID NO: 245] |
| ET140-p11 | SGSGEYFDSLLHACIPCQL | [SEQ ID NO: 246] |
| ET140-p12 | SGSGYFDSLLHACIPCQLR | [SEQ ID NO: 247] |
| ET140-p13 | SGSGFDSLLHACIPCQLRC | [SEQ ID NO: 248] |
| ET140-p14 | SGSGDSLLHACIPCQLRCS | [SEQ ID NO: 249] |
| ET140-p15 | SGSGSLLHACIPCQLRCSS | [SEQ ID NO: 250] |
| ET140-p16 | SGSGLLHACIPCQLRCSSN | [SEQ ID NO: 251] |
| ET140-p17 | SGSGLHACIPCQLRCSSNT | [SEQ ID NO: 252] |
| ET140-p18 | SGSGHACIPCQLRCSSNTP | [SEQ ID NO: 253] |
| ET140-p19 | SGSGACIPCQLRCSSNTPP | [SEQ ID NO: 254] |
| ET140-p20 | SGSGCIPCQLRCSSNTPPL | [SEQ ID NO: 255] |
| ET140-p21 | SGSGIPCQLRCSSNTPPLT | [SEQ ID NO: 256] |
| ET140-p22 | SGSGPCQLRCSSNTPPLTC | [SEQ ID NO: 257] |
| ET140-p23 | SGSGCQLRCSSNTPPLTCQ | [SEQ ID NO: 258] |
| ET140-p24 | SGSGQLRCSSNTPPLTCQR | [SEQ ID NO: 259] |
| ET140-p25 | SGSGLRCSSNTPPLTCQRY | [SEQ ID NO: 260] |
| ET140-p26 | SGSGRCSSNTPPLTCQRYC | [SEQ ID NO: 261] |
| ET140-p27 | SGSGCSSNTPPLTCQRYCN | [SEQ ID NO: 262] |
| ET140-p28 | SGSGSSNTPPLTCQRYCNA | [SEQ ID NO: 263] |
| ET140-p29 | SGSGSNTPPLTCQRYCNAS | [SEQ ID NO: 264] |

TABLE 24-continued

```
ET140-p30  SGSGNTPPLTCQRYCNASV    [SEQ ID NO: 265]
ET140-p31  SGSGTPPLTCQRYCNASVT    [SEQ ID NO: 266]
ET140-p32  SGSGPPLTCQRYCNASVTN    [SEQ ID NO: 267]
ET140-p33  SGSGPLTCQRYCNASVTNS    [SEQ ID NO: 268]
ET140-p34  SGSGLTCQRYCNASVTNSV    [SEQ ID NO: 269]
ET140-p35  SGSGTCQRYCNASVTNSVK    [SEQ ID NO: 270]
ET140-p36  SGSGCQRYCNASVTNSVKG    [SEQ ID NO: 271]
ET140-p37  SGSGQRYCNASVTNSVKGT    [SEQ ID NO: 272]
ET140-p38  SGSGRYCNASVTNSVKGTN    [SEQ ID NO: 273]
ET140-p39  SGSGYCNASVTNSVKGTNA    [SEQ ID NO: 274]
```

Figure 17:
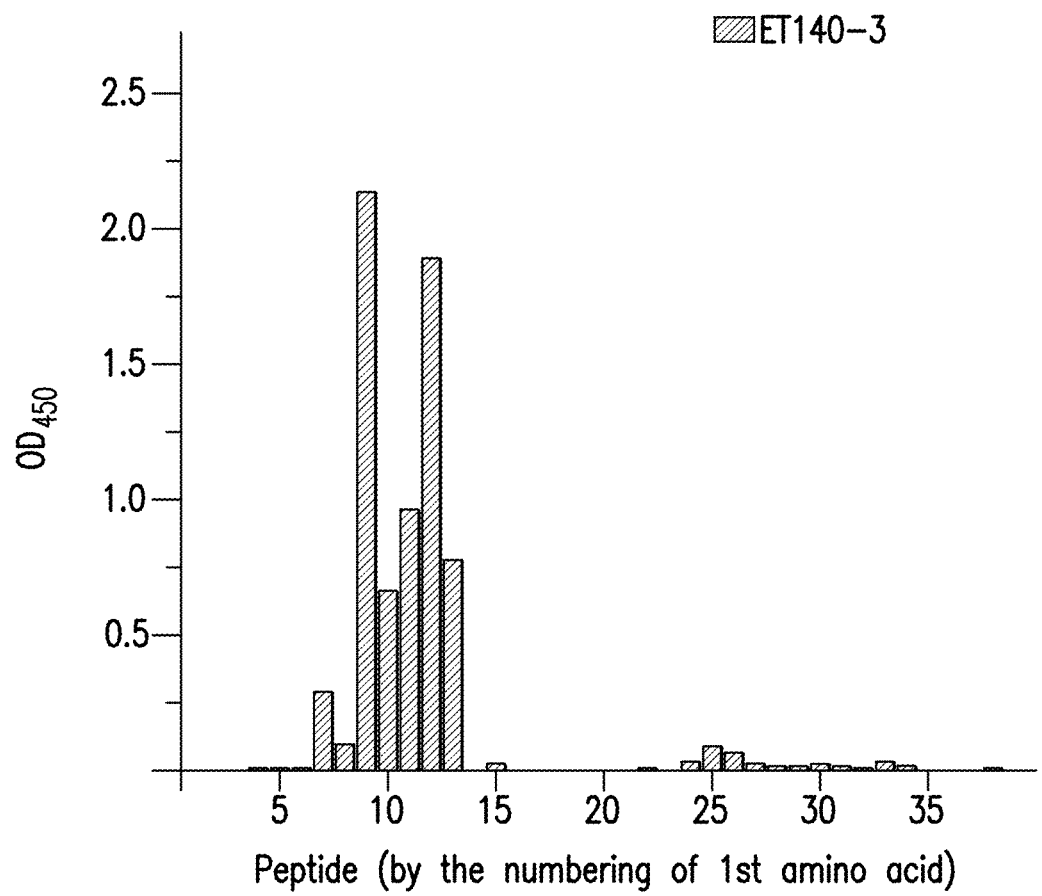
FIG. 17 depicts epitope mapping of ET140-3.
Figure 18:
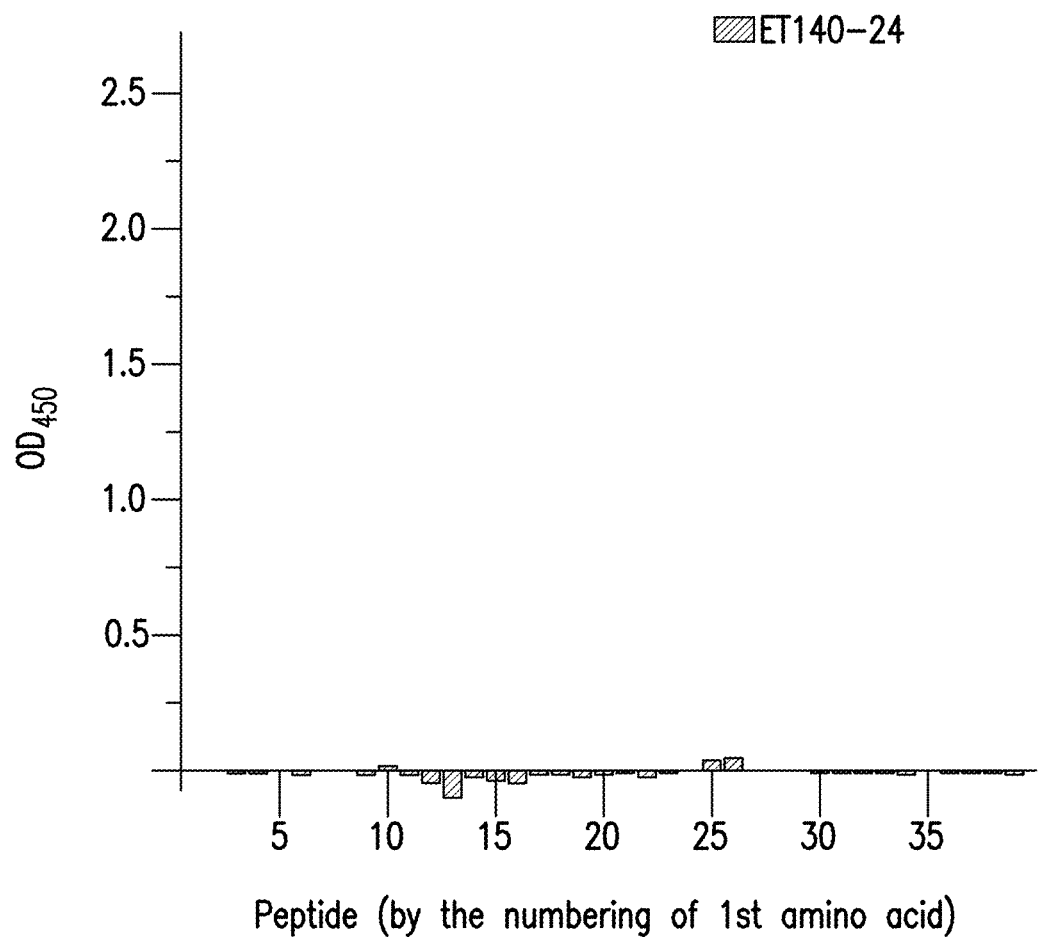
FIG. 18 depicts epitope mapping of ET140-24.
Figure 19:
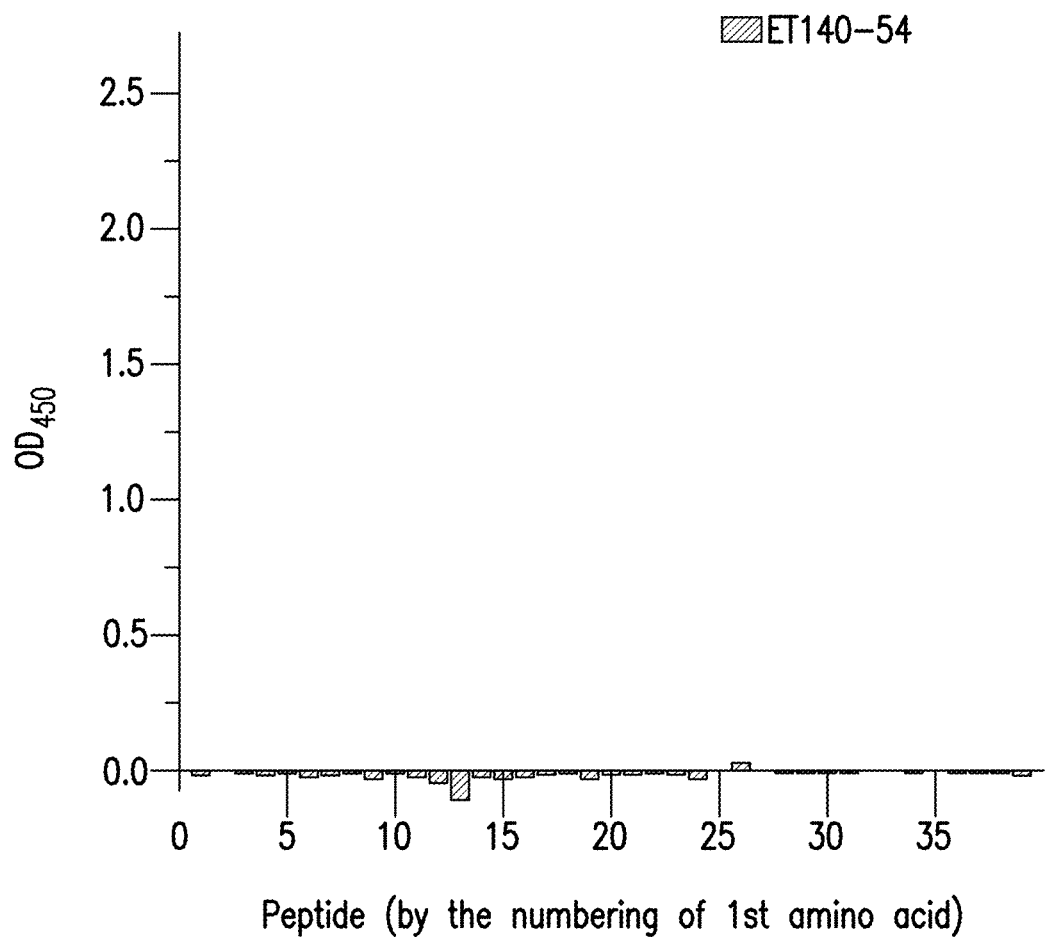
FIG. 19 depicts epitope mapping of ET140-54.

The peptides were coated onto Streptavidin plates at 2 ug/mL in PBST (PBS+0.05% Tween-20). After washing and blocking with 3% BSA. After washing, 1 ug/mL ET140-3, ET140-24, ET140-54 or ET901 mIgG1 was added to the wells, respectively. "mIgG1" used in all Examples represents that the variable region is fully human and the Fc part is mouse IgG1. Then HRP anti-mouse IgG detection antibody was added to each well. Finally, the color was developed using TMB substrate. A450 was recorded for data analysis. The results are shown in FIGS. 17-20. As shown in FIGS. 17 and 20, ET140-3 bound to peptidese 7-13 (i.e., amino acids 8-22, 9-23, 10-24, 11-25, 12-26, 13-27, and 14-28) of SEQ ID NO:71. As shown in FIGS. 18 and 19, no linear epitopes found for ET140-24 or ET140-54.

Summary:

3 ET140 antibodies (mIgG1) were tested together with isotype control ET901 mIgG1 for their binding epitope towards BCMA-ECD. A peptide library consisting of 39 peptides (N-terminal biotin+SGSG linker+15 amino acids, with 1 amino acid offset) was used for epitope mapping ELISA. This allows to search for the linear binding epitope of BCMA-ECD. ET901 mIgG1 was used as background reference for each peptide. Only ET140-3 can be identified for its epitope region: a region comprising amino acids 14-22 of SEQ ID NO:71, e.g., amino acids 8-28 of SEQ ID NO: 71.

ET140-24 and ET140-54 did not show any significant binding towards peptide library. This indicated that these two antibodies may recognize conformational epitope rather than linear epitope of BCMA.

Example 11—Anti-BCMA Antibodies Recombinant Antigen by Surface Plasmon Resonance Kinetics of interaction between ET140-153 mIgG1 (or "ET140-3 mIgG1"), ET140-174 mIgG1 (or "ET140-24 mIgG1"), ET140-204 mIgG1 (or "ET140-54 mIgG1") and BCMA recombinant antigen was measured using a BIAcore ×100 instrument. In brief, 50 µg/mL of modified streptavidin was immobilized onto a Sensor Chip CAP by flowing the Biotin CAPture Reagent through the flow cells at 2 µL/min for 5 minutes. 10 ug/mL biotinylated BCMA-Fc protein was loaded onto the flow cell at a rate of 30 µL/min for 3 minutes. Following the standard protocol for kinetics, a series of injection of ESK1 was performed between 0.6 and 15 µg/mL, each step consisting of a 3 minute injection at 30 µL/min and 3 minute disassociation. Afterwards, the surface was regenerated for 2 minutes with a solution consisting of 75% v/v of 8M guanidine-HCl and 25% v/v 1M NaOH. Kinetic constants were derived by the global fitting (1:1 Langmuir binding model) using BIAcore ×100 Evaluation Software (Version 2.0.1). The binding affinity data are shown in Table 25.

TABLE 25

| Protein | KD |
|---|---|
| ET140-24 mIgG1 | KD: 4.8 nM (BiaCore) |
| ET140-54 mIgG1 | KD: 8.1 nM (BiaCore) |
| ET140-3 mIgG1 | KD: 1.2 nM (BiaCore) |

Although the foregoing presently disclosed subject matter has been described in some detail by way of illustration and example for purposes of clarity of understanding, the descriptions and examples should not be construed as limiting the scope of the presently disclosed subject matter. The disclosures of all patent and scientific literature cited herein are expressly incorporated in their entirety by reference.

REFERENCES

1. Frigyesi, I., et al. Robust isolation of malignant plasma cells in multiple myeloma. *Blood* 123, 1336-1340 (2014).
2. Tai, Y. T., et al. Novel afucosylated anti-B cell maturation antigen-monomethyl auristatin F antibody-drug conjugate (GSK2857916) induces potent and selective anti-multiple myeloma activity. *Blood* (2014).
3. Carpenter, R. O., et al. B-cell maturation antigen is a promising target for adoptive T-cell therapy of multiple myeloma. *Clinical cancer research: an official journal of the American Association for Cancer Research* 19, 2048-2060 (2013).
4. Brentjens, R. J., et al. Safety and persistence of adoptively transferred autologous CD19-targeted T cells in patients with relapsed or chemotherapy refractory B-cell leukemias. *Blood* 118, 4817-4828 (2011).
5. Brentjens, R. J., et al. Eradication of systemic B-cell tumors by genetically targeted human T lymphocytes co-stimulated by CD80 and interleukin-15. *Nature medicine* 9, 279-286 (2003).
6. Brentjens, R. J., et al. CD19-Targeted T Cells Rapidly Induce Molecular Remissions in Adults with Chemotherapy-Refractory Acute Lymphoblastic Leukemia. *Science translational medicine* 5, 177ra138 (2013).
7. Davila, M. L., et al. Efficacy and Toxicity Management of 19-28z CAR T Cell Therapy in B Cell Acute Lymphoblastic Leukemia. *Science translational medicine* 6, 224ra225 (2014).
8. Siegel, R., Naishadham, D. & Jemal, A. Cancer statistics, 2013. *CA: a cancer journal for clinicians* 63, 11-30 (2013).
9. Boyd, K. D., et al. The clinical impact and molecular biology of del(17p) in multiple myeloma treated with conventional or thalidomide-based therapy. *Genes, chromosomes & cancer* 50, 765-774 (2011).
10. Shaughnessy, J. D., Jr., et al. A validated gene expression model of high-risk multiple myeloma is defined by deregulated expression of genes mapping to chromosome 1. *Blood* 109, 2276-2284 (2007).
11. Gahrton, G., et al. Allogeneic bone marrow transplantation in multiple myeloma. European Group for Bone Marrow Transplantation. *The New England journal of medicine* 325, 1267-1273 (1991).

12. Pegram, H. J., et al. Tumor-targeted T cells modified to secrete IL-12 eradicate systemic tumors without need for prior conditioning. *Blood* 119, 4133-4141 (2012).
13. Sabrina Bertilaccio, M. T., et al. Low-Dose Lenalidomide Improves CAR-Based Immunotherapy In CLL By Reverting T-Cell Defects In Vivo. *Blood* 122, 4171 (2013).
14. Bataille, R., et al. The phenotype of normal, reactive and malignant plasma cells. Identification of "many and multiple myelomas" and of new targets for myeloma therapy. *Haematologica* 91, 1234-1240 (2006).
15. Morgan, R. A., et al. Case report of a serious adverse event following the administration of T cells transduced with a chimeric antigen receptor recognizing ERBB2. *Molecular therapy: the journal of the American Society of Gene Therapy* 18, 843-851 (2010).
16. Brentjens, R. J., et al. Safety and persistence of adoptively transferred autologous CD19-targeted T cells in patients with relapsed or chemotherapy refractory B-cell leukemias. *Blood* 118, 4817-4828 (2011).
17. Brentjens, R. J., et al. CD19-targeted T cells rapidly induce molecular remissions in adults with chemotherapy-refractory acute lymphoblastic leukemia. *Science translational medicine* 5, 177ra138 (2013).
18. Hunder, N. N., et al. Treatment of metastatic melanoma with autologous CD4+ T cells against NY-ESO-1. *N. Engl. J. Med.* 358, 2698-2703 (2008).
19. Rosenberg, S. A., Restifo, N. P., Yang, J. C., Morgan, R. A. & Dudley, M. E. Adoptive cell transfer: a clinical path to effective cancer immunotherapy. *Nat. Rev. Cancer* 8, 299-308 (2008).
20. Dudley, M. E., et al. Adoptive cell therapy for patients with metastatic melanoma: evaluation of intensive myeloablative chemoradiation preparative regimens. *J Clin Oncol* 26, 5233-5239 (2008).
21. Brentjens, R. J., et al. Genetically targeted T cells eradicate systemic acute lymphoblastic leukemia xenografts. *Clin. Cancer Res.* 13, 5426-5435 (2007).
22. Gade, T. P., et al. Targeted elimination of prostate cancer by genetically directed human T lymphocytes. *Cancer Res.* 65, 9080-9088 (2005).
23. Maher, J., Brentjens, R. J., Gunset, G., Riviere, I. & Sadelain, M. Human T-lymphocyte cytotoxicity and proliferation directed by a single chimeric TCRzeta/CD28 receptor. *Nat. Biotechnol.* 20, 70-75 (2002).
24. Kershaw, M. H., et al. Gene-engineered T cells as a superior adjuvant therapy for metastatic cancer. *J Immunol* 173, 2143-2150 (2004).
25. Sadelain, M., Brentjens, R. & Riviere, I. The promise and potential pitfalls of chimeric antigen receptors. *Curr Opin Immunol* (2009).
26. Hollyman, D., et al. Manufacturing validation of biologically functional T cells targeted to CD19 antigen for autologous adoptive cell therapy. *J Immunother* 32, 169-180 (2009).
27. Sadelain, M., Brentjens, R. & Riviere, I. The basic principles of chimeric antigen receptor design. *Cancer discovery* 3, 388-398 (2013).
28. Riviere, I., Sadelain, M. & Brentjens, R. J. Novel strategies for cancer therapy: the potential of genetically modified T lymphocytes. *Curr Hematol Rep* 3, 290-297 (2004).
29. Stephan, M. T., et al. T cell-encoded CD80 and 4-1BBL induce auto- and transco-stimulation, resulting in potent tumor rejection. *Nat. Med.* 13, 1440-1449 (2007).
30. Krause, A., et al. Antigen-dependent CD28 signaling selectively enhances survival and proliferation in genetically modified activated human primary T lymphocytes. *J Exp Med* 188, 619-626 (1998).
31. Gong, M. C., et al. Cancer patient T cells genetically targeted to prostate-specific membrane antigen specifically lyse prostate cancer cells and release cytokines in response to prostate-specific membrane antigen. *Neoplasia.* 1, 123-127 (1999).
32. Lyddane, C., et al. Cutting Edge: CD28 controls dominant regulatory T cell activity during active immunization. *J. Immunol.* 176, 3306-3310 (2006).
33. Carpenter et al., B-cell maturation antigen is a promising target for adoptive T-cell therapy of multiple myeloma. *Clin Cancer Res.* 2013 Apr. 15; 19(8):2048-60.
34. WO2013/154760
35. Maus et al., *Cancer Immunol Res* (2003); 1(1):26-31

From the foregoing description, it will be apparent that variations and modifications may be made to the invention described herein to adopt it to various usages and conditions. Such embodiments are also within the scope of the following claims.

All patents and publications and sequences referred to by accession or reference number mentioned in this specification are herein incorporated by reference to the same extent as if each independent patent and publication and sequence was specifically and individually indicated to be incorporated by reference.

What is claimed is:

1. A chimeric antigen receptor (CAR), comprising an extracellular antigen-binding domain that binds to B cell maturation antigen (BCMA), a transmembrane domain, and an intracellular domain, wherein the extracellular antigen-binding domain comprises:

(a) a heavy chain variable region comprising a CDR1, a CDR2, and a CDR3 of the heavy chain variable region sequence set forth in SEQ ID NO:1, and a light chain variable region comprising a CDR1, a CDR2, and a CDR3 of the light chain variable region sequence set forth in SEQ ID NO:2;

(b) a heavy chain variable region comprising a CDR1, a CDR2, and a CDR3 of the heavy chain variable region sequence set forth in SEQ ID NO:5, and a light chain variable region comprising a CDR1, a CDR2, and a CDR3 of the light chain variable region sequence set forth in SEQ ID NO:6;

(c) a heavy chain variable region comprising a CDR1, a CDR2, and a CDR3 of the heavy chain variable region sequence set forth in SEQ ID NO:9, and a light chain variable region comprising a CDR1, a CDR2, and a CDR3 of the light chain variable region sequence set forth in SEQ ID NO:10;

(d) a heavy chain variable region comprising a CDR1, a CDR2, and a CDR3 of the heavy chain variable region sequence set forth in SEQ ID NO:13, and a light chain variable region comprising a CDR1, a CDR2, and a CDR3 of the light chain variable region sequence set forth in SEQ ID NO:14;

(e) a heavy chain variable region comprising a CDR1, a CDR2, and a CDR3 of the heavy chain variable region sequence set forth in SEQ ID NO:17, and a light chain variable region comprising a CDR1, a CDR2, and a CDR3 of the light chain variable region sequence set forth in SEQ ID NO:18;

(f) a heavy chain variable region comprising a CDR1, a CDR2, and a CDR3 of the heavy chain variable region sequence set forth in SEQ ID NO:21, and a light chain variable region comprising a CDR1, a CDR2, and a CDR3 of the light chain variable region sequence set forth in SEQ ID NO:22;

(g) a heavy chain variable region comprising a CDR1, a CDR2, and a CDR3 of the heavy chain variable region sequence set forth in SEQ ID NO:25, and a light chain variable region comprising a CDR1, a CDR2, and a CDR3 of the light chain variable region sequence set forth in SEQ ID NO:26;

(h) a heavy chain variable region comprising a CDR1, a CDR2, and a CDR3 of the heavy chain variable region sequence set forth in SEQ ID NO:29, and a light chain variable region comprising a CDR1, a CDR2, and a CDR3 of the light chain variable region sequence set forth in SEQ ID NO:30;

(i) a heavy chain variable region comprising a CDR1, a CDR2, and a CDR3 of the heavy chain variable region sequence set forth in SEQ ID NO:33, and a light chain variable region comprising a CDR1, a CDR2, and a CDR3 of the light chain variable region sequence set forth in SEQ ID NO:34;

(j) a heavy chain variable region comprising a CDR1, a CDR2, and a CDR3 of the heavy chain variable region sequence set forth in SEQ ID NO:37, and a light chain variable region comprising a CDR1, a CDR2, and a CDR3 of the light chain variable region sequence set forth in SEQ ID NO:38;

(k) a heavy chain variable region comprising a CDR1, a CDR2, and a CDR3 of the heavy chain variable region sequence set forth in SEQ ID NO:41, and a light chain variable region comprising a CDR1, a CDR2, and a CDR3 of the light chain variable region sequence set forth in SEQ ID NO:42;

(l) a heavy chain variable region comprising a CDR1, a CDR2, and a CDR3 of the heavy chain variable region sequence set forth in SEQ ID NO:45, and a light chain variable region comprising a CDR1, a CDR2, and a CDR3 of the light chain variable region sequence set forth in SEQ ID NO:46;

(m) a heavy chain variable region comprising a CDR1, a CDR2, and a CDR3 of the heavy chain variable region sequence set forth in SEQ ID NO:49, and a light chain variable region comprising a CDR1, a CDR2, and a CDR3 of the light chain variable region sequence set forth in SEQ ID NO:50;

(n) a heavy chain variable region comprising a CDR1, a CDR2, and a CDR3 of the heavy chain variable region sequence set forth in SEQ ID NO:53, and a light chain variable region comprising a CDR1, a CDR2, and a CDR3 of the light chain variable region sequence set forth in SEQ ID NO:54;

(o) a heavy chain variable region comprising a CDR1, a CDR2, and a CDR3 of the heavy chain variable region sequence set forth in SEQ ID NO:57, and a light chain variable region comprising a CDR1, a CDR2, and a CDR3 of the light chain variable region sequence set forth in SEQ ID NO:58;

(p) a heavy chain variable region comprising a CDR1, a CDR2, and a CDR3 of the heavy chain variable region sequence set forth in SEQ ID NO:61, and a light chain variable region comprising a CDR1, a CDR2, and a CDR3 of the light chain variable region sequence set forth in SEQ ID NO:62; or (q) a heavy chain variable region comprising a CDR1, a CDR2, and a CDR3 of the heavy chain variable region sequence set forth in SEQ ID NO:65, and a light chain variable region comprising a CDR1, a CDR2, and a CDR3 of the light chain variable region sequence set forth in SEQ ID NO:66.

2. A chimeric antigen receptor (CAR), comprising an extracellular antigen-binding domain that binds to B cell maturation antigen (BCMA), a transmembrane domain, and an intracellular domain, wherein the extracellular antigen-binding domain comprises:

(a) a heavy chain variable region comprising a CDR1, a CDR2, and a CDR3 sequence set forth in SEQ ID NOs: 89, 90, and 91, respectively; and a light chain variable region comprising a CDR1, a CDR2, and a CDR3 sequence set forth in SEQ ID NOs: 92, 93, and 94, respectively;

(b) a heavy chain variable region comprising a CDR1, a CDR2, and a CDR3 sequence set forth in SEQ ID NOs: 95, 96, and 97, respectively; and a light chain variable region comprising a CDR1, a CDR2, and a CDR3 sequence set forth in SEQ ID NOs: 98, 99, and 100, respectively;

(c) a heavy chain variable region comprising a CDR1, a CDR2, and a CDR3 sequence set forth in SEQ ID NOs: 101, 102, and 103, respectively; and a light chain variable region comprising a CDR1, a CDR2, and a CDR3 sequence set forth in SEQ ID NOs: 104, 105, and 106, respectively;

(d) a heavy chain variable region comprising a CDR1, a CDR2, and a CDR3 sequence set forth in SEQ ID NOs: 107, 108, and 109, respectively; and a light chain variable region comprising a CDR1, a CDR2, and a CDR3 sequence set forth in SEQ ID NOs: 110, 111, and 112, respectively;

(e) a heavy chain variable region comprising a CDR1, a CDR2, and a CDR3 sequence set forth in SEQ ID NOs: 113, 114, and 115, respectively; and a light chain variable region comprising a CDR1, a CDR2, and a CDR3 sequence set forth in SEQ ID NOs: 116, 117, and 118, respectively;

(f) a heavy chain variable region comprising a CDR1, a CDR2, and a CDR3 sequence set forth in SEQ ID NOs: 119, 120, and 121, respectively; and a light chain variable region comprising a CDR1, a CDR2, and a CDR3 sequence set forth in SEQ ID NOs: 122, 123, and 124, respectively;

(g) a heavy chain variable region comprising a CDR1, a CDR2, and a CDR3 sequence set forth in SEQ ID NOs: 125, 126, and 127, respectively; and a light chain variable region comprising a CDR1, a CDR2, and a CDR3 sequence set forth in SEQ ID NOs: 128, 129, and 130, respectively;

(h) a heavy chain variable region comprising a CDR1, a CDR2, and a CDR3 sequence set forth in SEQ ID NOs: 131, 132, and 133, respectively; and a light chain variable region comprising a CDR1, a CDR2, and a CDR3 sequence set forth in SEQ ID NOs: 134, 135, and 136, respectively;

(i) a heavy chain variable region comprising a CDR1, a CDR2, and a CDR3 sequence set forth in SEQ ID NOs: 137, 138, and 139, respectively; and a light chain variable region comprising a CDR1, a CDR2, and a CDR3 sequence set forth in SEQ ID NOs: 140, 141, and 142, respectively;

(j) a heavy chain variable region comprising a CDR1, a CDR2, and a CDR3 sequence set forth in SEQ ID NOs: 143, 144, and 145, respectively; and a light chain variable region comprising a CDR1, a CDR2, and a CDR3 sequence set forth in SEQ ID NOs: 146, 147, and 148, respectively;

(k) a heavy chain variable region comprising a CDR1, a CDR2, and a CDR3 sequence set forth in SEQ ID NOs: 149, 150, and 151, respectively; and a light chain variable region comprising a CDR1, a CDR2, and a CDR3 sequence set forth in SEQ ID NOs: 152, 153, and 154, respectively;

(l) a heavy chain variable region comprising a CDR1, a CDR2, and a CDR3 sequence set forth in SEQ ID NOs: 155, 156, and 157, respectively; and a light chain variable region comprising a CDR1, a CDR2, and a CDR3 sequence set forth in SEQ ID NOs: 158, 159, and 160, respectively;

(m) a heavy chain variable region comprising a CDR1, a CDR2, and a CDR3 sequence set forth in SEQ ID NOs: 161, 162, and 163, respectively; and a light chain variable region comprising a CDR1, a CDR2, and a CDR3 sequence set forth in SEQ ID NOs: 164, 165, and 166, respectively;

(n) a heavy chain variable region comprising a CDR1, a CDR2, and a CDR3 sequence set forth in SEQ ID NOs: 167, 168, and 169, respectively; and a light chain variable region comprising a CDR1, a CDR2, and a CDR3 sequence set forth in SEQ ID NOs: 170, 171, and 172, respectively (o) a heavy chain variable region comprising a CDR1, a CDR2, and a CDR3 sequence set forth in SEQ ID NOs: 173, 174, and 175, respectively; and a light chain variable region comprising a CDR1, a CDR2, and a CDR3 sequence set forth in SEQ ID NOs: 176, 177, and 178, respectively;

(p) a heavy chain variable region comprising a CDR1, a CDR2, and a CDR3 sequence set forth in SEQ ID NOs: 179, 180, and 181, respectively; and a light chain variable region comprising a CDR1, a CDR2, and a CDR3 sequence set forth in SEQ ID NOs: 182, 183, and 184, respectively; or (q) a heavy chain variable region comprising a CDR1, a CDR2, and a CDR3 sequence set forth in SEQ ID NOs: 185, 186, and 187, respectively; and a light chain variable region comprising a CDR1, a CDR2, and a CDR3 sequence set forth in SEQ ID NOs: 188, 189, and 190, respectively.

3. The CAR of claim 1, wherein:
(a) the heavy chain variable region comprises an amino acid sequence that has at least about 90% sequence identity to the sequence set forth in SEQ ID NO:1, and the light chain variable region comprises an amino acid sequence that has at least about 90% sequence identity to the sequence set forth in SEQ ID NO:2;
(b) the heavy chain variable region comprises an amino acid sequence that has at least about 90% sequence identity to the sequence set forth in SEQ ID NO:5, and the light chain variable region comprises an amino acid sequence that has at least about 90% sequence identity to the sequence set forth in SEQ ID NO:6;
(c) the heavy chain variable region comprises an amino acid sequence that has at least about 90% sequence identity to the sequence set forth in SEQ ID NO:9, and the light chain variable region comprises an amino acid sequence that has at least about 90% sequence identity to the sequence set forth in SEQ ID NO:10;
(d) the heavy chain variable region comprises an amino acid sequence that has at least about 90% sequence identity to the sequence set forth in SEQ ID NO:13, and the light chain variable region comprises an amino acid sequence that has at least about 90% sequence identity to the sequence set forth in SEQ ID NO:14;
(e) the heavy chain variable region comprises an amino acid sequence that has at least about 90% sequence identity to the sequence set forth in SEQ ID NO:17, and the light chain variable region comprises an amino acid sequence that has at least about 90% sequence identity to the sequence set forth in SEQ ID NO:18;
(f) the heavy chain variable region comprises an amino acid sequence that has at least about 90% sequence identity to the sequence set forth in SEQ ID NO:21, and the light chain variable region comprises an amino acid sequence that has at least about 90% sequence identity to the sequence set forth in SEQ ID NO:22;
(g) the heavy chain variable region comprises an amino acid sequence that has at least about 90% sequence identity to the sequence set forth in SEQ ID NO:25, and the light chain variable region comprises an amino acid sequence that has at least about 90% sequence identity to the sequence set forth in SEQ ID NO:26;
(h) the heavy chain variable region comprises an amino acid sequence that has at least about 90% sequence identity to the sequence set forth in SEQ ID NO:29, and the light chain variable region comprises an amino acid sequence that has at least about 90% sequence identity to the sequence set forth in SEQ ID NO:30;
(i) the heavy chain variable region comprises an amino acid sequence that has at least about 90% sequence identity to the sequence set forth in SEQ ID NO:33, and the light chain variable region comprises an amino acid sequence that has at least about 90% sequence identity to the sequence set forth in SEQ ID NO:34;
(j) the heavy chain variable region comprises an amino acid sequence that has at least about 90% sequence identity to the sequence set forth in SEQ ID NO:37, and the light chain variable region comprises an amino acid sequence that has at least about 90% sequence identity to the sequence set forth in SEQ ID NO:38;
(k) the heavy chain variable region comprises an amino acid sequence that has at least about 90% sequence identity to the sequence set forth in SEQ ID NO:41, and the light chain variable region comprises an amino acid sequence that has at least about 90% sequence identity to the sequence set forth in SEQ ID NO:42;
(l) the heavy chain variable region comprises an amino acid sequence that has at least about 90% sequence identity to the sequence set forth in SEQ ID NO:45, and the light chain variable region comprises an amino acid sequence that has at least about 90% sequence identity to the sequence set forth in SEQ ID NO:46;
(m) the heavy chain variable region comprises an amino acid sequence that has at least about 90% sequence identity to the sequence set forth in SEQ ID NO:49, and the light chain variable region comprises an amino acid sequence that has at least about 90% sequence identity to the sequence set forth in SEQ ID NO:50;
(n) the heavy chain variable region comprises an amino acid sequence that has at least about 90% sequence identity to the sequence set forth in SEQ ID NO:53, and the light chain variable region comprises an amino acid sequence that has at least about 90% sequence identity to the sequence set forth in SEQ ID NO:54
(o) the heavy chain variable region comprises an amino acid sequence that has at least about 90% sequence identity to the sequence set forth in SEQ ID NO:57, and the light chain variable region comprises an amino acid sequence that has at least about 90% sequence identity to the sequence set forth in SEQ ID NO:58;
(p) the heavy chain variable region comprises an amino acid sequence that has at least about 90% sequence identity to the sequence set forth in SEQ ID NO:61, and the light chain variable region comprises an amino acid sequence that has at least about 90% sequence identity to the sequence set forth in SEQ ID NO:62; or
(q) the heavy chain variable region comprises an amino acid sequence that has at least about 90% sequence identity to the sequence set forth in SEQ ID NO:65, and the light chain variable region comprises an amino acid sequence that has at least about 90% sequence identity to the sequence set forth in SEQ ID NO:66.

4. The CAR of claim 3, wherein:
(a) the heavy chain variable region comprises the amino acid sequence set forth in SEQ ID NO:1, and the light chain variable region comprises the amino acid sequence set forth in SEQ ID NO:2;
(b) the heavy chain variable region comprises the amino acid sequence set forth in SEQ ID NO:5, and the light chain variable region comprises the amino acid sequence set forth in SEQ ID NO:6;
(c) the heavy chain variable region comprises the amino acid sequence set forth in SEQ ID NO:9, and the light chain variable region comprises the amino acid sequence set forth in SEQ ID NO:10;
(d) the heavy chain variable region comprises the amino acid sequence set forth in SEQ ID NO:13, and the light chain variable region comprises the amino acid sequence set forth in SEQ ID NO:14;
(e) the heavy chain variable region comprises the amino acid sequence set forth in SEQ ID NO:17, and the light chain variable region comprises the amino acid sequence set forth in SEQ ID NO:18;
(f) the heavy chain variable region comprises the amino acid sequence set forth in SEQ ID NO:21, and the light chain variable region comprises the amino acid sequence set forth in SEQ ID NO:22;
(g) the heavy chain variable region comprises the amino acid sequence set forth in SEQ ID NO:25, and the light chain variable region comprises the amino acid sequence set forth in SEQ ID NO:26;
(h) the heavy chain variable region comprises the amino acid sequence set forth in SEQ ID NO:29, and the light chain variable region comprises the amino acid sequence set forth in SEQ ID NO:30;

(i) the heavy chain variable region comprises the amino acid sequence set forth in SEQ ID NO:33, and the light chain variable region comprises the amino acid sequence set forth in SEQ ID NO:34;

(j) the heavy chain variable region comprises the amino acid sequence set forth in SEQ ID NO:37, and the light chain variable region comprises the amino acid sequence set forth in SEQ ID NO:38;

(k) the heavy chain variable region comprises the amino acid sequence set forth in SEQ ID NO:41, and the light chain variable region comprises the amino acid sequence set forth in SEQ ID NO:42;

(l) the heavy chain variable region comprises the amino acid sequence set forth in SEQ ID NO:45, and the light chain variable region comprises the amino acid sequence set forth in SEQ ID NO:46;

(m) the heavy chain variable region comprises the amino acid sequence set forth in SEQ ID NO:49, and the light chain variable region comprises the amino acid sequence set forth in SEQ ID NO:50;

(n) the heavy chain variable region comprises the amino acid sequence set forth in SEQ ID NO:53, and the light chain variable region comprises the amino acid sequence set forth in SEQ ID NO:54;

(o) the heavy chain variable region comprises the amino acid sequence set forth in SEQ ID NO:57, and the light chain variable region comprises the amino acid sequence set forth in SEQ ID NO:58;

(p) the heavy chain variable region comprises the amino acid sequence set forth in SEQ ID NO:61, and the light chain variable region comprises the amino acid sequence set forth in SEQ ID NO:62; or (q) the heavy chain variable region comprises the amino acid sequence set forth in SEQ ID NO:65, and the light chain variable region comprises the amino acid sequence set forth in SEQ ID NO:66.

5. The CAR of claim 2, wherein the heavy chain variable region comprises a CDR1, a CDR2, and a CDR3 sequence set forth in SEQ ID NOs: 119, 120, and 121, respectively; and the light chain variable region comprises a CDR1, a CDR2, and a CDR3 sequence set forth in SEQ ID NOs: 122, 123, and 124, respectively.

6. The CAR of claim 2, wherein the heavy chain variable region comprises a CDR1, a CDR2, and a CDR3 sequence set forth in SEQ ID NOs: 167, 168, and 169, respectively; and the light chain variable region comprises a CDR1, a CDR2, and a CDR3 sequence set forth in SEQ ID NOs: 170, 171, and 172, respectively.

7. The CAR of claim 2, wherein the heavy chain variable region comprises a CDR1, a CDR2, and a CDR3 sequence set forth in SEQ ID NOs: 173, 174, and 175, respectively; and the light chain variable region comprises a CDR1, a CDR2, and a CDR3 sequence set forth in SEQ ID NOs: 176, 177, and 178, respectively.

8. The CAR of claim 2, wherein the heavy chain variable region comprises a CDR1, a CDR2, and a CDR3 sequence set forth in SEQ ID NOs: 179, 180, and 181, respectively; and the light chain variable region comprises a CDR1, a CDR2, and a CDR3 sequence set forth in SEQ ID NOs: 182, 183, and 184, respectively.

9. The CAR of claim 2, wherein the heavy chain variable region comprises a CDR1, a CDR2, and a CDR3 sequence set forth in SEQ ID NOs: 185, 186, and 187, respectively; and the light chain variable region comprises a CDR1, a CDR2, and a CDR3 sequence set forth in SEQ ID NOs: 188, 189, and 190, respectively.

10. The CAR of claim 4, wherein the heavy chain variable region comprises the amino acid sequence set forth in SEQ ID NO:21, and the light chain variable region comprises the amino acid sequence set forth in SEQ ID NO:22.

11. The CAR of claim 4, wherein the heavy chain variable region comprises the amino acid sequence set forth in SEQ ID NO: 53, and the light chain variable region comprises the amino acid sequence set forth in SEQ ID NO: 54.

12. The CAR of claim 4, wherein the heavy chain variable region comprises the amino acid sequence set forth in SEQ ID NO:57, and the light chain variable region comprises the amino acid sequence set forth in SEQ ID NO:58.

13. The CAR of claim 4, wherein the heavy chain variable region comprises the amino acid sequence set forth in SEQ ID NO: 61, and the light chain variable region comprises the amino acid sequence set forth in SEQ ID NO: 62.

14. The CAR of claim 4, wherein the heavy chain variable region comprises the amino acid sequence set forth in SEQ ID NO: 65, and the light chain variable region comprises the amino acid sequence set forth in SEQ ID NO: 66.

15. The CAR of claim 1, wherein the extracellular antigen-binding domain comprises a linker positioned between the heavy chain variable region and the light chain variable region.

16. The CAR of claim 1, wherein the extracellular antigen-binding domain is a single-chain variable fragment (scFv).

17. The CAR of claim 2, wherein the extracellular antigen-binding domain comprises a linker positioned between the heavy chain variable region and the light chain variable region.

18. The CAR of claim 2, wherein the extracellular antigen-binding domain is a single-chain variable fragment (scFv).

19. The CAR of claim 4, wherein the extracellular antigen-binding domain comprises a linker positioned between the heavy chain variable region and the light chain variable region.

20. The CAR of claim 4, wherein the extracellular antigen-binding domain is a single-chain variable fragment (scFv).

21. The CAR of claim 16, wherein the extracellular antigen-binding domain is a human scFv.

22. The CAR of claim 1, wherein the extracellular antigen-binding domain comprises the amino acid sequence set forth in SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, or SEQ ID NO: 88.

23. The CAR of claim 22, wherein the extracellular antigen-binding domain comprises the amino acid sequence set forth in SEQ ID NO:77.

24. The CAR of claim 22, wherein the extracellular antigen-binding domain comprises the amino acid sequence set forth in SEQ ID NO:85.

25. The CAR of claim 22, wherein the extracellular antigen-binding domain comprises the amino acid sequence set forth in SEQ ID NO:86.

26. The CAR of claim 22, wherein the extracellular antigen-binding domain comprises the amino acid sequence set forth in SEQ ID NO:87.

27. The CAR of claim 22, wherein the extracellular antigen-binding domain comprises the amino acid sequence set forth in SEQ ID NO:88.

28. The CAR of claim 1, wherein the BCMA comprises the amino acid sequence set forth in SEQ ID NO:71.

29. The CAR of claim 2, wherein the BCMA comprises the amino acid sequence set forth in SEQ ID NO:71.

30. The CAR of claim 4, wherein the BCMA comprises the amino acid sequence set forth in SEQ ID NO:71.

31. The CAR of claim 1, wherein the extracellular antigen-binding domain binds to a non-linear epitope of BCMA.

32. The CAR of claim 1, wherein the extracellular antigen-binding domain of the CAR binds to B cell maturation antigen (BCMA) with a binding affinity ($K_D$) of from about $1 \times 10^{-9}$ M to about $1 \times 10^{-8}$ M.

33. The CAR of claim 1, wherein the transmembrane domain comprises a CD8 polypeptide, a CD28 polypeptide, a CD3t polypeptide, a CD4 polypeptide, a 4-1BB polypeptide, an OX40 polypeptide, an ICOS polypeptide, a CTLA-4 polypeptide, a PD-1 polypeptide, a LAG-3 polypeptide, a 2B4 polypeptide, a BTLA polypeptide, a synthetic peptide, or a combination thereof.

34. The CAR of claim 33, wherein the transmembrane domain comprises a CD8 polypeptide.

35. The CAR of claim 33, wherein the transmembrane domain comprises a CD28 polypeptide.

36. The CAR of claim 1, wherein the intracellular domain comprises a CD3t polypeptide.

37. The CAR of claim 36, wherein the intracellular domain comprises at least one signaling region that is a co-stimulatory signaling region.

38. The CAR of claim 37, wherein the co-stimulatory signaling region comprises a CD28 polypeptide, a 4-1BB polypeptide, an OX40 polypeptide, an ICOS polypeptide, a DAP-10 polypeptide, or a combination thereof.

39. The CAR of claim 38, wherein the co-stimulatory signaling region comprises a CD28 polypeptide.

40. The CAR of claim 38, wherein the co-stimulatory signaling region comprises a 4-1BB polypeptide.

41. The CAR of claim 40, wherein the transmembrane domain comprises a CD28 polypeptide.

42. The CAR of claim 2, wherein the intracellular domain comprises a CD3ζ polypeptide and at least one signaling region that is a co-stimulatory signaling region.

43. The CAR of claim 42, wherein the co-stimulatory signaling region comprises a 4-1BB polypeptide.

44. The CAR of claim 43, wherein the transmembrane domain comprises a CD28 polypeptide.

45. The CAR of claim 4, wherein the intracellular domain comprises a CD3ζ polypeptide and at least one signaling region that is a co-stimulatory signaling region.

46. The CAR of claim 45, wherein the co-stimulatory signaling region comprises a 4-1BB polypeptide.

47. The CAR of claim 46, wherein the transmembrane domain comprises a CD28 polypeptide.

48. An immunoresponsive cell comprising the CAR of claim 1.

49. An immunoresponsive cell comprising the CAR of claim 2.

50. An immunoresponsive cell comprising the CAR of claim 4.

51. The immunoresponsive cell of claim 48, wherein the immunoresponsive cell is selected from the group consisting of a T cell, a Natural Killer (NK) cell, a human embryonic stem cell, a lymphoid progenitor cell, a T cell-precursor cell, and a stem cell from which a lymphoid cell may be differentiated.

52. A T cell comprising the CAR of claim 1.

53. A T cell comprising the CAR of claim 2.

54. A T cell comprising the CAR of claim 4.

55. A pharmaceutical composition comprising an effective amount of the immunoresponsive cell of claim 48 and a pharmaceutically acceptable excipient.

56. A pharmaceutical composition comprising an effective amount of the immunoresponsive cell of claim 49 and a pharmaceutically acceptable excipient.

57. A pharmaceutical composition comprising an effective amount of the immunoresponsive cell of claim 50 and a pharmaceutically acceptable excipient.

* * * * *